US007262192B2

(12) United States Patent
Bell et al.

(10) Patent No.: US 7,262,192 B2
(45) Date of Patent: Aug. 28, 2007

(54) SUBSTITUTED PYRAZOLO[4,3-D]PYRIMIDINES AND THEIR USE AS PDE-5 INHIBITORS

(75) Inventors: Andrew Simon Bell, Sandwich (GB); David Graham Brown, Sandwich (GB); David Nathan Abraham Fox, Sandwich (GB); Ian Roger Marsh, Sandwich (GB); Andrew Ian Morrell, Sandwich (GB); Michael John Palmer, Sandwich (GB); Carol Ann Winslow, Sandwich (GB)

(73) Assignee: Pfizer Inc., New York, NY (US)

( * ) Notice: Subject to any disclaimer, the term of this patent is extended or adjusted under 35 U.S.C. 154(b) by 472 days.

(21) Appl. No.: 10/834,484

(22) Filed: Apr. 29, 2004

(65) Prior Publication Data

US 2005/0043325 A1 Feb. 24, 2005

Related U.S. Application Data

(60) Provisional application No. 60/538,147, filed on Jan. 20, 2004, provisional application No. 60/476,678, filed on Jun. 6, 2003.

(30) Foreign Application Priority Data

| Apr. 29, 2003 | (GB) | ................................. 0309780.5 |
| Nov. 28, 2003 | (GB) | ................................. 0327748.0 |

(51) Int. Cl.
| *A61K 31/5355* | (2006.01) |
| *A61K 31/497* | (2006.01) |
| *A61K 31/519* | (2006.01) |
| *C07D 487/04* | (2006.01) |
| *C07D 413/04* | (2006.01) |
| *A61P 9/12* | (2006.01) |

(52) U.S. Cl. ............................... 514/234.2; 514/262.1; 514/252.16; 544/262; 544/118

(58) Field of Classification Search ............... 544/262; 514/262.1
See application file for complete search history.

(56) References Cited

U.S. PATENT DOCUMENTS

| 3,951,980 | A | 4/1976 | Henry et al. ................... 451/2 |
| 4,282,631 | A | 8/1981 | Uehara et al. ................... 13/2 |
| 5,091,431 | A | 2/1992 | Tulshian et al. ............ 514/262 |
| 5,442,044 | A | 8/1995 | Hoover et al. ................... 5/6 |
| 6,001,830 | A | 12/1999 | Lee et al. ...................... 31/50 |
| 6,106,864 | A | 8/2000 | Dolan et al. ................... 9/14 |
| 6,130,223 | A | 10/2000 | Jonas et al. ................ 514/258 |
| 6,184,338 | B1 | 2/2001 | Schwindeman et al. .... 528/392 |
| 6,288,078 | B1 | 9/2001 | Walsh et al. ............... 514/300 |
| 6,432,957 | B1 | 8/2002 | Kodoma et al. .............. 31/496 |
| 6,465,486 | B1 | 10/2002 | Baxter et al. ................... 31/47 |
| 6,566,360 | B1 | 5/2003 | Niewohner et al. ......... 514/243 |
| 6,777,419 | B1 | 8/2004 | Jonas et al. .............. 514/262.1 |
| 2001/0047013 | A1 | 11/2001 | Lang et al. ..................... 213/2 |
| 2002/0058668 | A1 | 5/2002 | Yuan .......................... 514/258 |
| 2002/0127593 | A1 | 9/2002 | Reich et al. .................... 435/6 |
| 2003/0187261 | A1 | 10/2003 | Havlicek et al. ............ 514/276 |
| 2004/0002990 | A1 | 1/2004 | Sander et al. .................. 17/30 |
| 2004/0023990 | A1 | 2/2004 | Eggenweiler et al. .... 514/262.1 |
| 2004/0029900 | A1 | 2/2004 | Jonas et al. .............. 514/262.1 |
| 2004/0063730 | A1 | 4/2004 | Eggenweiler et al. .... 514/262.1 |

FOREIGN PATENT DOCUMENTS

| DE | 10104095 | 1/2001 |
| EP | 0201188 A2 | 4/1986 |
| EP | 0296811 | 6/1987 |
| EP | 0297858 | 7/1987 |
| EP | 0349239 | 7/1988 |
| EP | 319479 | 6/1989 |
| EP | 400661 | 5/1990 |
| EP | 0937459 | 8/1999 |
| EP | 1072595 | 1/2001 |
| EP | 0579496 | 11/2001 |
| EP | 1176142 | 1/2002 |
| EP | 1176147 | 1/2002 |
| EP | 1241170 | 9/2002 |
| EP | 1348707 A1 * | 1/2003 |
| EP | 1348707 | 10/2003 |
| FR | 2638745 | 11/1988 |
| JP | 03142277 | 10/1989 |
| JP | 2002255932 | 9/2002 |
| WO | WO8605518 | 9/1986 |

(Continued)

OTHER PUBLICATIONS

Perry, M.J. et al, Current Opinion in Chemical Biology, 1998, 2,472-481.*

(Continued)

*Primary Examiner*—Mark L. Berch
*Assistant Examiner*—Susanna Moore
(74) *Attorney, Agent, or Firm*—Gregg C. Benson; Lisa A. Samuels

(57) ABSTRACT

The present invention comprises a class of 5,7-diaminopyrazolo[4,3-d]pyrimidine compounds. These compounds are useful as phosphodiesterase type 5 inhibitors. The present invention further comprises compositions containing the compounds use of the compounds and compositions to treat hypertension and other conditions, processes for the preparation of the compounds, and intermediates used in the preparation of the compounds.

42 Claims, No Drawings

FOREIGN PATENT DOCUMENTS

| | | |
|---|---|---|
| WO | WO8605519 | 9/1986 |
| WO | WO9301181 | 1/1993 |
| WO | WO93/06104 | 4/1993 |
| WO | WO93/07149 | 4/1993 |
| WO | WO93/12095 | 6/1993 |
| WO | WO94/00453 | 1/1994 |
| WO | WO94/05661 | 3/1994 |
| WO | WO95/19978 | 7/1995 |
| WO | WO9616657 | 6/1996 |
| WO | WO96/28429 | 9/1996 |
| WO | WO96/28448 | 9/1996 |
| WO | WO98/08847 | 3/1998 |
| WO | WO9817668 | 4/1998 |
| WO | WO98/49166 | 11/1998 |
| WO | WO9928325 | 6/1999 |
| WO | WO99/45006 | 9/1999 |
| WO | WO9954333 | 10/1999 |
| WO | WO 00/24745 | 5/2000 |
| WO | WO 01/23387 A2 | 4/2001 |
| WO | WO 01/23388 | 4/2001 |
| WO | WO 01/27112 | 4/2001 |
| WO | WO 01/27113 | 4/2001 |
| WO | WO 0123389 | 4/2001 |
| WO | WO 01/32646 | 5/2001 |
| WO | WO 01/47901 | 7/2001 |
| WO | WO 0147495 | 7/2001 |
| WO | WO 02/10171 | 2/2002 |
| WO | WO 0213798 | 2/2002 |
| WO | WO 02/42292 | 5/2002 |
| WO | WO 02066481 | 8/2002 |
| WO | WO 02102314 | 12/2002 |
| WO | WO 2004006867 | 3/2003 |
| WO | WO 2004096810 | 11/2004 |

OTHER PUBLICATIONS

Corbin JD, Francis SH., Int J Clin Pract. Jul.-Aug. 2002;56(6):453-459.*

Cremers B, Bohm M., Herz. Jun. 2003;28(4):325-333.*

Schudt, C.; Eur. Respir. J.; 1995; 8; 1179-1183. Torphy et. al.; Environ. Health Perspect.; 1994; 79-84.*

Organic Reactions, vol. 41 and vol. 42, p. 42, 1992.

Chambers et al. Journal Organic Chemistry, *Selective Sequential Demasking of the Ester Functions of 1-Methyl-3,4,5-tris(methoxycarbonyl) pyrazole*, 50, 4736-4738, 1985.

Zeitschrift fur Chemie 28; 2; 59-60, 1988.

Webber, R., et.al., Journal Med. Chem., *Substituted 2-Iminopiperidines as Inhibitors of Human Nitric Oxide Synthase Isoforms*, 41 (1); 96-101, 1998.

Singh, B., et. al., J Het. Chem., *Three Convenient and Novel Syntheses of 4-Amino-2-arylpyrimidines*, 14; 1413; 1977.

Hara, H., et. al., J. Het. Chem., *On the Amination of Azaheterocycles. A New Procedure for the Introduction of an Amino Group* (1), 19; 1285; 1982.

Orozco, M., et. al., J. Pharmaceutical Science, *Quantum Chemical Study of the Electronic and Conformational Characteristics of Adenosine and 8-Substituted Derivatives: Functional Implications in the Mechanism of Reaction of Adenosine Deaminase*, 79(2), 133-137, 1990.

Orozco, M., et. a., Quantitative Struct.-Act. Relat., *Theoretical Approximation to the Reaction Mechanism of Adenosine Deaminase*, 8: 109-114, 1989.

Orozco, M., et. al., Molecular Pharmacology, *Theoretical Study of the Protonation and Tautomerization of Adenosine, Formycin, and Their 2-$NH_2$ and 2-F Derivatives: Functional Implications in the Mechanism of Reaction of Adenosine Deaminase*, 35(2): 257-264, 1988.

Upadhya, K., et. al., Nucleic Acids Research, *Synthesis of 5-chloroformycin A, 5-chloro-2'-deoxyformycin A and certain related 5,7-disubstituted 3-β-D-ribofuranosylpyrazolo[4,3-d]pyrimidines from formycin A*, 14(4): 1747-1764, 1986.

Secrist III, J., et. al., Journal Med. Chem., *2-Fluoroformycin and 2-Aminoformycin. Synthesis and Biological Activity*, 28(11): 1740-1742, 1985.

Diederich, F., *Metal-Catalysed Cross-Coupling Reactions*, Wiley-VCH, 1998.

Norris, T., et. al., J. Chem. Soc. Perkin Trans. 1, *Synthesis of trovafloxacin using various (1α,5α,6α)-3-azabicyclo[3.1.0]hexane derivatives*, 1615-1622, 2000.

Bochis, R., et. al., J. Med. Chem., *Substituted Imidazo[1,2-a]pyridine-2-carbamate Anthelmintics*, 24(12) 1518-1521, 1981.

Yakovlev, M., et. a., Chemistry of. Heterocyclic Compound, *Synthesis of Substituted 2,5-Diazabicyclo[2.2.1]Heptanes*, 36(4): 429-431, 2000.

Smith, S., et. al., Tetrahedron Letters, *Tandem cyclisation and [2,3]-Stevens rearrangement to 2-substituted pyrrolidines*, 43, 899-902, 2002.

Barlocco, D., et. al., J. Med. Chem., *Mono- and Disubstituted-3,8-diazabicyclo[3.2.1]octane Derivatives as Analgesics Structurally Related to Epibatidine: Synthesis, Activity, and Modeling*, 41, 674-681, 1998.

Baraldi, P., et. al., IL Farmaco, *Synthesis, Antibacterial Activity and Structure-Activity Relationships of N-Substituted 4-Diazo-Pyrazole-5-Carboxamides*, 46(11), 1337-1350, 1991.

Brown, H., et. al., J. Org. Chem., *Hydroboration. 71. Hydroboration of Representative Heterocyclic Olefins with Borane-Methyl Sulfide, 9-Borabicyclo[3.3.1]nonane, Dicyclohexylborane, and Disiamylborane. Synthesis of Heterocyclic Alcohols*, 50, 1582-1589, 1985.

H.C.Van Der Plas, Rec.1. Trav. Chim. Pays-Bas., *Syntheses of Amino and Bromo Derivatives of 4-methyl-,4-t-butyl-and 4-phenyl-pyrimidine*, 84, 1101-1106, 1965.

Dumaitre, B., et. al., Journal of Medicinal Chemistry, American Chemical Society, *Synthesis and Cyclic GMP Phosphodiesterase Inhibitory Activity of a Series of 6-Phenylpyrazolou3, 4-Dpyrimidones*, 39(8), 1635-1644, 1996.

Czarniecki, M., et. al., Annu. Rep. Med. Chem., *Inhibitors of Types I and V Phosphodiesterase: Elevation of cGMP as a Therapeutic Strategy*, 31, 61-70, 1996.

* cited by examiner

SUBSTITUTED PYRAZOLO[4,3-D]PYRIMIDINES AND THEIR USE AS PDE-5 INHIBITORS

The present application claims priority under Title 35, United States Code § 119 of the U.S. Provisional application Ser. No. 60/476,678 filed Jun. 6, 2003 and U.S. Provisional application Ser. No. 60/538,147 filed Jan. 20, 2004. The present application also claims priority to United Kingdom provisional application Serial Number 0309780.5 filed Apr. 29, 2003, which is herein incorporated by reference, and United Kingdom provisional application Serial Number 0327748.0 filed Nov. 28, 2003, which is herein incorporated by reference.

The present invention relates to a series of novel 5,7-diaminopyrazolo[4,3-d]pyrimidines, which are cyclic guanylate monophosphate (cGMP)-specific phosphodiesterase type 5 inhibitors (hereinafter referred to as PDE-5 inhibitors) that are useful in the treatment of hypertension and other disorders, to processes for their preparation, intermediates used in their preparation, to compositions containing them and the uses of said compounds and compositions.

i) Hypertension

Blood pressure (BP) is defined by a number of haemodynamic parameters taken either in isolation or in combination. Systolic blood pressure (SBP) is the peak arterial pressure attained as the heart contracts. Diastolic blood pressure is the minimum arterial pressure attained as the heart relaxes. The difference between the SBP and the DBP is defined as the pulse pressure (PP).

Hypertension, or elevated BP, has been defined as a SBP of at least 140 mmHg and/or a DBP of at least 90 mmHg. By this definition, the prevalence of hypertension in developed countries is about 20% of the adult population, rising to about 60-70% of those aged 60 or more, although a significant fraction of these hypertensive subjects have normal BP when this is measured in a non-clinical setting. Some 60% of this older hypertensive population have isolated systolic hypertension (ISH), i.e. they have an elevated SBP and a normal DBP. Hypertension is associated with an increased risk of stroke, myocardial systolic hypertension (ISH), i.e. they have an elevated SBP and a normal DBP. Hypertension is associated with an increased risk of stroke, myocardial infarction, atrial fibrillation, heart failure, peripheral vascular disease and renal impairment (Fagard, R H; Am. J. Geriatric Cardiology 11(1), 23-28, 2002; Brown, M J and Haycock, S; Drugs 59(Suppl 2), 1-12, 2000).

The pathophysiology of hypertension is the subject of continuing debate. While it is generally agreed that hypertension is the result of an imbalance between cardiac output and peripheral vascular resistance, and that most hypertensive subjects have abnormal cardiac output and increased peripheral resistance there is uncertainty which parameter changes first (Beevers, G et al.; BMJ 322, 912-916, 2001).

Despite the large number of drugs available in various pharmacological categories, including diuretics, alpha-adrenergic antagonists, beta-adrenergic antagonists, calcium channel blockers, angiotensin converting enzyme (ACE) inhibitors and angiotensin receptor antagonists, the need for an effective treatment of hypertension is still not satisfied.

ii) PDE-5 Inhibitors

Vascular endothelial cells secrete nitric oxide (NO). This acts on vascular smooth muscle cells and leads to the activation of guanylate cyclase and the accumulation of cyclic guanosine monophosphate (cGMP). The accumulation of cGMP causes the muscles to relax and the blood vessels to dilate. This dilation reduces vascular resistance and so leads to a reduction in blood pressure.

The cGMP is inactivated by hydrolysis to guanosine 5'-monophosphate (GMP) by a cGMP-specific phosphodiesterase. One important phosphodiesterase has been identified as Phosphodiesterase type 5 (PDE-5). Inhibitors of PDE-5 decrease the rate of hydrolysis of cGMP and so potentiate the actions of nitric oxide.

Inhibitors of PDE-5 have been reported in several chemical classes, including: pyrazolo[4,3-d]pyrimidin-7-ones (e.g. published international patent applications WO 93/06104, WO 98/49166, WO 99/54333, WO 00/24745, WO 01/27112 and WO 01/27113); pyrazolo[3,4-d]pyrimidin-4-ones (e.g. published international patent application WO 93/07149); pyrazolo[4,3-d]pyrimidines (e.g. published international patent application WO 01/18004); quinazolin-4-ones (e.g. published international patent application WO 93/12095); pyrido[3,2-d]pyrimidin-4-ones (e.g. published international patent application WO 94/05661); purin-6-ones (e.g. published international patent application WO 94/00453); hexahydro-pyrazino[2',1':6,1]pyrido[3,4-b]indole-1,4-diones (e.g. published international application WO 95/19978) and imidazo[5,1-f][1,2,4]triazin-ones (e.g. published international application WO 99/24433).

Although they have been suggested as agents for the treatment of related conditions such as angina, PDE-5 inhibitors have not yet been adopted as agents for the treatment of hypertension. PDE-5 inhibitors are known for the treatment of male erectile dysfunction, e.g. sildenafil, tadalafil and vardenafil. There remains a demand for new PDE-5 inhibitors, particularly with improved pharmacokinetic and pharmacodynamic properties.

WO 02/00660 and WO 01/18004 disclose pyrazolo[4,3-d]pyrimidines with a PDE-5 inhibiting effect, which can be used for treating disorders of the cardiovascular system.

According to a first aspect, the present invention provides compounds of formula (I)

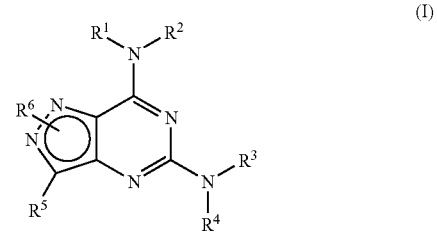

wherein $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ groups, or $R^E$, which is optionally substituted with one or more $R^9$ groups, or hydrogen;

or —$NR^3R^4$ forms $R^F$, which is optionally substituted with one or more $R^{10}$ groups;

$R^5$ is $C_1$-$C_6$ alkyl, $C_1$-$C_6$ haloalkyl, $C_2$-$C_6$ alkenyl, $C_2$-$C_6$ alkynyl or $C_3$-$C_7$ cycloalkyl, each of which is optionally substituted by one or more groups selected from hydroxy, $C_1$-$C_6$ alkoxy, $C_1$-$C_6$ haloalkoxy, $C_3$-$C_7$ cycloalkyl and $C_3$-$C_7$ cycloalkoxy, or hydrogen;

$R^6$, which may be attached at $N^1$ or $N^2$, is $R^{6A}$ or hydrogen;

$R^{6A}$ is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, ($C_3$-$C_6$ cycloalkyl)$C_1$-$C_6$ alkoxy, $C_1$-$C_6$ haloalkoxy or a cyclic group selected from $R^J$, $R^K$, $R^L$ and $R^M$, or $R^{6A}$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, oxo, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $C_3$-$C_6$ cycloalkyl, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is OH, phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ and $R^J$ are each independently a $C_3$-$C_{10}$ cycloalkyl or $C_3$-$C_{10}$ cycloalkenyl group, each of which may be either monocyclic or, when there are an appropriate number of ring atoms, polycyclic and which may be fused to either
  (a) a monocyclic aromatic ring selected from a benzene ring and a 5- or 6-membered heteroaromatic ring containing up to three heteroatoms selected from nitrogen, oxygen and sulphur, or
  (b) a 5-, 6- or 7-membered heteroalicyclic ring containing up to three heteroatoms selected from nitrogen, oxygen and sulphur;

$R^B$ and $R^K$ are each independently a phenyl or naphthyl group, each of which may be fused to
  (a) a $C_5$-$C_7$ cycloalkyl or $C_5$-$C_7$ cycloalkenyl ring,
  (b) a 5-, 6- or 7-membered heteroalicyclic ring containing up to three heteroatoms selected from nitrogen, oxygen and sulphur, or
  (c) a 5- or 6-membered heteroaromatic ring containing up to three heteroatoms selected from nitrogen, oxygen and sulphur;

$R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^D$ and $R^M$ are each independently a 5- or 6-membered heteroaromatic ring containing up to three heteroatoms independently selected from nitrogen, oxygen and sulphur, which ring may be further fused to
  (a) a second 5- or 6-membered heteroaromatic ring containing up to three heteroatoms selected from nitrogen, oxygen and sulphur;
  (b) $C_5$-$C_7$ cycloalkyl or $C_5$-$C_7$ cycloalkenyl ring;
  (c) a 5-, 6- or 7-membered heteroalicyclic ring containing up to three heteroatoms selected from nitrogen, oxygen and sulphur; or
  (d) a benzene ring;

$R^E$, $R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

and $R^H$ is a 5- or 6-membered heteroaromatic ring containing up to three heteroatoms independently selected from nitrogen, oxygen and sulphur;

a tautomer thereof or a pharmaceutically acceptable salt, solvate or polymorph of said compound or tautomer.

Unless otherwise indicated, an alkyl or alkoxy group may be straight or branched and contain 1 to 8 carbon atoms, preferably 1 to 6 and particularly 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Unless otherwise indicated, an alkenyl or alkynyl group may be straight or branched and contain 2 to 8 carbon atoms, preferably 2 to 6 and particularly 2 to 4 carbon atoms and may contain up to 3 double or triple bonds which may be conjugated. Examples of alkenyl and alkynyl include vinyl, allyl, butadienyl and propargyl.

Unless otherwise indicated, a cycloalkyl or cycloalkoxy group may contain 3 to 10 ring-atoms, may be either monocyclic or, when there are an appropriate number of ring atoms, polycyclic. Examples of cycloalkyl groups are cyclopropyl, cyclopentyl, cyclohexyl and adamantyl.

Unless otherwise indicated, a cycloalkenyl group may contain 3 to 10 ring-atoms, may be either monocyclic or, when there are an appropriate number of ring atoms, polycyclic and may contain up to 3 double bonds. Examples of cycloalkenyl groups are cyclopentenyl and cyclohexenyl.

Aryl includes phenyl, naphthyl, anthracenyl and phenanthrenyl.

Unless otherwise indicated, a heteroalicyclyl group contains 3 to 10 ring-atoms up to 4 of which may be heteroatoms such as nitrogen, oxygen and sulfur, and may be saturated or partially unsaturated. Examples of heteroalicyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Unless otherwise indicated, a heteroaryl group contains 3 to 10 ring-atoms up to 4 of which may be hetero-atoms such as nitrogen, oxygen and sulfur. Examples of heteroaryl groups are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, tetrazolyl, triazinyl. In addition, the term heteroaryl includes fused heteroaryl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, benzothiazolyl, phthalimido, benzofuranyl, benzodiazepinyl, indolyl and isoindolyl.

For the avoidance of doubt, oxo-substituted heteroaromatic systems such as pyridinonyl, pyranonyl, imidazolonyl and the like are also considered to be heteroaryl groups.

Halo means fluoro, chloro, bromo or iodo.

Haloalkyl includes monohaloalkyl, polyhaloalkyl and perhaloalkyl, such as 2-bromoethyl, 2,2,2-trifluoroethyl, chlorodifluoromethyl and trichloromethyl. Haloalkoxy includes monohaloalkoxy, polyhaloalkoxy and perhaloalkoxy, such as 2-bromoethoxy, 2,2,2-trifluoroethoxy, chlorodifluoromethoxy and trichloromethoxy. Halocycloalkyl includes monohalocycloalkyl, polyhalocycloalkyl and perhalocycloalkyl.

Unless otherwise indicated, the term substituted means substituted by one or more defined groups. In the case where groups may be selected from a number of alternative groups, the selected groups may be the same or different.

In one preferred embodiment, $R^1$ is $R^A$, which is optionally substituted with one or more $R^7$ groups; and $R^A$ is a $C_3$-$C_{10}$ cycloalkyl group, which may be either monocyclic or, when there are an appropriate number of ring atoms, polycyclic, which may be fused to either
 (a) a monocyclic aromatic ring selected from a benzene ring and a 5- or 6-membered heteroaromatic ring containing up to three heteroatoms selected from nitrogen, oxygen and sulphur, or
(b) a 5-, 6- or 7-membered heteroalicyclic ring containing up to three heteroatoms selected from nitrogen, oxygen and sulphur.

Preferably, $R^A$ is a monocyclic $C_3$-$C_8$ cycloalkyl group.

More preferably, $R^A$ is a monocyclic $C_5$-$C_7$ cycloalkyl group.

Most preferably, $R^A$ is cyclopentyl or cyclohexyl.

In another preferred embodiment, $R^1$ is $R^B$, which is optionally substituted with one or more $R^7$ groups.

Preferably, $R^B$ is phenyl.

In another preferred embodiment, $R^1$ is $R^C$, which is optionally substituted with one or more $R^7$ groups.

Preferably, $R^C$ is a monocyclic saturated or partly unsaturated ring system containing between 3 and 8 ring atoms, of which at least one is a heteroatom selected from nitrogen, oxygen and sulphur.

More preferably, $R^C$ is a monocyclic saturated or partly unsaturated ring system containing between 5 and 7 ring atoms, of which at least one is a heteroatom selected from nitrogen, oxygen and sulphur.

More preferably, $R^C$ is a monocyclic saturated ring system containing between 5 and 7 ring atoms, of which at least one is a heteroatom selected from nitrogen, oxygen and sulphur.

Most preferably, $R^C$ is piperidinyl.

In another preferred embodiment, $R^1$ is $R^D$, which is optionally substituted with one or more $R^7$ groups.

Preferably, $R^D$ is a 5- or 6-membered heteroaromatic ring containing up to three heteroatoms independently selected from nitrogen, oxygen and sulphur.

More preferably, $R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms.

More preferably $R^D$ is furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl or pyrazinyl.

Most preferably, $R^D$ is pyrazolyl, imidazolyl, isoxazolyl, oxazolyl, oxadiazolyl, pyridyl, pyridazinyl, pyrimidyl or pyrazinyl.

Preferably, $R^7$ is halo, $C_1$-$C_6$ alkyl, $C_1$-$C_6$ haloalkyl, oxo, $OR^{12}$ or $CONR^{12}R^{13}$.

More preferably, $R^7$ is halo, $C_1$-$C_3$ alkyl, $C_1$-$C_3$-haloalkyl, oxo, $C_1$-$C_3$ alkoxy, hydroxy or $CONH(C_1$-$C_3$ alkyl).

Most preferably, $R^7$ is fluoro, methyl, ethyl, hydroxy, methoxy, propoxy, trifluoromethyl, oxo or CONHMe.

Preferably, $R^2$ is hydrogen or methyl.

More preferably, $R^2$ is hydrogen.

Preferably, $R^3$ is hydrogen, $C_1$-$C_6$ alkyl, which is optionally substituted with one or more $R^8$ groups, or $R^E$, which is optionally substituted with one or more $R^9$ groups; and wherein $R^E$ is a monocyclic or, when there are an appropriate number of ring atoms, polycyclic saturated ring system containing between 3 and 7 ring atoms, of which at least one is a heteroatom selected from nitrogen, oxygen and sulphur.

More preferably, $R^3$ is hydrogen, $C_1$-$C_4$ alkyl, which is optionally substituted with one or more $R^8$ groups, or $R^E$, which is optionally substituted with one or more $R^9$ groups; and wherein $R^E$ is a monocyclic saturated ring system containing between 3 and 7 ring atoms, of which at least one is a heteroatom selected from nitrogen, oxygen and sulphur.

In one preferred embodiment, $R^3$ is $R^E$, which is optionally substituted with one or more $R^9$ groups and wherein $R^E$ is a monocyclic saturated ring system containing between 3 and 7 ring atoms containing one nitrogen atom.

More preferably, $R^E$ is azetidinyl, pyrrolidinyl or piperidinyl.

In another preferred embodiment, $R^3$ is $C_1$-$C_4$ alkyl, which is optionally substituted with one or more $R^8$ groups and wherein $R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups.

More preferably, $R^8$ is hydroxy, methoxy, methoxyphenyl, $NH_2$, NHMe, $NMe_2$, $NHCO_2^tBu$, $NMeCO_2^tBu$, $CO_2H$, CONHMe, $R^G$ or $R^H$, the last two of which are optionally substituted with one or more $R^9$ groups.

In one preferred embodiment, $R^8$ is $R^G$, which is optionally substituted with one or more $R^9$ groups and wherein $R^G$ is a monocyclic saturated ring system containing between 3 and 7 ring atoms, of which at least one is a heteroatom selected from nitrogen, oxygen and sulphur.

More preferably, $R^G$ is a monocyclic saturated ring system containing between 3 and 7 ring atoms containing one nitrogen atom and optionally one oxygen atom.

Most preferably, $R^G$ is pyrrolidinyl, piperidinyl or morpholinyl.

In another preferred embodiment, $R^8$ is $R^H$, which is optionally substituted with one or more $R^9$ groups and wherein $R^H$ is a 5- or 6-membered heteroaromatic ring containing up to two nitrogen atoms.

More preferably, $R^H$ is pyrazolyl.

Preferably, $R^9$ is methyl or $CO_2^tBu$.

In another preferred embodiment, $R^3$ is hydrogen or $C_1$-$C_4$ alkyl, which is optionally substituted with one or more $R^8$ groups, or $R^3$ is azetidinyl, pyrrolidinyl or piperidinyl, each of which is optionally substituted with one or more $R^9$ groups, wherein $R^8$ is hydroxy, methoxy, methoxyphenyl, $NH_2$, NHMe, $NMe_2$, $NHCO_2{}^tBu$, $NMeCO_2{}^tBu$, $CO_2H$, CONHMe, pyrrolidinyl, piperidinyl, morpholinyl or pyrazolyl, the last four of which are optionally substituted with one or more $R^9$ groups and wherein $R^9$ is methyl or $CO_2{}^tBu$.

In one preferred embodiment, $R^4$ is hydrogen, $C_1$-$C_6$ alkyl, $C_1$-$C_6$ haloalkyl, $C_2$-$C_6$ alkenyl or $C_2$-$C_6$ alkynyl.

More preferably, $R^4$ is hydrogen, $C_1$-$C_6$ alkyl or $C_1$-$C_6$ haloalkyl.

Most preferably, $R^4$ is hydrogen, methyl or ethyl.

In another preferred embodiment, —$NR^3R^4$ forms $R^F$, which is optionally substituted with one or more $R^{10}$ groups and wherein $R^F$ is a monocyclic or, when there are an appropriate number of ring atoms, polycyclic saturated ring system containing between 3 and 10 ring atoms containing at least one nitrogen atom and optionally one other atom selected from oxygen and sulphur.

More preferably, $R^F$ is a monocyclic or, when there are an appropriate number of ring atoms, polycyclic saturated ring system containing between 3 and 10 ring atoms containing one or two nitrogen atoms and optionally one other atom selected from oxygen and sulphur.

Most preferably, $R^F$ is selected from azetidinyl, pyrrolidinyl, piperidinyl, piperazinyl, morpholinyl, 3-azabicyclo[3.1.0]hex-3-yl, homopiperazinyl, 2,5-diazabicyclo[2.2.1]hept-2-yl, 2,5-diazabicyclo[2.2.2]oct-2-yl, 2,5-diazabicyclo[4.3.0]non-2-yl, 3,8-diazabicyclo[3.2.1]oct-3-yl, 3,8-diazabicyclo[3.2.1]oct-8-yl, 1,4-diazabicyclo[4.3.0]non-4-yl and 1,4-diazabicyclo[3.2.2]non-4-yl.

Preferably $R^{10}$ is halo, $OR^{12}$, $NR^{12}R^{13}$, $NR^{12}CO_2R^{14}$, $CO_2R^{13}$, oxo, $C_1$-$C_6$ alkyl or $C_1$-$C_6$ haloalkyl, the last two of which are optionally substituted by $R^{11}$.

More preferably, $R^{10}$ is halo, methyl, ethyl, isopropyl, hydroxy, methoxy, $NH_2$, NHMe, $NMe_2$, $NHCO_2{}^tBu$, $CO_2H$, $CO_2{}^tBu$, oxo, benzyl, —$CH_2OH$, —$CH_2NH_2$, —$CH_2NHMe$, —$CH_2NMe_2$ or —$CH_2NMeCO_2{}^tBu$.

In a particularly preferred —$NR^3R^4$ forms a piperazine ring that is optionally substituted by one or two methyl groups, and/or is bridged by a —$CH_2$— or —$CH_2CH_2$— group. Suitable bridged piperazines include 2,5-diazabicyclo[2.2.1]hept-2-yl, 2,5-diazabicyclo[2.2.2]oct-2-yl, 3,8-diazabicyclo[3.2.1]oct-3-yl and 3,8-diazabicyclo[3.2.1]oct-8-yl ring systems.

In another preferred embodiment, $R^3$ is $C_1$-$C_6$ alkyl, which is substituted by one $R^8$ group, or $R^E$, which is substituted by one $R^9$ group; or —$NR^3R^4$ forms a cyclic group $R^F$, which is substituted with one $R^{10}$ group, and $R^8$, $R^9$ and $R^{10}$ are all $CO_2H$.

Preferably, $R^5$ is $C_1$-$C_4$ alkyl or $C_1$-$C_4$ haloalkyl, each of which is optionally substituted by hydroxy, $C_1$-$C_4$ alkoxy or $C_1$-$C_4$ haloalkoxy.

In one more preferred embodiment, $R^5$ is $C_1$-$C_4$ alkyl, hydroxymethyl or $C_1$-$C_4$ alkoxymethyl.

In another more preferred embodiment, $R^5$ is methyl, ethyl or propyl, each of which is optionally substituted by hydroxy, methoxy or ethoxy.

Most preferably, $R^5$ is methyl, ethyl, n-propyl, isopropyl, hydroxymethyl, methoxymethyl or ethoxymethyl.

Preferably, $R^6$ is $R^{6A}$.

When $R^6$ is hydrogen, the compounds of formula (I) wherein $R^6$ is attached at $N^1$ and at $N^2$ are tautomers. These tautomers will tend to co-exist in both the solid and solution state, and will not be readily separable. The amounts of each tautomer present in any equilibrium mixture will be determined by the relative thermodynamic stabilities of the two forms. In most cases, the 1H-tautomer will tend to be the predominant form.

When $R^6$ is $R^{6A}$, two regioisomers of the compounds of formula (I) can be distinguished. In one, preferred, embodiment of the invention, $R^{6A}$ is positioned on $N^1$ to give the compounds of formula ($I^A$):

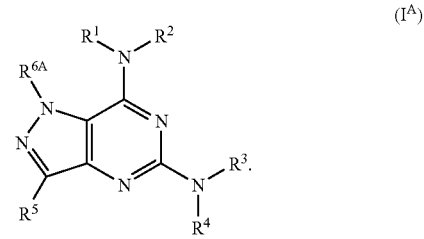

(I$^A$)

In an alternative embodiment, $R^{6A}$ is positioned on $N^2$ to give the compounds of formula ($I^B$):

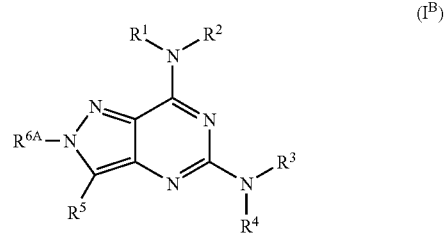

(I$^B$)

Preferably, $R^{6A}$ is $C_1$-$C_6$ alkyl or $C_1$-$C_6$ haloalkyl, each of which is optionally substituted by $C_1$-$C_6$ alkoxy, $C_1$-$C_6$ haloalkoxy, ($C_3$-$C_6$ cycloalkyl)$C_1$-$C_6$ alkoxy or a cyclic group selected from $R^J$, $R^L$ and $R^M$, or $R^{6A}$ is $R^N$;

$R^J$ is a $C_3$-$C_7$ monocyclic cycloalkyl group;

$R^L$ and $R^N$ are each independently a monocyclic, saturated or partly unsaturated ring system containing between 4 and 7 ring atoms, of which at least one is a heteroatom selected from nitrogen, oxygen and sulphur; and $R^M$ is a 5- or 6-membered heteroaromatic ring containing up to three heteroatoms independently selected from nitrogen, oxygen and sulphur.

More preferably, $R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy, ($C_3$-$C_6$ cycloalkyl)$C_1$-$C_6$ alkoxy or a cyclic group selected from $R^J$, $R^L$ and $R^M$, or $R^{6A}$ is $R^N$;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur; and $R^M$ is a 5- or 6-membered heteroaromatic ring containing a heteroatom selected from nitrogen, oxygen and sulphur.

More preferably, $R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy, ($C_3$-$C_6$ cycloalkyl)methoxy or a cyclic group selected from $R^J$, $R^L$ and $R^M$, or $R^{6A}$ is $R^N$;

$R^J$ is cyclopropyl or cyclobutyl;

$R^L$ and $R^N$ are each independently a monocyclic saturated ring system containing either 5 or 6 ring atoms containing one heteroatom selected from nitrogen, oxygen and sulphur; and $R^M$ is a 5- or 6-membered heteroaromatic ring containing one nitrogen atom.

More preferably, $R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy, ($C_3$-$C_6$ cycloalkyl)methoxy, cyclopropyl, cyclobutyl, tetrahydrofuranyl, tetrahydropyranyl or pyridinyl, or $R^{6A}$ is tetrahydropyranyl.

Most preferably, $R^{6A}$ is methyl, ethyl, isopropyl, isobutyl, methoxyethyl, methoxypropyl, ethoxyethyl, ethoxypropyl, n-propoxyethyl, isopropoxyethyl, 2,2,2-trifluoroethyl, 2,2,2-trifluoroethoxyethyl, tetrahydrofuranylmethyl, tetrahydropyranylmethyl, tetrahydropyranyl or pyridinylmethyl.

A particularly preferred embodiment is a compound of formula (I) wherein $R^6$ is $R^{6A}$ attached at the $N^1$-position, and $R^{6A}$ is 2-(2,2,2-trifluoroethoxy)ethyl.

Preferred embodiments of compounds of formula (I) are those that incorporate two or more of the foregoing preferences.

A particularly preferred embodiment is a compound of formula (I) wherein $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is $C_1$-$C_6$ alkyl, $C_1$-$C_6$ haloalkyl, $C_2$-$C_6$ alkenyl, $C_2$-$C_6$ alkynyl or $C_3$-$C_7$ cycloalkyl, each of which is optionally substituted by one or more groups selected from hydroxy, $C_1$-$C_6$ alkoxy, $C_1$-$C_6$ haloalkoxy, $C_3$-$C_7$ cycloalkyl and $C_3$-$C_7$ cycloalkoxy, or hydrogen;

$R^6$ is $R^{6A}$ or hydrogen;

$R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^{6A}$ is $R^N$;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, oxo, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is OH, phenyl, $NR^{12}R^{13}$ or $NR^{12}CO_2R^{14}$;

$R^{12}$ and $R^{13}$ are each independently hydrogen, $C_1$-$C_6$alkyl or $C_1$-$C_6$ haloalkyl;

$R^{14}$ is $C_1$-$C_6$ alkyl or $C_1$-$C_6$ haloalkyl;

$R^A$ is a monocyclic $C_3$-$C_8$ cycloalkyl group;

$R^B$ is phenyl;

$R^C$ is a monocyclic saturated or partly unsaturated ring system containing between 3 and 8 ring atoms, of which at least one is a heteroatom selected from nitrogen, oxygen and sulphur;

$R^D$ is a 5- or 6-membered heteroaromatic ring containing up to three heteroatoms independently selected from nitrogen, oxygen and sulphur;

$R^E$ is a monocyclic saturated ring system containing between 3 and 7 ring atoms, of which at least one is a heteroatom selected from nitrogen, oxygen and sulphur;

$R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

and $R^M$ is a 5- or 6-membered heteroaromatic ring containing a heteroatom selected from nitrogen, oxygen and sulphur.

More preferably, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is $C_1$-$C_4$ alkyl or $C_1$-$C_4$ haloalkyl, each of which is optionally substituted by hydroxy, $C_1$-$C_4$ alkoxy or $C_1$-$C_4$ haloalkoxy;

$R^6$ is $R^{6A}$ or hydrogen;

$R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^{6A}$ is $R^N$;

$R^7$ is halo, $C_1$-$C_6$ alkyl, $C_1$-$C_6$ haloalkyl, oxo, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is OH, phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^L$ and $R^N$ are each independently a monocyclic saturated ring system containing either 5 or 6 ring atoms, of which at least one is a heteroatom selected from nitrogen, oxygen and sulphur;

and $R^M$ is a 5- or 6-membered heteroaromatic ring containing a heteroatom selected from nitrogen, oxygen and sulphur.

Most preferred compounds are:

1-(2-ethoxyethyl)-3-methyl-5-[(3R)-3-methylpiperazin-1-yl]-N-pyrimidin-4-yl-1H-pyrazolo[4,3-d]pyrimidin-7-amine, 1-(2-ethoxyethyl)-3-ethyl-5-[(3R)-3-methylpiperazin-1-yl]-N-pyrimidin-4-yl-1H-pyrazolo[4,3-d]pyrimidin-7-amine, 1-(2-ethoxyethyl)-3-ethyl-$N^5$-methyl-$N^5$-(1-methylpiperidin-4-yl)-$N^7$-pyrimidin-4-yl-1H-pyrazolo[4,3-d]pyrimidine-5,7-diamine, 3-methyl-5-[(3R)-3-methylpiperazin-1-yl]-1-(2-n-propoxyethyl)-N-pyrimidin-4-yl-1H-pyrazolo[4,3-d]pyrimidin-7-amine, 5-[(2R,5S)-2,5-dimethylpiperazin-1-yl]-1-(2-ethoxyethyl)-3-methyl-N-pyrimidin-4-yl-1H-pyrazolo[4,3-d]pyrimidin-7-amine, 5-[(2R,5S)-2,5-dimethylpiperazin-1-yl]-1-(2-ethoxyethyl)-3-ethyl-N-pyrimidin-4-yl-1H-pyrazolo[4,3-d]pyrimidin-7-amine, 1-(2-ethoxyethyl)-$N^5$,3-dimethyl-$N^7$-(4-methylpyridin-2-yl)-$N^5$-[(3S)-1-methylpyrrolidin-3-yl]-1H-pyrazolo[4,3-d]pyrimidine-5,7-diamine, 1-(2-ethoxyethyl)-3-ethyl-$N^5$-methyl-$N^7$-(4-methylpyridin-2-yl)-$N^5$-[(3S)-1-methylpyrrolidin-3-yl]-1H-pyrazolo[4,3-d]pyrimidine-5,7-diamine, 1-(2-ethoxyethyl)-3-(methoxymethyl)-5-[(3R)-3-methylpiperazin-1-yl]-N-(4-methylpyridin-2-yl)-1H-pyrazolo[4,3-d]pyrimidin-7-amine, 1-(2-ethoxyethyl)-3-(methoxymethyl)-$N^5$,$N^5$-dimethyl-$N^7$-(4-methylpyridin-2-yl)-1H-pyrazolo[4,3-d]pyrimidine-5,7-diamine, {1-(2-ethoxyethyl)-5-[N-ethyl-N-methylamino]-7-[(4-methylpyridin-2-yl)amino]-1H-pyrazolo[4,3-d]pyrimidin-3-yl}methanol, 1-(2-isopropoxyethyl)-3-methyl-5-[(3R)-3-methylpiperazin-1-yl]-N-pyrimidin-4-yl-1H-pyrazolo[4,3-d]pyrimidin-7-amine, 1-(2-ethoxyethyl)-$N^5$,3-dimethyl-$N^5$-[(3S)-1-methylpyrrolidin-3-yl]-$N^7$-pyrimidin-4-yl-1H-pyrazolo[4,3-d]pyrimidine-5,7-diamine, 1-(2-ethoxyethyl)-3-ethyl-$N^5$-methyl-$N^7$-(5-methylpyridin-2-yl)-$N^5$-[(3S)-1-methylpyrrolidin-3-yl]-1H-pyrazolo[4,3-d]pyrimidine-5,7-diamine, 1-methyl-5-[(3R)-3-methylpiperazin-1-yl]-3-propyl-N-pyrimidin-4-yl-1H-pyrazolo[4,3-d]pyrimidin-7-amine, N-[5-((1R, 4R)-2,5-diazabicyclo[2.2.1]hept-2-yl)-1-(2-ethoxyethyl)-3-ethyl-1H-pyrazolo[4,3-d]pyrimidin-7-yl]-4-methylpyridin-2-ylamine, N-[5-((1S, 4S)-2,5-diazabicyclo[2.2.1]hept-2-yl)-1-(2-ethoxyethyl)-3-ethyl-1H-pyrazolo[4,3-d]pyrimidin-7-yl]-4-methylpyridin-2-ylamine, N-{1-(2-ethoxyethyl)-3-methoxymethyl-5-[(3R)-3-methylpiperazin-1-yl]-1H-pyrazolo[4,3-d]pyrimidin-7-yl}-6-methylpyridin-2-ylamine, N-{3-methyl-5-[(3R)-3-methylpiperazin-1-yl]-1-[2-(2,2,2-trifluoroethoxy)ethyl]-1H-pyrazolo[4,3-d]pyrimidin-7-yl}pyrimidin-4-ylamine, N-{5-(3,8-diazabicyclo[3.2.1]oct-3-yl)-3-methyl-1-[2-(2,2,2-trifluoroethoxy)ethyl]-1H-pyrazolo[4,3-d]pyrimidin-7-yl}-6-methylpyridin-2-ylamine, N-{3-ethyl-5-[(3R)-3-methylpiperazin-1-yl]-1-[2-(2,2,2-trifluoroethoxy)ethyl]-1H-pyrazolo[4,3-d]pyrimidin-7-yl}pyrimidin-4-ylamine, N-{3-methyl-5-(piperazin-1-yl)-1-[2-(2,2,2-trifluoroethoxy)ethyl]-1H-pyrazolo[4,3-d]pyrimidin-7-yl}-6-methylpyridin-2-ylamine, 1-{3-methyl-7-(6-methylpyrimidin-4-ylamino)-1-[2-(2,2,2-trifluoroethoxy)ethyl]-1H-pyrazolo[4,3-d]pyrimidin-5-yl}piperidine-4-carboxylic acid, N-{3-ethyl-5-[(3R)-3-methylpiperazin-1-yl]-1-[2-(2,2,2-trifluoroethoxy)ethyl]-1H-pyrazolo[4,3-d]pyrimidin-7-yl}pyridazin-4-ylamine, N-{3-ethyl-5-[(3R)-3-methylpiperazin-1-yl]-1-[2-(2,2,2-trifluoroethoxy)ethyl]-1H-pyrazolo[4,3-d]pyrimidin-7-yl}-2-methylpyrimidin-4-ylamine, 3-ethyl-$N^5$-methyl-$N^5$-(1-methylpiperidin-4-yl)-$N^7$-(6-methylpyrimidin-4-yl)-1-[2-(2,2,2-trifluoroethoxy)ethyl]-1H-pyrazolo[4,3-d]pyrimidine-5,7-diamine, N-{3-methoxymethyl-5-[(3R)-3-methylpiperazin-1-yl]-1-[2-(2,2,2-trifluoroethoxy)-ethyl]-1H-pyrazolo[4,3-d]pyrimidin-7-yl}-6-methylpyridin-2-ylamine, N-{3-ethoxymethyl-5-[(3R)-3-methylpiperazin-1-yl]-1-[2-(2,2,2-trifluoroethoxy)-ethyl]-1H-pyrazolo[4,3-d]pyrimidin-7-yl}-6-methylpyridin-2-ylamine, N-{3-methoxymethyl-5-[(3R)-3-methylpiperazin-1-yl]-1-[2-(2,2,2-trifluoroethoxy)-ethyl]-1H-pyrazolo[4,3-d]pyrimidin-7-yl}-4-methylpyridin-2-ylamine, 1-{3-methyl-7-(4-methylpyridin-2-ylamino)-1-[2-(2,2,2-trifluoroethoxy)ethyl]-1H-pyrazolo[4,3-d]pyrimidin-5-yl}piperidine-4-carboxylic acid, N-{3-ethoxymethyl-5-[(3R)-3-methylpiperazin-1-yl]-1-[2-(2,2,2-trifluoroethoxy)-ethyl]-1H-pyrazolo[4,3-d]pyrimidin-7-yl}-4-methylpyridin-2-ylamine, 1-{3-ethyl-7-(6-methylpyrimidin-4-ylamino)-1-[2-(2,2,2-trifluoroethoxy)ethyl]-1H-pyrazolo[4,3-d]pyrimidin-5-yl}piperidine-4-carboxylic acid, and 3,$N^5$-dimethyl-$N^5$-(1-methylpiperidin-4-yl)-$N^7$-(6-methylpyrimidin-4-yl)-1-[2-(2,2,2-trifluoroethoxy)ethyl]-1H-pyrazolo[4,3-d]pyrimidine-5,7-diamine and tautomers thereof and pharmaceutically acceptable salts, solvates and polymorphs of said compounds or tautomer.

Pharmaceutically acceptable salts of the compounds of formula (I) include the acid addition and base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, pamoate, phosphate, saccharate, stearate, succinate, sulphate, D- and L-tartrate, and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, acetone-$d_6$, DMSO-$d_6$.

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula (I), including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{36}Cl$.

Substitution of the compounds of the invention with isotopes such as deuterium, i.e. $^2H$, may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

The compounds of formula (I) may be freeze-dried, spray-dried, or evaporatively dried to provide a solid plug, powder, or film of crystalline or amorphous material. Microwave or radio frequency drying may be used for this purpose.

The compounds of formula (I) are inhibitors of PDE-5. Accordingly, in a further aspect the present invention provides for the use of a compound of formula (I), or a tautomer, salt or solvate thereof, as a medicament, and particularly as a medicament for the treatment of a disease or condition where inhibition of PDE-5 is known, or can be shown, to produce a beneficial effect.

The term "treatment" includes palliative, curative and prophylactic treatment.

Diseases and conditions suitable for treatment with the compounds of the invention include hypertension (including essential hypertension, pulmonary hypertension, secondary hypertension, isolated systolic hypertension, hypertension associated with diabetes, hypertension associated with atherosclerosis, and renovascular hypertension), congestive heart failure, angina (including stable, unstable and variant (Prinzmetal) angina), stroke, coronary artery disease, congestive heart failure, conditions of reduced blood vessel patency (such as post-percutaneous coronary angioplasty), peripheral vascular disease, atherosclerosis, nitrate-induced tolerance, nitrate tolerance, diabetes, impaired glucose tolerance, metabolic syndrome, obesity, sexual dysfunction (including male erectile disorder, impotence, female sexual arousal disorder, clitoral dysfunction, female hypoactive sexual desire disorder, female sexual pain disorder, female sexual orgasmic dysfunction and sexual dysfunction due to spinal cord injury), premature labour, pre-eclampsia, dysmenorrhea, polycystic ovary syndrome, benign prostatic hyperplasia, bladder outlet obstruction, incontinence, chronic obstructive pulmonary disease, acute respiratory failure, bronchitis, chronic asthma, allergic asthma, allergic rhinitis, gut motility disorders (including irritable bowel syndrome), Kawasaki's syndrome, multiple sclerosis, Alzheimer's disease, psoriasis, skin necrosis, scarring, fibrosis, pain (particularly neuropathic pain), cancer, metastasis, baldness, nutcraker oesophagus, anal fissure and haemorrhoids.

In a further aspect, the present invention provides for the use of a compound of formula (I), or a tautomer, salt or solvate thereof, for the manufacture of a medicament for the treatment of a disease or condition where inhibition of PDE-5 is known, or can be shown, to produce a beneficial effect, and in particular those diseases and conditions listed in the preceding paragraph.

In a preferred embodiment, the disease or condition is hypertension. More preferably it is essential hypertension, pulmonary hypertension, secondary hypertension, isolated systolic hypertension, hypertension associated with diabetes, hypertension associated with atherosclerosis, or renovascular hypertension.

In another preferred embodiment, the disease or condition is diabetes.

In a further aspect, the present invention provides a method of treatment of a disorder or condition where inhibition of PDE-5 is known, or can be shown, to produce a beneficial effect, in a mammal, which method comprises administering to said mammal a therapeutically effective amount of a compound of formula (I) or a pharmaceutically acceptable salt, solvate or polymorph thereof.

In a preferred embodiment, the disease or condition is hypertension. More preferably it is essential hypertension, pulmonary hypertension, secondary hypertension, isolated systolic hypertension, hypertension associated with diabetes, hypertension associated with atherosclerosis, or renovascular hypertension.

In another preferred embodiment, the disease or condition is diabetes.

The compounds of the present invention may be used alone or in combination with other therapeutic agents. When used in combination with another therapeutic agent the administration of the two agents may be simultaneous or sequential. Simultaneous administration includes the administration of a single dosage form that comprises both agents and the administration of the two agents in separate dosage forms at substantially the same time. Sequential administration includes the administration of the two agents according to different schedules provided that there is an overlap in the periods during which the treatment is provided. Suitable agents with which the compounds of formula (I) can be co-administered include aspirin, angiotensin II receptor antagonists (such as losartan, candesartan, telmisartan, valsartan, irbesartan and eprosartan), calcium channel blockers (such as amlodipine), beta-blockers (i.e. beta-adrenergic receptor antagonists such as sotalol, propranolol, timolol, atenolol, carvedilol and metoprolol), CI1027, CCR5 receptor antagonists, imidazolines, soluble guanylate cyclase activators, diuretics (such as hydrochlorothiazide, torsemide, chlorothiazide, chlorthalidone and amiloride), alpha adrenergic antagonists (such as doxazosin), ACE (angiotensin converting enzyme) inhibitors (such as quinapril, enalapril, ramipril and lisinopril), aldosterone receptor antagonists (such as eplerenone and spironolactone), neutral endopeptidase inhibitors, antidiabetic agents (such as insulin, sulfonylureas (such as glyburide, glipizide and glimepiride), glitazones (such as rosiglitazone and pioglitazone) and metformin), cholesterol lowering agents (such as atorvastatin, pravastatin, lovastatin, simvastatin, clofibrate and rosuvastatin), and alpha-2-delta ligands (such as gabapentin, pregabalin, [(1R,5R,6S)-6-(aminomethyl)bicyclo[3.2.0]hept-6-yl]acetic acid, 3-(1-(aminomethyl)cyclohexylmethyl)-4H-[1,2,4]oxadiazol-5-one, C-[1-(1H-tetrazol-5-ylmethyl)cycloheptyl]methylamine, (3S,4S)-(1-aminomethyl-3,4-dimethyl-cyclopentyl)acetic acid, (1α,3α,5α)-(3-(aminomethyl)bicyclo[3.2.0]hept-3-yl)acetic acid, (3S,5R)-3-aminomethyl-5-methyloctanoic acid, (3S,5R)-3-amino-5-methylheptanoic acid, (3S,5R)-3-amino-5-methylnonanoic acid and (3S,5R)-3-amino-5-methyloctanoic acid).

In a further aspect, the present invention provides for a pharmaceutical composition comprising a compound of formula (I), or a pharmaceutically acceptable salt, solvate or polymorph thereof, and a second pharmaceutically active agent selected from those listed in the preceding paragraph.

The compounds of the invention may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those-described in Expert Opinion in Therapeutic Patents, 11 (6), 981-986 by Liang and Chen (2001).

The composition of a typical tablet in accordance with the invention may comprise:

| Ingredient | % w/w |
|---|---|
| Compound of formula (I) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1-14 (2001). Other modified release formulations are described in U.S. Pat. No. 6,106,864.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, Finnin and Morgan, J Pharm Sci, 88 (10), 955-958 (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus compounds of the invention may be formulated in a more solid form for administration as an implanted depot providing long-term release of the active compound.

The compounds of the invention can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the compound of the invention, a suitable powder base such as lactose or starch and a performance modifier such as l-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff" containing from 1 µg to 20 mg of the compound of formula (I). The overall daily dose will typically be in the range 1 µg to 80 mg which may be administered in a single dose or, more usually, as divided doses throughout the day.

Formulations for inhaled/intranasal administration may be formulated to be immediate and/or modified release. Modified release formulations include delayed-, sustained-, pulsed-, controlled dual-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

The compounds of the invention may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

The compounds of the invention may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.1 mg to 500 mg depending, of course, on the mode of administration. For example, oral administration may require a total daily dose of from 0.1 mg to 500 mg, while an intravenous dose may only require from 0.01 mg to 50 mg. The total daily dose may be administered in single or divided doses.

These dosages are based on an average human subject having a weight of about 65 to 70 kg. The physician will readily be able to determine doses for subjects whose weight falls outside this range, such as infants and the elderly.

Compounds of the invention may be prepared, in known manner in a variety of ways. In the following reaction schemes and hereafter, unless otherwise stated $R^1$ to $R^6$ are as defined in the first aspect. These processes form further aspects of the invention.

1. Scheme 1 summarises a synthetic route that is applicable to the synthesis of compounds of formula (I), and particularly for those compounds of formula (I) wherein $R^5$ is hydrogen or unsubstituted alkyl or cycloalkyl. The starting materials are pyrazolecarboxylic acids of formula (II). Some compounds of formula (II) are items of commerce, and others are known in the literature. Where they are not known they may be prepared according to one or more of the methods that are available in the art, such as those discussed in part 2 below.

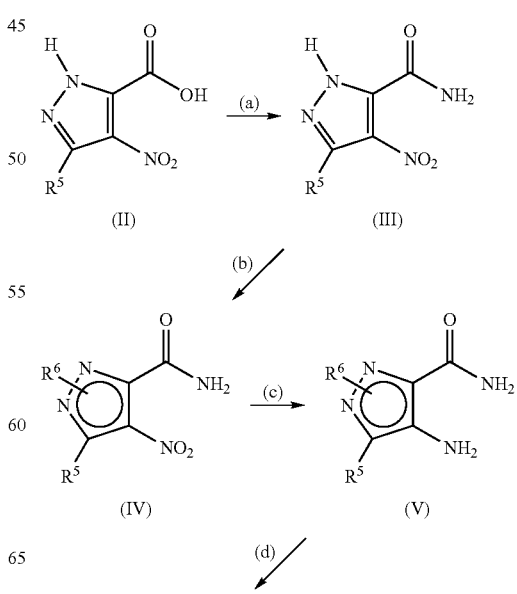

Scheme 1

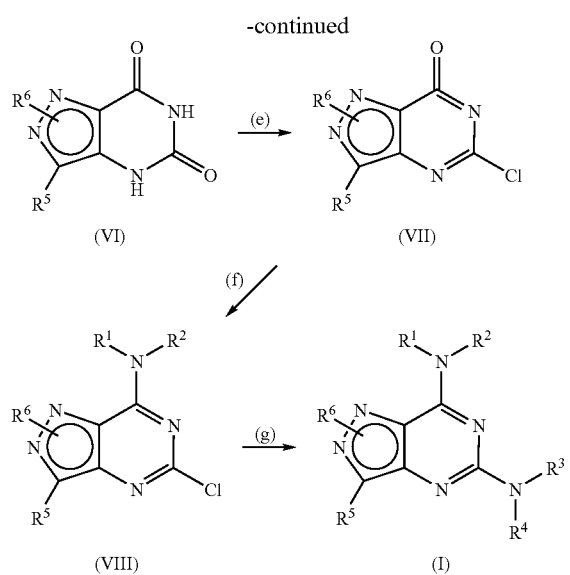

Step (a)

The carboxylic acid of formula (II) is converted to the corresponding amide of formula (III) either directly or, preferably, via an acid chloride intermediate. Direct conversion may be achieved by treating a solution of the acid with excess ammonia in the presence of a coupling agent such as a carbodiimide (e.g dicyclohexylcarbodiimide or 1-(3-dimethylaminopropyl)-3-ethylcarbodiimide) and optionally a hydroxytriazole such as HOBT or HOAT. Suitable solvents include dichloromethane and ethyl acetate. Indirect conversion may be achieved by forming an acid chloride by treatment with oxalyl chloride and N,N-dimethylformamide in a suitable solvent such as dichloromethane, or with thionyl chloride. A solution of the acid chloride in a suitable solvent such as dichloromethane, tetrahydrofuran or dioxan is then treated with gaseous ammonia or aqueous ammonia to provide the amide of formula (III).

Preferably, a solution of the acid of formula (II) in dichloromethane is treated at room temperature with oxalyl chloride and a catalytic quantity of N,N-dimethylformamide for 2 hours. The mixture is then cooled to −20° C., excess ammonia is added, and the mixture is stirred for 2 hours at a temperature of between −20° C. and room temperature.

Step (b)

When $R^6$ is $R^{6A}$, this group may be introduced in an N-alkylation step. The compound of formula (III) may be treated with a base such as an alkaline metal carbonate or bicarbonate, for example potassium carbonate or caesium carbonate, or a tertiary amine, for example triethylamine, N-ethyl-diisopropylamine or pyridine, and the appropriate chloride ($R^{6A}$—Cl), bromide ($R^{6A}$—Br), iodide ($R^{6A}$—I), mesylate ($R^{6A}$—OSO$_2$CH$_3$) or tosylate ($R^{6A}$—OSO$_2$Tol) in a suitable solvent at a temperature of between −20° C. and 100° C. Suitable solvents include ethers such as tetrahydrofuran and dioxan, lower alcohols such as methanol, ethanol and butanol, ketones such as acetone and 2-butanone, N-methylpyrrolidinone, N,N-dimethylformamide and acetonitrile.

Alternatively, an alkali metal hydroxide such as sodium hydroxide or potassium hydroxide may be used as the base. Suitable solvents then include water and mixtures of water and water-miscible organic solvents.

Alternatively, an alkali metal (C$_1$-C$_4$)alkoxide such as sodium methoxide or potassium tert-butoxide may be used as the base. Suitable solvents then include the corresponding lower alcohols (i.e. methanol for sodium methoxide), ethers such as tetrahydrofuran and dioxan, N-methylpyrrolidinone, N,N-dimethylformamide and acetonitrile.

Stronger bases such as sodium hydride and sodium or potassium hexamethyldisilazide may also be used. Suitable solvents then include ethers such as tetrahydrofuran and dioxan, N-methylpyrrolidinone, and N,N-dimethylformamide.

The reaction may also be carried out under phase transfer conditions using aqueous sodium or potassium hydroxide as base, dichloromethane or chloroform as organic solvent, and a tetraalkylammonium chloride or hydroxide as phase transfer catalyst.

Alternatively, the transformation may be achieved using the Mitsunobu reaction (Organic Reactions 1992, 42), in which a solution of the compound of formula (III) and the appropriate alcohol $R^{6A}$—OH in a suitable solvent is treated with triphenylphosphine and a dialkyl azodicarboxylate such as diethyl azodicarboxylate or diisopropyl azodicarboxylate. Suitable solvents include tetrahydrofuran and dioxan. The reaction is preferably performed at a temperature of between −10° C. and ambient temperature.

Preferably, the compounds of formula (III) is treated with either 1 equivalent of $R^{6A}$—Br and 1 equivalent of potassium carbonate in N,N-dimethylformamide at room temperature for 18 hours, or with 1.2 equivalents of $R^{6A}$—OH, 1.4 equivalents of diisopropyl azodicarboxylate and 1.4 equivalents of triphenylphosphine in tetrahydrofuran at a temperature of between 0° C. and 25° C. for 2 hours.

Depending on the precise choice of reagents and conditions chosen, the reaction may give the $N^1$- or $N^2$-alkylated product, or a mixture of the two.

Where a mixture is produced then the individual components may be separated using conventional methods such as chromatography or fractional crystallisation.

Step (c)

Reduction of the nitro group of compounds of formula (IV) to provide the amines of formula (V) can be achieved by, for example, transfer or catalytic hydrogenation, or by a dissolving metal reduction.

For transfer hydrogenation, the nitro compound is reacted with a suitable hydrogen donor, such as ammonium formate or cyclohexene, in a polar solvent, such as tetrahydrofuran, methanol or ethanol, in the presence of a transition metal or transition metal salt catalyst, such as palladium or palladium (II) hydroxide, optionally at elevated temperature and pressure.

For catalytic hydrogenation, a solution of the nitro compound in a polar solvent, such as tetrahydrofuran, methanol or ethanol, is stirred under a hydrogen atmosphere in the presence of a transition metal or transition metal salt catalyst, such as palladium or Raney® nickel, optionally at elevated pressure. The catalyst may be in solution (homogeneous catalysis) or in suspension (heterogeneous catalysis).

For dissolving metal reduction, the nitro compound in ethanol is treated with a suitable reactive metal, such as zinc or tin, in the presence of an acid such as acetic acid or hydrochloric acid. Other reducing agents, such as tin(II) chloride, may also be used.

Preferably, a solution of the compound of formula (IV) in methanol or ethanol is treated with 10% (by weight) of 10% Pd(OH)$_2$-on-carbon and 5 equivalents of ammonium formate, and the mixture is heated at reflux for between 2 and 18 hours.

Step (d)

A solution of the pyrazolecarboxamide (V) and phosgene or an equivalent thereof, such as 1,1'-carbonyldiimidazole, trichloromethyl chloroformate or bis(trichloromethyl) carbonate, in a suitable solvent is stirred at a temperature of between ambient temperature and the boiling point of the solvent, optionally at elevated pressure, for between 2 and 18 hours to provide the corresponding pyrazolopyrimidinedione of formula (VI). Suitable solvents include acetonitrile, dichloromethane and N,N-dimethylformamide. Preferably, a solution of the dione and 1 to 2 equivalents of carbonyl diimidazole in acetonitrile, N,N-dimethylformamide or dichloromethane is heated at a temperature of between 50° C. and 80° C. for 18 hours.

Step (e)

The dione of formula (VI) is treated with a large excess of a suitable chlorinating reagent such as phosphorus oxychloride (POCl$_3$) or phenylphosphonyl dichloride (PhP(O)Cl$_2$) in the presence of a tertiary amine such as N-ethyldiisopropylamine, N-methylmorpholine, triethylamine or N,N-dimethylaniline at elevated temperature for 8-48 hours to provide the corresponding dichloropyrazolopyrimidine of formula (VII). N,N-dimethylformamide can optionally be added as a catalyst. Alternatively, the dione is treated with POCl$_3$ or PhP(O)Cl$_2$ in a suitable solvent in the presence of a tetraalkylammonium chloride, such as tetraethylammonium chloride, at elevated temperature. Suitable solvents include acetonitrile and propionitrile.

Preferably, the dione is treated with 10-30 equivalents of POCl$_3$ and 3-5 equivalents of tetraethylammonium chloride in propionitrile at reflux for 4-18 hours.

Step (f)

A solution of the dichloride of formula (VII), the amine HNR$^1$R$^2$ and an excess of a tertiary amine such as N-ethyldiisopropylamine, N-methylmorpholine or triethylamine in a suitable solvent are stirred at ambient or elevated temperature for between 1 and 24 hours to provide the corresponding compound of formula (VIII). Suitable solvents include dichloromethane, dimethylsulfoxide, N,N-dimethylformamide, tetrahydrofuran and N-methylpyrrolidinone.

Alternatively, a solution of the amine HNR$^1$R$^2$ in a suitable solvent is treated with butyllithium or sodium hexamethyldisilazide at low temperature, and the dichloride is added to the resulting solution. Suitable solvents include tetrahydrofuran, dioxan and N-methylpyrrolidinone.

Preferably, either the dichloride is treated with 3-5 equivalents of the amine HNR$^1$R$^2$ and optionally 3-5 equivalents of N-ethyldiisopropylamine in dichloromethane, dimethylsulfoxide or a mixture of dimethylsulfoxide and N-methylpyrrolidinone at 20-90° C. for 1-18 hours, or a solution of 2-4 equivalents of HNR$^1$R$^2$ in tetrahydrofuran is treated with an equimolar amount of butyllithium or sodium hexamethyldisilazide, 1 equivalent of the dichloride is added, and the mixture is stirred at a temperature of between 0° C. and room temperature for between 2 and 3 hours.

It will be appreciated that any functional groups that are substituents on R$^1$, and particularly any primary or secondary amine groups, may need to be protected in order to allow this reaction to proceed successfully. Suitable protecting groups are well known in the art, and are described in, for example, "Protective Groups in Organic Synthesis", Greene, T. W. and Wutts, P. G. M., 3$^{rd}$ edition, John Wiley & Sons, Ltd, Chichester, 1999. Examples of protecting groups for primary and secondary amines include tert-butyloxycarbonyl (BOC), benzyloxycarbonyl (CBZ or Z) and 9-fluorenylmethyloxycarbonyl (Fmoc) groups. Carboxylic acids may be protected as their methyl, ethyl, benzyl or tert-butyl esters. Alcohols may be protected as ester or ether derivatives.

Step (g)

A solution of the monochloride (VIII) and the amine HNR$^3$R$^4$ in a suitable dipolar aprotic solvent are stirred at elevated temperature for between 1 and 24 hours to provide the corresponding compound of formula (I). Suitable solvents include dimethylsulfoxide, N,N-dimethylformamide and N-methylpyrrolidinone. An excess of a tertiary amine such as N-ethyldiisopropylamine, N-methylmorpholine or triethylamine and/or a fluoride source such as caesium fluoride or tetraethylammonium fluoride may optionally be included. It is sometimes necessary to perform the reaction at elevated pressure in a closed vessel, particularly when the amine HNR$^3$R$^4$ or the solvent is volatile.

Alternatively, the reaction may be carried out under microwave irradiation.

Preferred conditions are:

the monochloride is treated with 3-5 equivalents of the amine HNR$^3$R$^4$ and optionally with 3-5 equivalents of N-ethyldiisopropylamine in dimethylsulfoxide or N-methylpyrrolidinone, optionally in a sealed vessel, at 80-125° C. for 12-18 hours; or the monochloride is treated with 3-5 equivalents of the amine HNR$^3$R$^4$ and 1 equivalent of caesium fluoride in dimethylsulfoxide or N-methylpyrrolidinone, optionally in a sealed vessel, at 100-120° C.; or the monochloride is treated with 3-5 equivalents of the amine HNR$^3$R$^4$ and optionally with 3-5 equivalents of N-ethyldiisopropylamine and/or optionally in the presence of caesium fluoride or tetraethylammonium fluoride in N-methyl-pyrrolidinone under microwave irradiation for 40 minutes.

It will be appreciated that, as for step (f) above, any functional groups in —NR$^3$R$^4$, and particularly any primary or secondary amine groups, may need to be protected in order to allow this reaction to proceed successfully.

In some cases, it is possible to perform the transformations of steps (f) and (g) as a "one-pot" operation, i.e. without isolating the monochloride of formula (VIII). The compound of formula (VII) is treated with the amine HNR$^1$R$^2$, as described in step (f), then the amine HNR$^3$R$^4$ is added to the mixture and the reaction is carried forward as described in step (g).

When one or more protecting groups have been used in the course of the synthesis, there will be a final deprotection protocol to unmask the functional groups of the target compound. This protocol may be a single operation or may proceed in several steps. It may also be combined with the preceding synthetic manipulation.

Deprotection is well known in the art, as described in "Protective Groups in Organic Synthesis", Greene, T. W. and Wutts, P. G. M., 3$^{rd}$ edition, John Wiley & Sons, Ltd, Chichester, 1999. For example, tert-butyloxycarbonyl-protected amines and tert-butyl esters of carboxylic acids may be deprotected by treatment with acids such as trifluoroacetic acid or anhydrous hydrogen chloride in a suitable solvent, benzyloxycarbonyl-protected amines and benzyl esters of carboxylic acids may be deprotected by catalytic hydrogenolysis, 9-fluorenylmethyloxycarbonyl-protected amines may be deprotected by treatment with piperidine, and methyl and ethyl esters of carboxylic acids may be deprotected by treatment with an alkali metal hydroxide.

Preferably, tert-butyloxycarbonyl and tert-butyl protecting groups are removed by treatment with trifluoroacetic acid in dichloromethane at room temperature for between 1 and 18 hours, or, for tert-butyloxycarbonyl protecting groups, by treatment with excess hydrogen chloride in dioxan at room temperature for 18 hours. Benzyl protecting groups are preferably removed by hydrogenation at 60 psi in the presence of Pd(OH)$_2$ in ethanolic hydrogen chloride at room temperature for 18 hours.

2. Scheme 2 summarises two methods, the Knorr and the Pechmann syntheses, available for the synthesis pyrazole-carboxylic acids of formula (II). Other methods known in the art may also be used.

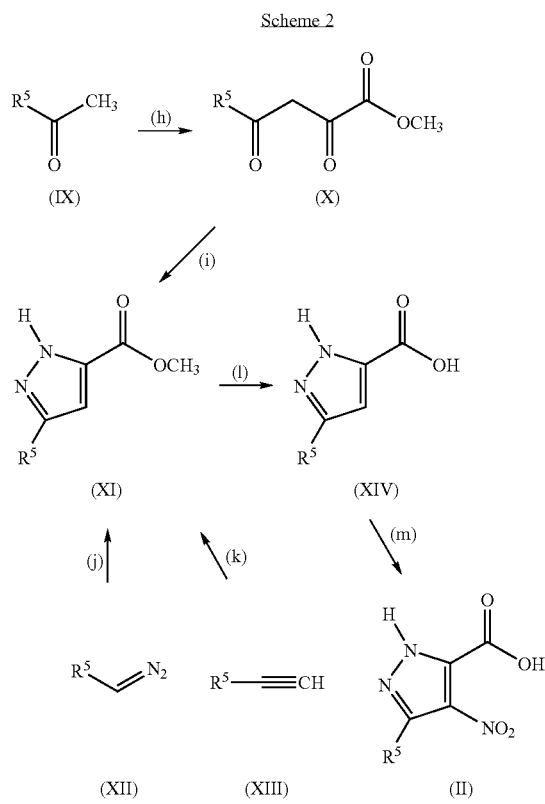

Scheme 2

Step (h)

The 1,3-diketones of formula (X) that are the starting materials for the Knorr pyrazole synthesis can be prepared from the corresponding methyl ketones of formula (IX) using a crossed Claisen condensation. The methyl ketone of formula (IX) is reacted with dimethyl oxalate in a suitable solvent in the presence of a suitable base. Suitable solvents include ethers, such as tetrahydrofuran. Suitable bases include sodium hydride, potassium tert-butoxide and lithium diisopropylamide. Alternatively, sodium methoxide may be used as the base and methanol as the solvent.

Step (i)

The 1,3-diketone of formula (X) may be reacted with hydrazine to give a pyrazole of formula (XI) following the well known methodology of the Knorr pyrazole synthesis.

It will be appreciated that substituted hydrazines R$^{6d}$NHNH$_2$ may also be used in the Knorr pyrazole synthesis to provide analogues of the compounds of formula (XI) which are N-alkylated. A mixture of N$^1$- and N$^2$-alkylated product is normally produced and the individual components may be separated using conventional methods such as chromatography or fractional crystallisation. Hydrolysis and nitration according to the methods described for steps (l) and (m) below, followed by amide formation according to the method described in part 1, step (a), above, then provides the compounds of formula (IV) without the need for the alkylation reaction of part 1, step (b).

Step (j)

In this variant of the Pechmann pyrazole synthesis, a diazo compound of formula (XII) is reacted with methyl propiolate to provide a pyrazole of formula (XI). The diazo compounds of formula (XII) can be prepared by known methods, such as from the corresponding primary amine R$^5$CH$_2$NH$_2$ via an N-arylsulfonyl-N-nitroso derivative.

Step (k)

In this alternative variant of the Pechmann pyrazole synthesis, an acetylene of formula (XIII) is reacted with methyl diazoacetate to provide a pyrazole of formula (XI).

Step (l)

Hydrolysis of the ester of the compounds of formula (XI) then provides the compounds of formula (XIV). The conversion may conveniently be accomplished by treating the compound of formula (XI) with an alkaline metal hydroxide such as lithium hydroxide, sodium hydroxide or potassium hydroxide in a suitable solvent at a temperature of between about 10° C. and the boiling point of the solvent. Suitable solvents include water, methanol, ethanol and mixtures of water with methanol, ethanol, tetrahydrofuran and dioxan.

Step (m)

The nitration of pyrazoles is well known. The compounds of formula (XIV) are treated with a nitrating agent such as nitric acid or a mixture of nitric acid and sulphuric acid to provide the compounds of formula (II).

3. Scheme 3 provides a variation to the synthetic route of Scheme 1 that is applicable to the synthesis of compounds of formula (I) wherein R$^6$ is R$^{6A}$, in which this group is introduced in the final step.

Scheme 3

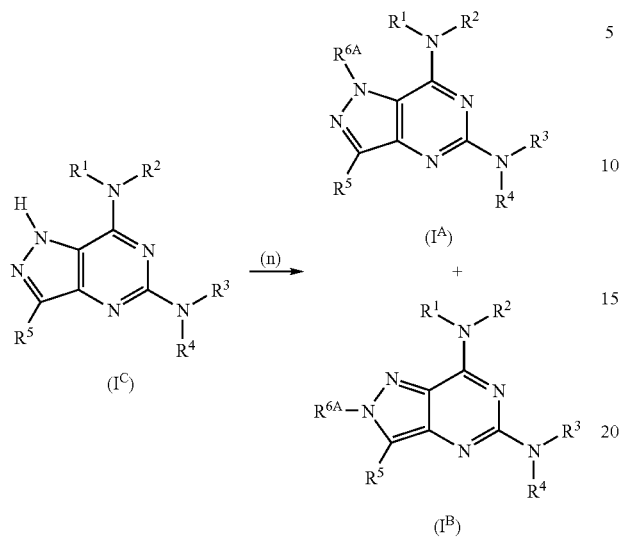

Scheme 4

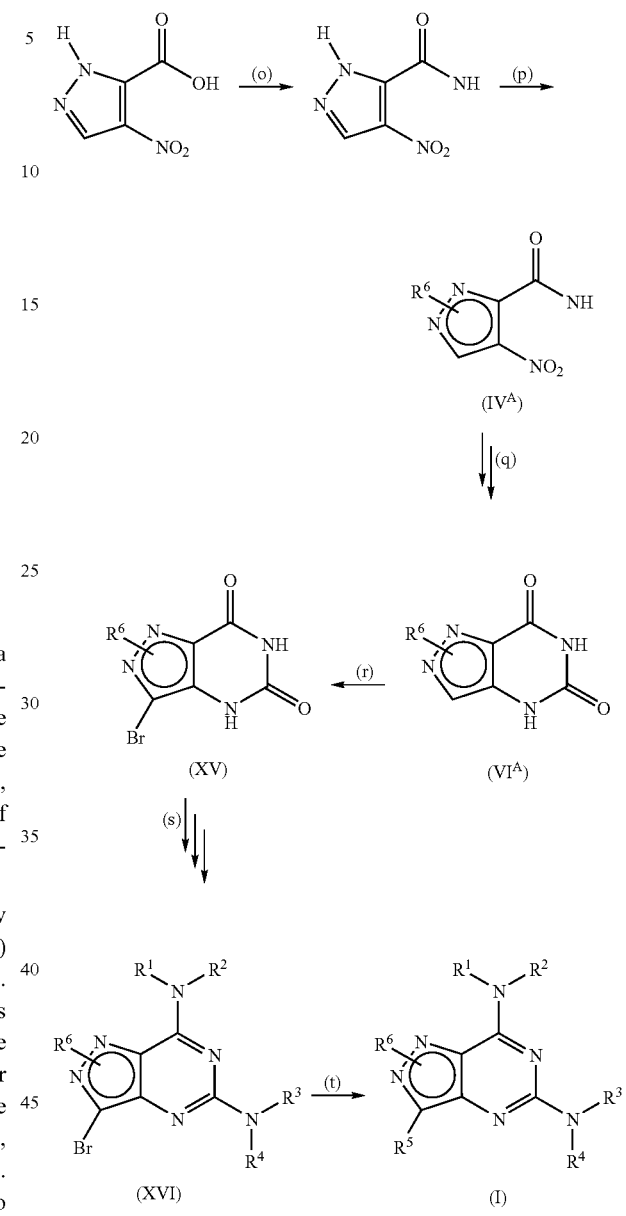

Step (n)

Compounds of formula (I$^C$), i.e. compounds of formula (I) wherein R$^6$ is hydrogen, can be converted to the N-alkylated compounds of formulae (I$^A$) and (I$^B$) following the methods described in part 1, step (b), above. When the reaction gives a mixture of the two products (I$^A$) and (I$^B$), these can be separated using standard techniques. The use of more reactive alkylating agents tends to promote the formation of the N$^2$-substuituted compounds of formula (I$^B$).

4. The methodology of Schemes 1 and 2 is generally applicable to the synthesis of compounds of formula (I) wherein R$^5$ is hydrogen or unsubstituted alkyl or cycloalkyl. It may also be applied to the synthesis of other compounds of formula (I) provided that any functional groups in R$^5$ are compatible with the chemical manipulations involved. For example, polyfluoroalkyl and perfluoroalkyl groups are likely to be compatible, as are ether functional groups, particularly if remote from the pyrazolopyrimidine nucleus. In some cases, however, it may be desirable or necessary to introduce or elaborate R$^5$ at an intermediate stage in the overall synthesis. Representative methods are described below in Schemes 4 to 11. It will be appreciated that many of the transformations could be performed at points in the overall synthesis other than those illustrated.

Scheme 4 summarises a synthetic route for the synthesis of compounds of formula (I) in which the group R$^5$ is introduced in the final step by a cross-coupling reaction. The method is particularly suited to instances of R$^5$ that are branched or unsaturated at the point of attachment to the pyrazolopyrimidine nucleus. Saturated alkyl and cycloalkyl groups may also be obtained following this method by introducing them as their alkenyl and cycloalkenyl analogues and then reducing the unwanted double bond in a subsequent catalytic hydrogenation step.

Step (o)

Commercially available 4-nitro-(2H)-pyrazole-3-carboxylic acid is converted to 4-nitro-(2H)-pyrazole-3-carboxamide following the methods described in part 1, step (a), above.

Step (p)

The compounds of formula (IV$^A$), i.e. compounds of formula (IV) wherein R$^5$ is hydrogen, are obtained following the methods described in part 1, step (b), above.

Step (q)

The compounds of formula (VI$^A$), I.e. compounds of formula (VI) wherein R$^5$ is hydrogen, are obtained in two steps following the methods described in part 1, steps (c) and (d), above

Step (r)

The compounds of formula (VI⁴) may be brominated to provide the corresponding compounds of formula (XV) by treatment with N-bromosuccinimide in N,N-dimethylformamide at elevated temperature, or with bromine and excess sodium acetate in acetic acid at reflux. Preferably the compound of formula (VI⁴) is treated with N-bromosuccinimide in N,N-dimethylformamide at 50° C. for 18 hours.

Step (s)

The compounds of formula (XVI) are obtained following the methods described in part 1, steps (e), (f) and (g), above.

Step (t)

The compounds of formula (XVI) may be coupled to a suitable reagent $R^5$—M, where M is a metal, a metal derivative or a boron derivative such as: lithium (M=Li); halomagnesium, particularly chloromagnesium, bromomagnesium and iodomagnesium (M=ClMg, BrMg and IMg); halozinc, particularly chlorozinc, bromozinc and iodozinc (M=ClZn, BrZn and IZn); trialkyltin, for example tri-n-butyltin (M=n-Bu₃Sn); dialkylboron, for example diethylboron (M=Et₂B); and dialkoxyboron, for example dimethoxyboron (M=(H₃CO)₂B). The reaction is generally carried out in the presence of a transition metal catalyst such as a palladium or nickel, or derivatives thereof, and may additionally call for the use of a base such as potassium carbonate, caesium fluoride or triethylamine. Representative coupling methods include the "Suzuki" and "Stille" protocols, which are described in detail in "Metal-Catalysed Cross-Coupling Reactions", F. Diederich (ed.), Wiley-VCH, 1998 (and references cited therein).

5. Scheme 5 summarises synthetic routes that are particularly useful for the preparation of compounds of formula (I) wherein $R^5$ is hydroxymethyl, alkoxymethyl, haloalkoxymethyl or cycloalkoxymethyl. In Scheme 5, X represents a leaving group such as a chlorine, bromine or iodine atom or an alkyl, aryl or perfluoroalkylsulfonate group (for example a methanesulfonate, toluenesulfonate or trifluoromethanesulfonate group), and $R^8$ represents an alkyl, cycloalkyl or haloalkyl group.

Scheme 5

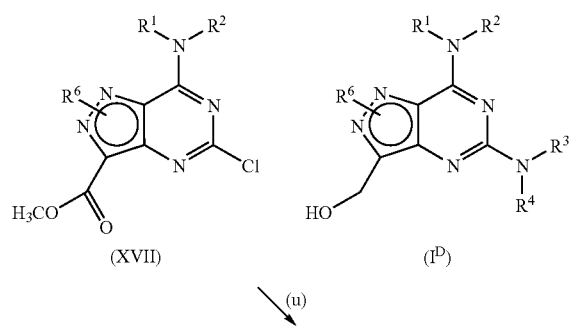

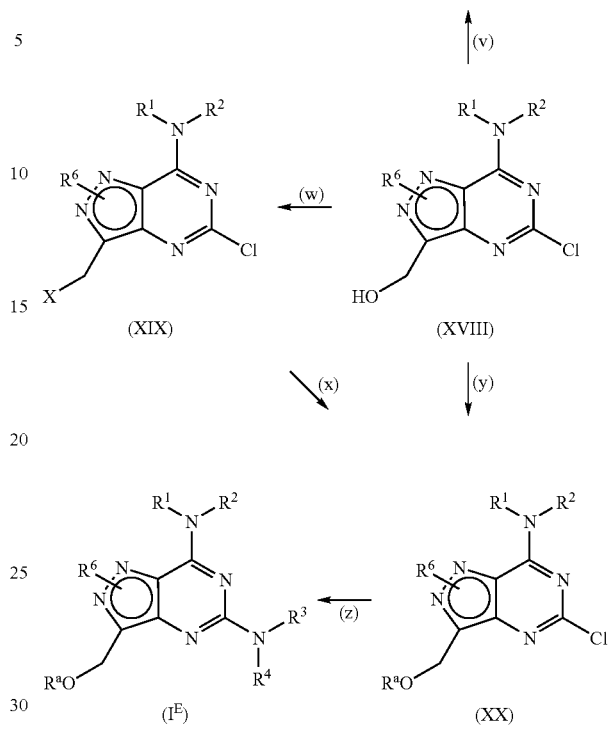

Step (u)

The reduction of the esters of formula (XVII) to provide the primary alcohols of formula (XVIII) can be achieved using a metal hydride reagent such as lithium aluminiumhydride, lithium borohydride, lithium triethylborohydride or diisobutylaluminium hydride (DIBAL) in a suitable solvent at a temperature of less than 0° C. Suitable solvents include hydrocarbons such as pentane, hexane and toluene, ethers such as tetrahydrofuran, and mixtures thereof. Alternatively, the ester can be reduced by hydrogenation over a copper chromite catalyst at elevated temperature and pressure. Preferably, the ester is treated with 8-10 equivalents of DIBAL in tetrahydrofuran at a temperature of between −78° C. and −5° C. for 15 minutes to 1 hour.

The esters of formula (XVII) can be prepared according to the methods described in part 6, below.

Step (v)

Compounds of formula (I^D), i.e. compounds of formula (I) wherein $R^5$ is hydroxymethyl, may be obtained from the alcohols of formula (XVIII) following the methods of part 1, step (g).

Step (w)

Compounds of formula (XIX) wherein X is Br may be prepared from the alcohols of formula (XVIII) by treatment with hydrogen bromide or a mixture of triphenylphosphine and bromine, tetrabromomethane or N-bromosuccinimide, optionally in the presence of pyridine, in a suitable solvent such as diethyl ether, dichloromethane or propionitrile. Preferably the alcohol is treated with triphenylphosphine and tetrabromomethane in dichloromethane at room temperature for 1 hour.

Compounds of formula (XIX) wherein X is Cl may be prepared from the alcohols of formula (XVIII) by treatment with thionyl chloride, phosphorus trichloride or a mixture of triphenylphosphine and N-chlorosuccinimide in a suitable solvent such as dichloromethane. Preferably the alcohol is treated with excess thionyl chloride in dichloromethane for 2-18 hours.

Compounds of formula (XIX) wherein X is I may be prepared from the corresponding bromide or chloride by treatment with sodium iodide.

Compounds of formula (XIX) wherein X is an alkylsulfonate, arylsulfonate or perfluoroalkylsulfonate may be prepared from the alcohols of formula (XVIII) by treatment with a sulfonyl chloride or anhydride, such as methanesulfonyl chloride (mesyl chloride), toluenesulfonyl chloride (tosyl chloride) or trifluoromethanesulfonic anhydride (triflic anhydride), in the presence of a tertiary amine such as triethylamine, N-ethyldiisopropylamine or N-methylmorpholine, in a suitable solvent, for example dichloromethane. Alternatively, pyridine may be used as solvent, in which case there is no need for the use of a tertiary amine.

Step (x)

Compounds of formula (XX) may be obtained by treating the corresponding compounds of formula (XIX) with a sodium or potassium alkoxide, NaOR$^a$ or KOR$^a$. Alternatively, the compounds of formula (XIX) may be treated with an excess of the alcohol R$^a$H and a catalyst such as silver tetrafluoroborate (AgBF$_4$). Suitable solvents include acetonitrile, N-methylpyrrolidinone and N,N-dimethylformamide. Alternatively, the alcohol R$^a$OH may be used as solvent provided that it can be removed easily after the reaction, for example by evaporation.

Preferably, a compound of formula (XIX) wherein X is Cl or Br is treated with an excess of NaOR$^a$ in N,N-dimethylformamide or R$^a$OH at room temperature for between 30 minutes and 72 hours.

Step (y)

Compounds of formula (XX) may also be obtained from the primary alcohols of formula (XVIII) by reaction with an alkylating agent R$^a$—X, using methods analogous to those discussed in part (y) above. Thus a solution of the alcohol of formula (XVIII) in a suitable solvent, for example N,N-dimethylformamide or acetonitrile, may be treated with a strong base such as sodium hydride to form the sodium alkoxide, and then with the alkylating agent R$^a$—X.

It will be appreciated that this transformation may also be carried out using the primary alcohols of formula (I$^D$) as starting materials, which transformation leads to the production of compounds of formula (I$^E$).

Step (z)

Compounds of formula (I$^E$), i.e. compounds of formula (I) wherein R$^5$ is R$^a$OCH$_2$—, may be obtained from the alcohols of formula (XX) following the methods of part 1, step (g).

6. The esters of formula (XVII$^A$), i.e. compounds of formula (XVII) wherein R$^6$ is attached at the N$^1$-position, and of formula (XVII$^B$), i.e. compounds of formula (XVII) wherein R$^6$ is attached at the N$^2$-position, can be prepared according to the methods summarised in Scheme 6.

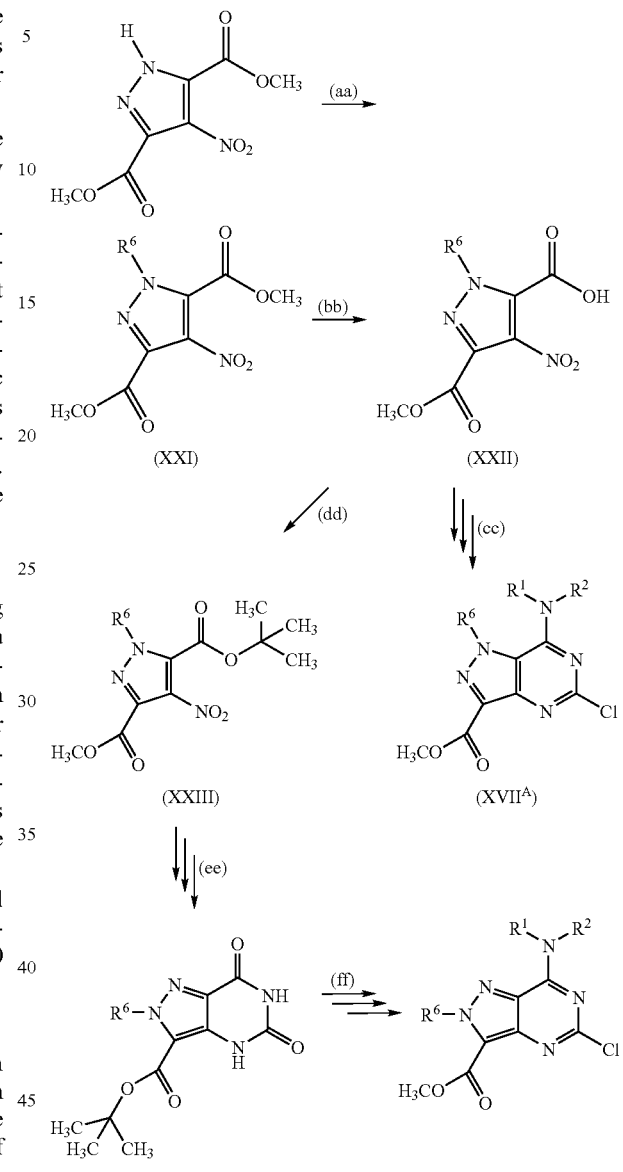

Scheme 6

Step (aa)

Dimethyl 4-nitropyrazole-3,5-dicarboxylate, which is readily prepared according to the method described in published international patent application WO00/24745 (see preparation 2, page 48), can be N-alkylated according to the methods described in part 1, step (b), above. It will be appreciated that the sensitivity of the ester groups to hydrolysis and trans-esterification means that alkali metal hydroxides and alkoxides (other than methoxides) cannot be used as bases, and water and alcohols (other than methanol) cannot be used as a solvents or cosolvents.

Because the two nitrogen atoms of the pyrazole are equivalent, a single alkylation product is obtained.

Step (bb)

Selective hydrolysis of the diesters of formula (XXI) with one equivalent of alkali metal hydroxide according to the method of Chambers et al. (J. Org. Chem. 50, 4736-4738, 1985) cleaves the ester adjacent to the substituted nitrogen to provide the monoacids of formula (XXII).

Preferably, the diester is treated with 1 equivalent of potassium hydroxide in methanol at room temperature for 18 hours.

Step (cc)

Compounds of formula (XVII$^4$), i.e. compounds of formula (XVII) wherein $R^6$ is attached at the $N^1$-position of the pyrazolopyrimidine, may be obtained from the compounds of formula (XXII) following the methods of part 1, steps (b) to (f).

The introduction of the —$NR^1R^2$ group is preferably achieved by treating the corresponding dichloride with 3-5 equivalents of $HNR^1R^2$ in dimethylsulfoxide at 30° C. for 1 hour.

Step (dd)

The compounds of formula (XXIII) may be prepared by treating the monoacids of formula (XXII) with tert-butyl acetate or isobutene in the presence of a mineral acid.

Step (ee)

Hydrolysis of the methyl ester of the compounds of formula (XXIII) according to the methods described in part 2, step (I), above, followed by elaboration of the resulting monoacid following the methods of part 1, steps (a) to (d), above, provides the $N^2$-substituted pyrazolopyrimidine-5,7-diones of formula (XXIV).

Step (ff)

The tert-butyl ester of the compounds of formula (XXIV) is cleaved by treatment with acid such as trifluoroacetic acid or a solution of hydrogen chloride in a suitable solvent such as dioxan. The resulting carboxylic acid is converted to the methyl ester using any of the methods well known in the art, such as by formation of the acid chloride using oxalyl chloride or thionyl chloride followed by treatment with methanol, or by treatment with methanol and a carbodiimide. The methyl ester is then carried forward as described in part 1, steps ((e) and (f) above, to provide the compounds of formula (XVII$^B$).

7. The synthetic route illustrated in Scheme 6 can be low-yielding in cases where the amine $HNR^1R^2$ is only weakly nucleophilic, such as when $R^1$ is a pyrimidine, or pyrazine ring. In these cases, it is necessary to reduce the ester group prior to the introduction of the —$NR^1R^2$ group, as illustrated in Scheme 7.

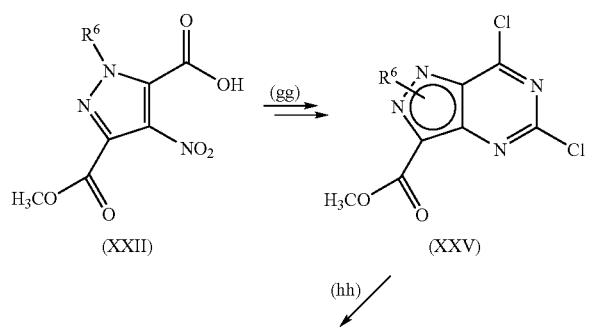

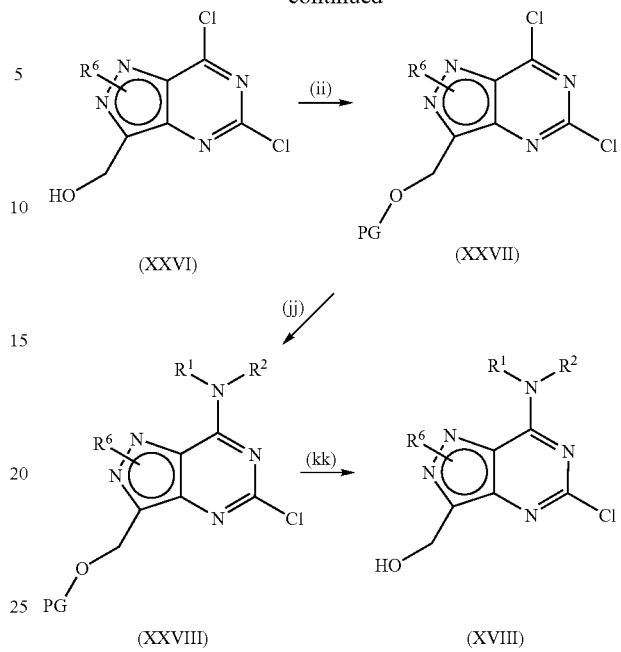

Step (gg)

Compounds of formula (XXV) may be obtained from the compounds of formula (XXII) following the methods of part 1, steps (b) to (e), above.

Step (hh)

Compounds of formula (XXVI) may be obtained from the compounds of formula (XXV) following the methods of part 5, step (v), above.

Step (ii)

The primary alcohol is then protected to give compounds of formula (XXVII), wherein PG is an alcohol protecting group. A preferred protecting group is a trialkylsilyl group, particularly a tert-butyldimethylsilyl group. Preferably, the alcohol is treated with 1.1 equivalents of tert-butyldimethylsilyl chloride and 1.1 equivalents of imidazole in dichloromethane at room temperature for 18 hours.

Step (jj)

Compounds of formula (XXVIII) may be obtained from the compounds of formula (XXVII) following the methods of part 1, step (f), above.

Step (kk)

The compounds of formula (XXVIII) are deprotected to provide the primary alcohols of formula (XVIII) using appropriate conditions. When PG is a trialkylsilyl group it may be removed by treatment with a fluoride salt, such as tetrabutylammonium fluoride, or with hydrogen chloride in methanol. Preferably, when PG is a tert-butyldimethylsilyl group it is removed by treatment with 2 equivalents of tetrabutylammonium fluorie in tetrahydrofuran at room temperature for 18 hours, or with hydrogen chloride in methanol at room temperature for 18 hours.

8. The alcohols of formula (XVIII) and ($I^D$) can be oxidised to the corresponding aldehydes of formula (XXIX), which are particularly versatile intermediates in the preparation of compounds of formula (I). Some representative transformations are shown in Scheme 8. Unless otherwise indicated, in schemes 8 to 11 Y is either Cl or —NR³R⁴, and may preferably to be Cl.

DIBAL at low temperature, but in practice it is very difficult to stop the reduction at the aldehyde stage, and the primary alcohol is generally the major product.

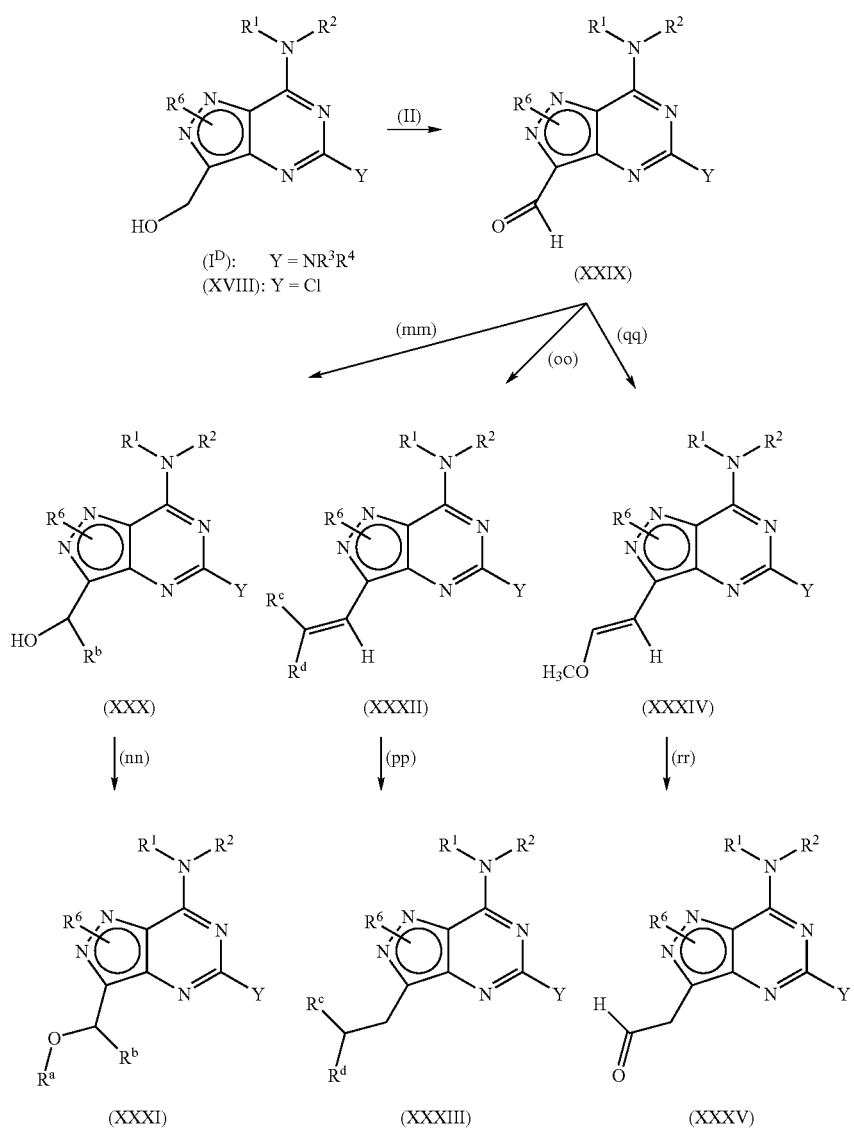

Step (ll)

The oxidation of the alcohols of formula (XIX) can be achieved using a chromium(VI) reagent such as pyridinium chlorochromate, an activated dimethylsulfoxide reagent as in the Swern oxidation protocol, a hypervalent iodine reagent such as the Dess-Martin periodinane, or a combination of tetra-n-propylammonium perruthenate and N-methylmorpholine-N-oxide in a suitable solvent at a temperature of between 0° C. and ambient temperature. Suitable solvents include dichloromethane.

A preferred reagent is the Dess-Martin periodinane.

In principle, the aldehydes of formula (XXIX) may also be prepared from the corresponding esters by reduction with Step (mm)

Reaction of the aldehydes of formula (XXIX) with a Grignard reagent $R^bMgHal$, where $R^b$ is an alkyl or cycloalkyl group and Hal is Cl, Br or I, or with an organolithium reagent $R^bLi$, provides the secondary alcohols of formula (XXX).

The compounds of formula (XXX) wherein Y is $NR^3R^4$ are themselves compounds of formula (I) wherein $R^5$ is alkyl substituted with a hydroxyl group.

Step (nn)

The compounds of formula (XXX) may be carried forward as discussed in part 5 above for the primary alcohol analogues. For example, they may be alkylated to provide the compounds of formula (XXXI) following the methods described in part 5, steps (x) and (y), or part 5, step (z), above.

Another possibility, not illustrated in Scheme 8, is to oxidise the secondary alcohol using the methods of step (ll) to obtain a ketone, which may be further elaborated in a manner analogous to the aldehydes of formula (XXIX).

Step (oo)

Using the Wittig reaction methodology, the aldehydes of formula (XXIX) may be treated with a phosphorane reagent $Ph_3P{:}C(R^c)R^d$, where $R^c$ and $R^d$ are hydrogen, alkyl or cycloalkyl, to provide compounds of formula (XXXII), in which there is a double bond adjacent to the pyrazolopyrimidine nucleus.

Analogous compounds may also be prepared from the alcohols of formula (XXX) when $R^a$ is $CH(R^c)R^d$ by acid-catalysed dehydration, or by base-catalysed elimination from the corresponding chloride or mesylate.

Step (pp)

If not required in the final product, the double bond in compounds of formula (XXXII) may be reduced by catalytic hydrogenation.

Step (qq)

The use of (methoxymethylene)triphenylphosphorane in the Wittig reaction of step (oo) provides the enol ethers of formula (XXXIV).

Step (rr)

The enol ethers of formula (XXXIV) may be hydrolysed in acid solution to provide the aldehydes of formula (XXXV). These may then be elaborated in the same ways as discussed above for the aldehydes of formula (XXIX).

9. The aldehydes of formula (XXIX) can also be homologated to provide esters, as illustrated in Scheme 9. The esters so obtained can then be elaborated to provide compounds of formula (I) following the methods outlined in parts 5 and 8 above.

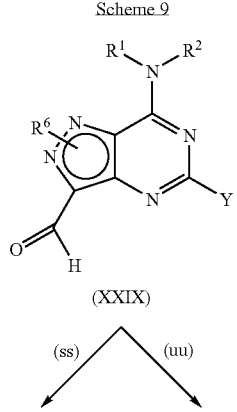

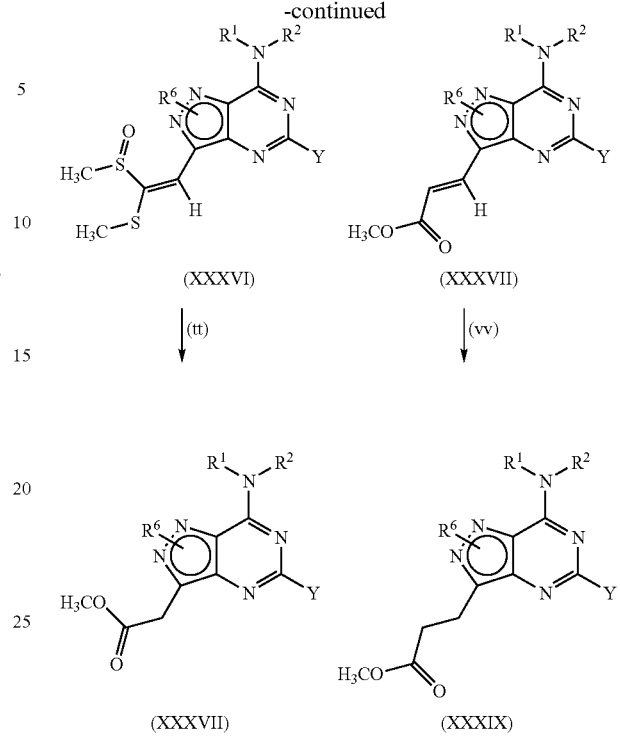

Step (ss)

The aldehydes of formula (XXIX) are treated with methyl methylmercaptomethyl sulfoxide ($CH_3SCH_2S(O)CH_3$) and triton B in tetrahydrofuran to give intermediates of formula (XXXVI).

Step (tt)

The intermediates of formula (XXXVI) are treated with methanol and acetyl chloride to provide the ester of formula (XXXVII).

Step (uu)

The aldehydes of formula (XXIX) can be converted to the acrylate ester of formula (XXXVIII) by reaction with a phosphorus reagent following the protocols of the Wittig, Horner or Wadsworth-Horner-Emmons reactions. The reagent is prepared by treating a triphenylphosphonium salt $Ph_3P^+CH_2CO_2CH_3.X^-$ (Wittig), a phosphine oxide $Ph_2P(O)CH_2CO_2CH_3$ (Horner), or a phosphonate $(EtO)_2P(O)CH_2CO_2CH_3$ (Wadsworth-Horner-Emmons), with a base such as butyllithium, a lithium dialkylamide or an alkaline metal alkoxide, in a suitable solvent such as tetrahydrofuran.

The method is not limited to the preparation of α-unsubstituted acrylate esters. The use of an alkyl-substituted phosphorus reagent such as $Ph_3P^+CH(R)CO_2CH_3.X^-$ or the equivalent phosphine oxide or phosphonate, wherein R is alkyl, gives access to the corresponding α-alkyl acrylate derivative.

The conversion of the aldehydes of formula (XXIX) to acrylate esters of formula (XXXVIII) can also be achieved by reaction with a malonate derivative following the method of the Knoevenagel condensation.

Step (vv)

The reduction of the carbon-carbon double bond of (XXXVIII) to give the compounds of formula (XXXIX) can be accomplished by catalytic hydrogenation using molecular hydrogen in the presence of a transition metal catalyst such as palladium, platinum or nickel.

The acrylates of formula (XXXVIII) can also be treated with alkylcopper reagents to give analogues of the compounds of formula (XXXIX) in which an alkyl substituent is introduced on the carbon atom adjacent to the pyrazolopyrimidine ring system, or with a sulphonium ylid or a carbene equivalent to give a 2-(pyrazolopyrimidinyl)-cyclopropane-1-carboxylate derivative.

10. The homologated esters of formula (XXXVII) can also be prepared by the method illustrated in Scheme 10.

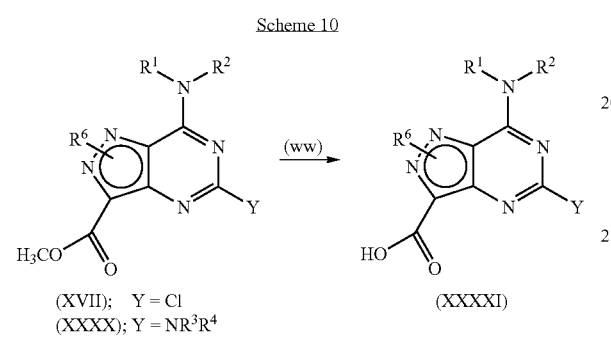

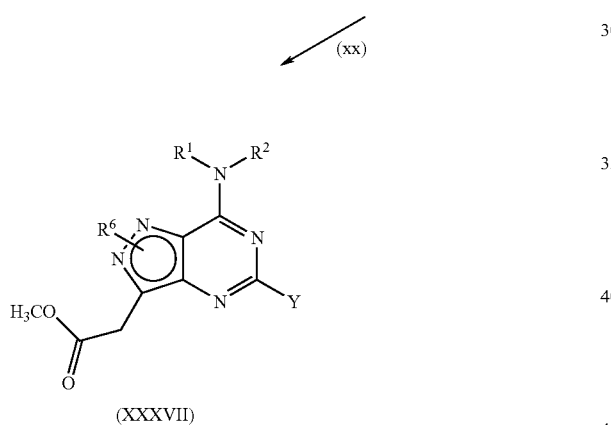

11. The homologated esters of formula (XXXIX) can also be prepared by the method illustrated in Scheme 11.

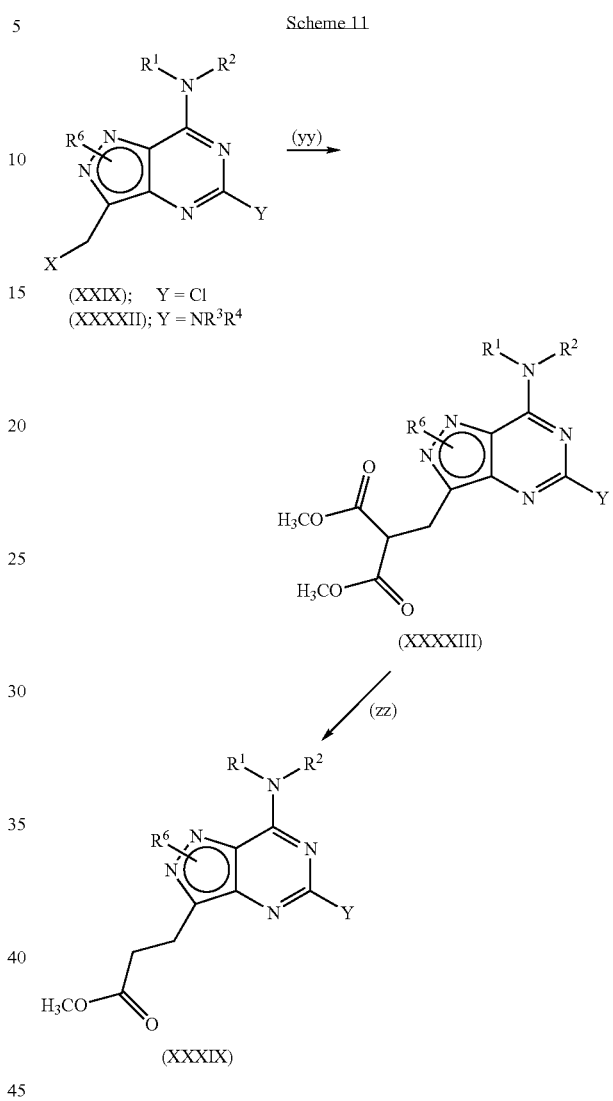

Step (ww)

The methyl esters of formulae (XVII) and (XXXX) may be hydrolysed to provide the acids of formula (XXXXI) following the methods of part 2, step (n), above. (The esters of formula (XXXX) may be obtained from the esters of formula (XVII) following the methods of part 1, step (g) above.)

Step (xx)

The acids of formula (XXXXI) may be homologated following the methods of the Arndt-Eistert reaction. The carboxylic acid is converted to a reactive intermediate such as the acid chloride (by reaction with oxalyl chloride) or a mixed anhydride (by reaction with isobutyl chloroformate). The intermediate is reacted with diazomethane to provide an α-diazoketone. This is treated with silver oxide in the presence of methanol to give the homologated ester of formula (XXXVII).

Step (yy)

The chlorides of formulae (XXIX) and (XXXXII) are reacted with a dialkyl malonate $(CH_3O_2C)_2CH_2$ and a base in a suitable solvent. Typically, the base is an alkaline metal alkoxide such as sodium ethoxide or potassium tert-butoxide, and the solvent is an alcohol such as methanol or ethanol, or an ether such as tetrahydrofuran. Preferably the base and the solvent are chosen such as to minimise transesterification with the malonate reagent and the intermediate (XXXXIII).

The method can be extended to substituted malonates $(CH_3O_2C)_2CHR$, where R is an alkyl group. This gives access to compounds analogous to (XXXIX) in which the group R is a substituent on the carbon atom adjacent to the $R^4O_2C$ group. These compounds can also be prepared by alkylating the intermediate (XXXXIII) with R—Br or R—I in the presence of an alkaline metal alkoxide base.

Step (zz)

The intermediate (XXXXIII) is then decarboxylated to give the product (XXXIX). This can be achieved by selective hydrolysis using one equivalent of an alkaline metal hydroxide, such as sodium hydroxide, followed by acidification, or by any other method known in the art.

The following compounds form further aspects of the present invention:

A compound of formula (VII)

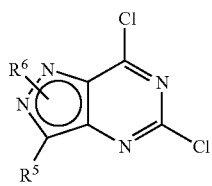

(VII)

wherein $R^5$ and $R^6$ are as defined above.

Preferred is a compound of formula (VII$^A$)

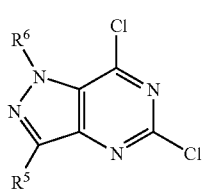

(VII$^A$)

wherein $R^5$ and $R^6$ are as defined above.

A compound of formula (VIII)

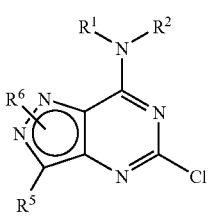

(VIII)

wherein $R^1$, $R^2$, $R^5$ and $R^6$ are as defined above.

Preferred is a compound of formula (VIII$^A$)

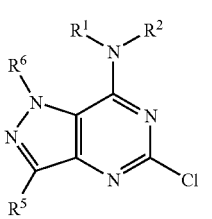

(VIII$^A$)

wherein $R^1$, $R^2$, $R^5$ and $R^6$ are as defined above.

The invention is further illustrated by the following, non-limiting examples. Melting points were determined on a Gallenkamp melting point apparatus using glass capillary tubes and are uncorrected. Unless otherwise indicated all reactions were carried out under a nitrogen atmosphere, using commercially available anhydrous solvents. Reactions performed under microwave irradiation were carried out using an Emrys Creator machine (Personal Chemistry Ltd.) with a power output of 15 to 300 W at 2.45 GHz. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40-63 μm silica gel (Merck silica gel 60). Ion exchange chromatography was performed using with the specified ion exchange resin which had been pre-washed with deionised water. Proton NMR spectra were measured on a Varian Inova 300, Varian Inova 400, or Varian Mercury 400 spectrometer in the solvents specified. In the NMR spectra, only non-exchangeable protons which appeared distinct from the solvent peaks are reported. Low resolution mass spectra were recorded on either a Fisons Trio 1000, using thermospray positive ionisation, or a Finnigan Navigator, using electrospray positive or negative ionisation. High resolution mass spectra were recorded on a Bruker Apex II FT-MS using electrospray positive ionisation. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in a suitable solvent.

Abbreviations and Definitions

Arbocel™ Filtration agent, from J. Rettenmaier & Sohne, Germany

Amberlyst® 15 Ion exchange resin, available from Aldrich Chemical Company

APCI Atmospheric Pressure Chemical Ionisation atm Pressure in atmospheres (1 atm=760 Torr=101.3 kPa)

Biotage™ Chromatography performed using Flash 75 silica gel cartridge, from Biotage, UK BOC tert-Butyloxycarbonyl group br Broad c Concentration used for optical rotation measurements in g per 100 ml (1 Mg/ml is c 0.10)

cat Catalytic d Doublet dd Doublet of doublets

Degussa® 101 10 wt % palladium on activated carbon, Degussa type E101 available from Aldrich Chemical Company Develosil Supplied by Phenomenex—manufactured by Nomura Chemical Combi-RP $C_{30}$ Co. Composed of spherical silica particles (size 3 μm or 5 μm)

hplc column which have a chemically bonded surface of C30 chains. These particles are packed into stainless steel columns of dimensions 2 cm internal diameter and 25 cm long.

Dowex® Ion exchange resin, from Aldrich Chemical Company ee Enantiomeric excess

HRMS High Resolution Mass Spectrocopy (electrospray ionisation positive scan)

Hyflo™ Hyflo supercel®, from Aldrich Chemical Company liq Liquid

LRMS Low Resolution Mass Spectroscopy (electrospray or thermospray ionisation positive scan)

LRMS (ES⁻) Low Resolution Mass Spectroscopy (electrospray ionisation negative scan)

m Multiplet m/z Mass spectrum peak

MCI™ gel High porous polymer, CHP20P 75-150 μm, from Mitsubishi Chemical Corporation Phenomenex Supplied by Phenomenex. Composed of spherical silica particles Luna C18 hplc (size 5 μm or 10 μm) which have a chemically bonded surface of column C18 chains. These particles are packed into a stainless steel column of dimensions 2.1 cm internal diameter and 25 cm long.

psi Pounds per square inch (1 psi=6.9 kPa)

q Quartet $R_f$ Retention factor on TLC s Singlet

Sep-Pak® Reverse phase $C_{18}$ silica gel cartridge, Waters Corporation t Triplet TLC Thin Layer Chromatography δ Chemical shift Unless otherwise provided herein:
  PyBOP® means Benzotriazol-1-yloxytris(pyrrolidino)phosphonium hexafluorophosphate;
  PyBrOP® means bromo-tris-pyrrolidino-phosphonium hexafluorophosphate;
  CDI means N,N'-carbonyldiimidazole;
  WSCDI means 1-(3-dimethylaminopropyl)-3-ethylcarbodiimide hydrochloride;
  Mukaiyama's reagent means 2-chloro-1-methylpyridinium iodide;
  DCC means N,N'-dicyclohexylcarbodiimide;
  HOAT means 1-hydroxy-7-azabenzotriazole;
  HOBT means 1-hydroxybenzotriazole hydrate;
  Hünig's base means N-ethyldiisopropylamine;
  $Et_3N$ means triethylamine;
  NMM means N-methylmorpholine;
  NMP means 1-methyl-2-pyrrolidinone;
  DMAP means 4-dimethylaminopyridine;
  NMO means 4-methylmorpholine N-oxide;
  KHMDS means potassium bis(trimethylsilyl)amide;
  NaHMDS means sodium bis(trimethylsilyl)amide;
  DIAD means diisopropyl azodicarboxylate;
  DEAD means diethyl azodicarboxylate,
  DIBAL means diisobutylaluminium hydride;
  Dess-Martin periodinane means 1,1,1-triacetoxy-1,1-dihydro-1,2-benziodoxol-3(1H)-one;
  TBDMS-Cl means tert-butyldimethylchlorosilane;
  TMS-Cl means chlorotrimethylsilane;
  BOC means tert-butoxycarbonyl;
  CBz means benzyloxycarbonyl;
  MeOH means methanol, EtOH means ethanol, and EtOAc means ethyl acetate;
  THF means tetrahydrofuran, DMSO means dimethylsulfoxide, and DCM means dichloromethane; DMF means N,N-dimethylformamide;

AcOH means acetic acid, TFA means trifluoroacetic acid.

The following Examples illustrate the preparation of the compounds of the formula (I):—

EXAMPLES 1-28

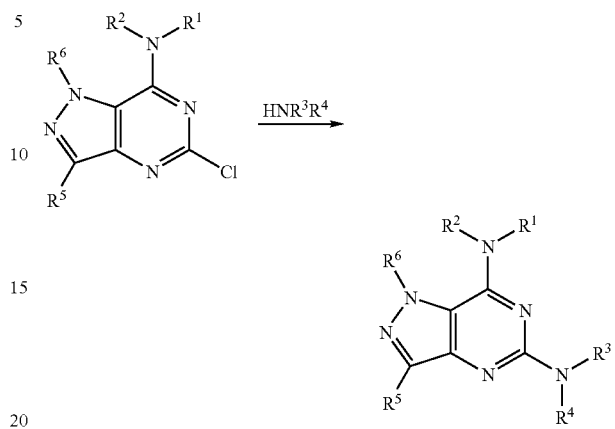

A solution of the required monochloride (see preparations 68, 70-82, 85, 86 and 90) (1 eq), the required $HNR^3R^4$ amine (5 eq) and N-ethyldiisopropylamine (5 eq) in dimethylsulfoxide (3-4 mL.mmol$^{-1}$) was heated in a sealed vessel at 120° C. for 18 hours. The reaction mixture was diluted with water and the product extracted with ethyl acetate (×3). The organics were combined, washed with water dried over magnesium sulphate and concentrated in vacuo. The crude product was purified using column chromatography on silica gel eluting with dichloromethane:ethyl acetate, dichloromethane:methanol or pentane:ethyl acetate as solvents.

The following compounds were made by the method described above:

| Ex | |
|---|---|
| 1 | |
| 2 | |

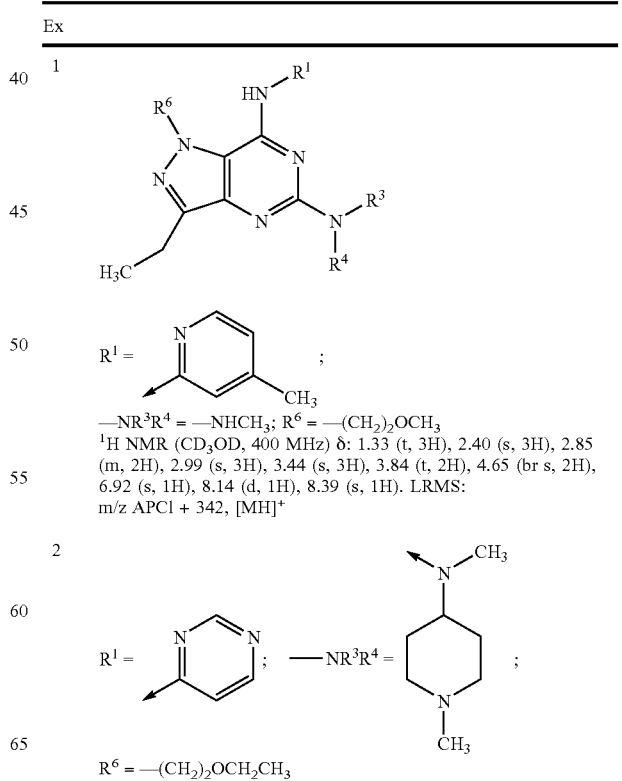

Ex 1:
$R^1$ = pyridinyl with $CH_3$;
—$NR^3R^4$ = —$NHCH_3$; $R^6$ = —$(CH_2)_2OCH_3$
$^1$H NMR (CD$_3$OD, 400 MHz) δ: 1.33 (t, 3H), 2.40 (s, 3H), 2.85 (m, 2H), 2.99 (s, 3H), 3.44 (s, 3H), 3.84 (t, 2H), 4.65 (br s, 2H), 6.92 (s, 1H), 8.14 (d, 1H), 8.39 (s, 1H). LRMS: m/z APCI + 342, [MH]$^+$ Ex 2:
$R^1$ = pyrimidinyl; —$NR^3R^4$ = piperidinyl-$CH_3$/$CH_3$
$R^6$ = —$(CH_2)_2OCH_2CH_3$

| Ex | |
|---|---|
| | $^1$H NMR (CDCl$_3$, 400 MHz) δ: 1.25 (t, 3H), 1.40 (t, 3H), 1.78 (m, 2H), 2.02 (m, 2H), 2.22 (m, 2H), 2.40 (s, 3H), 2.92 (q, 2H), 3.07 (m, 2H), 3.11 (s, 3H), 3.66 (q, 2H), 3.90 (m, 2H), 4.62 (m, 2H), 4.65 (m, 1H), 8.28 (dd, 1H), 8.55 (d, 1H), 8.86 (s, 1H), 10.08 (s, 1H). LRMS: m/z ES+ 440, [MH]$^+$ |
| 3 | 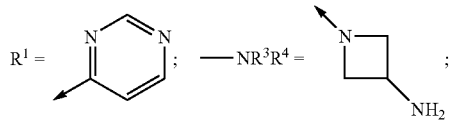<br>R$^6$ = —(CH$_2$)$_2$OCH$_2$CH$_3$<br>$^1$H NMR (CDCl$_3$, 400 MHz) δ: 1.22 (t, 3H), 1.38 (t, 3H), 2.92 (q, 2H), 3.65 (m, 2H), 3.81 (m, 2H), 3.92 (m, 3H), 4.42 (m, 2H), 4.63 (t, 2H), 8.43 (m, 1H), 8.53 (m, 1H), 8.85 (s, 1H)<br>LRMS APCl m/z 384 [MH]$^+$ |
| 4 | 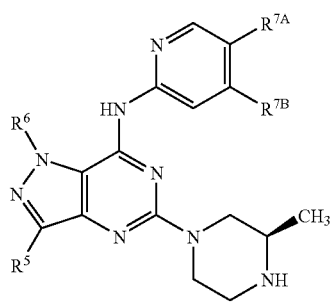<br>R$^5$ = —CH$_3$; R$^6$ = —(CH$_2$)$_2$O(CH$_2$)$_2$CH$_3$; R$^{7A}$ = H; R$^{7B}$ = —CH$_3$<br>$^1$H NMR (CDCl$_3$, 400 MHz) δ: 0.75 (t, 3H), 1.49 (d, 3H), 1.61 (m, 2H), 2.37 (s, 3H), 2.47 (s, 3H), 3.07–3.41 (m, 5H), 3.52 (t, 2H), 3.89 (t, 2H), 4.64 (t, 2H), 4.74 (d, 2H), 6.81 (d, 1H), 8.10 (s, 1H), 8.20 (d, 1H), 9.68 (s, 1H).<br>LRMS: m/z APCl+ 425, [MH]$^+$ |
| 5 | R$^5$ = —CH(CH$_3$)$_2$; R$^6$ = —(CH$_2$)$_2$OCH$_3$; R$^{7A}$ = H; R$^{7B}$ = —CH$_3$<br>$^1$H NMR (DMSO-d$_6$, 400 MHz) δ: 1.02 (d, 3H), 1.33 (d, 6H), 2.32 (s, 3H), 2.43 (m, 1H), 2.67 (m, 2H), 2.76 (m, 1H), 2.91 (m, 1H), 3.19 (m, 1H), 3.35 (s, 3H) 3.74 (t, 2H), 4.35 (m, 2H), 4.57 (br s, 2H) 6.91 (d, 1H), 8.03 (br s, 1H), 8.17 (d, 1H), 9.79 (br 1H).<br>LRMS: m/z APCl+ 425, [MH]$^+$ |
| 6 | R$^5$ = —CH$_3$; R$^6$ = H; R$^{7A}$ = H; R$^{7B}$ = —CH$_3$<br>$^1$H NMR (DMSO-d$_6$, 400 MHz) δ: 1.05 (d, 3H), 2.34 (d, 6H), 2.56 (m, 1H) 2.70 (m, 2H), 2.78–2.95 (m, 2H), 4.45 (d, 2H), 6.93 (d, 1H), 8.22 (d, 1H), 8.27 (s, 1H), 9.94 (br s, 1H), 12.23 (br s, 1H). LRMS: m/z APCl+ 339, [MH]$^+$ |
| 7 | R$^5$ = —CH$_3$; R$^6$ = —(CH$_2$)$_2$O(CH$_2$)$_2$CH$_3$; R$^{7A}$ = —CH$_3$; R$^{7B}$ = H<br>$^1$H NMR (CDCl$_3$, 400 MHz) δ: 0.75 (t, 3H), 1.21 (d, 3H), 1.62 (m, 2H), 2.30 (s, 3H), 2.47 (s, 3H), 2.65 (m, 1H), 2.97 (m, 3H), 3.15 (m, 1H), 3.51 (t, 2H), 3.88 (t, 2H), 4.63 (m, 4H), 7.50 (d, 1H), 8.14 (s, 1H), 8.18 (d, 1H), 9.57 (s, 1H). LRMS: m/z APCl+ 425, [MH]$^+$ |
| 8 | R$^5$ = —CH(CH$_3$)$_2$; R$^6$ = —(CH$_2$)$_2$OCH$_3$; R$^{7A}$ = —CH$_3$; R$^{7B}$ = H<br>$^1$H NMR (DMSO-d$_6$, 400 MHz) δ: 1.00 (d, 3H), 1.32 (d, 6H), 2.25 (s, 3H), 2.40 (m, 1H), 2.65 (m, 2H), 2.76 (m, 1H), 2.89 (m, 1H), 3.19 (m, 1H), 3.35 (s, 3H), 3.75 (t, 2H), 4.33 (br d, 2H), 4.57 (br s, 2H), 7.62 (br d, 1H), 8.00 (br d, 1H), 8.15 (s, 1H) 9.67 (br s, 1H). LRMS: m/z APCl+ 425, [MH]$^+$ |
| 9 | R$^5$ = —CH$_3$; R$^6$ = —CH(CH$_3$)$_2$; R$^{7A}$ = —CH$_3$; R$^{7B}$ = H<br>$^1$H NMR (CD$_3$OD, 400 MHz) δ: 1.25 (d, 3H), 1.52 (d, 6H), 2.34 (s, 3H), 2.42 (s, 3H), 2.73 (m, 1H), 2.95 (m, 1H), 3.04 (m, 2H), 3.20 (m, 2H), 4.59 (br s, 2H), 5.03 (br s, 1H), 7.69 (d, 1H), 7.95 (br s, 1H), 8.16 (s, 1H).<br>LRMS: m/z APCl+ 381, [MH]$^+$ |
| 10 | 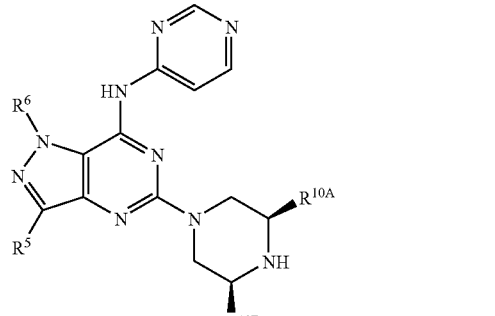<br>R$^5$ = —CH$_3$; R$^6$ = —(CH$_2$)$_3$OCH$_3$; R$^{10A}$ ; = —CH$_3$; R$^{10B}$ = H<br>$^1$H NMR (DMSO-d$_6$, 400 MHz) δ: 1.01 (d, 3H), 1.94 (t, 2H), 2.33 (s, 3H), 2.46 (br d, 1H), 2.66 (br m, 2H), 2.80 (br m, 1H), 2.92 (br d, 1H), 3.17 (m, 5H), 4.37 (br d, 2H), 4.43 (t, 2H), 7.85 (br d, 1H), 8.59 (d, 1H), 8.81 (s, 1H). LRMS: m/z APCl+ 398, [MH]$^+$ |
| 11 | R$^5$ = —CH$_3$; R$^6$ = —(CH$_2$)$_2$OCH$_2$CH$_3$; R$^{10A}$ = —CH$_3$; R$^{10B}$ = H<br>$^1$H NMR (CDCl$_3$, 400 MHz) δ: 1.25 (t, 3H), 1.34 (d, 3H), 2.48 (s, 3H), 2.87 (m, 1H), 3.01 (m, 2H), 3.26 (m, 2H), 3.66 (q, 2H), 3.91 (t, 2H), 4.63 (m, 4H), 8.13 (d, 1H), 8.56 (d, 1H), 8.87 (s, 1H), 10.13 (br s, 1H).<br>LRMS: m/z ES+: 398, [MH]$^+$ |
| 12 | R$^5$ = —CH$_3$; R$^6$ = —(CH$_2$)$_2$OCH$_2$CH$_3$; R$^{10A}$ = H; R$^{10B}$ = —CH$_3$<br>$^1$H NMR (CDCl$_3$, 400 MHz) δ: 1.25 (t, 3H), 1.40 (d, 3H), 2.48 (s, 3H), 3.01 (m, 2H), 3.17 (m, 1H), 3.26 (m, 2H), 3.66 (q, 2H), 3.91 (t, 2H), 4.63 (m, 4H), 8.13 (d, 1H), 8.56 (d, 1H), 8.87 (s, 1H), 10.15 (br s, 1H). LRMS: m/z ES+: 398, [MH]$^+$ |
| 13 | R$^5$= —CH$_3$;<br>R$^6$ = —(CH$_2$)$_2$OCH$_2$CH$_3$; R$^{10A}$ = —CH(CH$_3$)$_2$; R$^{10B}$ = H<br>$^1$H NMR (CDCl$_3$, 400 MHz) δ: 1.12 (m, 1H), 1.18 (m, 6H), 1.26 (t, 3H), 2.10 (br m, 1H), 2.47 (s, 3H), 3.04 (m, 2H), 3.44 (m, 2H), 3.67 (m, 2H), 3.91 (t, 2H), 4.64 (t, 2H), 4.70–4.86 (br m, 2H), 8.14 (d, 1H), 8.54 (d, 1H), 8.88 (s, 1H), 10.17 (br s, 1H). LRMS: m/z ES+: 426, [MH]$^+$ |
| 14 | R$^5$ = —CH$_3$;<br>R$^6$ = —(CH$_2$)$_2$OCH$_2$CH$_3$; R$^{10A}$ = H; R$^{10B}$ = —CH(CH$_3$)$_2$<br>$^1$H NMR (CDCl$_3$, 400 MHz) δ: 1.08 (m, 1H), 1.18 (m, 6H), 1.26 (t, 3H), 2.30 (m, 1H), 2.47 (s, 3H), 3.10 (m, 2H), 3.25 (m, 2H), 3.67 (m, 2H), 3.91 (t, 2H), 4.64 (t, 2H), 4.76 (m, 1H), 4.92 (m, 1H), 8.14 (d, 1H), 8.54 (d, 1H), 8.88 (s, 1H), 10.20 (s, 1H).<br>LRMS: m/z ES+: 426, [MH]$^+$ |
| 15 | R$^5$ = —CH$_2$CH; R$^6$ = —(CH$_2$)$_2$OCH$_2$CH$_3$; R$^{10A}$ = —CH$_3$, R$^{10B}$ = H<br>$^1$H NMR (CDCl$_3$, 400 MHz) δ: 1.26 (t, 3H), 1.30 (d, 3H), 1.39 (t, 3H), 2.78–3.02 (br m, 7H), 3.66 (q, 2H), 3.91 (t, 2H), 4.62 (m, 4H), 8.15 (d, 1H), 8.55 (d, 1H), 8.86 (s, 1H), 10.13 (br s, 1H).<br>LRMS: m/z ES+: 412, [MH]$^+$ |
| 16 | R$^5$ = —CH$_2$CH$_3$; R$^6$ = —(CH$_2$)$_2$OCH$_2$CH$_3$; R$^{10A}$ = H; R$^{10B}$ = —CH$_3$<br>$^1$H NMR (CDCl$_3$, 400 MHz) δ: 1.26 (t, 3H), 1.30 (d, 3H), 1.39 (t, 3H), 2.78–3.02 (br m, 7H), 3.66 (q, 2H), 3.91 (t, 2H), 4.62 (m, 4H), 8.15 (d, 1H), 8.55 (d, 1H), 8.86 (s, 1H), 10.13 (brs, 1H).<br>LRMS: m/z ES+: 412, [MH]$^+$ |
| 17 | R$^5$ = —CH$_2$CH$_3$;<br>R$^6$ = —(CH$_2$)$_2$OCH$_2$CH$_3$; R$^{10A}$ = —CH(CH$_3$)$_2$; R$^{10B}$ = H<br>$^1$H NMR (CDCl$_3$, 400 MHz) δ: 1.21 (d, 6H), 1.27 (t, 3H), 1.39 (t, 3H), 2.30 (m, 1H), 2.90 (m, 2H), 3.00 (m, 1H), 3.10 (m, 1H), 3.33 (m, 1H), 3.69 (m, 4H), 3.93 (t, 2H), 4.66 (m, 2H), 4.84 (m, 1H), 8.14 (d, 1H), 8.62 (d, 1H), 8.91 (s, 1H), 10.46 (br s, 1H).<br>LRMS: m/z ES+: 440, [MH]$^+$ |
| 18 | R$^5$ = —CH$_2$CH$_3$;<br>R$^6$ = —(CH$_2$)$_2$OCH$_2$CH$_3$; R$^{10A}$ = H; R$^{10B}$ = —CH(CH$_3$)$_2$<br>$^1$H NMR (CDCl$_3$, 400 MHz) δ: 1.08 (d, 6H), 1.21 (t, |

| Ex | |
|---|---|
| | 3H), 1.39 (t, 3H), 2.90 (m, 4H), 3.11 (m, 2H), 3.21 (m, 2H), 3.63 (m, 2H), 3.90 (t, 2H), 4.61 (m, 3H), 4.78 (br d, 1H), 8.18 (d, 1H), 8.51 (d, 1H), 8.83 (s, 1H), 10.12 (br s, 1H). LRMS: m/z ES+: 440, [MH]$^+$ |
| 19 | $R^5$ = —CH$_2$CH$_3$; $R^6$ = —(CH$_2$)$_2$OCH$_2$CH$_3$; $R^{10A}$ = —CH$_2$CH$_3$; $R^{10B}$ = H <br> $^1$H NMR (CDCl$_3$, 400 MHz) δ: 1.16 (t, 3H), 1.25 (m, 5H), 1.39 (t, 3H), 2.91 (q, 2H), 3.10 (m, 2H), 3.30 (m, 1H), 3.50 (m, 2H), 3.68 (m, 2H), 3.92 (m, H), 4.65 (t, 2H), 4.77 (m, 2H), 8.06 (d, 1H), 8.55 (d, 1H), 8.88 (s, 1H), 10.23 (br s, 1H). LRMS: m/z ES+: 426, [MH]$^+$ |
| 20$^A$ | $R^5$ = —CH$_3$; $R^6$ = —(CH$_2$)$_2$OCH(CH$_3$)$_2$; $R^{10A}$ = —CH$_3$; $R^{10B}$ = H <br> $^1$H NMR (DMSO-d$_6$, 400 MHz) δ: 1.04 (d, 6H), 1.33 (d, 3H), 2.38 (s, 3H), 3.08–3.11 (m, 2H), 3.30–3.40 (m, 3H), 3.59 (m, 1H), 3.75 (t, 2H), 4.55 (d, 2H), 4.61 (m, 2H), 8.08 (d, 1H), 8.70 (d, 1H), 9.01 (s, 1H), 9.30 (br 1H), 9.54 (br, 1H). LRMS: m/z APCl+ 412, [MH]$^+$ |
| 21$^A$ | $R^5$ = H; $R^6$ = —(CH$_2$)$_2$OCH$_2$CH$_3$; $R^{10A}$ = —CH$_3$; $R^{10B}$ = H <br> $^1$H NMR (DMSO-d$_6$, 400 MHz) δ: 1.05 (t, 3H), 1.32 (d, 3H), 3.03 (m, 1H), 3.14 (m, 1H), 3.35 (m, 2H), 3.47 (q, 2H), 3.79 (t, 2H), 4.50 (m, 2H), 4.73 (t, 2H), 7.98 (s, 1H), 8.05 (d, 1H), 8.72 (d, 1H), 9.01 (s, 1H), 9.40 (br s, 1H), 9.52 (br s, 1H). LRMS: m/z APCl+ 384, [MH]$^+$ |
| 22 | $R^5$ = —CH$_2$CH$_3$; $R^6$ = —(CH$_2$)$_2$OCH$_2$CH$_3$; $R^{10A}$ = —CH$_3$; $R^{10B}$ = —CH$_3$ <br> $^1$H NMR (CD$_3$OD, 400 MHz) δ: 1.18 (d, 6H), 1.22 (1, 3H), 1.36 (t, 3H), 2.53 (t, 2H), 2.89 (m, 4H), 3.65 (q, 2H), 3.88 (m, 2H), 4.63 (m, 4H), 8.20 (d, 1H), 8.57 (d, 1H), 8.79 (s, 1H). LRMS: m/z ES+ 426, [MH]$^+$ |
| 23 | $R^5$ = —CH$_3$; $R^6$ = —(CH$_2$)$_2$O(CH$_2$)$_2$CH$_3$; $R^{10A}$ = —CH$_3$; $R^{10B}$ = H <br> $^1$H NMR (CD$_3$OD, 400 MHz) δ: 0.76 (t, 3H), 1.19 (d, 3H), 1.63 (m, 2H), 2.43 (s, 3H), 2.68 (m, 1H), 2.89 (m, 2H), 3.06 (m, 2H), 3.54 (t, 2H), 3.87 (t, 2H), 4.59 (m, 2H), 4.65 (t, 2H), 8.20 (d, 1H), 8.58 (d, 1H), 8.79 (s, 1H). LRMS: m/z APCl+ 412, [MHz]$^+$ |
| 24 | $R^5$ = —CH$_3$; $R^6$ = —CH(CH$_3$)$_2$; $R^{10A}$ = —CH$_3$; $R^{10B}$ = H <br> $^1$H NMR (CD$_3$OD, 400 MHz) δ: 1.18 (d, 3H), 1.47 (dd, 6H), 2.43 (s, 3H), 2.64 (m, 1H), 2.87 (m, 2H), 3.06 (m, 2H), 4.50 (br s, 2H), 5.00 (br, 1H), 7.88 (br s, 1H), 8.53 (d, 1H), 8.79 (s, 1H). LRMS: m/z APCl+ 368, [MH]$^+$ |
| 25$^A$ | $R^5$ = —CH$_3$; $R^6$ = —(CH$_2$)$_3$OCH$_2$CH$_3$; $R^{10A}$ = —CH$_3$; $R^{10B}$ = H <br> $^1$H NMR (DMSO-d$_6$, 400 MHz) δ: 0.96 (t, 3H), 1.32 (d, 3H), 1.88 (m, 2H), 2.41 (s, 3H), 2.94–3.20 (br m, 3H), 3.23–3.42 (br m, 6H), 4.44–4.59 (br m, 4H), 7.81 (d, 1H), 8.62 (d, 1H), 8.95 (s, 1H). LRMS APCl m/z 412 [MH]$^+$ |
| 26 | 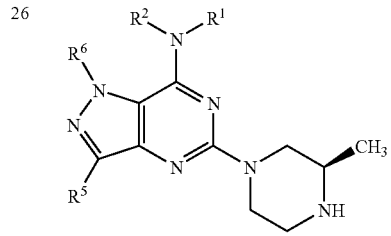 <br> —NR$^1$R$^2$ = 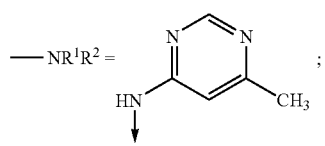; <br> $R^5$ = —CH$_3$; <br> $R^6$ = —(CH$_2$)$_2$OCH$_2$CH$_3$ <br> $^1$H NMR (CD$_3$OD, 400 MHz) δ: 1.20 (m, 6H), 2.42 (s, 3H), 2.50 (s, 3H), 2.66 (m, 1H), 2.88 (m, 2H), 3.00 (m, 1H), 3.10 (m, 1H), 3.64 (q, 2H), 3.87 (t, 2H), 4.58 (d, 2H), 4.64 (t, 2H), 8.18 (s, 1H), 8.67 (s, 1H). LRMS: m/z APCl+ 412, [MH]$^+$. |
| 27 | —NR$^1$R$^2$ = (4-pyrimidinylamino group); <br> $R^5$ = —(CH$_2$)$_2$CH$_3$; <br> $R^6$ = —CH$_3$ <br> $^1$H NMR (DMSO-d$_6$, 400 MHz) δ: 0.92 (t, 3H), 0.99 (d, 3H), 1.72 (q, 2H), 2.38 (bt, 1H), 2.63 (br d, 2H), 2.71 (t, 2H), 2.88 (br d, 2H), 4.13 (s, 3H), 4.24 (br d, 2H), 7.66 (m, 1H), 8.01 (br d, 1H), 8.82 (br s, 1H). LRMS: m/z APCl+ 368, [MH]$^+$ |
| 28 | —NR$^1$R$^2$ = (N-methyl-4-pyrimidinylamino group); <br> $R^5$ = —CH$_2$CH$_3$; $R^6$ = —(CH$_2$)$_2$OCH$_2$CH$_3$ <br> $^1$H NMR (CDCl$_3$, 400 MHz) δ: 0.97 (t, 3H), 1.15 (d, 3H), 1.41 (t, 3H), 2.56 (m, 1H), 2.91 (m, 4H), 3.10 (m, 1H), 3.22 (m, 2H), 3.48 (m, 3H), 3.61 (s, 3H), 3.97 (t, 2H), 4.59 (t, 2H), 6.39 (d, 1H), 8.24 (d, 1H), 8.77 (s, 1H). LRMS: m/z APCl+ 426, [MH]$^+$ |

$^A$the products were dissolved in dichloromethane, and treated with ethereal HCl, then evaporated in vacuo to provide the HCl salts

NOTES FOR EXAMPLES 1-28

EXAMPLE 3 tert-Butyl azetidin-3-ylcarbamate used as HNR$^3$R$^4$ amine. The product was treated with 9 eq of trifluoroacetic acid in sufficient dichloromethane to achieve solution, and stirred for 18 hours. The reaction mixture was concentrated in vacuo to yield the trifluoroacetate salt of the compound shown.

EXAMPLES 13 and 17

(2R)-2-Isopropylpiperazine (WO 01/32646, pg. 19, description 54) used as HNR$^3$R$^4$ amine.

EXAMPLES 14 and 18

(2S)-2-Isopropylpiperazine (U.S. Pat. No. 6,432,957, pg. 29, preparation 65) used as HNR$^3$R$^4$ amine.

EXAMPLE 19

(2R)-2-Ethylpiperazine (Preparation 124) used as HNR$^3$R$^4$ amine

EXAMPLES 29-90

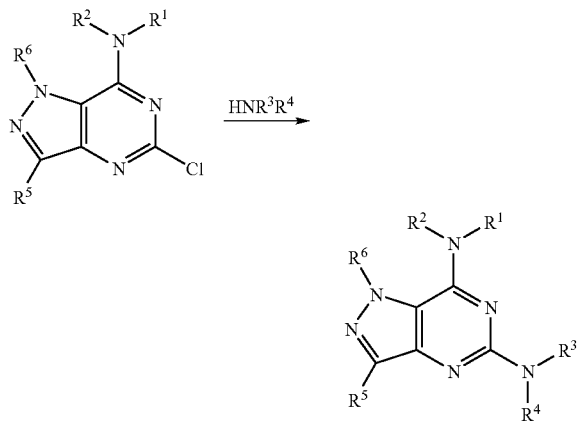

A solution of the required monochloride (see preparations 60, 66, 67, 69, 83, 84, 86-89) (1 eq.), and N-ethyldiisopropylamine (5 eq) in dimethylsulfoxide (3.5-4 mL.mmol$^{-1}$) was added to a solution of the appropriate amine (HNR$^3$R$^4$) or BOC-protected amine (2-4 eq), washing in with dimethylsulfoxide as required. The reaction vessel was sealed and heated to 120° C. for 18 hours and the cooled mixture concentrated in vacuo. The crude product was purified by column chromatography on silica gel using an elution gradient of dichloromethane:acetonitrile:methanol, or by HPLC using a Develosil Combi-RP C$_{30}$ column, and methanol:water:diethylamine as eluant, to afford the title compound.

When deprotection of the amine was required the crude products were either treated with a solution of trifluoroacetic acid:dichloromethane (20:80 to 50:50 by volume) and the reaction stirred for 6 hours or dissolved in dichloromethane and treated with a solution of HCl in ether, at room temperature for 18 hours. The solutions were then evaporated in vacuo and purified either by column chromatography on silica gel using dichloromethane:methanol:0.88 ammonia as eluant, or by HPLC using a Phenomenex Luna C18 2×15 cm 5 μm column using an elution gradient of 0.1% aqueous trifluoroacetic acid: acetonitrile to give the trifluoroacetate salt of the title compound (B).

| Ex | |
|---|---|
| 29$^A$ | 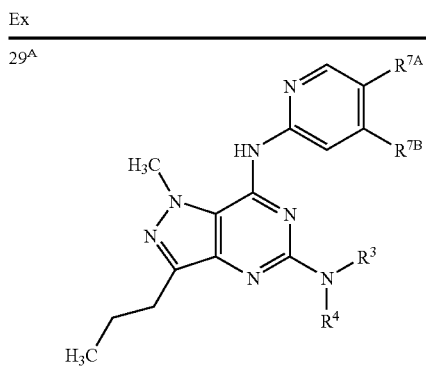 |

| Ex | |
|---|---|
| 30$^A$ | —NR$^3$R$^4$ = [structure: 2,5-dimethylpiperazine]; R$^{7A}$ = —CH$_3$; R$^{7B}$ = H<br>$^1$H NMR (D$_2$O, 400 MHz) δ: 0.77 (t, 3H), 1.21 (d, 6H), 1.57 (m, 2H), 2.25 (s, 3H), 2.70 (t, 2H), 3.06 (m, 1H), 3.40 (m, 1H), 3.56 (m, 1H), 3.72 (m, 1H), 4.05 (m, 2H), 4.10 (s, 3H), 7.59 (d, 1H), 7.87 (d, 1H), 8.09 (s, 1H).<br>LRMS: m/z ES+ 395, [MH]$^+$ |
| 30$^A$ | —NR$^3$R$^4$ = [structure: 2-methylpiperazine]; R$^{7A}$ = —CH$_3$; R$^{7B}$ = H<br>$^1$H NMR (D$_2$O, 400 MHz) δ: 0.77 (t, 3H), 1.21 (d, 3H), 1.57 (q, 2H), 2.24 (s, 3H), 2.68 (1, 2H), 3.11 (m, 2H), 3.35 (m, 3H), 4.08 (s, 3H), 4.29 (m, 2H), 7.55 (d, 1H), 7.83 (d, 1H), 8.06 (s, 1H).<br>LRMS: m/z ES+ 381, [MH]$^+$ |
| 31$^A$ | —NR$^3$R$^4$ = [structure: 3-methylpiperazine]; R$^{7A}$ = —CH$_3$; R$^{7B}$ = H<br>$^1$H NMR(D$_2$O, 400 MHz) δ: 0.77 (t, 3H), 1.22 (d, 3H), 1.58 (q, 2H), 2.25 (s, 3H), 2.68 (t, 2H), 3.11 (m, 2H), 3.35 (m, 3H), 4.08 (s, 3H), 4.29 (m, 2H), 7.60 (d, 1H), 7.90 (d, 1H), 8.05 (s, 1H).<br>LRMS: m/z ES+ 381, [MH]$^+$ |
| 32$^A$ | —NR$^3$R$^4$ = [structure: 3,5-dimethylpiperazine]; R$^{7A}$ = —CH$_3$; R$^{7B}$ = H<br>$^1$H NMR (D$_2$O, 400 MHz) δ: 0.78 (t, 3H), 1.21 (d, 6H), 1.56 (q, 2H), 2.27 (s, 3H), 2.68 (t, 2H), 2.94 (t, 2H), 3.28 (m, 2H), 4.06 (s, 3H), 4.39 (m, 2H), 7.60 (m, 1H), 7.92 (m, 1H), 8.05 (m, 1H). LRMS APCl+ m/z 395 [MH]$^+$ |
| 33$^A$ | —NR$^3$R$^4$ = [structure: 2,6-dimethylpiperazine]; R$^{7A}$ = —CH$_3$; R$^{7B}$ = H<br>$^1$H NMR (DMSO-d$_6$, 400 MHz) δ: 0.89(t, 3H), 1.28 (d, 6H), 1.71 (q, 2H), 2.27 (s, 3H) 2.76 (t, 2H), 2.80 (m, 2H), 3.33 (m, 2H), 4.14 (m, 3H), 4.60 (m, 2H), 8.08 (m, 1H). MS ES+ 395 m/z [MH]$^+$ |
| 34$^A$ | —NR$^3$R$^4$ = [structure: piperazine]; R$^{7A}$ = —CH$_3$; R$^{7B}$ = H<br>$^1$H NMR (DMSO-d$_6$ 400 MHz) δ: 1.94 (t, 3H), 1.72 (m, 2H), 2.25 (s, 3H), 2.80 (m, 2H), 3.20 (m, 4H), 3.95 (m, 4H), 4.25 (s, 3H), 7.95 (m, 2H), 8.21 (s, 1H). MS ES+ m/z 367 [MH]$^+$ |

| Ex | | |
|---|---|---|
| 35 | —NR³R⁴ = 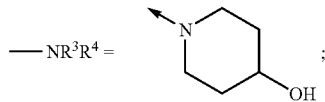 ; | |

R⁷ᴬ = —CH₃; R⁷ᴮ = H
¹H NMR (CD₃OD, 400 MHz) δ: 0.97 (t, 3H),
1.52 (m, 2H), 1.77 (q, 2H), 1.89 (m, 2H), 2.32 (s, 3H), 2.81 (m, 2H), 3.21 (m, 2H), 3.82 (m, 1H), 4.18 (s, 3H), 4.42 (m, 2H), 7.66 (m, 1H), 8.16 (m, 2H). MS ES+ m/z 382 [MH]⁺

| 36 | —NR³R⁴ = 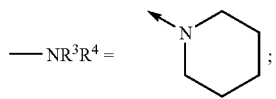 ; | |

R⁷ᴬ = —CH₃; R⁷ᴮ = H
¹H NMR (CD₃OD, 400 MHz) δ: 0.96 (t, 3H), 1.64 (m, 6H), 1.78 (m, 2H), 2.31 (s, 3H), 2.81 (m, 2H), 3.75 (m, 4H), 4.19 (s, 3H), 7.63 (m, 1H), 8.15 (m, 2H).
MS ES+ m/z 366 [MH]⁺

| 37 | —NR³R⁴ = 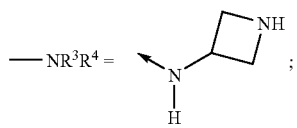 ; | |

R⁷ᴬ = —CH₃; R⁷ᴮ = H
¹H NMR (D₂O, 400 MHz) δ: 0.85 (t, 3H), 1.61 (q, 2H), 2.26 (s, 3H), 2.57 (m, 1H), 2.69 (t, 2H), 3.08 (m, 2H), 4.12 (s, 3H), 4.40 (m, 1H), 4.58 (m, 1H), 7.39 (d, 1H), 7.81 (d, 1H), 7.99 (s, 1H).
MS ES+ m/z 353 [MH]⁺

| 38 | —NR³R⁴ = 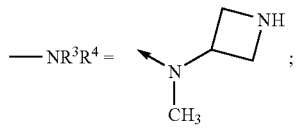 ; | |

R⁷ᴬ = —CH₃; R⁷ᴮ = H
¹H NMR (DMSO-d₆, 400 MHz) δ: 0.93 (t, 3H), 1.66 (q, 2H), 2.32 (s, 3H), 2.70 (m, 2H), 3.01 (s, 3H), 3.29 (m, 2H), 4.24 (s, 3H), 4.38 (m, 2H), 4.56 (m, 1H), 7.56 (m, 2H), 8.20 (m, 2H), 8.80 (m, 1H). MS ES+ m/z 367 [MH]⁺

| 39 | —NR³R⁴ = 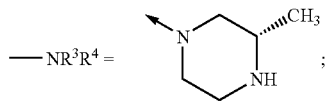 ; | |

R⁷ᴬ = H; R⁷ᴮ = —CH₃
¹H NMR (CDCl₃, 400 MHz) δ: 1.00 (t, 3H), 1.34 (d, 3H), 1.83 (q, 2H), 2.40 (s, 3H), 2.84 (m, 3H), 3.01 (m, 2H), 3.25 (m, 2H), 4.27 (s, 3H), 4.67 (m, 2H), 6.87 (d, 1H), 7.50 (s, 1H), 8.16 (d, 1H), 8.24 (s, 1H).
LRMS: m/z ES+: 381, [MH]⁺

| 40 | —NR³R⁴ = 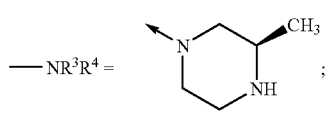 ; | |

R⁷ᴬ = H; R⁷ᴮ = —CH₃
¹H NMR (CDCl₃, 400 MHz) δ: 1.00 (t, 3H), 1.34 (d, 3H), 1.83 (q, 2H), 2.40 (s, 3H), 2.84 (m, 3H), 3.01 (m, 2H), 3.25 (m, 2H), 4.27 (s, 3H), 4.67 (m, H), 6.87 (d, 1H), 7.50 (s, 1H), 8.16 (d, 1H), 8.24 (brs, 1H). LRMS: m/z ES+ : 381, [MH]⁺

| 41 | —NR³R⁴ = 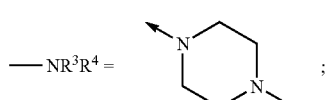 ; | |

R⁷ᴬ = H; R⁷ᴮ = —CH₃
¹H NMR (CDCl₃, 400 MHz) δ: 1.00 (t, 3H), 1.82 (q,

| Ex | | |
|---|---|---|
| | 2H), 2.38 (s, 3H), 2.42 (s, 3H), 2.62 (m, 4H), 2.83 (t, 2H), 3.95 (br m, 4H), 4.27 (br s, 3H), 6.85 (br s, 1H), 7.50 (br s, 1H), 8.15 (br s, 1H), 8.24 (brs, 1H). LRMS: m/z ES+: 381, [MH]⁺ | |
| 42ᴮ | —NR³R⁴ = 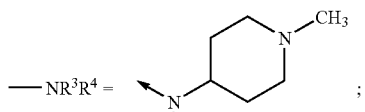 ; | |

R⁷ᴬ = H; R⁷ᴮ = —CH₃
¹H NMR (DMSO-d₆, 400 MHz) δ: 0.91 (t, 3H), 1.64 (m, 4H), 2.00–2.20 (m, 2H), 2.45 (s, 3H), 2.69 (t, 2H), 2.78 (s, 3H), 3.00 (m, 2H), 3.20–3.60 (m, 2H), 3.96 (m, 1H), 4.21 (s, 3H), 7.10 (d, 1H), 7.80 (s, 1H), 8.18 (d, 1H).
LRMS: m/z ES+ 395, [MH]⁺

| 43ᴮ | —NR³R⁴ = 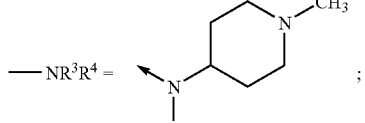 ; | |

R⁷ᴬ = H; R⁷ᴮ = —CH₃
¹H NMR (DMSO-d₆, 400 MHz) δ: 0.93 (t, 3H), 1.51 (m, 1H), 1.71 (q, 2H), 1.92 (m, 2H), 2.39 (s, 3H), 2.76 (m, 2H), 2.80 (m, 2H), 3.00 (s, 3H), 3.45 (m, 5H), 4.19 (s, 3H), 4.60 (m, 1H), 7.02 (m, 1H), 7.83(s, 1H), 8.18 (d, 1H).
LRMS: m/z ES+ 409, [MH]⁺

| 44ᴮ | —NR³R⁴ = 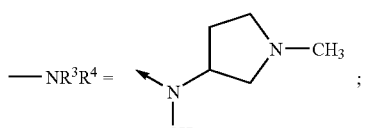 ; | |

R⁷ᴬ = H; R⁷ᴮ = —CH₃
¹H NMR (DMSO-d₆ 400 MHz) δ: 0.94 (t, 3H), 1.72 (q, 2H), 2.20 (m, 2H), 2.40 (s, 3H), 2.75 (t, 2H), 2.90 (m, 2H), 3.10 (s, 3H), 3.20–3.95 (complex, 5H), 4.15 (s, 3H), 5.33 (t, 1H), 6.98 (d, 1H), 7.84 (s, 1H), 8.19 (d, 1H).
LRMS: m/z ES+ 395, [MH]⁺

| 45ᴮ | —NR³R⁴ = 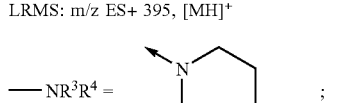 ; | |

R⁷ᴬ = H; R⁷ᴮ = —CH₃
¹H NMR (CDCl₃, 400 MHz) δ: 0.92 (t, 3H), 1.65 (m, 2H), 1.98 (m, 2H), 2.23 (m, 2H), 2.52 (s, 3H), 2.81 (m, 2H), 3.23 (m, 2H), 3.50 (m, 2H), 4.31 (s, 3H), 4.55 (m, 1H), 7.16 (br s, 1H), 7.69 (br s, 1H), 8.13 (br s, 1H).
LRMS: m/z ES+ 381, [MH]⁺

| 46ᴮ | —NR³R⁴ = 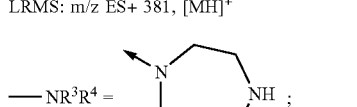 ; | |

R⁷ᴬ = H; R⁷ᴮ = —CH₃
¹H NMR (CDCl₃, 400 MHz) δ: 0.95 (t, 3H), 1.72 (q, 2H), 2.06 (br m, 2H), 2.51 (s, 3H), 2.82 (t, 2H), 3.31 (br m, 2H), 3.48 (br m, 2H), 3.92 (br m, 2H), 4.15 (br m, 2H), 4.27 (s, 3H), 7.07 (br s, 1H), 7.76 (s, 1H), 8.04 (s, 1H). LRMS: m/z ES+ 381, [MH]⁺

| 47ᴮ | —NR³R⁴ = 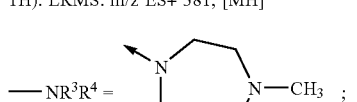 ; | |

R⁷ᴬ = H; R⁷ᴮ = —CH₃
¹H NMR (DMSO-d₆, 400 MHz) δ: 0.92, (t, 3H), 1.70 (q,

| Ex | |
|---|---|
| | 2H), 2.17 t, 2H), 2.39 (s, 3H), 2.75 (t, 2H), 2.82 (s, 3H), 3.24–3.75 (complex, 8H), 4.17 (s, 3H), 7.01 (br s, 1H), 7.86 (s, 1H), 8.18 (d, 1H). LRMS: m/z ES+ 395, [MH]$^+$ |
| 48$^B$ | —NR$^3$R$^4$ = 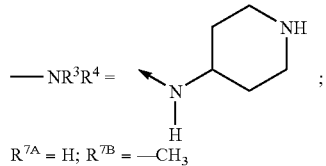 ; <br> R$^{7A}$ = H; R$^{7B}$ = —CH$_3$ <br> $^1$H NMR (CDCl$_3$, 400 MHz) δ: 0.95 (t, 3H), 1.65 (m, 2H), 2.05 (m, 2H), 2.30 (m, 2H), 2.45–2.5 (m, 3H), 2.65 (t, 2H), 2.80 (t, 2H), 3.25 (m, 2H), 3.50 (m, 2H), 4.20 (s, 3H), 4.30 (m, 1H), 7.05 (m, 1H), 7.15 (s, 1H), 8.20 (m, 1H). HRMS: 381, [MH]$^+$ |
| 49$^B$ | —NR$^3$R$^4$ = 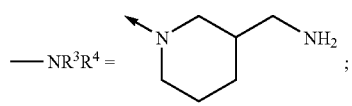 ; <br> R$^{7A}$ = H; R$^{7B}$ = —CH$_3$ <br> $^1$H NMR (DMSO-d$_6$ 400 MHz) δ: 0.93 (t, 3H), 1.30–1.95 (m, 7H), 2.40 (s, 3H), 2.74 (t, 2H), 2.97 (t, 2H), 3.14 (t, 2H), 4.17 (s, 3H), 4.25 (m, 2H), 7.04 (d, 1H), 7.83 (br s, 1H), 8.19 (d, 1H). HRMS: 395, [MH]$^+$ |
| 50$^B$ | R$^3$ = —(CH$_2$)$_2$NHCH$_3$; R$^4$ = H; <br> R$^{7A}$ = H; R$^{7B}$ = —CH$_3$ <br> $^1$H NMR (DMSO-d$_6$ 400 MHz) δ: 0.92 (t, 3H), 1.65 (q, 2H), 2.44 (s, 3H), 2.57 (s, 3H), 2.70 (t, 2H), 3.15 (m, 2H), 3.60 (m, 2H), 4.21 (s, 3H), 7.10 (d, 1H), 7.84 (s, 1H), 8.19 (d, 1H). HRMS: 355, MH$^+$ |
| 51$^B$ | R$^3$ = —(CH$_2$)$_3$NH$_2$; R$^4$ = H; <br> R$^{7A}$ = H; R$^{7B}$ = —CH$_3$ <br> $^1$H NMR (DMSO-d$_6$, 400 MHz) δ: 0.91 (t, 3H), 1.64 (q, 2H), 1.86 (t, 2H), 2.43 (s, 3H), 2.69 (t, 2H), 2.85 (br m, 2H), 3.43 (br m, 2H), 4.21 (s, 3H), 7.09 (d, 1H), 7.74 (s, 1H), 8.18 (s, 1H). HRMS: 355, MH$^+$ |
| 52$^B$ | —NR$^3$R$^4$ = 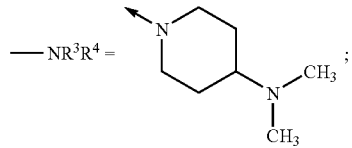 ; <br> R$^{7A}$ = H; R$^{7B}$ = —CH$_3$ <br> $^1$H NMR (DMSO-d$_6$, 400 MHz) δ: 0.93 (t, 3H), 1.59 (q, 2H), 1.72 (q, 2H), 2.05 (m, 2H) 2.36 (s, 3H), 2.75 (m, 8H), 2.92 (m, 2H), 3.42 (m, 2H), 4.14 (s, 3H), 4.68 (s, 1H), 6.96 (d, 1H), 7.83 (s, 1H), 8.18 (s, 1H). HRMS: 409, MH$^+$ |
| 53$^B$ | —NR$^3$R$^4$ = 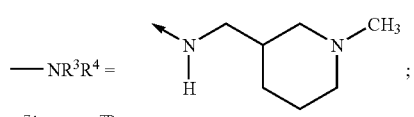 ; <br> R$^{7A}$ = H; R$^{7B}$ = —CH$_3$ <br> $^1$H NMR (DMSO-d$_6$, 400 MHz) δ: 0.92 (t, 3H), 1.09 (m, 1H), 1.55–1.90 (m, 5H), 2.10 (m, 1H), 2.45 (s, 3H), 2.80 (s, 3H), 3.20–3.60 (complex, 4H), 4.22 (s, 3H), 7.12 (d, 1H), 7.88 (br s, 1H), 8.18 (d, 1H). LRMS ES+ m/z 409 [MH]$^+$ |
| 54$^B$ | —NR$^3$R$^4$ = 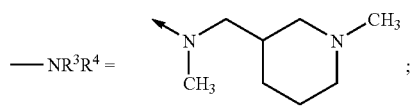 ; <br> R$^{7A}$ = H; R$^{7B}$ = —CH$_3$ <br> $^1$H NMR (DMSO-d$_6$, 400 MHz) δ: 0.93 (t, 3H), 1.10 (m, 1H), 1.60–1.90 (m, 4H), 2.20 (m, 1H), 2.41 (s, 3H), 2.60 (m, 1H), 2.72 (s, 3H), 2.76 (m, 2H), 3.17 (s, 3H), 3.26–3.77 (m, 6H), 4.19 (s, 3H), 7.04 (m, 1H), 7.85 (s, 1H), 8.21 (d, 1H). LRMS ES+ m/z 423 [MH]$^+$ |
| 55$^B$ | —NR$^3$R$^4$ = 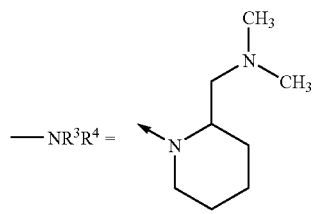 ; <br> R$^{7A}$ = H; R$^{7B}$ = —CH$_3$ <br> $^1$H NMR (DMSO-d$_6$, 400 MHz) δ: 0.90 (t, 3H), 1.57–1.78 (m, 8H), 2.34 (s, 3H), 2.72 (t, 2H), 2.78 (s, 6H), 3.06–3.22 (m, 2H), 3.80 (m, 2H), 4.12 (m, 2H), 4.46 (br s, 1H), 5.19 (br s, 1H), 6.99 (m, 1H), 7.72 (m, 1H), 8.18 (m, 1H). LRMS ES+ m/z 423 [MH]$^+$ |
| 56$^B$ | —NR$^3$R$^4$ = 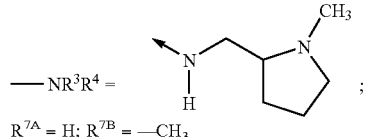 ; <br> R$^{7A}$ = H; R$^{7B}$ = —CH$_3$ <br> $^1$H NMR (DMSO-d$_6$, 400 MHz) δ: 0.93 (t, 3H), 1.66 (q, 2H), 1.74–2.40 (m, 4H), 2.42 (s, 3H), 2.71 (t, 2H), 2.83 (s, 3H), 3.10–3.80 (m, 4H), 4.20 (s, 3H), 7.07 (m, 1H), 7.78 (br s, 1H), 8.18 (d, 1H). LRMS ES+ m/z 395 [MH]$^+$ |
| 57$^B$ | —NR$^3$R$^4$ = 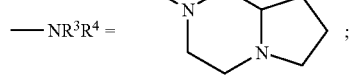 ; <br> R$^{7A}$ = H; R$^{7B}$ = —CH$_3$ <br> $^1$H NMR (DMSO-d$_6$, 400 MHz) δ: 0.93 (t, 3H), 1.74 (q, 2H), 1.82–2.25 (br m, 4H), 2.36 (s, 3H), 2.74 (t, 2H), 2.97–3.91 (complex, 9H) 4.15 (s, 3H), 6.97 (d, 1H), 7.81 (s, 1H), 8.18 (d, 1H). LRMS ES+ m/z 407 [MH]$^+$ |
| 58$^B$ | R$^3$ = —(CH$_2$)$_2$N(CH$_3$)$_2$; R$^4$ = H; <br> R$^{7A}$ = H; R$^{7B}$ = —CH$_3$ <br> $^1$H NMR (DMSO-d$_6$, 400 MHz) δ: 0.91 (t, 3H), 1.65 (q, 2H), 2.40 (s, 3H), 2.67 (t, 2H), 2.80 (s, 6H), 3.28 (m, 2H), 3.72 (t, 2H), 4.19 (s, 3H), 7.09 (m, 1H), 7.77 (m, 1H), 8.18 (d, 1H). LRMS ES+ m/z 369 [MH]$^+$ |
| 59$^B$ | R$^3$ = —(CH$_2$)$_2$N(CH$_3$)$_2$; R$^4$ = —CH$_3$; <br> R$^{7A}$ = H; R$^{7B}$ = —CH$_3$ <br> $^1$H NMR (DMSO-d$_6$, 400 MHz) δ: 0.93 (t, 3H), 1.72 (q, 2H), 2.36 (s, 3H), 2.74 (t, 2H), 2.82 (s, 6H), 3.14 (s, 3H), 3.33 (m, 2H), 3.91 (t, 2H), 4.14 (s, 3H), 6.96 (d, 1H), 7.80 (s, 1H), 8.18 (d, 1H). LRMS ES+ m/z 383 [MH]$^+$ |
| 60$^B$ | R$^3$ = —(CH$_2$)$_3$N(CH$_3$)$_2$; R$^4$ = H; <br> R$^{7A}$ = H; R$^{7B}$ = —CH$_3$ <br> $^1$H NMR (DMSO-d$_6$, 400 MHz) δ: 0.93 (t, 3H), 1.64 (m, 2H), 1.94 (m, 2H), 2.48 (s, 3H), 2.72 (m, 2H), 2.76 (s, 6H), 3.08 (m, 2H), 3.43 (m, 2H), 4.21 (s, 3H), 7.09 (d, 1H), 7.88 (s, 1H), 8.17 (d, 1H). LRMS ES+ m/z 383 [MH]$^+$ |
| 61$^B$ | R$^3$ = —(CH$_2$)$_3$N(CH$_3$)$_2$; R$^4$ = —CH$_3$; <br> R$^{7A}$ = H; R$^{7B}$ = —CH$_3$ <br> $^1$H NMR (DMSO-d$_6$, 400 MHz) δ: 0.92 (t, 3H), 1.64 (m, 2H), 1.95 (m, 2H), 2.40 (s, 3H), 2.73 (s, 6H), 2.75 (m, 2H), 3.00 (m, 2H), 3.14 (s, 3H), 3.65 (m, 2H), 4.18 (m, 3H), 7.02 (m, 1H), 7.90 (m, 1H), 8.18 (d, 1H). LRMS ES+ m/z 397 [MH]$^+$ |
| 62$^B$ | R$^3$ = —(CH$_2$)$_2$NH(CH$_3$); R$^4$ = —CH$_3$; <br> R$^{7A}$ = H; R$^{7B}$ = —CH$_3$ <br> $^1$H NMR (CDCl$_3$, 400 MHz) δ: 0.97 (t, 3H), 1.72 (q, 2H), 2.53 (s, 3H), 2.76 (t, 3H), 2.90 (t, 2H), 3.29 (s, 3H), 3.35 (m, 2H), 4.28 (t, 2H), 4.31 (s, 3H), 7.04 (d, 1H), 7.54, (s, 1H), 8.02 (d, 1H). LRMS: m/z ES+ 369, [MH]$^+$ |
| 63$^B$ | —NR$^3$R$^4$ = 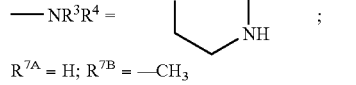 ; <br> R$^{7A}$ = H; R$^{7B}$ = —CH$_3$ |

| Ex | | Ex | |
|---|---|---|---|
| | ¹H NMR (CDCl₃, 400 MHz) δ: 0.92 (t, 3H), 1.43 (m, 3H), 1.77 (m, 2H), 2.58 (m, 1H), 2.85 (t, 2H), 3.18–3.75 (m, 5H), 4.30 (s, 3H), 4.58 (m, 2H), 7.18 (m, 1H), 7.79 (m, 1H), 8.18 (m, 1H). LRMS APCl m/z 381 [MH]⁺ | 70ᴮ | —NR³R⁴ = 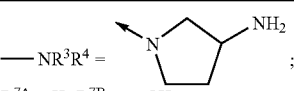;<br>R⁷ᴬ = H; R⁷ᴮ = —CH₃<br>¹H NMR (CDCl₃, 400 MHz) δ: 0.87 (t, 3H), 1.62 (q, 2H), 2.43 (m, 2H), 2.48 (s, 3H), 2.72 (t, 2H), 3.77 (m, 1H), 3.95 (m, 1H), 4.00–4.24 (m, 3H), 4.29 (s, 3H), 7.00 (d, 1H), 7.42 (s, 1H), 8.14 (d, 1H). LRMS APCl m/z: 367 [MH]⁺ |
| 64ᴮ | —NR³R⁴ = 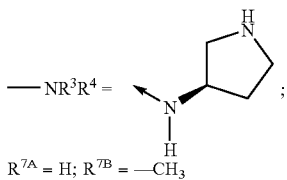;<br>R⁷ᴬ = H; R⁷ᴮ = —CH₃<br>¹H NMR (CDCl₃, 400 MHz) δ: 0.97 (t, 3H), 1.06 (m, 1H), 1.73 (m, 2H), 1.85 (m, 1H), 2.27 (m, 1H), 2.53 (s, 3H), 2.80 (t, 2H), 2.85 (m, 1H), 3.37–3.88 (complex 3H), 4.38 (s, 3H), 7.03 (m, 1H), 7.26 (s, 1H), 8.28 (br s, 1H).<br>LRMS APCl m/z 367 [MH]⁺ | 71 | —NR³R⁴ = 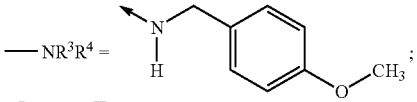;<br>R⁷ᴬ = H; R⁷ᴮ = —CH₃<br>¹H NMR (CDCl₃, 400 MHz) δ: 1.00 (t, 3H), 1.82 (q, 2H), 2.34 (s, 3H), 2.84 (t, 2H), 3.79 (s, 3H), 4.29 (s, 3H), 4.65 (d, 2H), 6.74 (br s, 1H), 6.89 (d, 2H), 7.34 (d, 2H).<br>LRMS: m/z ES+ 418, [MH]⁺ |
| 65ᴮ | —NR³R⁴ = 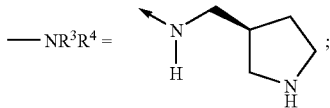;<br>R⁷ᴬ = H; R⁷ᴮ = —CH₃<br>¹H NMR (CDCl₃, 400 MHz) δ: 0.96 (t, 3H), 1.68 (q, 2H), 1.93 (m, 1H), 2.25 (m, 1H), 2.52 (s, 3H), 2.76 (t, 2H), 2.92 (m, 1H), 3.31 (m, 2H), 3.50–3.60 (m, 4H), 4.32 (s, 3H), 7.05 (s, 1H), 7.50 (br s, 1H), 8.05 (d, 1H).<br>LRMS APCl m/z: 381, [MH]⁺ | 72ᴮ | R³ = —(CH₂)₂OCH₃;<br>R⁷ᴬ = H; R⁷ᴮ = —CH₃<br>¹H NMR (CDCl₃, 400 MHz) δ: 1.00 (t, 3H), 1.81 (q, 2H), 2.41 (s, 3H), 2.80 (m, 2H), 3.41 (s, 3H) 3.66 (m, 4H), 4.29 (s, 3H),<br>6.82 (s, 1H), 7.60 (br s, 1H), 8.12 (br s, 1H).<br>LRMS: m/z ES+ 356, [MH]⁺ |
| 66ᴮ | —NR³R⁴ = 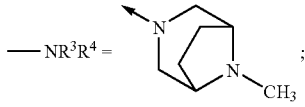;<br>R⁷ᴬ = H; R⁷ᴮ = —CH₃<br>¹H NMR (CDCl₃, 400 MHz) δ: 0.98 (t, 3H), 1.78 (q, 2H), 2.18 (m, 4H), 2.52 (s, 3H), 2.85 (m, 5H), 3.78 (d, 2H), 3.99 (s, 2H), 4.29 (s, 3H), 4.56 (d, 2H) 7.07 (d, 1H), 7.93 (s, 1H) 8.05 (d, 1H). LRMS APCl m/z 407 [MH]⁺ | 73ᴮ | —NR³R⁴ = 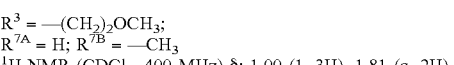;<br>R⁷ᴬ = H; R⁷ᴮ = —CH₃<br>¹H NMR (CDCl₃, 400 MHz) δ: 0.98 (m, 3H), 1.77 (m, 2H), 1.81–2.16 (m, 5H), 2.53 (s, 3H), 2.84 (m, 2H), 2.95 (s, 3H), 3.73 (m, 1H), 3.85 (m, 2H), 4.05–4.58 (m, 4H), 4.29 (s, 3H), 7.08 (m, 1H), 7.79 (s, 1H), 8.11 (m, 1H).<br>LRMS: m/z ES+ 421, [MH]⁺ |
| 67ᴮ | —NR³R⁴ = 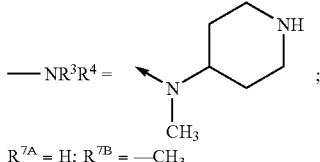;<br>R⁷ᴬ = H; R⁷ᴮ = —CH₃<br>LRMS: m/z ES+ 395, [MH]⁺ | 74ᴮ | —NR³R⁴ = 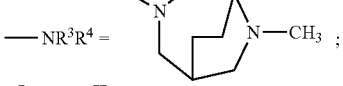;<br>R⁷ᴬ = H; R⁷ᴮ = —CH₃<br>¹H NMR (DMSO-d₆ 400 MHz) δ: 0.91 (t, 3H), 1.33 (m, 2H), 1.63 (m, 2H), 1.75–1.87 (m, 3H), 2.44 (s, 3H), 2.69 (t, 2H), 2.81 (m, 2H), 3.25–3.55 (m, 4H), 4.22 (s, 3H), 7.10 (d, 1H), 8.18 (d, 1H), 8.53 (br d, 1H). LRMS: m/z ES+ 395, [MH]⁺ |
| 68ᴮ | —NR³R⁴ = 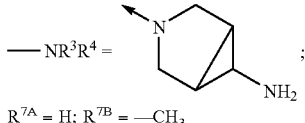;<br>R⁷ᴬ = H; R⁷ᴮ = —CH₃<br>¹H NMR (CDCl₃, 400 MHz) δ: 0.8 (t, 3H), 1.62 (q, 2H), 2.48 (s, 3H), 2.52 (m, 2H), 2.77 (t, 2H), 3.03 (m, 1H), 3.85 (d, 2H), 4.15 (d, 2H), 4.27 (s, 3H), 6.99 (d, 1H), 7.34 (d, 1H), 8.13 (d, 1H). LRMS: m/z ES+ 379, [MH]⁺ | 75ᴮ | —NR³R⁴ = 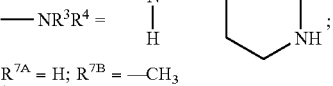;<br>R⁷ᴬ = H; R⁷ᴮ = —CH₃<br>¹H NMR (CDCl₃, 400 MHz) δ: 0.99 (t, 3H), 1.45 (m, 3H), 1.74 (m, 2H), 2.56 (s, 3H), 2.87 (t, 2H) 3.17–3.70 (m, 4H), 4.32 (s, 3H), 4.50–5.10 (m, 3H), 7.17 (m, 1H), 7.83 (m, 1H), 8.15 (s, 1H). LRMS: m/z ES+ 381, [MH]⁺ |
| 69ᴮ | —NR³R⁴ = 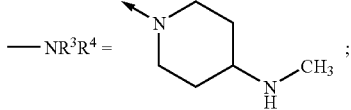;<br>R⁷ᴬ = H; R⁷ᴮ = —CH₃<br>¹H NMR (CDCl₃, 400 MHz) δ: 0.94 (t, 3H), 1.68 (q, 2H), 1.99 (m, 2H), 2.28 (m, 2H), 2.50 (s, 3H), 2.68 (s, 3H), 2.85 (t, 2H), 3.15 (t, 2H), 3.26 (m, 1H), 4.27 (s, 3H), 4.68 (d, 2H), 7.02 (d, 1H), 7.57 (s, 1H), 8.11 (d, 1H).<br>LRMS: m/z ES+ 395, [MH]⁺ | 76 | —NR³R⁴ = 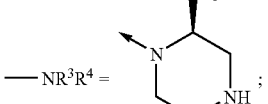;<br>LRMS: m/z ES+ 409, [MH]⁺ 407, [MH]⁻ |
| | | 77 | R³ = H; R⁴ = H; R⁷ᴬ = H; R⁷ᴮ = —CH₃<br>¹H NMR (CDCl₃, 400 MHz) δ: 0.95 (t, 3H), 2.68 (m, 2H), 2.45 (s, 3H), 2.68 (t, 2H), 4.30 (s, 3H), 6.88 (d, 1H), 7.18 (s, 1H), 8.20 (d, 1H). LRMS: m/z ES+ 298, [MH]⁺ |
| | | 78 | R³ = —CH₃; R⁴ = H; R⁷ᴬ = H; R⁷ᴮ = —CH₃<br>¹H NMR (CDCl₃, 400 MHz) δ: 1.00 (t, 3H), 1.81 (q, |

| Ex | |
|---|---|
| | 2H), 2.42 (s, 3H), 2.82 (m, 2H), 3.10 (s, 3H), 4.30 (s, 3H), 6.84 (s, 1H), 8.06 (s, 1H). LRMS: m/z ES+ 312, [MH]⁺ |
| 79ᴬ | 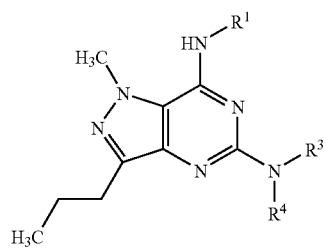 |
| | R¹ = 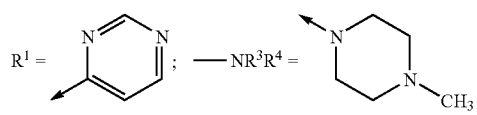; —NR³R⁴ = (piperazinyl)<br>¹H NMR (CD₃OD, 400 MHz) δ: 0.98 (t, 3H), 1.82 (m, 2H), 2.82 (t, 2H), 2.95 (t, 4H), 3.79 (m, 4H), 4.17 (s, 3H), 8.02 (br s, 1H), 8.56 (d, 1H), 8.79 (s, 1H). LRMS (ES+) 354, [MH]⁺ |
| 80 | R¹ = 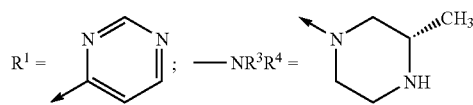; —NR³R⁴ = (N-methylpiperazinyl)<br>¹H NMR (CD₃OD, 400 MHz) δ: 0.97 (t, 3H), 1.78 (m, 2H), 2.38 (s, 3H), 2.62 (m, 4H), 2.80 (t, 2H), 3.80 (m, 4H), 4.15 (s, 3H), 8.01 (br s, 1H), 8.54 (d, 1H), 8.79 (s, 1H). LRMS: m/z ES+ :368, [MH]⁺ |
| 81 | R¹ = (pyrimidinyl); —NR³R⁴ = (3-methylpiperazinyl)<br>¹H NMR (CD₃OD, 400 MHz) δ: 0.97 (t, 3H), 1.17 (d, 3H), 1.78 (m, 2H), 2.62 (m, 1H), 2.75–2.90 (m, 4H), 2.95–3.10 (m, 2H), 4.15 (s, 3H), 4.51 (m, 2H), 7.99 (br s, 1H), 8.54 (d, 1H), 8.79 (s, 1H). LRMS: m/z ES+: 368, [MH]⁺ |
| 82ᴬ | R¹ = (pyrimidinyl); —NR³R⁴ = 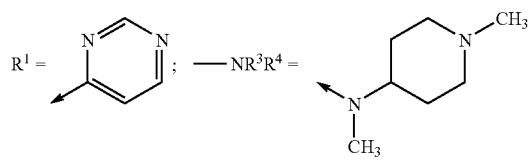<br>¹H NMR (CD₃OD, 400 MHz) δ: 1.00 (t, 3H), 1.80 (m, 2H), 2.10 (m, 2H), 2.25 (m, 2H), 2.85 (m, 2H), 2.90 (s, 3H), 3.21 (s, 3H), 3.55 (m, 2H), 3.65 (m, 2H), 4.20 (s, 3H), 4.95 (br m, 1H), 8.10 (br s, 1H), 8.75 (br s, 1H), 9.10 (s, 1H). LRMS: m/z ES+ 396, [MH]⁺ |
| 83 | R¹ = 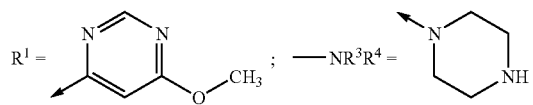; —NR³R⁴ = (piperazinyl)<br>¹H NMR (DMSO-d₆, 400 MHz) δ: 0.91 (t, 3H), 1.73 (q, 2H), 2.71 (t, 2H), 2.75 (m, 4H), 3.59 (m, 4H), 3.89 (s, 3H), 4.08 (s, 3H), 7.30 (s, 1H), 8.50 (s, 1H). LRMS: m/z ES+ 384, [MH]⁺ |
| 84 | R¹ = 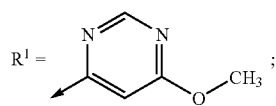;<br>R³ = —CH₃; R⁴ = H<br>¹H NMR (DMSO-d₆, 400 MHz) δ: 0.91 (t, 3H), 1.72 (q, 2H), 2.70 (t, 2H), 2.81 (s, 3H), 3.91 (s, 3H), 4.09 (s, |

| Ex | |
|---|---|
| | 3H), 6.70 (br s, 1H), 7.60 (s, 1H), 8.49 (s, 1H), 9.36 (s, 1H). LRMS: m/z ES+ 329, [MH]⁺ |
| 85 | R¹ = 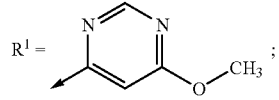;<br>R³ = —CH₃; R⁴ = —CH₃<br>¹H NMR (DMSO-d₆, 400 MHz) δ: 0.91 (t, 3H), 1.73 (q, 2H), 2.72 (t, 2H), 3.12 (s, 6H), 3.90 (s, 3H), 4.10 (s, 3H), 7.50 (s, 1H), 8.51 (s, 1H), 9.52 (s, 1H). LRMS: m/z ES+ 365, [MNa]⁺ |
| 86 | R¹ = 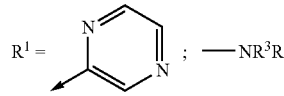; —NR³R⁴ = (piperazinyl)<br>¹H NMR (CD₃OD, 400 MHz) δ: 0.98 (t, 3H), 1.81 (t, 2H), 2.80 (t, 2H), 2.91 (m, 4H), 3.73 (m, 4H), 4.21 (s, 3H), 8.23 (d, 1H), 8.37 (d, 1H), 9.36 (br s, 1H). LRMS: m/z ES− 352, [M − H]⁻ |
| 87ᴬ | R¹ = 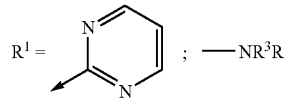; —NR³R⁴ = (piperazinyl)<br>¹H NMR (CD₃OD, 400 MHz) δ: 0.98 (t, 3H), 1.80 (m, 2H), 2.78 (m, 6H), 3.76 (m, 4H), 4.07 (s, 3H), 7.04 (br s, 1H), 8.57 (br s, 2H). LRMS ES+ m/z 354 [MH]⁺ |
| 88 | R¹ = 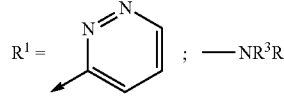; —NR³R⁴ = (piperazinyl)<br>¹H NMR (DMSO-d₆, 400 MHz) δ: 0.91 (t, 3H), 1.71 (m, 2H), 2.73 (m, 2H), 2.78 (m, 4H), 3.52 (m, 4H), 4.16 (s, 3H), 7.61 (m, H), 8.02 (d, 1H), 8.79 (d, 1H). LRMS APCl+ m/z 354 [MH]⁺ |
| 89 | R¹ = 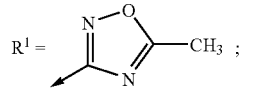;<br>R³ = —CH₃; R⁴ = —CH₃<br>¹H NMR (DMSO-d₆, 400 MHz) δ: 0.92 (t, 3H), 1.78 (m, 2H), 2.16 (s, 3H), 2.81 (m, 2H), 3.21 (s, 6H), 4.16 (s, 3H). LRMS ES+ m/z 339 [MNa]⁺ |
| 90 | R¹ = 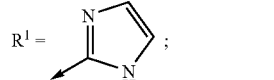;<br>R³ = —CH₃; R⁴ = H<br>¹H NMR (CD₃OD, 400 MHz) δ: 0.97 (t, 3H), 1.74 (m, 2H), 2.77 (m, 2H), 3.00 (s, 3H), 4.26 (s, 3H), 6.89 (s, 2H). LRMS ES+ m/z 287 [MH]⁺ |

ᴬThe products were dissolved in dichloromethane, treated with ethereal HCl, and the solutions evaporated in vacuo to afford the hydrochloride salts.

ᴮTrifluoroacetate salt was isolated

NOTES FOR EXAMPLES 29-90

EXAMPLE 30 tert-Butyl 3-methylpiperazine-1-carboxylate used as HNR³R⁴ amine

EXAMPLE 33 tert-Butyl 3,5-dimethylpiperazine-1-carboxylate (WO 93/01181, pg. 30, prep. 76) used as HNR³R⁴ amine EXAMPLES 34, 79, 83, 86, 87 and 88 tert-Butyl piperazine-1-carboxylate used as HNR³R⁴ amine

EXAMPLE 37 tert-Butyl 3-aminoazetidine-1-carboxylate (WO 01/47901, pg. 136, preparation 78) used as HNR³R⁴ amine

EXAMPLE 38 tert-Butyl 3-(methylamino)azetidine-1-carboxylate used as HNR³R⁴ amine, see preparation 6

EXAMPLE 39

(2S)-2-Methylpiperazine used as HNR³R⁴ amine

EXAMPLE 45 tert-Butyl (piperidin-4-yl)carbamate used as HNR³R⁴ amine

EXAMPLE 46 tert-Butyl [1,4]diazepane-1-carboxylate used as HNR³R⁴ amine

EXAMPLE 48 tert-Butyl 4-aminopiperidine-1-carboxylate used as HNR³R⁴ amine

EXAMPLE 49 tert-Butyl (piperidin-3-ylmethyl)carbamate used as HNR³R⁴ amine

EXAMPLE 50 tert-Butyl N-(2-aminoethyl)-N-methylcarbamate used as HNR³R⁴ amine

EXAMPLE 53

3-(Aminomethyl)-1-methylpiperidine (J. Am. Chem. Soc., 94 (26), 1972, 9151-9158) used as HNR³R⁴ amine

EXAMPLE 54

1-Methyl-3-(methylaminomethyl)piperidine used as HNR³R⁴ amine, see preparation 5

EXAMPLE 62 tert-Butyl N-methyl-N-(2-(methylamino)ethyl)carbamate (EP 0296811 ex. 1, step A) used as HNR³R⁴ amine

EXAMPLE 64 tert-Butyl (3R)-3-aminopyrrolidine-1-carboxylate used as HNR³R⁴ amine

EXAMPLE 65 tert-Butyl (3S)-3-(aminomethyl)pyrrolidine-1-carboxylate used as HNR³R⁴ amine

EXAMPLE 66

8-Methyl-3,8-diazabicylo[3.2.1]octane (U.S. Pat. No. 3,951,980, pg. 3, ex. 1) used as HNR³R⁴ amine

EXAMPLE 67 tert-Butyl 4-(methylamino)piperidine-1-carboxylate used as HNR³R⁴ amine

EXAMPLE 68 tert-Butyl (3-azabicyclo[3.1.0]hex-6-yl)carbamate (J. Chem. Soc Perkin 1, 2000, 1615) used as HNR³R⁴ amine

EXAMPLE 70 tert-Butyl (pyrrolidin-3-yl)carbamate used as HNR³R⁴ amine

EXAMPLE 73

6-Methyl-3,6-diazabicyclo[3.2.2]nonane (EP 0297858, pg. 8, ex. 4) used as HNR³R⁴ amine

EXAMPLE 74 tert-Butyl 4-(aminomethyl)piperidine-1-carboxylate used as HNR³R⁴ amine

EXAMPLE 75 tert-Butyl (3S)-3-methylpiperazine-1-carboxylate used as HN R³R⁴ amine

EXAMPLE 76 tert-Butyl N-methyl-N-(piperidin-4-ylmethyl)carbamate (U.S. Pat. No. 5,442,044, pg. 37, ex. 108) used as HNR³R⁴ amine

EXAMPLE 91

N-[1-Methyl-5-((3R)-3-methylpiperazin-1-yl)-3-propyl-1H-pyrazolo[4,3-d]pyrimidin-7-yl]pyrimidin-4-ylamine

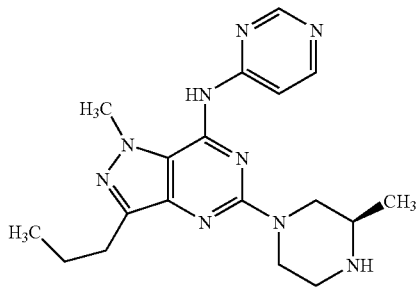

N-Ethyldiisopropylamine (625 μL, 4.5 mmol) and (2R)-2-methylpiperazine (450 mg, 4.5 mmol) were added to a solution of the monochloro compound of preparation 69 (270 mg, 0.89 mmol) in dimethylsulfoxide (8 mL) and the reaction mixture heated to 120° C. for 18 hours under nitrogen. The reaction mixture was diluted with ethyl acetate, washed with water (2×30 mL) and then brine (30 mL). The organic solution was dried over magnesium sulphate and concentrated in vacuo. The crude product was purified by column chromatography on silica gel eluting with dichloromethane:methanol:ammonia 100:0:0 to 95:5:0.5 to yield the title compound, 142 mg.

$^1$H NMR (CD$_3$OD, 400 MHz) δ: 0.97 (t, 3H), 1.17 (d, 3H), 1.78 (m, 2H), 2.62-3.20 (m, 7H), 4.15 (s, 3H), 4.51 (m, 2H), 7.99 (br s, 1H), 8.54 (d, 1H), 8.79 (s, 1H). LRMS:m/z ES+368, [MH]$^+$

EXAMPLES 92-122

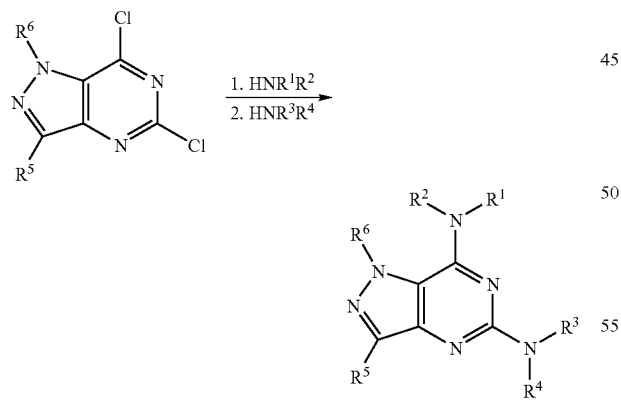

A solution of the appropriate HNR$^1$R$^2$ amine (50 μmol) in 1-methyl-2-pyrrolidinone (100 μL) was added to a solution of the appropriate dichloro compound (see preparations 52, 55, 56 and 59) (50 μL) in 1-methyl-2-pyrrolidinone (100 μL) followed by N-ethyldiisopropylamine (50 μL). The reaction mixture was heated under nitrogen for 36 hours at 90° C. The reaction mixture was cooled and a solution of the appropriate HNR$^3$R$^4$ amine (150 μmol) in dimethylsulfoxide (125 μL) added, followed by more N-ethyldiisopropylamine (50 μL). The reaction mixture was heated at 120° C. for 72 hours and then allowed to cool. The crude product was purified using HPLC on a Phenomenex Luna C18 column, 5 μm, 30×4.6 mm id at 40° C., eluting with acetonitrile: 0.05% ammonium acetate(aq.) with a gradient of 90:10 to 5:95 over 2.20 minutes with a flow rate of 3 mL/min.

The following compounds were prepared by the method described above:

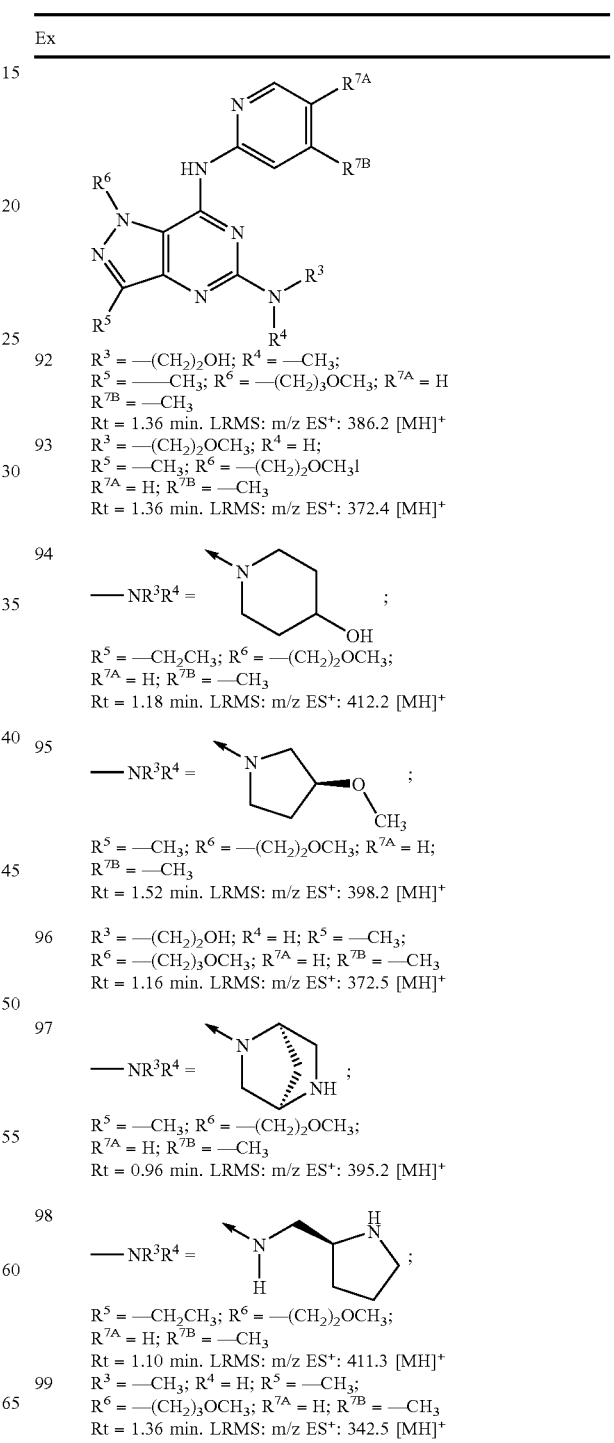

-continued

| Ex | |
|---|---|
| 100 | —NR³R⁴ =  ;<br>R⁵ = —CH₃; R⁶ = —(CH₂)₃OCH₃;<br>R⁷ᴬ = H; R⁷ᴮ = —CH₃<br>Rt = 1.27 min. LRMS: m/z ES⁺: 398.4 [MH]⁺ |
| 101 | R³ = —(CH₂)₂CO₂H; R⁴ = H; R⁵ = —CH₃;<br>R⁶ = —(CH₂)₂OCH₃; R⁷ᴬ = H;<br>R⁷ᴮ = —CH₃<br>Rt = 0.78 min. LRMS: m/z ES⁺: 386.2 [MH]⁺ |
| 102 | —NR³R⁴ =  ;<br>R⁵ = —CH₃; R⁶ = —(CH₂)₂OCH₃;<br>R⁷ᴬ = H; R⁷ᴮ = —CH₃<br>Rt = 1.20 min. LRMS: m/z ES: 384.2 [MH]⁺ |
| 103 | R³ = —(CH₂)₃OH; R⁴ = H; R⁵ = —CH₂CH₃;<br>R⁶ = —(CH₂)₂OCH₃; R⁷ᴬ = —CH₃;<br>R⁷ᴮ = H<br>Rt = 1.32 min. LRMS: m/z ES⁺: 386.3 [MH]⁺ |
| 104 | R³ = H; R⁴ = H; R⁵ = —CH₃;<br>R⁶ = —(CH₂)₃OCH₃; R⁷ᴬ = —CH₃;<br>R⁷ᴮ = H<br>Rt = 1.19 min. LRMS: m/z ES⁺: 328.5 [MH]⁺ |
| 105 | —NR³R⁴ =  ;<br>R⁵ = —CH₃; R⁶ = —(CH₂)₂OCH₃;<br>R⁷ᴬ = —CH₃; R⁷ᴮ = H<br>Rt = 1.30 min. LRMS: m/z ES⁺: 398.3 [MH]⁺ |
| 106 | —NR³R⁴ =  ;<br>R⁵ = —CH₃; R⁶ = —(CH₂)₂OCH₃;<br>R⁷ᴬ = —CH₃; R⁷ᴮ = H<br>Rt = 1.13 min. LRMS: m/z ES⁺: 397.2 [MH]⁺ |
| 107 | R³ = —(CH₂)₂CONHCH₃; R⁴ = H;<br>R⁵ = —CH₂CH₃; R⁶ = —(CH₂)₂OCH₃;<br>R⁷ᴬ = —CH₃; R⁷ᴮ = H<br>Rt = 1.13 min. LRMS: m/z ES⁺: 413.3 [MH]⁺ |
| 108 | —NR³R⁴ =  ;<br>R⁵ = —CH₂CH₃; R⁶ = —(CH₂)₂OCH₃;<br>R⁷ᴬ = —CH₃; R⁷ᴮ = H<br>Rt = 1.45 min. LRMS: m/z ES⁺: 398.2 [MH]⁺ |
| 109 | R³ = —(CH₂)₂OH; R⁴ = —CH₃;<br>R⁵ = —CH₂CH₃; R⁶ = —(CH₂)₂OCH₃;<br>R⁷ᴬ = H; R⁷ᴮ = H<br>Rt = 1.39 min. LRMS: m/z ES⁺: 372.4 [MH]⁺ |
| 110 | R³ = —(CH₂)₂OCH₃; R⁴ = H;<br>R⁵ = —CH₂CH₃; R⁶ = —(CH₂)₂OCH₃;<br>R⁷ᴬ = F; R⁷ᴮ = H<br>Rt = 1.26 min. LRMS: m/z ES⁺: 390.2 [MH]⁺ |
| 111 | R³ = H; R⁴ = H; R⁵ = —CH₂CH₃;<br>R⁶ = —(CH₂)₂OCH₃; R⁷ᴬ = —O(CH₂)₂CH₃;<br>R⁷ᴮ = H<br>Rt = 1.17 min. LRMS: m/z ES⁺: 372.2 [MH]⁺ |

-continued

| Ex | |
|---|---|
| 112 | —NR³R⁴ = 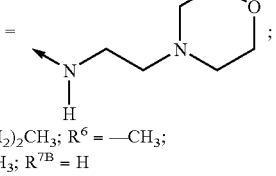 ;<br>R⁵ = —(CH₂)₂CH₃; R⁶ = —CH₃;<br>R⁷ᴬ = —CH₃; R⁷ᴮ = H<br>Rt: 1.23 min. LRMS m/z ES+: 411.2 [MH]⁺ |
| 113 | —NR³R⁴ = 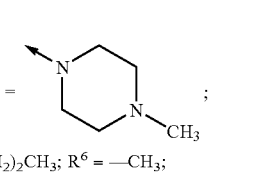 ;<br>R⁵ = —(CH₂)₂CH₃; R⁶ = —CH₃;<br>R⁷ᴬ = —CH₃; R⁷ᴮ = H<br>Rt: 1.34 min. LRMS m/z ES+: 381.2 [MH]⁺ |
| 114 | 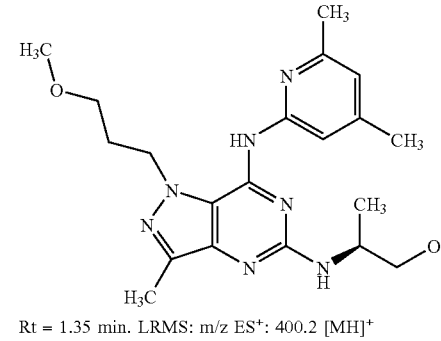<br>Rt = 1.35 min. LRMS: m/z ES⁺: 400.2 [MH]⁺ |
| | 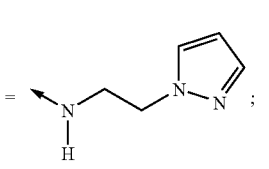 |
| 115 | —NR³R⁴ = 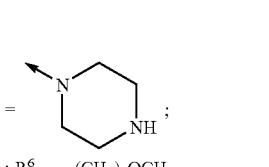 ;<br>R⁵ = —CH₂CH₃; R⁶ = —(CH₂)₂OCH₃<br>Rt = 0.92 min. LRMS: m/z ES⁺: 411.2 [MH]⁺ |
| 116 | —NR³R⁴ =  ;<br>R⁵ = —CH₃; R⁶ = —(CH₂)₃OCH₃<br>Rt = 0.82 min. LRMS: m/z ES⁺: 386.6 [MH]⁺ |

| Ex | | |
|---|---|---|
| 117 | 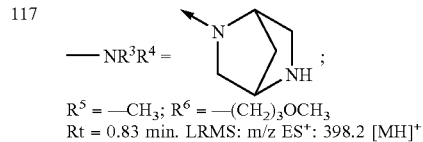 —NR³R⁴ = ; R⁵ = —CH₃; R⁶ = —(CH₂)₃OCH₃ Rt = 0.83 min. LRMS: m/z ES⁺: 398.2 [MH]⁺ | |
| 118 | 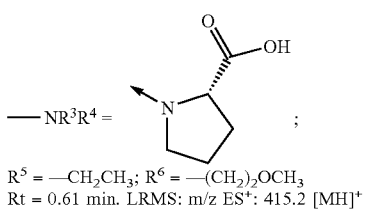 —NR³R⁴ = ; R⁵ = —CH₂CH₃; R⁶ = —(CH₂)₂OCH₃ Rt = 0.61 min. LRMS: m/z ES⁺: 415.2 [MH]⁺ | |
| 119 | 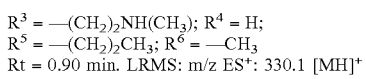 R³ = —(CH₂)₂NH(CH₃); R⁴ = H; R⁵ = —(CH₂)₂CH₃; R⁶ = —CH₃ Rt = 0.90 min. LRMS: m/z ES⁺: 330.1 [MH]⁺ | |
| 120 | 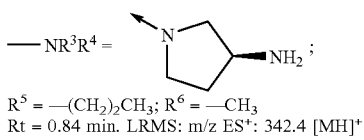 —NR³R⁴ = ; R⁵ = —(CH₂)₂CH₃; R⁶ = —CH₃ Rt = 0.84 min. LRMS: m/z ES⁺: 342.4 [MH]⁺ | |
| 121 | 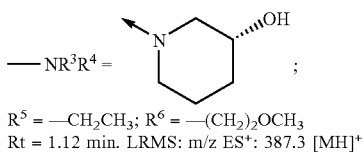 —NR³R⁴ = ; R⁵ = —CH₂CH₃; R⁶ = —(CH₂)₂OCH₃ Rt = 1.12 min. LRMS: m/z ES⁺: 387.3 [MH]⁺ | |
| 122 | 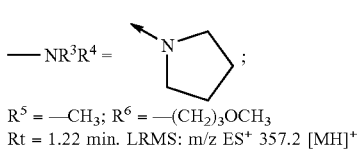 —NR³R⁴ = ; R⁵ = —CH₃; R⁶ = —(CH₂)₃OCH₃ Rt = 1.22 min. LRMS: m/z ES⁺ 357.2 [MH]⁺ | |

Notes for Examples 92–122
Example 95: (3S)-3-Methoxypyrrolidine used as HNR³R⁴ amine, see preparation 7.
Example 101: tert-Butyl 3-aminopropionate used as HNR³R⁴.
Example 107: 3-Amino-N-methylpropionamide used as HNR³R⁴ amine, see preparation 8.
Example 111: 2-Amino-5-propoxypyridine (J.Med.Chem., 1981, 24 (12), 1518–1521) used as the HNR¹R² amine.
Example 114: (S)-(+)-2-Amino-1-propanol was used as the HNR³R⁴ amine.
Example 115: 2-(Pyrazol-1-yl)ethylamine (WO 02/066481, pg. 60, method 44) used as HNR³R⁴ amine.
Example 116: ted-Butyl piperazine-1-carboxylate used as HNR³R⁴ amine.
Example 117: tert-Butyl (1S,4S)-2,5-diazabicyclo[2.2.1]heptane-2-carboxylate used as HNR³R⁴ amine.
Example 118: L-Proline tert-butyl ester used as the HNR³R⁴ amine.
Example 119: tert-Butyl N-(2-aminoethyl)-N-methylcarbamate used as HNR³R⁴ amine.
Example 120: (3S)-3-(tert-Butyloxycarbonylamino)pyrrolidine was used as HNR³R⁴ amine.

EXAMPLES 123–130

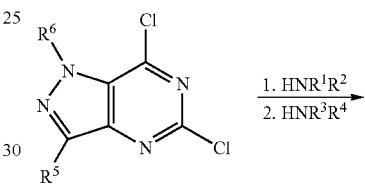

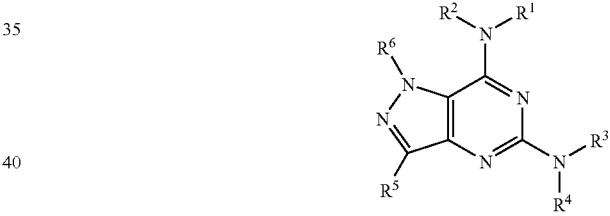

A solution of the dichloride of preparation 52 (1 eq) in dimethylsulfoxide (1 mL.mmol⁻¹) was added to a solution of the appropriate amine HNR¹R² (2 eq) in dimethylsulfoxide (0.75 mL.mmol⁻¹). N-Ethyldiisopropylamine (1 eq) was added and the reaction vessel sealed and shaken at 140 rpm at 80° C. for 12 hours. The reaction mixture was then allowed to cool. A solution of tert-butyl piperazine carboxylate or 33% methylamine in ethanol (5 eq) in dimethylsulfoxide (0.66 mL.mmol⁻¹) followed by N-ethyldiisopropylamine (3 eq) was then added to the reaction mixture and the reaction vessel sealed, heated to 120° C. and left for 18 hours. The reaction mixture was evaporated to dryness. When deprotection was required (ex 123 to 129), dichloromethane (2.5 mL.mmol⁻¹) and trifluoroacetic acid (2.5 mL.mmol⁻¹) were added and the reaction mixture sealed and stirred for 24 hours. The reaction mixture was concentrated in vacuo. The residues were purified using a Phenomenex Luna C18 2×15 cm 5 µm column eluting with acetonitrile: diethylamine to afford the title compounds.

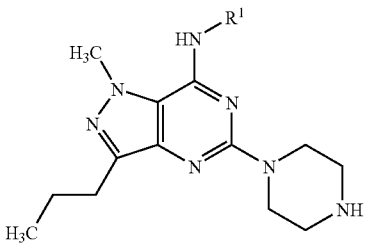

| Ex | R¹ = | |
|---|---|---|
| 123 | 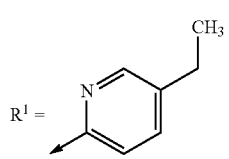 | ¹H NMR (DMSO-d$_6$, 400 MHz) δ: 0.90 (t, 3H), 1.20 (m, 3H), 1.70 (m, 2H), 2.56 (m, 2H), 2.67 (m, 2H), 2.75 (m, 4H), 3.56 (m, 4H), 4.10 (s, 3H), 7.76 (d, 1H), 7.90 (br s, 1H), 8.16 (s, 1H). LRMS: m/z APCl+ 381, [MH]$^+$ |
| 124 |  | ¹H NMR (DMSO-d$_6$, 400 MHz) δ: 0.90 (t, 3H), 1.1–1.5 (m, 6H), 1.6–1.8 (m, 4H), 1.96 (d, 2H), 2.63 (t, 2H), 2.75 (m, 4H), 3.56 (m, 4H), 4.0 (m, 1H), 4.05 (s, 3H), 6.30 (d, 1H). LRMS: m/z (ES+) 358, [MH]$^+$ |
| 125 | 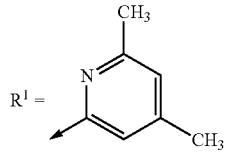 | ¹H NMR (DMSO-d$_6$, 400 MHz) δ: 0.93 (t, 3H), 1.72 (m, 2H), 2.27 (s, 3H), 2.38 (s, 3H), 2.75 (t, 2H), 2.77 (m, 4H), 3.56 (m, 4H), 4.13 (s, 3H), 6.74 (s, 1H), 7.59 (br s, 1H). LRMS: m/z (ES+) 381, [MH]$^+$ |
| 126 | 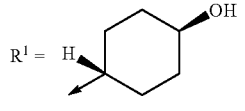 | ¹H NMR (CD$_3$OD, 400 MHz) δ: 0.96 (t, 3H), 1.44 (m, 4H), 1.76 (m, 4H), 2.08 (br s, 1H), 2.22 (br s, 1H), 2.76 (t, 2H), 2.85 (t, 4H), 3.68 (m, 1H), 3.74 (m, 4H), 4.07 (m, 1H), 4.13 (s, 3H). LRMS ES+ m/z 374 [MH]$^+$ |
| 127 | 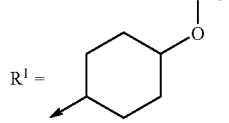 | ¹H NMR (CD$_3$OD, 400 MHz) δ: 0.96 (t, 3H), 1.37 (m, 2H), 1.58 (m, 2H), 1.76 (m, 2H), 1.95 (m, 1H), 2.19 (m, 4H), 2.78 (m, 2H), 2.93 (m, 4H), 3.25 (m, 1H), 3.37 (s, 3H), 3.78 (m, 4H), 4.10 (s, 3H). LRMS ES+ m/z 388 [MH]$^+$ |
| 128 | 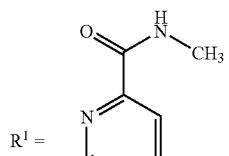 | ¹H NMR (DMSO-d$_6$, 400 MHz) δ: 0.98 (t, 3H), 1.77 (m, 2H), 2.77 (m, 6H), 2.82 (s, 3H), 3.57 (m, 4H), 4.18 (s, 3H), 7.64 (m, 1H), 7.98 (m, 1H), 8.13 (m, 1H), 8.44 (m, 1H). LRMS ES m/z: 410 [MH]$^+$ |
| 129 | 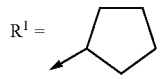 | ¹H NMR (CD$_3$OD, 400 MHz) δ: 0.97 (t, 3H), 1.65 (m, 6H), 1.78 (m, 2H), 2.15 (m, 2H), 2.81 (t, 2H), 2.90 (m, 4H), 3.75 (m, 4H), 4.09 (s, 3H), 4.49 (m, 1H). LRMS ES+ m/z 344 [MH]$^+$ |
| 130 | 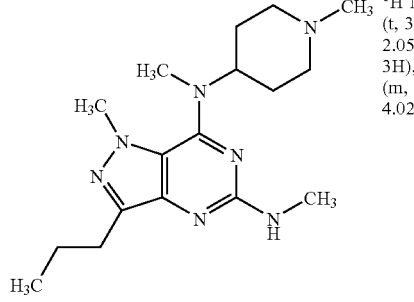 | ¹H NMR (CD$_3$OD, 400 MHz) δ: 0.99 (t, 3H), 1.75 (m, 2H), 1.88 (m, 2H), 2.05 (m, 2H), 2.22 (t, 2H), 2.34 (s, 3H), 2.79 (t, 2H), 2.94 (s, 3H), 3.01 (m, 2H), 3.05 (s, 3H), 3.94 (s, 3H), 4.02 (m, 1H) |

Notes for Examples 123–130

Example 123–129: tert-Butyl piperazme-1-carboxylate as HNR³R⁴ amine.

EXAMPLE 123

2-Amino-5-ethylpyridine used as HNR¹R² amine, see preparation 10

EXAMPLE 131

N-[1-(2-Methoxyethyl)-5-(piperazin-1-yl)-3-propyl-1H-pyrazolo[4,3-d]pyrimidin-7-yl]-4-methylpyridin-2-ylamine dihydrochloride

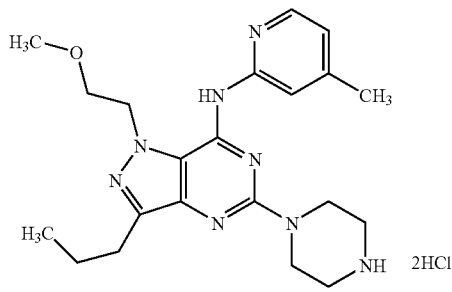

4-Methylpyridin-2-ylamine (112 mg, 1.037 mmol) was added to a solution of the dichloride of preparation 65 (100 mg, 0.346 mmol) in dimethylsulfoxide (1 mL) and the reaction mixture stirred at 70° C. for 18 hours. Piperazine-1-carboxylic acid tert butyl ester (322 mg, 1.73 mmol) and N-ethyldiisopropylamine (1 mL) were added and the reaction mixture stirred at 120° C. for 8 hours. The cooled reaction mixture was diluted with ethanol and ethyl acetate, the organic phase washed with water (2×15 mL), dried over magnesium sulphate and concentrated in vacuo. The residue was dissolved in dichloromethane (1 mL) and added trifluoroacetic acid (1 mL) under nitrogen at room temperature. The reaction mixture was stirred for 2 hours at room temperature and concentrated in vacuo. The residue was dissolved dichloromethane (15 mL) and 2M sodium hydrogencarbonate added until the aqueous phase was basic. The organic phase was washed with water (10 mL), dried over magnesium sulphate and concentrated in vacuo. The crude product was purified by column chromatography on silica gel using ethyl acetate:methanol:diethylamine 98:1:1 to yield a gum which was dissolved in dichloromethane (2 mL). 2M Hydrogen chloride in ether (1 mL) was added and the mixture blown dry and concentrated in vacuo to give a yellow solid, 50 mg.

¹H NMR (DMSO-d₆, 400 MHz) δ: 0.87 (t, 3H), 1.67 (m, 2H), 2.36 (s, 3H), 2.72 (t, 2H), 3.20 (m, 4H), 3.24 (s, 3H), 3.71 (m, 2H), 3.89 (m, 4H), 4.65 (m, 2H), 7.05 (m, 1H), 7.81 (s, 1H), 8.13 (m, 1H). LRMS:m/z ES+: 411, [MH]⁺

EXAMPLE 132

N-[1-(2-Methoxyethyl)-5-(piperazin-1-yl)-3-propyl-1H-pyrazolo[4,3-d]pyrimidin-7-yl]-(5-methylpyridin-2-yl)amine dihydrochloride

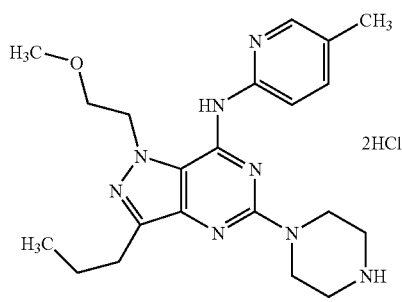

Made by the method of example 131 using 2-amino-5-methylpyridine as a starting material.

¹H NMR (DMSO-d₆, 400 MHz) δ: 0.87 (t, 3H), 1.66 (m, 2H), 2.25 (s, 3H), 2.73 (t, 2H), 3.16 (m, 4H), 3.26 (s, 3H), 3.71 (m, 2H), 3.84 (m, 4H), 4.63 (m, 2H), 7.78 (m, 1H), 7.91 (m, 1H), 8.12 (s, 1H). LRMS ES m/z 411 [MH]⁺

EXAMPLES 133-150

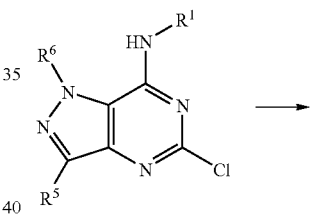

→

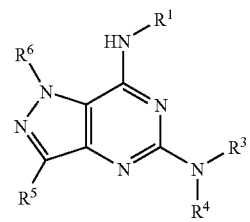

A solution of appropriate homochiral amine (0.5 mmol) (tert-butyl (2R, 5S)-2,5-dimethylpiperazine-1-carboxylate (WO 02/42292 preparation 51) or the protected piperazine from preparation 3) (for resolution see WO 02/42292) in dimethylsulfoxide (0.75 mL) was added to the appropriate monochloride (Preparations 72, 74, 117-123) (0.2 mmol). N-Ethyldiisopropylamine (1 mmol) was added, the reaction vessels sealed and heated at 130° C. for 18 hours. The reaction mixtures were concentrated in vacuo and the residues treated with a solution of trifluoroacetic acid in dichloromethane (0.5 mL/1.5 mL), and the solutions stirred at room temperature for 18 hours. The mixtures were evaporated in vacuo. The residues were purified using a Phenomenex Luna C18 2×15 cm 5 μm column eluting with acetonitrile:diethylamine to afford the title compounds.

| Ex | |
|---|---|
| | [Structure: pyrazolo[3,4-d]pyrimidine core with HN-R¹ at 7-position, R⁶ on N1, R⁵ at 3-position, and 2,5-dimethylpiperazine at 2-position, with CH₃ groups shown with stereochemistry] |
| 133 | R¹ = [4-methylpyridin-2-yl]; <br> R⁵ = —CH₃; R⁶ = —(CH₂)₂OCH₃ <br> ¹H NMR (DMSO-d₆, 400 MHz) δ: 1.09 (d, 3H), 1.19 (d, 3H), 2.29 (s, 3H), 2.32 (s, 3H), 3.11 (m, 2H), 3.22 (m, 1H), 327–3.36 (m, 4H), 3.72 (m, 2H), 4.04 (m, 1H), 4.57 (m, 3H), 6.88 (d, 1H), 7.99 (m, 1H), 8.18 (d, 1H). HRMS 411.26 [MH]+ |
| 134 | R¹ = [5-methylpyridin-2-yl]; <br> R⁵ = —CH₃; R⁶ = —(CH₂)₂OCH₃ <br> ¹H NMR (DMSO-d₆, 400 MHz) δ: 1.07 (d, 3H), 1.17 (d, 3H), 2.25 (s, 3H), 2.31 (s, 3H), 3.13 (m, 2H), 3.22 (m, 1H), 3.27–3.38 (m, 4H), 3.72 (m, 2H), 4.02 (m, 1H), 4.58 (m, 3H), 7.63 (d, 1H), 7.98 (m, 1H), 8.16 (s, 1H), 9.63 (br s, 1H). HRMS 411.26 [MH]+ |
| 135 | R¹ = [pyrimidin-5-yl]; <br> R⁵ = —CH₃; R⁶ = —(CH₂)₂OCH₃ <br> ¹H NMR (DMSO-d₆, 400 MHz) δ: 1.09 (d, 3H), 1.17 (d, 3H), 2.31 (s, 3H), 3.14 (m, 2H), 3.24 (m, 2H), 3.30 (s, 3H), 3.74 (m, 2H), 4.01 (d, 1H), 4.58 (m, 3H), 8.01 (m, 1H), 8.62 (d, 1H), 8.83 (s, 1H). <br> HRMS: m/z (ESI+) 398.24, MH+ |
| 136 | R¹ = [4-methylpyridin-2-yl]; <br> R⁵ = —CH₃; R⁶ = —(CH₂)₂OCH₂CH₃ <br> ¹H NMR (DMSO-d₆, 400 MHz) δ: 1.08 (m, 6H), 1.19 (d, 3H), 2.28 (m, 6H), 3.16 (m, 2H), 3.22 (m, 2H), 3.50 (m, 2H), 3.76 (m, 2H), 4.02 (d, 1H), 4.62 (m, 3H), 6.88 (d, 1H), 8.03 (br s, 1H), 8.17 (d, 1H), 9.58 (br s, 1H). HRMS 425.27 [MH]+ |
| 137 | R¹ = [5-methylpyridin-2-yl]; <br> R⁵ = —CH₃; R⁶ = —(CH₂)₂OCH₂CH₃ <br> ¹H NMR (DMSO-d₆, 400 MHz) δ: 1.08 (m, 6H), 1.17 (d, 3H), 2.24 (s, 3H), 2.29 (s, 3H), 3.12 (m, 2H), 3.15 (m, 2H), 3.51 (m, 2H), 3.76 (m, 2H), 4.00 (m, 1H), 4.54 (m, 3H), 7.63 (d, 1H), 8.03 (d, 1H), 8.14 (s, 1H), 9.53 (br s, 1H). HRMS 425.27 [MH]+ |
| 138 | R¹ = [pyrimidin-5-yl]; <br> R⁵ = —CH₃; R⁶ = —(CH₂)₂OCH₂CH₃ <br> ¹H NMR (DMSO-d₆, 400 MHz) δ: 1.08 (m, 6H), 1.17 (d, 3H), 2.31 (s, 3H), 3.14 (m, 2H), 3.25 (m, 2H), 3.53 (m, 2H), 3.74 (m, 2H), 4.02 (d, 1H), 4.57 (m, 3H), 8.03 (d, 1H), 8.61 (d, 1H), 8.82 (s, 1H). <br> HRMS 412.25 [MH]+ |
| 139 | R¹ = [4-methylpyridin-2-yl]; <br> R⁵ = —CH₂CH₃; R⁶ = —(CH₂)₂OCH₂CH₃ <br> ¹H NMR (DMSO-d₆, 400 MHz) δ: 1.09 (m, 6H), 1.21 (d, 3H), 1.29 (t, 3H), 2.31 (s, 3H), 2.74 (q, 2H), 3.13 (m, 2H), 3.23 (m, 2H), 3.51 (m, 2H), 3.76 (m, 2H), 4.02 (m, 1H) 4.56 (m, 3H), 6.89 (d, 1H), 8.05 (s, 1H), 8.16 (d, 1H), 9.60 (s, 1H). <br> HRMS 439.29 [MH]+ |
| 140 | R¹ = [5-methylpyridin-2-yl]; <br> R⁵ = —CH₂CH₃; R⁶ = —(CH₂)₂OCH₂CH₃ <br> ¹H NMR (CDCl₃, 400 MHz) δ; 1.10 (m, 6H), 1.18 (m, 3H), 1.31 (t, 3H), 2.24 (s, 3H), 2.50 (m, 1H), 2.74 (m, 2H), 3.12 (m, 2H), 3.23 (m, 1H), 3.54 (m, 2H), 3.77 (m, 2H), 4.01 (m, 1H), 4.55 (m, 3H), 7.63 (d, 1H), 8.04 (d, 1H), 8.12 (s, 1H), 9.52 (br s, 1H). <br> HRMS 439.29 [MH]+ |
| 141 | R¹ = [pyrimidin-5-yl]; <br> R⁵ = —CH₂CH₃; R⁶ = —(CH₂)₂OCH₂CH₃ <br> ¹H NMR (CDCl₃, 400 MHz) δ: 1.09 (m, 6H), 1.21 (d, 3H), 1.29 (t, 3H), 2.77 (q, 2H), 3.13 (m, 2H), 3.23 (m, 2H), 3.53 (m, 2H), 3.76 (m, 2H), 4.02 (d, 1H) 4.55 (m, 1H), 4.58 (m, 2H), 8.03 (s, 1H), 8.63 (d, 1H), 8.82 (s, 1H). HRMS 426.27 [MH]+ |
| | [Structure: pyrazolo[3,4-d]pyrimidine core with HN-R¹ at 7-position, R⁶ on N1, R⁵ at 3-position, and 2,5-dimethylpiperazine at 2-position with alternate stereochemistry] |
| 142 | R¹ = [4-methylpyridin-2-yl]; <br> R⁵ = —CH₃; R⁶ = —(CH₂)₂OCH₃ <br> ¹H NMR (DMSO-d₆, 400 MHz) δ: 1.08 (d, 3H), 1.19 (d, 3H), 2.29 (s, 3H), 2.32 (s, 3H), 3.16 (m, 2H), 3.23 (m, 2H), 3.31 (s, 3H), 3.68 (m, 2H), 4.03 (m, 1H), 4.58 (m, 3H), 6.92 (m, 1H), 8.00 (m, 1H), 8.17 (m, 1H). HRMS 411.26 [MH]+ |

| Ex | | |
|---|---|---|
| 143 | R¹ = (5-methyl-pyridin-2-yl);<br>R⁵ = —CH₃; R⁶ = —(CH₂)₂OCH₃<br>¹H NMR (CDCl₃, 400 MHz) δ: 1.06 (d, 3H), 1.13 (d, 3H), 2.24 (s, 3H), 2.27 (s, 3H), 3.14 (m, 2H), 3.20 (m, 2H), 3.30 (s, 3H), 3.75 (m, 2H), 4.03 (m, 1H), 4.56 (m, 3H), 7.62 (m, 1H), 8.00 (m, 1H), 8.16 (m, 1H), 9.62 (s, 1H). HRMS 411.26 [MH]⁺ | |
| 144 | R¹ = (pyrimidin-5-yl);<br>R⁵ = —CH₃; R⁶ = —(CH₂)₂OCH₃<br>¹H NMR (DMSO-d₆, 400 MHz) δ: 1.05 (d, 3H), 1.18 (d, 3H), 2.27 (s, 3H), 2.48 (m, 1H), 3.16 (m, 2H), 3.23 (m, 1H), 3.35 (s, 3H), 3.72 (m, 2H), 4.00 (d, 1H), 4.60 (m, 3H), 8.01 (d, 1H), 8.62 (d, 1H), 8.84 (s, 1H).<br>HRMS 398.24 [MH]⁺ | |
| 145 | R¹ = (4-methyl-pyridin-2-yl);<br>R⁵ = —CH₃; R⁶ = —(CH₂)₂OCH₃<br>¹H NMR (DMSO-d₆, 400 MHz) δ: 1.08 (m, 6H), 1.21 (s, 3H), 2.29 (m, 6H), 3.17 (m, 2H), 3.23 (m, 2H), 3.30 (s, 3H), 3.57 (m, 2H), 3.77 (m, 2H), 4.02 (m, 1H), 4.56 (m, 3H), 6.86 (m, 1H), 8.03 (m, 1H), 8.17 (m, 1H).<br>HRMS 425.27 [MH]⁺ | |
| 146 | R¹ = (5-methyl-pyridin-2-yl);<br>R⁵ = —CH₃; R⁶ = —(CH₂)₂OCH₃<br>¹H NMR (DMSO-d₆, 400 MHz) δ: 1.07 (m, 6H), 1.18 (d, 3H), 2.24 (s, 3H), 2.32 (s, 3H), 3.17 (m, 2H), 3.23 (m, 2H), 3.31 (s, 3H), 3.57 (m, 2H), 3.77 (m, 2H), 4.02 (m, 1H), 4.56 (m, 3H), 7.64 (m, 1H), 8.03 (m, 1H), 8.16 (m, 1H). HRMS 425.27 [MH]⁺ | |
| 147 | R¹ = (pyrimidin-5-yl);<br>R⁵ = —CH₃; R⁶ = —(CH₂)₂OCH₃<br>¹H NMR (DMSO-d₆, 400 MHz) δ: 1.08 (m, 6H), 1.17 (d, 3H), 2.31 (s, 3H), 3.14 (m, 2H), 3.26 (m, 2H), 3.53 (m, 2H), 3.74 (m, 2H), 4.02 (m, 1H), 4.57 (m, 3H), 8.03 (d, 1H), 8.61 (d, 1H), 8.82 (s, 1H). HRMS 412.26 [MH]⁺ | |
| 148 | R¹ = (4-methyl-pyridin-2-yl);<br>R⁵ = —CH₂CH₃; R⁶ = —(CH₂)₂OCH₂CH₃<br>¹H NMR (DMSO-d₆, 400 MHz) δ:1.03 (m, 6H), 1.20 (m, 3H), 1.26 (m, 3H), 2.29 (s, 3H), 2.50 (m, 1H), 2.74 (m, 2H), 3.15 (m, 2H), 3.27 (m, 1H), 3.52 (m, 2H), 3.77 (m, 2H), 4.02 (m, 1H), 4.57 (m, 3H), 6.90 (m, 1H), 8.04 (m, 1H), 8.18 (m, 1H), 9.58 (m, 1H). HRMS 439.29 [MH]⁺ | |
| 149 | R¹ = (5-methyl-pyridin-2-yl);<br>R⁵ = —CH₂CH₃; R⁶ = —(CH₂)₂OCH₂CH₃<br>¹H NMR (DMSO-d₆, 400 MHz) δ: 1.07 (m, 6H), 1.17 (m, 3H), 1.29 (m, 3H), 2.22 (s, 3H), 2.48 (m, 1H), 2.77 | |

| Ex | | |
|---|---|---|
| | (m, 2H), 3.15 (m, 2H), 3.21 (m, 1H), 3.52 (m, 2H), 3.77 (m, 2H), 4.02 (m, 1H), 4.55 (m, 3H), 7.81 (m, 1H), 8.03 (d, 1H), 8.14 (s, 1H), 9.54 (br s, 1H). HRMS 439.29 [MH]⁺ | |
| 150 | R¹ = (pyrimidin-5-yl);<br>R⁵ = —CH₂CH₃; R⁶ = —(CH₂)₂OCH₂CH₃<br>¹H NMR (DMSO-d₆, 400 MHz) δ: 1.09 (m, 6H), 1.21 (d, 3H), 1.27 (t, 3H), 2.48 (m, 1H), 2.77 (q, 2H), 3.13 (m, 2H), 3.23 (m, 1H), 3.53 (m, 2H), 3.76 (m, 2H), 4.02 (d, 1H) 4.57 (m, 3H), 8.03 (s, 1H), 8.63 (d, 1H), 8.82 (s, 1H). HRMS 426.27 [MH]⁺ | |

EXAMPLES 151 AND 152

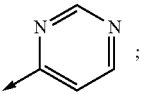

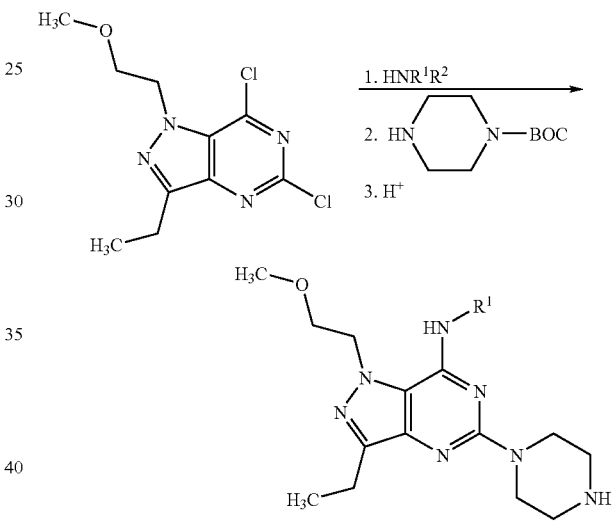

The following compounds were prepared by the method of example 131 using the dichloride of preparation 56, tert-butyl piperazine-1-carboxylate and the appropriate HNR¹R² amine as starting materials, except, the products were isolated as the free base.

| Ex | |
|---|---|
| 151 | R⁷ᴬ = —CH₃; R⁷ᴮ = H<br>¹H NMR (CDCl₃, 400 MHz) δ: 1.38 (t, 3H), 2.31 |

-continued

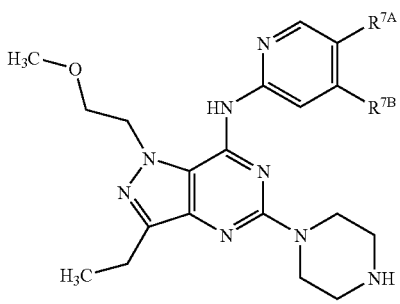

| Ex | |
|---|---|
| 152 | (s, 3H), 2.90 (q, 2H), 3.04 (m, 4H), 3.50 (s, 3H), 3.86 (1, 2H), 3.92 (m, 4H), 4.64 (m, 2H), 7.51 (d, 1H), 8.14 (m, 2H), 9.78 (s, 1H). LRMS: m/z ES+ 397, [MH]$^+$<br>$R^{7A}$ = H; $R^{7B}$ = —CH$_3$<br>$^1$H NMR (CDCl$_3$, 400 MHz) δ: 1.39 (t, 3H), 2.36 (s, 3H), 2.90 (q, 2H), 3.08 (m, 4H), 3.50 (s, 3H), 3.88 (t, 2H), 3.92 (m, 4H), 4.64 (m,2H), 6.79 (d, 1H), 8.13 (s, 1H), 8.19 (d, 1H), 9.80 (s, 1H). LRMS: m/z ES+: 397, [MH] |

EXAMPLE 153

3-Ethyl-1-(2-methoxyethyl)-N$^7$-(4-methylpyridin-2-yl)-N$^5$-(2-(pyrazol-1-yl)ethyl)-1H-pyrazolo[4,3-d]pyrimidine-5,7-diamine

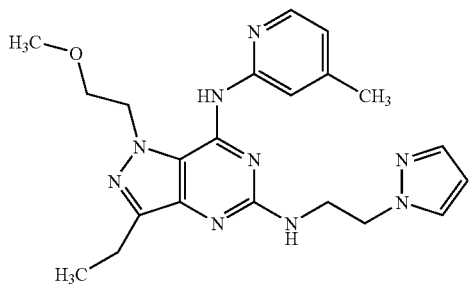

2-Amino-4-methylpyridine (118 mg, 1.09 mmol) was added to a solution of the dichloride of preparation 56 (10 mg, 0.36 mmol) in dimethylsulfoxide (1 mL) and the reaction mixture stirred at 70° C. for 18 hours. 2-(Pyrazol-1-yl)ethylamine (WO 02/066481, pg. 60, method 44) (202 mg, 1.82 mmol) and N-ethyldiisopropylamine (632 µL, 3.64 mmol) were added and the reaction mixture stirred at 120° C. for 18 hours. The reaction mixture was partitioned between ethyl acetate and water, the organics were separated, washed with water and brine, dried over magnesium sulphate and concentrated in vacuo to yield the title product.

$^1$H NMR (CD$_3$OD, 400 MHz) δ: 1.34 (t, 3H), 2.37 (s, 3H), 2.85 (q, 2H), 3.46 (s, 3H), 3.84 (m, 4H), 4.40 (t, 2H), 4.63 (br s, 2H), 6.23 (s, 1H), 6.90 (d, 1H), 7.47 (s, 1H), 7.53 (s, 1H), 8.12 (d, 1H), 8.23 (s, 1H). LRMS:m/z APCI+422, [MH]$^+$

EXAMPLE 154

(2S)-2-[3-Ethyl-1-(2-methoxyethyl)-7-(4-methylpyridin-2-ylamino)-1H-pyrazolo[4,3-d]pyrimidin-5-ylamino]propan-1-ol

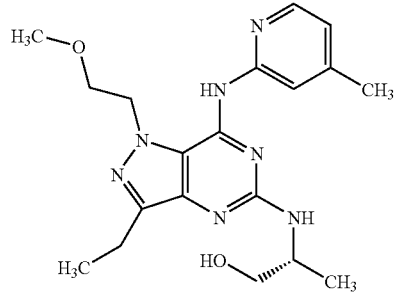

Made by the method of example 153 using (S)-2-aminopropanol as a starting material.

$^1$H NMR (CD$_3$OD, 400 MHz) δ: 1.32 (m, 6H), 2.49 (s, 3H), 2.82 (q, 2H), 3.39 (s, 3H), 3.65 (dd, 1H), 3.73 (dd, 1H), 3.87 (t, 2H), 4.16 (m, 1H), 4.86 (t, 2H), 7.10 (d, 1H), 7.75 (br s, 1H), 8.12 (d, 1H). LRMS:m/z APCI+386, [MH]$^+$

EXAMPLES 155 to 162

The following compounds of general formula shown below were prepared by the method of examples 1-28 using the appropriate monochloride starting materials (Preparation 72, 74, 117, 120, 122 and 123) and HNR$^3$R$^4$ amines (preparations 114 and 115), but were purified initially using a Phenomenex C$_{18}$ 5 µm column, and acetonitrile:water:trifluoroacetic acid (5:95:0.95 to 95:5:0.05) as eluant, followed by a Phenomenex C$_{18}$ 5 µm column and an elution gradient of acetonitrile:50 mM ammonium acetate (5:95 to 95:5) to give the title compounds.

| Ex | |
|---|---|
| | 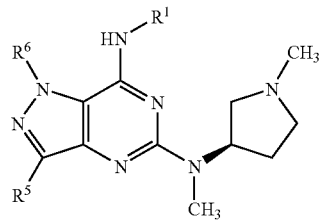 |
| | $R^1$ = 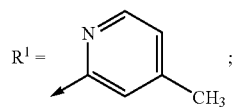 ;<br>$R^5$ = —CH$_3$; $R^6$ = —(CH$_2$)$_2$OCH$_3$<br>$^1$H NMR (CDCl$_3$, 400 MHz) δ: 2.30 (m, 2H), 2.36 (s, 3H), 2.43 (s, 3H), 2.71 (s, 3H), 3.0–3.5 (m, 4H), 3.17 (s, 3H), 3.46 (s, 3H), 3.82 (m, 2H), 4.60 (m, 2H), 5.40 (m, 1H), 6.77 (m, 1H), 8.17 (m, 2H). LRMS ES+ m/z 411 [MH]$^+$ |
| 156 | $R^1$ = 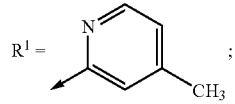 ; |

| Ex | |
|---|---|
| | R⁵ = —CH₃; R⁶ = —(CH₂)₂OCH₂CH₃<br>¹H NMR (CDCl₃, 400 MHz) δ: 1.16 (t, 3H), 2.02 (s, 3H), 2.1–2.4 (m, 2H), 2.36 (m, 3H), 2.43 (s, 3H), 2.59 (s, 3H), 2.68–3.14 (m, 4H), 3.59 (m, 2H), 3.87 (m, 2H), 4.60 (m, 2H), 5.53 (m, 1H), 6.77 (d, 1H), 8.15 (d, 1H), 8.27 (br s, 1H), 9.64 (br s, 1H).<br>LRMS ES+ m/z 425 [MH]⁺ |
| 157 | 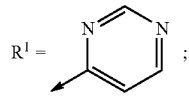<br>R⁵ = —CH₃; R⁶ = —(CH₂)₂OCH₂CH₃<br>¹H NMR (CDCl₃, 400 MHz) δ: 1.23 (t, 3H), 2.10–2.40 (m, 2H), 2.4 (s, 3H), 2.58 (s, 3H), 2.67 (s, 3H), 2.80–3.60 (m, 4H), 3.64 (m, 2H), 3.94 (m, 2H), 4.62 (m, 2H), 5.43 (m, 1H), 8.24 (m, 1H), 8.60 (m, 1H), 8.85 (m, 1H).<br>LRMS ES+ m/z 412 [MH]⁺ |
| 158 | 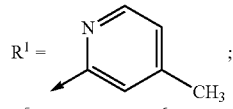<br>R⁵ = —CH₂CH₃; R⁶ = —(CH₂)₂OCH₂CH₃<br>LRMS ES+ m/z 439 [MH]⁺ |
| 159 | 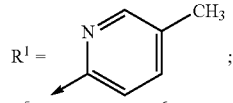<br>R⁵ = —CH₂CH₃; R⁶ = —(CH₂)₂OCH₂CH₃<br>¹H NMR (CDCl₃, 400 MHz) δ: 1.23 (t, 3H), 1.39 (t, 3H), 2.30–2.40 (m, 2H), 2.37 (s, 3H), 2.74 (s, 3H), 2.86 (q, 2H), 3.17 (s, 3H), 3.34 (d, 2H), 3.49 (m, 1H), 3.61 (q, 2H), 3.88 (m, 2H), 4.63 (m, 2H), 5.38 (m, 1H), 8.15 (s, 1H), 8.28 (d, 1H). LRMS ES+ m/z 439 [MH]⁺ |
| 160 | 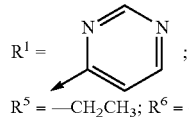<br>R⁵ = —CH₂CH₃; R⁶ = —(CH₂)₂OCH₂CH₃<br>¹H NMR (CDCl₃, 400 MHz) δ: 1.24 (t, 3H), 1.39 (t, 3H), 2.1–2.2 (m, 2H), 2.64 (s, 3H), 2.90 (q, 2H), 3.07–3.42 (m, 4H), 3.19 (s, 3H), 3.67 (m, 2H), 3.88 (m, 2H), 4.61 (m, 2H), 5.44 (m, 1H), 8.24 (d, 1H), 8.60 (d, 1H), 8.86 (s, 1H).<br>LRMS ES+ m/z 426 [MH]⁺ |
| | 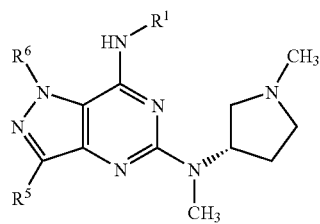 |
| 161 | 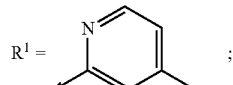<br>R⁵ = —CH₃; R⁶ = —(CH₂)₂OCH₂CH₃<br>¹H NMR (CDCl₃, 400 MHz) δ: 1.18 (t, 3H), 2.25 (m, 2H), 2.37 (s, 3H), 2.43 (s, 3H), 2.57 (s, 3H), 2.80–3.10 (m, 4H), 3.20 (s, 3H), 3.60 (m, 2H), 3.86 (m, 2H), 4.62 (m, 2H), 5.55 (m, 1H), 6.79 (d, 1H), 8.18 (d, 1H), 8.30 (s, 1H), 9.63 (br s 1H). LRMS ES+ m/z 425 [MH]⁺ |

| Ex | |
|---|---|
| 162 | R¹ = (pyridine with CH₃);<br>R⁵ = —CH₂CH₃; R⁶ = —(CH₂)₂OCH₂CH₃<br>¹H NMR (CDCl₃, 400 MHz) δ: 1.19 (t, 3H), 1.39 (t, 3H), 2.1–2.3 (m, 2H), 2.37 (s, 3H), 2.55 (s, 3H), 2.80–3.10 (m, 4H), 2.89 (q, 2H), 3.21 (s, 3H), 3.62 (q, 2H), 3.89 (m, 2H), 4.63 (m, 2H), 5.50 (m, 1H), 6.80 (d, 1H), 8.19 (d, 1H), 8.30 (s, 1H), 9.68 (br s 1H).<br>LRMS ES+ m/z 439 [MH]⁺ |

Examples 155 to 160 prepared using the pyrrolidine of preparation 114 as the HNR³R⁴ amine. Examples 161 and 162 were prepared using the pyrrolidine of preparation 115 as the HNR³R⁴ amine

EXAMPLE 163

N-[3-Methyl-5-(piperazin-1-yl)-1-(tetrahydropyran-2-ylmethyl)-1H-pyrazolo[4,3-d]pyrimidin-7-yl]-5-methylpyridin-2-ylamine dihydrochloride

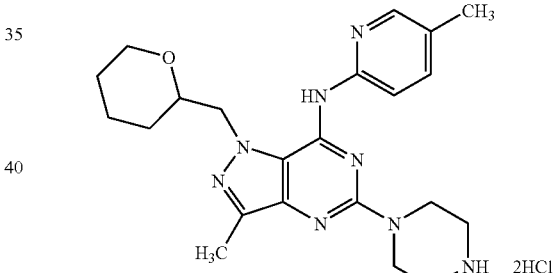

Potassium carbonate (57 mg, 0.33 mmol) and 2-(bromomethyl)tetrahydro-2H-pyran (50 μL, 0.39 mmol) were added to a solution of the protected piperazine of preparation 94 (150 mg, 0.35 mmol) in N,N-dimethylformamide (10 mL) and the reaction mixture stirred at 90° C. for 18 hours. The reaction mixture was partitioned between ethyl acetate (50 mL) and water (50 mL), the organics were separated, dried over magnesium sulphate and concentrated in vacuo. The crude product was purified by column chromatography on silica gel using pentane:ethyl acetate 100:0 to 40:60. The product was dissolved in dichloromethane (10 mL), and hydrogen chloride bubbled through until saturated, and the reaction stirred at room temperature for 3 hours. The solution was concentrated in vacuo, the product triturated with ether, the ether decanted off, and the product dried in vacuo.

¹H NMR (D₂O, 400 MHz) δ: 1.20-1.90 (m, 6H), 2.31 (s, 3H), 2.38 (s, 3H), 3.49 (m, 4H), 3.50 (m, 1H), 3.76 (m, 1H), 4.00 (m, 4H), 4.18 (m, 1H), 4.50 (m, 2H), 7.62 (d, 1H), 8.04 (d, 1H), 8.13 (s, 1H). LRMS:m/z APCI+423, [MH]⁺

EXAMPLES 164-177

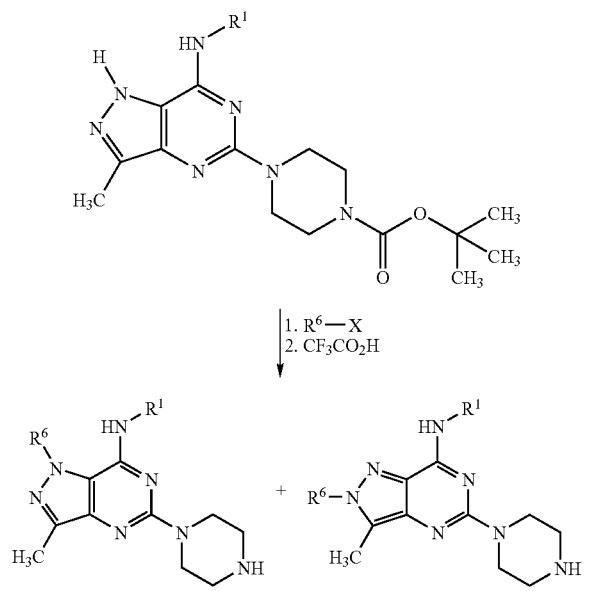

1. R⁶—X
2. CF₃CO₂H

Potassium carbonate (59 mg, 0.42 mmol) and the appropriate R⁶ bromide (0.35 mmol) were added to a solution of the protected piperazine of preparation 97 (150 mg, 0.35 mmol) in N,N-dimethylformamide (3 mL) and the reaction mixture shaken at 550 rpm at 100° C. for 36 hours. The reaction mixture was concentrated in vacuo. The product was taken up in dichloromethane (2 mL) and trifluoroacetic acid (2 mL) added. The reaction mixture was shaken for 2 hours and concentrated in vacuo. The residues were purified using a Phenomenex Luna C18 2×15 cm 5 μm column eluting with acetonitrile:diethylamine to afford the title compounds.

| Ex | |
|---|---|
| | 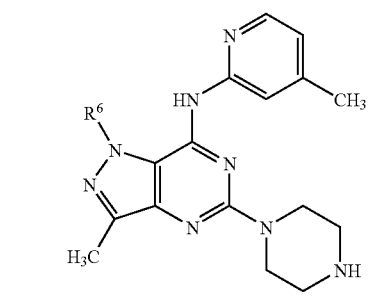 |
| 164 | R⁶ = —(CH₂)₂OCH₂CH₃<br>¹H NMR (DMSO-d₆, 400 MHz) δ: 1.07 (t, 3H), 2.31 (s, 3H), 2.41 (s, 3H), 2.76 (t, 4H), 3.51 (q, 2H), 3.62 (t, 4H), 3.77 (1, 2H), 4.57 (t, 2H), 6.89 (d, 1H), 8.02 (s, 1H), 8.16 (d, 1H). LRMS: m/z ES+ 397, [MH]⁺ |
| 165 | R⁶ = —(CH₂)₂OCH₃<br>¹H NMR (DMSO-d₆, 400 MHz) δ: 2.30 (s, 3H), 2.31 (s, 3H), 2.75 (t, 4H), 3.33 (s, 3H), 3.60 (t, 4H), 3.74 (t, 2H), 4.58 (t, 2H), 6.90 (d, 1H), 7.96 (s, 1H), 8.17 (d, 1H). LRMS: m/z ES+ 383, [MH]⁺ |

-continued

| Ex | |
|---|---|
| 166 | R⁶ = [tetrahydrofuran-2-ylmethyl]<br>¹H NMR (DMSO-d₆, 400 MHz) δ: 1.68 (m, 2H), 1.79 (m, 1H), 2.02 (m, 1H), 2.31 (s, 6H), 2.75 (t, 4H), 3.61 (t, 4H), 3.69 (m, 1H), 3.90 (m, 1H), 4.24 (m, 1H), 4.44 (m, 1H), 4.61 (m, 1H), 6.89 (d, 1H), 8.00 (s, 1H), 8.17 (d, 1H). LRMS: m/z ES+ 409, [MH]⁺ |
| 167 | R⁶ = [pyridin-3-ylmethyl]<br>¹H NMR (DMSO-d₆, 400 MHz) δ: 2.28 (s, 3H), 2.32 (s, 3H), 2.76 (m, 4H), 3.26 (s, 2H), 3.61 (t, 4H), 6.90 (d, 1H), 7.42 (m, 1H), 7.53 (d, 1H), 7.88 (t, 1H), 7.98 (s, 1H), 8.18 (d, 1H), 8.61 (d 1H). LRMS: m/z ES+ 416, [MH]⁺ |
| 168 | R⁶ = [tetrahydropyran-2-ylmethyl]<br>LRMS: m/z ES+ 423, [MH]⁺ |
| 169 | R⁶ = [tetrahydrofuran-3-ylmethyl]<br>¹H NMR (DMSO-d₆, 400 MHz) δ: 1.64 (m, 2H), 1.93 (m, 2H), 2.40 (m, 3H), 2.45 (s, 3H), 2.80–2.90 (m, 4H), 3.48 (m, 2H), 3.65 (m, 2H), 3.78 (m, 2H), 4.20 (m,1H), 4.35 (m, 2H), 7.09 (m, 1H), 7.96 (m, 1H), 8.28 (m, 1H) 8.80 (br, 1H). LRMS ES+ m/z 409 [MH]⁺ |
| 170 | R⁶ = —CH₂CF₃<br>¹H NMR (DMSO-d₆, 400 MHz) δ: 2.38 (s, 3H), 2.45 (s, 3H), 3.24 (m, 4H), 3.90 (m, 4H), 5.41 (m, 2H), 7.04 (m, 1H), 8.08 (m, 1H), 8.23 (m, 1H). LRMS ES4+ m/z 407 [MH]⁺ |
| 171 | R⁶ = [tetrahydropyran-2-ylmethyl]<br>¹H NMR (DMSO-d₆, 400 MHz) δ: 1.28 (m, 1H), 1.43 (m, 3H), 1.59 (m, 1H), 1.76 (m, 1H), 2.34 (s, 3H), 2.41 (s, 3H), 2.53 (m, 1H), 2.77 (t, 4H), 3.64 (1, 4H), 3.80 (m, 2H), 4.29 (m, 2H), 6.94 (d, 1H), 8.19 (d, 1H), 8.25 (s, 1H). LRMS: m/z ES+ 423, [MH]⁺ |

-continued

| Ex | | |
|---|---|---|
| 172 | $R^6 = -(CH_2)_2OCH_2CH_3$ $^1$H NMR (DMSO-$d_6$, 400 MHz) δ: 1.02 (t, 3H), 2.34 (s, 3H), 2.42 (s, 3H), 2.78 (t, 4H), 3.39 (q, 2H), 3.64 (t, 4H), 3.80 (t, 2H), 4.43 (t, 2H), 6.94 (d, 1H), 8.18 (d, 1H), 8.25 (s, 1H). LRMS: m/z ES+ 397, [MH]$^+$ | |
| 173 | $R^6 =$ 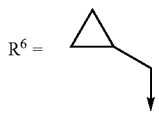 $^1$H NMR (CD$_3$OD, 400 MHz) δ: 0.48 (q, 2H), 0.63 (q, 2H), 1.37 (m, 1H), 2.41 (s, 3H), 2.53 (s, 3H), 3.13 (t, 4H), 3.95 (t, 4H), 4.23 (d, 2H), 6.97 (d, 1H), 8.18 (d, 1H), 8.32 (s, 1H). LRMS: m/z ES+ 379, [MH]$^+$ | |
| 174 | $R^6 = -(CH_2)_2CH(CH_3)_2$ $^1$H NMR (DMSO-$d_6$, 400 MHz) δ: 0.91 (s, 3H), 0.93 (s, 3H), 1.59 (m, 1H), 1.72 (q, 2H), 2.34 (s, 3H), 2.42 (s, 3H), 2.76 (t, 4H), 3.64 (t, 4H), 4.29 (t, 2H), 6.94 (d, 1H), 8.18 (d, 1H), 8.25 (s, 1H). LRMS: m/z ES+ 395, [MH]$^+$ | |
| 175 | $R^6 =$ 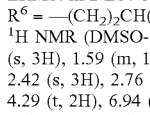 $^1$H NMR (CD$_3$OD, 400 MHz) δ: 1.99 (m, 2H), 2.31 (m, 2H), 2.43 (s, 3H), 2.56 (s, 3H), 3.27 (t, 4H), 3.66 (t, 2H), 4.06 (t, 4H), 4.14 (m, 2H), 4.74 (m, 1H), 7.06 (d, 1H), 8.19 (d, 1H), 8.25 (s, 1H). LRMS: m/z ES+ 409, [MH]$^+$ | |
| 176 | $R^6 =$ 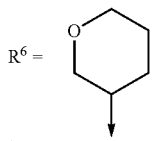 $^1$H NMR (CD$_3$OD, 400 MHz) δ: 2.43 (s, 3H), 2.50 (s, 3H), 3.33 (t, 4H), 4.08 (t, 4H), 4.87 (s, 2H), 6.99 (d, 1H), 7.16 (d, 1H), 7.36 (t, 1H), 7.81 (t, 1H), 8.18 (d, 1H), 8.23 (s, 1H), 8.54 (d 1H). LRMS: m/z ES+ 416, [MH]$^+$ | |
| 177 | $R^6 =$ 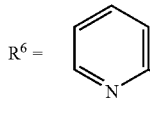 $^1$H NMR (DMSO-$d_6$, 400 MHz) δ: 1.82 (q, 4H), 1.98 (m, 2H), 2.34 (s, 3H), 2.41 (s, 3H), 2.77 (t, 4H), 2.87 (m, 1H), 3.64 (t, 4H), 4.30 (d, 2H), 7.94 (d, 1H), 8.18 (d, 1H), 8.25 (s, 1H). LRMS: m/z ES+ 393, [MH]$^+$ | |

NOTES FOR EXAMPLES 164 to 177

EXAMPLE 167 and 176

2-(Bromomethyl)pyridine (U.S. Pat. No. 6,465,486, pg. 12, ex. 5) used as the $R^6$ bromide

EXAMPLE 169

3-(Bromomethyl)tetrahydrofuran (WO 99/45006, pg. 117, preparation 9) used as the $R^6$ bromide

EXAMPLE 175

3-Bromotetrahydropyran (Preparation 125) used as the $R^6$ bromide

EXAMPLE 178

N-[3-Isopropyl-1-(2-methoxyethyl)-5-(piperazin-1-yl)-1H-pyrazolo[4,3-d]pyrimidin-7-yl]-4-methylpyridin-2-ylamine bis(trifluoroacetate)

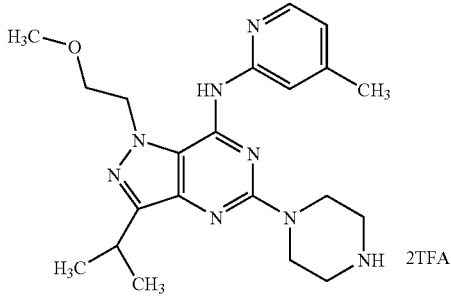

A solution of the BOC protected compound from preparation 92 (150 mg, 0.3 mmol) in dichloromethane (5 mL) and trifluoroacetic acid (5 mL) was stirred at room temperature for 2 hours. The reaction mixture was concetrated in vacuo and the residue azeotroped with toluene. The product was purified by column chromatography on silica gel using dichloromethane:methanol (100:0 to 95:5) to afford the title compound as a gum, 30 mg.

$^1$H NMR (DMSO-$d_6$, 400 MHz) δ: 1.34 (d, 6H), 2.31 (s, 3H), 2.86 (m, 4H), 3.18 (m, 1H), 3.35 (s, 3H), 3.62 (m, 4H), 3.74 (m, 2H), 4.58 (m, 2H), 6.90 (s, 1H), 7.99 (s, 1H), 8.17 (d, 1H). LRMS:m/z APCI+411, [MH]$^+$

EXAMPLE 179

N-[3-Isopropyl-1-(2-methoxyethyl)-5-(piperazin-1-yl)-1H-pyrazolo[4,3-d]pyrimidin-7-yl]-5-methylpyridin-2-ylamine

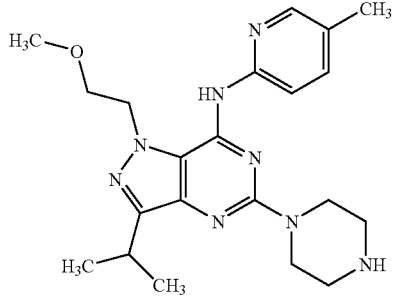

A solution of the BOC protected compound from preparation 93 (150 mg, 0.3 mmol) in dichloromethane (5 mL) and trifluoroacetic acid (5 mL) was stirred at room temperature for 2 hours. The reaction mixture was concentrated in vacuo and the residue azeotroped with toluene. The product was purified by column chromatography on silica gel using ethyl acetate:methanol:diethylamine (100:0:0 to 96:2:2) to afford the title compound, 14.5 mg.

¹H NMR (DMSO-d₆, 400 MHz) δ: 1.34 (d, 6H), 2.26 (s, 3H), 2.95 (s, 4H), 3.18 (m, 1H), 3.35 (s, 3H), 3.71 (m, 4H), 3.76 (t, 2H), 4.60 (t, 2H), 7.63 (d, 1H), 7.97 (d, 1H), 8.16 (s, 1H). LRMS:m/z APCI+411, [MH]⁺

EXAMPLE 180

N-[3-Ethyl-1-(2-methoxyethyl)-5-(piperazin-1-yl)-1H-pyrazolo[4,3-d]pyrimidin-7-yl]-5-methyl-2H-pyrazol-3-ylamine

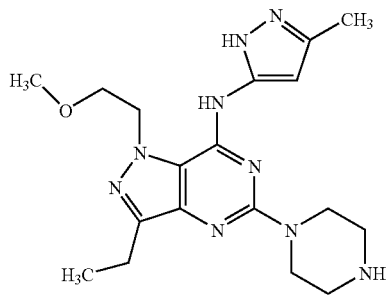

The BOC protected compound of preparation 95 was triturated with hydrogen chloride in ether (8 mL, 2M) for 30 minutes. The resulting gum was washed with ether, dissolved in sodium hydroxide (1M) and extracted with ethyl acetate (2×10 mL). The organics were combined, dried over magnesium sulphate and concentrated in vacuo to give the product.

¹H NMR (DMSO-d₆, 400 MHz) δ: 1.25 (t, 3H), 2.20 (s, 3H), 2.72 (m, 6H), 3.30 (s, 3H), 3.60 (m, 4H), 3.72 (t, 2H), 4.56 (m, 2H), 6.36 (s, 1H), 9.42 (s, 1H). LRMS:m/z ES+: 386, [MH]⁺,

EXAMPLE 181

[1-(2-Ethoxyethyl)-5-(N-ethyl-N-methylamino)-7-(4-methylpyridin-2-ylamino)-1H-pyrazolo[4,3-d]pyrimidin-3-yl]methanol

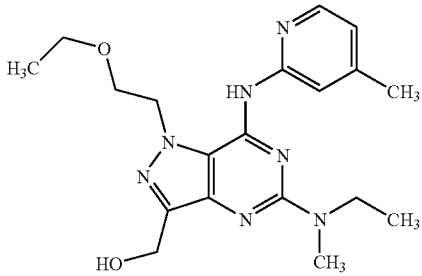

N-Ethyldiisopropylamine (1.3 mL, 7.5 mmol) and N-ethylmethylamine (642 μL, 7.5 mmol) were added to a solution of the monochloride of preparation 106 (544 mg, 1.5 mmol) in dimethylsulfoxide (4 mL) and the reaction mixture stirred at 120° C. for 18 hours. The reaction mixture was cooled and partitioned between dichloromethane (200 mL) and water (50 mL). The organic layer was washed with water (2×50 mL), dried over magnesium sulphate and concentrated in vacuo. The crude product was purified by column chromatography on silica gel eluting with dichloromethane:methanol 100:0 to 94:6 to yield the title product, 525 mg.

¹H NMR (CD₃OD, 400 MHz) δ: 1.10 (t, 3H), 1.22 (t, 3H), 2.39 (s, 3H), 3.21 (s, 3H), 3.60 (q, 2H), 3.78 (q, 2H), 3.89 (m, 2H), 4.76 (t, 2H), 4.80 (s, 2H), 6.92 (d, 1H), 8.15 (d, 1H), 8.19 (s, 1H). LRMS APCI+m/z 386 [MH]⁺

EXAMPLE 182

[5-Dimethylamino-1-(2-ethoxyethyl)-7-(4-methylpyridin-2-ylamino)-1H-pyrazolo[4.3-d]pyrimidin-3-yl]methanol

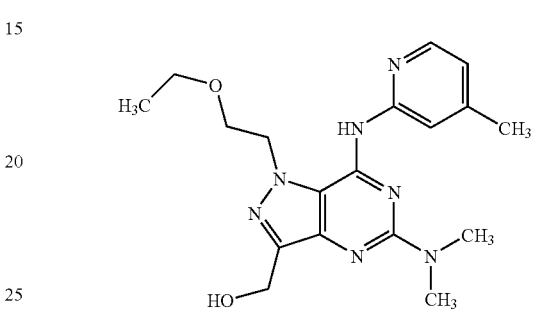

The title compound was prepared by the method of example 181 using dimethylamine as a starting material.

¹H NMR (CD₃OD, 400 MHz) δ: 1.10 (t, 3H), 2.38 (s, 3H), 3.23 (s, 6H), 3.58 (q, 2H), 3.87 (t, 2H), 4.66 (m, 2H), 4.81 (m, 2H), 6.93 (d, 1H), 8.15 (d, 1H), 8.41 (s, 1H)

EXAMPLE 183

N-[1-(2-Ethoxyethyl)-3-methoxymethyl-5-(piperazin-1-yl)-1H-pyrazolo[4,3-d]pyrimidin-7-yl]-4-methylpyridin-2-ylamine dihydrochloride

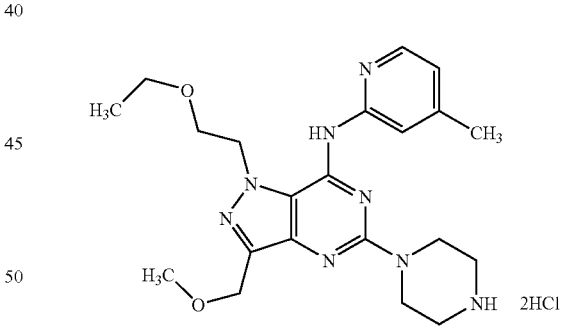

The compound of preparation 111 (150 mg, 0.35 mmol) was added to a solution of 25% sodium methoxide solution in methanol (350 μL, 1.4 mmol) in 1-methyl-2-pyrrolidinone (3.5 mL) and the reaction mixture left at room temperature for 15 minutes. The reaction mixture was quenched with acetic acid (60 μL), treated with N-ethyldiisopropylamine (174 μL) and the solution diluted to a volume of 9 mL with 1-methyl-2-pyrrolidinone. This solution (3 mL) was treated with tert-butyl piperazine-1-carboxylate (93 mg, 0.5 mmol) and the reaction mixture sealed and heated to 110° C. for 12 hours. The reaction mixture was concentrated in vacuo and the crude product partitioned between dichloromethane (10 mL) and water (10 mL). The layers were separated and the organic phase dried over magnesium sulphate and evaporated in vacuo. The product was dissolved in a mixture of dichloromethane (2 mL) and trifluoroacetic acid (2 mL) and left for 1 hour. The reaction mixture was concentrated in vacuo and partitioned between dichloromethane and sodium hydrogencarbonate solution. The organic layer was separated and concentrated in vacuo. The crude product was purified by column chromatography on silica gel eluting with ethyl acetate:methanol:dichloromethane 96:2:2. The product was dissolved in ether, treated with 2M ethereal HCl, and the solution evaporated in vacuo to yield the title product, 53 mg.

$^1$H NMR (D$_2$O, 400 MHz) δ: 0.95 (t, 3H), 2.45 (s, 3H), 3.30 (m, 4H), 3.35 (s, 3H), 3.48 (q, 2H), 3.84 (t, 2H), 3.95 (m, 4H), 4.72 (s, 2H), 4.75 (m, 2H), 7.21 (d, 1H), 7.55 (s, 1H), 8.10 (d, 1H). LRMS:m/z APCI+427, [MH]$^+$

EXAMPLE 184

N-[1-(2-Ethoxyethyl)-3-methoxymethyl-5-((3R)-(3-methylpiperazin-1-yl))-1H-pyrazolo[4,3-d]pyrimidin-7-yl]-4-methylpyridin-2-ylamine dihydrochloride

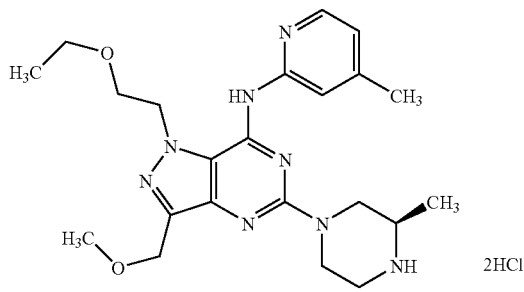

This compound was made by the method of example 183 using (R)-2-methyl-piperazine.

$^1$H NMR (D$_2$O, 400 MHz) δ: 0.92 (t, 3H), 1.32 (d, 3H), 2.45 (s, 3H), 3.17 (m, 2H), 3.35 (s, 3H), 3.40-3.50 (m, 5H), 3.87 (m, 2H), 4.46 (m, 2H), 4.68 (s, 2H), 4.73 (m, 2H), 7.21 (d, 1H), 7.57 (s, 1H), 8.10 (d, 1H). LRMS:m/z APCI+441, [MH]$^+$

EXAMPLE 185

1-(2-Ethoxyethyl)-3-methoxymethyl-N$^5$,N$^5$-dimethyl-N$^7$-(4-methylpyridin-2-yl)-1H-pyrazolo[4,3-d]pyrimidine-5,7-diamine

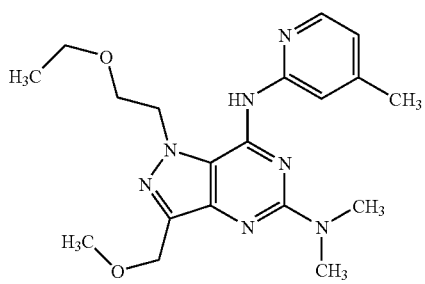

This compound was made by the method of example 183 using N,N-dimethylamine. After heating the reaction mixture was concentrated in vacuo and the crude product purified by column chromatography on silica gel eluting with dichloromethane:methanol 98:2 to yield the title product.

$^1$H NMR (CD$_3$OD, 400 MHz) δ: 1.11 (t, 3H), 2.39 (s, 3H), 3.24 (s, 6H), 3.44 (s, 3H), 3.60 (q, 2H), 3.90 (t, 2H), 4.70 (m, 4H), 6.93 (d, 1H), 8.15 (d, 1H), 8.41 (s, 1H). LRMS:m/z APCI+386, [MH]$^+$

EXAMPLE 186

N-[1-(2-Ethoxyethyl)-3-ethoxymethyl-5-(piperazin-1-yl)-1H-pyrazolo[4,3-d]pyrimidin-7-yl]-4-methylpyridin-2-ylamine dihydrochloride

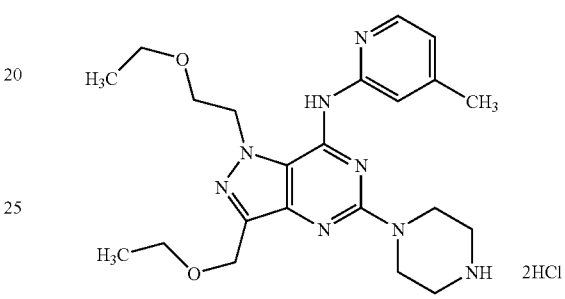

This compound was made by the method of example 183 using 21% sodium ethoxide in ethanol. The crude product was purified by column chromatography on silica gel eluting with dichloromethane:methanol 100:0 to 94:6. Appropriate combined fractions were concentrated in vacuo, dissolved in ether and treated with 2M hydrogen chloride in ether. The reaction mixture was concentrated in vacuo to yield the title product.

$^1$H NMR (D$_2$O, 400 MHz) δ: 0.88 (t, 3H), 1.08 (t, 3H), 2.39 (s, 3H), 3.26 (m, 4H), 3.42 (q, 2H), 3.58 (q, 2H), 3.83 (t, 2H), 3.90 (m, 4H), 4.70 (m, 4H), 7.14 (d, 1H), 7.50 (s, 1H), 8.04 (d, 1H). LRMS:m/z APCI+441, [MH]$^+$

EXAMPLE 187

N-[1-(2-Ethoxyethyl)-3-ethoxymethyl-5-((3R)-(3-methylpiperazin-1-yl))-1H-pyrazolo[4,3-d]pyrimidin-7-yl]-4-methylpyridin-2-ylamine dihydrochloride

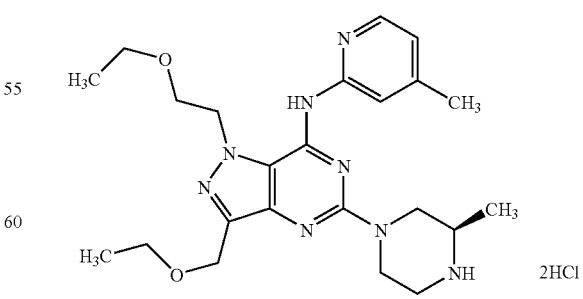

This compound was made by the method of example 183 using 21% sodium ethoxide in ethanol and (R)-2-methylpiperazine.

¹H NMR (D₂O, 400 MHz) δ: 0.88 (t, 3H), 1.06 (t, 3H), 1.28 (d, 3H), 2.40 (s, 3H), 3.12 (m, 2H), 3.30-3.50 (m, 5H), 3.55 (q, 2H), 3.82 (t, 2H), 4.42 (m, 2H), 4.73 (m, 4H), 7.14 (d, 1H), 7.50 (s, 1H), 8.05 (d, 1H). LRMS:m/z APCI+455, [MH]⁺

EXAMPLE 188

1-(2-Ethoxyethyl)-3-ethoxymethyl-N⁵,N⁵-dimethyl-N⁷-(4-methylpyridin-2-yl)-1H-pyrazolo[4,3-d]pyrimidine-5,7-diamine

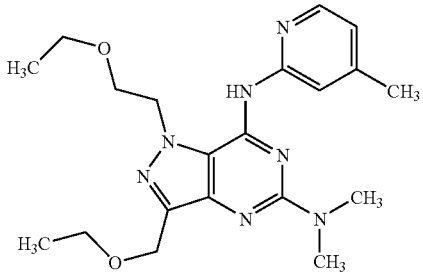

This compound was made by the method of example 183 using 21% sodium ethoxide in ethanol and dimethylamine.

¹H NMR (CD₃OD, 400 MHz) δ: 1.09 (t, 3H), 1.22 (s, 3H), 2.38 (s, 3H), 3.22 (s, 6H), 3.57 (q, 2H), 3.64 (q, 2H), 3.87 (t, 2H), 4.68 (t, 2H), 4.72 (s, 2H), 6.93 (d, 1H), 8.15 (d, 1H), 8.41 (s, 1H). LRMS:m/z APCI+400, [MH]⁺

EXAMPLE 189

N-[1-(2-Ethoxyethyl)-3-methoxymethyl-5-((3R)-3-methylpiperazin-1-yl)-1H-pyrazolo[4,3-d]pyrimidin-7-yl]pyrimidin-4-ylamine dihydrochloride

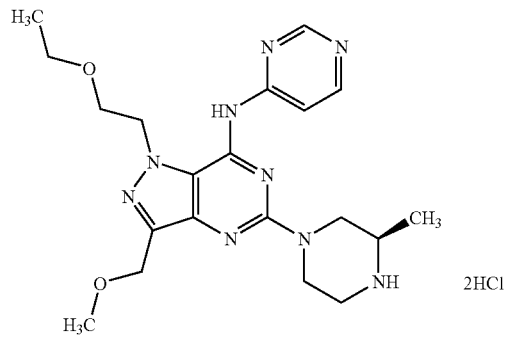

This compound was made by the method of example 183 using (R)-2-methylpiperazine and the monochloro compound of preparation 112 as starting materials.

¹H NMR (CD₃OD, 400 MHz) δ: 1.22 (m, 6H), 2.64-3.17 (br m, 4H), 3.44 (s, 3H), 3.67 (q, 2H), 3.78, 4.35 (2d, 1H), 3.91 (t, 2H), 4.60 (d, 2H), 4.78 (m, 4H), 8.21 (d, 1H), 8.60 (d, 1H), 8.83 (s, 1H). LRMS APCI+m/z 428 [MH]⁺

EXAMPLE 190

N-[1-(2-Ethoxyethyl)-3-methoxymethyl-5-(piperazin-1-yl)-1H-pyrazolo[4,3-d]pyrimidin-7-yl]pyrimidin-4-ylamine dihydrochloride

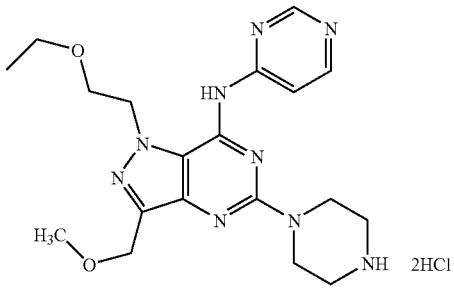

This compound was made by the method of example 183 using tert-butyl piperazine-1-carboxylate and the monochloro compound of preparation 112 as starting materials.

¹H NMR (CD₃OD, 400 MHz) δ: 1.21 (t, 3H), 2.97 (m, 4H), 3.43 (s, 3H), 3.66 (q, 2H), 3.81 (m, 4H), 3.94 (t, 2H), 4.83 (m, 4H), 8.20 (d, 1H), 8.59 (d, 1H), 8.80 (s, 1H). LRMS APCI+m/z 414 [MH]⁺

EXAMPLE 191

1-(2-Ethoxyethyl)-N⁵,3-dimethyl-N⁵-[(3S)-1-methylpyrrolidin-3-yl]-N⁷-pyrimidin-4-yl-1H-pyrazolo[4,3-d]pyrimidine-5,7-diamine

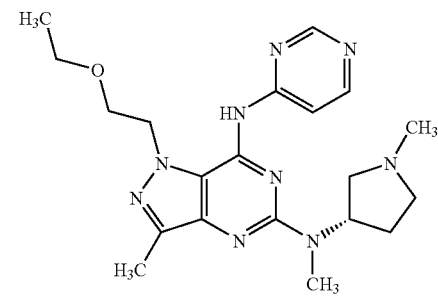

The monochloride of preparation 72 (115 mg, 0.35 mmol) was combined with the amine from preparation 115 (197 mg, 1.73 mmol) and N-ethyldiisopropylamine (0.3 mL, 1.73 mmol) in dimethylsulfoxide (4 mL) and the reaction mixture stirred at 120° C. for 16 hours. The cooled reaction mixture was diluted with ethyl acetate (10 mL) and water (10 mL). The organic phase was separated and the aqueous was further extracted with ethyl acetate (3×10 mL). The combined organic solutions were washed with water (3×15 mL), dried over magnesium sulphate and concentrated in vacuo.

The crude product was purified by column chromatography on silica gel using dichloromethane:methanol 99:1 to 85:15 to yield a gum, 21 mg.

$^1$H NMR (CD$_3$OD, 400 MHz) δ: 1.20 (t, 3H), 2.01-2.28 (m, 2H), 2.42 (s, 3H), 2.48 (s, 3H), 2.76 (m, 2H), 2.95 (m, 2H), 3.16 (s, 3H), 3.64 (q, 2H), 3.87 (t, 2H), 4.63 (t, 2H), 5.32 (m, 1H), 8.31 (d, 1H), 8.59 (d, 1H), 8.79 (s, 1H). LRMS:m/z ES+: 412, [MH]$^+$

EXAMPLE 192

1-(2-Ethoxyethyl)-3-ethyl-N$^5$-methyl-N$^7$-(5-methylpyridin-2-yl)-N$^5$-[(3S)-1-methylpyrrolidin-3-yl]-1H-pyrazolo[4,3-d]pyrimidine-5,7-diamine

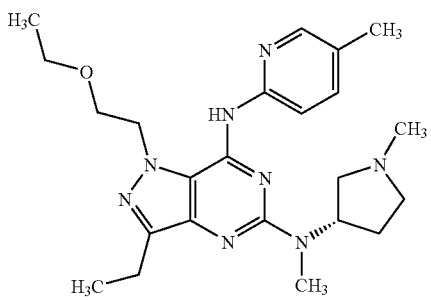

The title compound was made from the dichloro compound from preparation 54, the amine from preparation 115, and 2-amino-5-methylpyridine, following the method of example 131.

$^1$H NMR (CDCl$_3$, 400 MHz) δ: 1.20 (t, 3H), 1.39 (t, 3H), 2.1-2.3 (m, 2H), 2.37 (s, 3H), 2.54 (s, 3H), 2.91 (m, 2H), 2.80-3.25 (m, 4H), 3.20 (s, 3H), 3.61 (m, 2H), 3.95 (m, 2H), 4.63 (m, 2H), 5.50 (m, 1H), 7.53 (d, 1H), 8.14 (s, 1H), 8.28 (d, 1H) 9.65 (br s, 1H). HRMS:m/z ES+: 439.29, [MH]$^+$

EXAMPLE 193

1-(2-Ethoxyethyl)-3-ethyl-N$^5$-methyl-N$^5$-[(3S)-1-methylpyrrolidin-3-yl]-N$^7$-pyrimidin-4-yl-1H-pyrazolo[4,3-d]pyrimidine-5,7-diamine

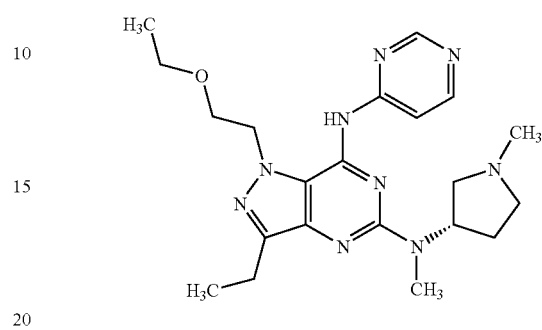

The title compound was made from the dichloro compound from preparation 54, the amine from preparation 115 and 4-aminopyrimidine, following the method of example 131.

$^1$H NMR (CDCl$_3$, 400 MHz) δ: 1.26 (t, 3H), 1.39 (t, 3H), 2.20-2.40 (m, 2H), 2.68 (s, 3H), 2.90 (q, 2H), 3.11 (s, 3H), 3.05-3.40 (m, 4H), 3.67 (q, 2H), 3.92 (m, 2H), 4.64 (m, 2H), 5.46 (m, 1H), 8.28 (d, 1H), 8.60 (d, 1H), 8.88 (s, 1H). HRMS:m/z ES+: 426.27, [MH]$^+$

EXAMPLES 194-215

The appropriate chloro compound (preparations 72, 120, 134, 137, 139, 142, 143, 144, 159 and 161) (1 eq), the appropriate HNR$^3$R$^4$ amine (3-5 eq) and N-ethyldiisopropylamine (3-5 eq) were dissolved in dimethylsulfoxide (3.5-6.9 mL.mmol$^{-1}$) and the reaction mixture stirred at 120° C. for 18 hours in a sealed vessel. The reaction mixture was partitioned between water and dichloromethane, the organic phase was separated and the aqueous washed with dichloromethane (×2). The organics were combined, dried over magnesium sulphate and concentrated in vacuo. The residue was purified by column chromatography on silica gel eluting with dichloromethane:methanol:0.880 ammonia 98:2:0 to 90:10:1 to yield the title product.

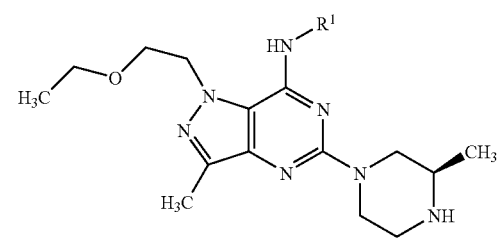

| No. | R$^1$ | Data |
|---|---|---|
| 194A | 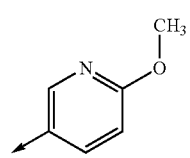 | $^1$H NMR (CD$_3$OD, 400 MHz) δ: 1.12 (t, 3H), 1.16 (d, 3H), 2.40 (s, 3H), 2.61 (m, 1H), 2.85 (m, 2H), 2.94 (m, 1H), 3.08 (m, 1H), 3.58 (q, 2H), 3.87 (t, 2H), 3.92 (s, 3H), 4.51 (m, 2H), 4.65 (m, 2H), 6.85 (m, 1H), 7.95 (m, 1H), 8.42 (m, 1H) LRMS: m/z APCl+ 427 [MH]$^+$ |

| No. | | Data |
|---|---|---|
| 195[B] | (5-methoxypyridin-2-yl) | $^1$H NMR (CD$_3$OD, 400 MHz) δ: 1.13 (m, 6H), 2.40 (s, 3H), 2.58 (m, 1H), 2.82 (m, 2H), 2.95 (m, 1H), 3.02 (m, 1H), 3.60 (q, 2H), 3.87 (m, 5H), 4.53 (m, 2H), 4.63 (t, 2H), 7.44 (m, 1H), 8.01 (m, 1H), 8.18 (m, 1H). LRMS: m/z APCl+ 427 [MH]$^+$ |
| 196[B] | (6-methoxypyridin-2-yl) | $^1$H NMR (CD$_3$OD, 400 MHz) δ: 1.14 (d, 3H), 1.20 (t, 3H), 2.40 (s, 3H), 2.58 (m, 1H), 2.82 (m, 2H), 2.95 (m, 1H), 3.02 (m, 1H), 3.66 (q, 2H), 3.87 (t, 2H), 3.90 (s, 3H), 4.54 (m, 2H), 4.60 (t, 2H), 6.44 (m, 1H), 7.63 (m, 1H), 7.76 (m, 1H) LRMS: m/z APCl+ 427 [MH]$^+$ |
| 197[E] | (6-methylpyridin-2-yl) | $^1$H NMR (CD$_3$OD, 400 MHz) δ: 1.20 (m, 6H), 2.41 (s, 3H), 2.46 (s, 3H), 2.61 (m, 1H), 2.83 (m, 2H), 3.00 (m, 2H), 3.61 (q, 2H), 3.87 (t, 2H), 4.55 (m, 2H), 4.65 (t, 2H), 6.93 (d, 1H), 7.67 (dd, 1H), 8.05 (d, 1H). LRMS: m/z ES+ 411 [MNa]$^+$ |
| 198[3] | (4,6-dimethylpyridin-2-yl) | $^1$H NMR (CD$_3$OD, 400 MHz) δ: 1.14 (m, 6H), 2.33 (s, 3H), 2.41 (s, 3H), 2.43 (s, 3H), 2.61 (m, 1H), 2.82 (m, 2H), 2.96 (m, 1H), 3.04 (m, 1H), 3.58 (q, 2H), 3.83 (m, 2H), 4.57 (m, 2H), 4.63 (m, 2H), 6.80 (s, 1H), 8.01 (s, 1H). LRMS: m/z ES+ 425 [MH]$^+$ |
| 199 | (5,6-dimethylpyridin-3-yl) | $^1$H NMR (CD$_3$OD, 400 MHz) δ: 1.10–1.17 (m, 6H), 2.35 (s, 3H), 2.40 (s, 3H), 2.48 (s, 3H), 2.59 (m, 1H), 2.79–3.07 (m, 4H), 3.59 (q, 2H), 3.88 (t, 2H), 4.52 (m, 2H), 4.65 (t, 2H), 7.97 (d, 1H), 8.61 (d, 1H). LRMS: m/z APCl+ 425 [MH]$^+$ |
| 200 | (6-methylpyrimidin-4-yl) | $^1$H NMR (CD$_3$OD, 400 MHz) δ: 1.19 (m, 6H), 2.42 (s, 3H), 2.50 (s, 3H), 2.65 (m, 1H), 2.82–3.11 (m, 4H), 3.64 (q, 2H), 3.87 (t, 2H), 4.57 (m, 2H), 4.63 (t, 2H), 8.18 (s, 1H), 8.67 (s, 1H). LRMS: m/z APCl+ m/z 412 [MH]$^+$ |

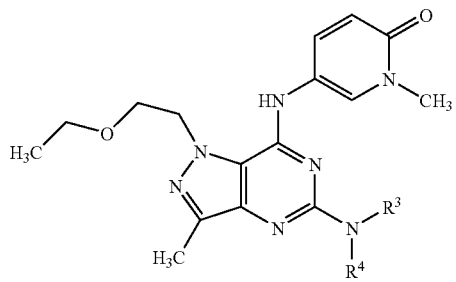

| No. | —NR$^3$R$^4$ | Data |
|---|---|---|
| 201 | (3-methylpiperazin-1-yl) | $^1$H NMR (CD$_3$OD, 400 MHz) δ: 1.10 (t, 3H), 1.16 (d, 3H), 2.40 (s, 3H), 2.59 (m, 1H), 2.80–2.97 (m, 3H), 3.07 (d, 1H), 3.54 (q, 2H), 3.62 (s, 3H), 3.84 (t, 2H), 4.48 (d, 2H), 4.63 (t, 2H), 6.61 (d, 1H), 7.71 (dd, 1H), 8.10 (d, 1H). LRMS: m/z APCl+ 427 [MH]$^+$ |
| 202 | N-methyl-N-(2-methoxyethyl) | $^1$H NMR (CD$_3$OD, 400 MHz) δ: 1.10 (t, 3H), 2.39 (s, 3H), 3.18 (s, 3H), 3.34 (s, 3H), 3.55 (m, 4H), 3.62 (s, 3H), 3.78 (t, 2H), 3.85 (t, 2H), 4.62 (t, 2H), 6.61 (d, 1H), 7.69 (dd, 1H), 8.34 (d, 1H). LRMS: m/z APCl+ 416 [MH]$^+$ |

-continued

| | | |
|---|---|---|
| 203 | 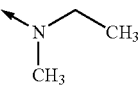 | ¹H NMR (CD₃OD, 400 MHz) δ: 1.11 (t, 3H), 1.20 (t, 3H), 2.49 (s, 3H), 3.24 (s, 3H), 3.56 (q, 2H), 3.62 (s, 3H), 3.67 (q, 2H), 3.88 (t, 2H), 4.76 (t, 2H), 6.63 (d, 1H), 7.73 (dd, 1H), 8.04 (d, 1H). LRMS: m/z APCl+ 386 [MH]⁺ |

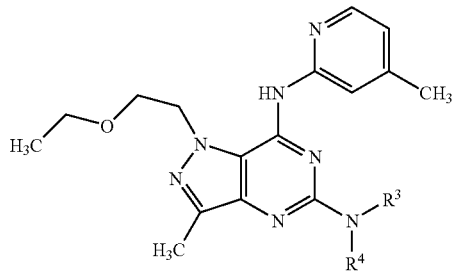

| No. | —NR³R⁴ | Data |
|---|---|---|
| 204ᶜ | 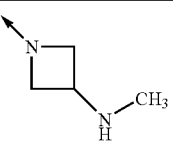 | ¹H NMR (CD₃OD, 400 MHz) δ: 1.08 (t, 3H), 2.41 (s, 3H), 2.42 (s, 3H), 2.51 (s, 3H), 3.70 (q, 2H), 3.82 (m, 1H), 3.86 (t, 2H), 4.02 (m, 2H), 4.40 (m, 2H), 4.67 (t, 2H), 6.94 (d, 1H), 8.15 (d, 1H), 8.47 (m, 1H). LRMS: m/z APCl+ 397 [MH]⁺ |
| 205ᶜ | 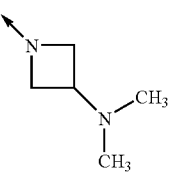 | ¹H NMR (CD₃OD, 400 MHz) δ: 1.08 (t, 3H), 2.23 (s, 6H), 2.38 (s, 3H), 2.42 (s, 3H), 3.26 (m, 1H), 3.56 (q, 2H), 3.84 (t, 2H), 4.00 (m, 2H), 4.22 (m, 2H), 4.64 (t, 2H), 6.92 (d, 1H), 8.14 (d, 1H), 8.46 (s, 1H). LRMS: m/z ES+ 411 [MH]⁺ |
| 206 | 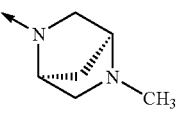 | ¹H NMR (CD₃OD, 400 MHz) δ: 1.12 (t, 3H), 2.00 (m, 2H), 2.40 (s, 3H), 2.42 (s, 3H), 2.44 (s, 3H), 2.92 (m, 2H), 3.59 (m, 4H), 3.84 (m, 2H), 4.63 (m, 2H), 4.82 (m, 1H), 6.93 (m, 1H), 8.15 (m, 1H), 8.37 (m, 1H). LRMS: m/z ES+ 423 [MH]⁺ |
| 207ᴰ | 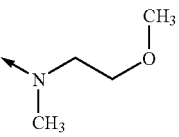 | ¹H NMR (CD₃OD, 400 MHz) δ: 1.10 (t, 3H), 2.39 (s, 3H), 2.41 (s, 3H), 3.24 (s, 3H), 3.35 (s, 3H), 3.58 (q, 2H), 3.66 (t, 2H), 3.87 (m, 4H), 4.63 (t, 2H), 6.92 (d, 1H), 8.13 (d, 1H), 8.35 (s, 1H). LRMS: m/z APCl+ 400 [MH]⁺ |
| 208ᴰ,ᶠ | 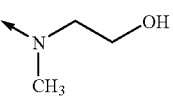 | ¹H NMR (CD₃OD, 400 MHz) δ: 1.10 (t, 3H), 2.39 (s, 6H), 3.30 (m, 2H), 3.57 (q, 2H), 3.83 (m, 7H), 4.63 (t, 2H), 6.92 (d, 1H), 8.14 (d, 1H), 8.36 (s, 1H). LRMS: m/z APCl+ 386 [MH]⁺ |

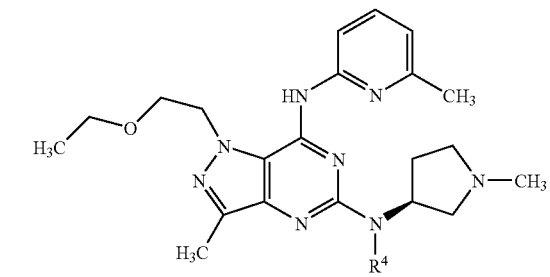

209 ¹H NMR (CD₃OD, 400 MHz): δ 1.16 (t, 3H), 1.95 (m, 1H), 2.23 (m, 1H), 2.41 (s, 3H), 2.44 (s, 3H), 2.47 (s, 3H), 2.71 (m, 2H), 2.80 (m, 1H), 2.88 (m, 1H), 3.14 (s, 3H), 3.62 (q, 2H), 3.86 (m, 2H), 4.66 (m, 2H), 5.59 (m, 1H), 6.93 (d, 1H), 7.70 (m, 1H), 8.16 (br, d, 1H).
LRMS: m/z APCl+ 425

-continued

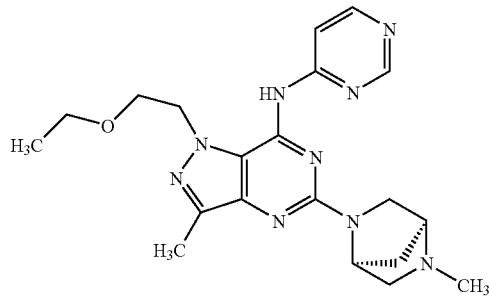

| 210 | ¹H NMR (CD₃OD, 400 MHz) δ: 1.10 (t, 3H), 2.00 (m, 2H), 2.43 (s, 3H), 2.44 (s, 3H), 2.98 (m, 2H), 3.53–3.68 (m, 4H), 3.81 (m, 1H), 3.88 (1, 2H), 4.62 (t, 2H), 4.82 (m, 1H), 8.36 (m, 1H), 8.77 (d, 1H), 8.80 (s, 1H). LRMS: m/z ES+ 410 [MH]⁺ |

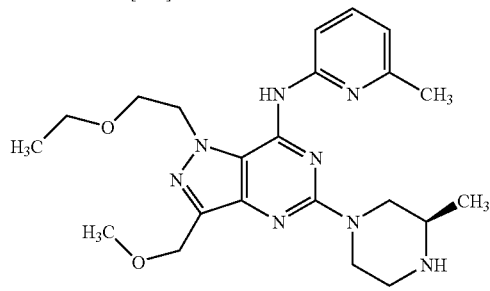

| 211 | ¹H NMR (CD₃OD, 400 MHz) δ: 1.16 (m, 6H), 2.46 (s, 3H), 2.59 (m, 1H), 2.82 (m, 2H), 2.92–3.04 (m, 2H), 3.43 (s, 3H), 3.61 (q, 2H), 3.88 (t, 2H), 4.55 (m, 2H), 4.67 (s, 2H), 4.70 (1, 2H), 6.91 (d, 1H), 7.64 (m, 1H), 8.03 (m, 1H). LRMS: m/z APCl° 441 [MH]⁺ |

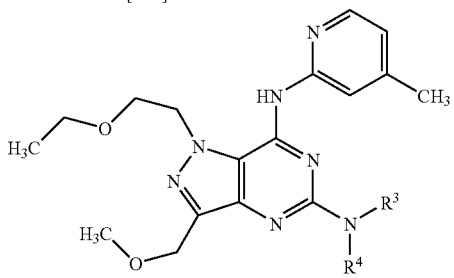

| No. | —NR³R⁴ | Data |
|---|---|---|
| 212 | N(CH₃)(CH₂CH₃) | ¹H NMR (CD₃OD, 400 MHz) δ: 1.09 (t, 3H), 1.21 (t, 3H), 2.36 (s, 3H), 3.17 (s, 3H), 3.43 (s, 3H), 3.57 (q, 2H), 3.72 (q, 2H), 3.87 (t, 2H), 4.67 (m, 4H), 6.89 (d, 1H), 8.12 (d, 1H), 8.35 (s, 1H). LRMS: m/z APCl+ 400 [MH]⁺ |
| 213 | (S)-2-(hydroxymethyl)pyrrolidin-1-yl | ¹H NMR (CD₃OD, 400 MHz) δ: 1.09 (t, 3H), 1.94 (m, 2H), 2.10 (m, 2H), 2.40 (s, 3H), 3.42 (s, 3H), 3.58 (q, 2H), 3.67–3.79 (m, 4H), 3.88 (t, 2H), 4.26 (m, 1H), 4.64 (s, 2H), 4.70 (t, 2H), 6.92 (d, 1H), 8.15 (d, 1H), 8.44 (s, 1H). LRMS: m/z APCl+ 442 [MH]⁺ |
| 214^{D,F} | 4-(N-methyl-N-(1-methylpiperidin-4-yl))amino | ¹H NMR (CD₃OD, 400 MHz) δ: 1.12 (t, 3H), 1.74 (m, 2H), 1.93 (m, 2H), 2.19 (m, 2H), 2.32 (s, 3H), 2.44 (s, 3H), 3.00 (m, 2H), 3.09 (s, 3H), 3.44 (s, 3H), 3.59 (q, 2H), 3.88 (t, 2H), 4.69 (m, 5H), 6.93 (d, 1H), 8.15 (d, 1H), 8.23 (m, 1H). LRMS: m/z APCl+ 469 [MH]⁺ |

| | -continued | |
|---|---|---|
| 215[F] | 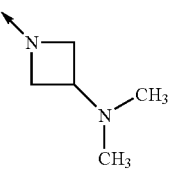 | $^1$H NMR (CD$_3$OD, 400 MHz) δ: 1.09 (t, 3H), 2.25 (s, 6H), 2.40 (s, 3H), 3.26 (m, 1H), 3.42 (s, 3H), 3.58 (q, 2H), 3.88 (t, 2H), 4.01 (m, 2H), 4.24 (m, 2H), 4.68 (s, 2H), 4.72 (m, 2H), 6.93 (d, 1H), 8.14 (d, 1H), 8.47 (s, 1H) |

[A] reaction not heated in a sealed vessel
[B] 1 eq caesium fluoride was used in place of N-ethyldiisopropylamine.
[C] the trifluoroacetate salt of the HNR$^3$R$^4$ amine was used, and 9 eq of N-ethyldiisopropylamine.
[D] reaction performed in NMP under microwave radiation for 40 mins at 180° C.
[E] product isolated by trituration from ether/pentane.
[F] 1 eq tetraethylammonium fluoride added Ex 204: N-methyl-3-azetidinamine bis(trifluoroacetate) used as described in JP 2002 255932, pg 5.

Ex 205 and 215: see prep 170.

Ex 206 and 210: (1S,4S)-2-methyl-2,5-diazabicyclo[2.2.1] heptane used as described in Chem. Heterocyclo.Compd (Eng. Trans) 36; 4; 2000; 429-431

Ex 209: (3S)-1-methyl-3-(methylamino)pyrrolidine used from preparation 115.

EXAMPLES 216-228

The appropriate monochloro compound (preparations 72, 110, 135, 136, 138, 140, 159 and 162 (1 eq) and the appropriate HNR$^3$R$^4$ amine (5-6 eq) were dissolved in dimethylsulfoxide (5-10 mL.mmol$^{-1}$) and the reaction mixture heated to 110-120° C. for 18 hours in a sealed vessel. The reaction mixture was diluted with ethyl acetate, washed with water (×2) and the organic phase dried over magnesium sulphate and concentrated in vacuo. The residue was purified by column chromatography on silica gel eluting with dichloromethane:methanol:0.880ammonia 99:1:0.125 to 95:5:0.5, then triturated with ether/pentane to yield the desired product.

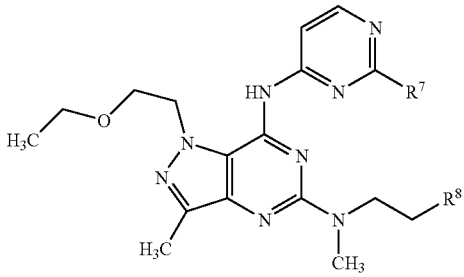

| No. | R$^7$ | R$^8$ | Data |
|---|---|---|---|
| 216[A] | H | —N(CH$_3$)$_2$ | $^1$H NMR (CD$_3$OD, 400 MHz) δ: 1.20 (t, 3H), 2.33 (s, 6H), 2.41 (s, 3H), 2.62 (t, 2H), 3.23 (s, 3H), 3.64 (q, 2H), 3.87 (m, 4H), 4.63 (t, 2H), 8.34 (d, 1H), 8.56 (d, 1H), 8.79 (s, 1H). LRMS: m/z APCl+ 400 [MH]$^+$ |
| 217[A] | H | H | $^1$H NMR (CD$_3$OD, 400 MHz) δ: 1.21 (m, 6H), 2.42 (s, 3H), 3.19 (s, 3H), 3.64 (q, 2H), 3.74 (q, 2H), 3.87 (t, 2H), 4.61 (t, 2H), 8.35 (d, 1H), 8.55 (d, 1H), 8.78 (s, 1H). LRMS: m/z APCl+ 357 [MH]$^+$ |
| 218[B] | —CH$_3$ | H | $^1$H NMR (CD$_3$OD, 400 MHz) δ: 1.20 (m, 6H), 2.41 (s, 3H), 2.57 (s, 3H), 3.18 (s, 3H), 3.64 (q, 2H), 3.72 (q, 2H), 3.88 (t, 2H), 4.61 (t, 2H), 8.17 (d, 1H), 8.44 (d, 1H). LRMS: m/z ES+ 371 [MH]$^+$ |
| 219 | —CH$_3$ | —OCH$_3$ | $^1$H NMR (CD$_3$OD, 400 MHz) δ: 1.23 (t, 3H), 2.41 (s, 3H), 2.57 (s, 3H), 3.24 (s, 3H), 3.36 (s, 3H), 3.65 (m, 4H), 3.87 (m, 4H), 4.61 (m, 2H), 8.17 (d, 1H), 8.43 (d, 1H). LRMS: m/z APCl+ 401 [MH]$^+$ |

-continued

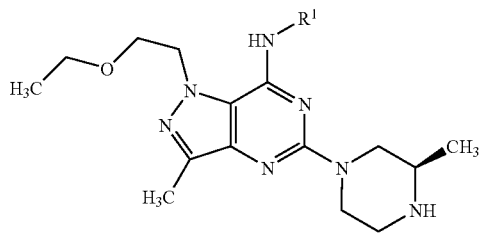

| No. | R¹ | Data |
|---|---|---|
| 220 | 2-methylpyrimidin-4-yl (CH₃ at 2-position) | ¹H NMR (CD₃OD, 400 MHz) δ: 1.17 (t, 3H), 1.24 (t, 3H), 2.41 (s, 3H), 2.58 (s, 3H), 2.62 (m, 1H), 2.84 (m, 2H), 2.96 (m, 1H), 3.05 (m, 1H), 3.64 (q, 2H), 3.88 (m, 2H), 4.53 (m, 2H), 4.63 (m, 2H), 8.03 (d, 1H), 8.46 (d, 1H). LRMS: m/z ES+ 412 [MH]⁺ |
| 221 | 4-methylpyrimidin-2-yl | ¹H NMR (CD₃OD, 400 MHz) δ: 1.13 (d, 3H), 1.25 (t, 3H), 2.43 (s, 3H), 2.49 (s, 3H), 2.56 (m, 1H), 2.82 (m, 2H), 2.89 (m, 1H), 3.00 (m, 1H), 3.61 (q, 2H), 3.85 (m, 2H), 4.57 (m, 2H), 4.64 (m, 2H), 6.99 (d, 1H), 8.43 (d, 1H). LRMS: m/z ES+ 412 [MH]⁺ |
| 222 | 4-(trifluoromethyl)pyridin-2-yl | ¹H NMR (CD₃OD, 400 MHz): δ 1.18 (m, 6H), 2.41 (s, 3H), 2.68 (m, 1H), 2.90–3.20 (m, 4H), 3.63 (m, 2H), 3.88 (m, 2H), 4.57 (m, 2H), 4.64 (m, 2H), 7.30 (d, 1H), 8.51 (d, 1H), 8.65 (br, s 1H). LRMS: m/z APCl+ 465 [MH]⁺ |

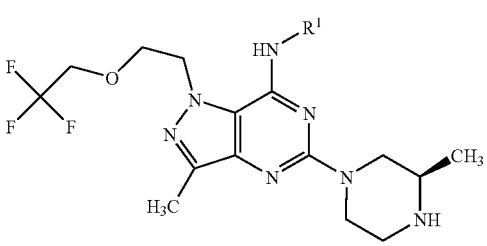

| No. | R¹ | Data |
|---|---|---|
| 223ᶜ | 6-methylpyridin-2-yl | ¹H NMR (CD₃OD, 400 MHz) δ: 1.41 (d, 3H), 2.43 (s, 3H), 2.49 (s, 3H), 3.10 (m, 1H), 3.15–3.50 (m, 4H), 4.07 (m, 4H), 4.77 (m, 4H), 6.97 (d, 1H), 7.73 (dd, 1H), 7.98 (m, 1H). LRMS: m/z ES+ 465 [MH]⁺ |
| 224ᴰ | pyrimidin-4-yl | ¹H NMR (CD₃OD, 400 MHz) δ: 1.00 (d, 3H), 2.40 (s, 3H), 2.60 (m, 1H), 2.80 (m, 2H), 3.00–3.50 (m, 2H), 4.00 (m, 2H), 4.10 (t, 2H), 4.55 (d, 2H), 4.70 (t, 2H), 8.20 (m, 1H), 8.60 (d, 1H), 8.80 (s, 1H). LRMS: m/z APCl+ 452 [MH]⁺ |

-continued

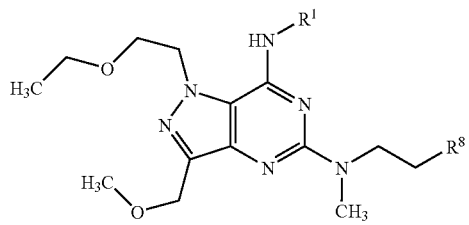

| No. | R¹ | R⁸ | Data |
|---|---|---|---|
| 225 | pyrimidin-4-yl | H | ¹H NMR (CD₃OD, 400 MHz) δ: 1.21 (t, 6H), 3.19 (s, 3H), 3.45 (s, 3H), 3.65 (q, 2H), 3.74 (q, 2H), 3.91 (t, 2H), 4.69 (m, 4H), 8.33 (d, 1H), 8.55 (d, 1H), 8.78 (s, 1H). LRMS: m/z APCl+ 387 [MH]⁺ |
| 226 | 4-methylpyridin-2-yl | —OCH₃ | ¹H NMR (CD₃OD, 400 MHz) δ: 1.11 (t, 3H), 2.40 (s, 3H), 3.25 (s, 3H), 3.35 (s, 3H), 3.44 (s, 3H), 3.59 (q, 2H), 3.66 (t, 2H), 3.89 (m, 4H), 4.70 (m, 4H), 6.92 (d, 1H), 8.15 (d, 1H), 8.35 (d, 1H). LRMS: m/z APCl+ 430 [MH]⁺ |
| 227 | 4-methylpyridin-2-yl | —OH | ¹H NMR (CD₃OD, 400 MHz) δ: 1.12 (t, 3H), 2.41 (s, 3H), 3.30 (s, 3H), 3.44 (s, 3H), 3.59 (q, 2H), 3.83 (m, 4H), 3.89 (t, 2H), 4.70 (m, 4H), 6.92 (d, 1H), 8.13 (d, 1H), 8.35 (d, 1H). LRMS: m/z APCl+ 416 [MH]⁺ |

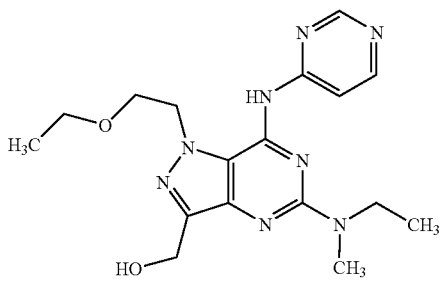

| 228 | ¹H NMR (CD₃OD, 400 MHz) δ: 1.22 (m, 6H), 3.20 (S, 3H), 3.65 (q, 2H), 3.76 (q, 2H), 3.91 (t, 2H), 4.69 (t, 2H), 4.85 (m, 2H), 8.36 (dd, 1H), 8.57 (d, 1H), 8.79 (s, 1H). LRMS: m/z ES+ 395 [MNa]⁺ |
|---|---|

ᴬthe reaction was diluted with dichloromethane not ethyl acetate.
ᴮpurified by HPLC using 0.1 aq trifluoroacetic acid and acetonitrile as eluant.
ᶜisolated as the HCl salt
ᴰ1eq caesium fluoride added to the reaction

EXAMPLE 229

N-[5-((1S,4S)-2,5-Diazabicyclo[2.2.1]hept-2-yl)-1-(2-ethoxyethyl)-3-ethyl-1H-pyrazolo[4,3-d]pyrimidin-7-yl]-4-methylpyridin-2-ylamine hydrochloride

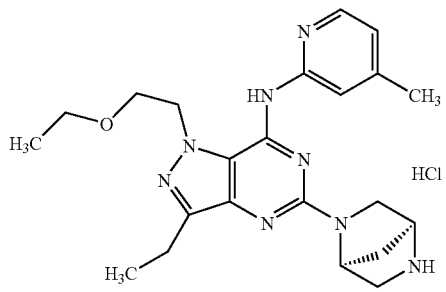

The chloro compound from preparation 122 (2.3 g, 6.37 mmol), tert butyl (1S,4S)-(−)-2,5-diazabicyclo[2.2.1]heptane-2-carboxylate (3.8 g, 19.11 mmol) and caesium fluoride (967 mg, 6.37 mmol) were dissolved in dimethylsulfoxide (15 mL) and the reaction mixture heated to 110° C. for 18 hours. The cooled reaction mixture was partitioned between 10% citric acid solution and ethyl acetate (400 mL) and the layers separated. The aqueous phase was extracted with ethyl acetate (200 mL) and the combined organic solutions were washed with water (200 mL), brine (200 mL) then dried over magnesium sulphate and concentrated in vacuo. The residue was dissolved in dichloromethane (40 mL) and trifluoroacetic acid (10 mL) and the solution stirred at room temperature for 2 hours. The reaction mixture was concentrated in vacuo and the residue partitioned between dichloromethane (100 mL) and sodium carbonate solution (100 mL). The organic solution was dried over magnesium sulphate and evaporated in vacuo. The crude product was purified by column chromatography on silica gel eluting with dichloromethane:methanol:0.880 ammonia (97.5:2.5:0.25 to 95:5:0.5). The product was then dissolved in methanol, and 2N hydrochloric acid (1 eq) added and the solution evaporated in vacuo. The solid was recrystallised from isopropyl acetate/ether to afford the title compound as a pale yellow solid, 1.15 g.

$^1$H NMR (CD$_3$OD, 400 MHz) δ: 1.10 (t, 3H), 1.34 (t, 3H), 2.17 (m, 1H), 2.35 (m, 1H), 2.53 (s, 3H), 2.91 (q, 2H), 3.52 (m, 2H), 3.59 (m, 2H), 3.90 (t, 2H), 3.98 (m, 2H), 4.64 (m, 1H), 4.86 (m, 2H), 5.20 (m, 1H), 7.15 (d, 1H), 7.97 (s, 1H), 8.22 (m, 1H)

Microanalysis found: C, 54.53; H, 7.05; N, 22.82. C$_{22}$H$_{30}$N$_8$O;HCl;1.5H$_2$O requires C, 54.37; H, 7.05; N, 23.06%.

EXAMPLE 230

N-[5-((1S, 4S)-2,5-Diazabicyclo[2.2.1]hept-2-yl)-3-methoxymethyl-1-(2-propoxyethyl)-1H-pyrazolo[4,3-d]pyrimidin-7-yl]-4-methylpyridin-2-ylamine

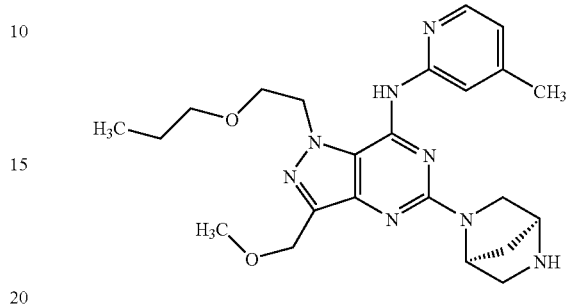

The title compound was obtained from the chloro compound from preparation 160, and tert-butyl (1S,4S)-(−)-2,5-diazabicyclo[2.2.1]heptane-2-carboxylate following the procedure described in example 229, except the compound was isolated as the free base.

$^1$H NMR (CD$_3$OD, 400 MHz) δ: 0.71 (t, 3H), 1.53 (m, 2H), 1.92 (m, 1H), 2.10 (m, 1H), 2.42 (s, 3H), 3.17 (q, 2H), 3.43 (s, 3H), 3.50 (m, 2H), 3.66 (m, 1H), 3.68 (m, 1H), 3.89 (m, 2H), 4.02 (s, 1H), 4.69 (m, 2H), 4.74 (m, 2H), 4.95 (s, 1H), 6.94 (d, 1H), 8.14 (d, 1H), 8.33 (m, 1H). LRMS:m/z ES+453 [MH]$^+$

EXAMPLE 231

N-{5-((1S, 4S)-2.5-Diazabicyclo[2.2.1]hept-2-yl)-3-methyl-1-[2-(2,2,2-trifluoroethoxy)ethyl]-1H-pyrazolo[4,3-d]pyrimidin-7-yl}-4-methylpyridin-2-ylamine

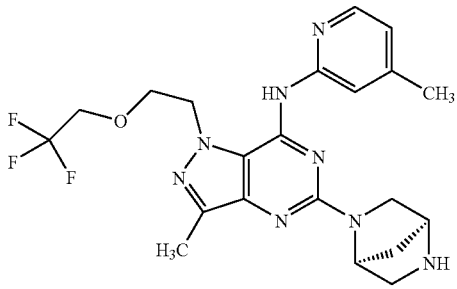

The title product was prepared by a method similar to that described for example 230 using the monochloro compound of preparation 141 and tert-butyl (1S, 4S)-(−)-2,5-diazabicyclo[2.2.1]heptane-2-carboxylate.

$^1$H NMR (CD$_3$OD, 400 MHz) δ: 1.84 (m, 1H), 1.97 (m, 1H), 2.40 (s, 3H), 2.41 (s, 3H), 3.06 (q, 2H), 3.58 (m, 1H), 3.70 (m, 1H), 3.82 (s, 1H), 4.00 (q, 2H), 4.06 (t, 2H), 4.72 (m, 2H), 4.84 (m, 1H), 6.92 (d, 1H), 8.13 (d, 1H), 8.25 (m, 1H) LRMS:m/z ES+463 [MH]$^+$

EXAMPLE 232

N-[5-(3,8-Diazabicyclo[3.2.1]oct-3-yl)-1-(2-ethoxyethyl)-3-methyl-1H-pyrazolo[4,3-d]pyrimidin-7-yl]-4-methylpyridin-2-ylamine

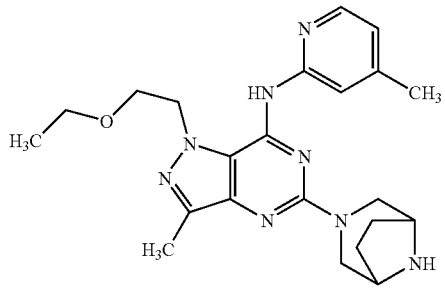

The title compound was obtained as a yellow foam from the chloro compound from preparation 120 and tert-butyl 3,8-diazabicyclo[3.2.1]octane-8-carboxylate (Tet. Lett. 43 (2002), 899-902) following the procedure described in example 231.

$^1$H NMR (CD$_3$OD, 400 MHz) δ: 1.12 (t, 3H), 1.89 (m, 4H), 2.41 (2×s, 6H), 3.19 (m, 2H), 3.60 (q, 2H), 3.75 (m, 2H), 3.86 (t, 2H), 4.36 (m, 2H), 4.65 (t, 2H), 6.92 (d, 1H), 7.39 (d, 1H), 8.20 (br s, 1H). LRMS:m/z ES+423 [MH]$^+$

EXAMPLES 233-238

The appropriate monochloro precursor (preparations 120, 134, 139, 140 and 143) (1 eq), the appropriate HNR$^3$R$^4$ amine (3 eq) and N-ethyldiisopropylamine (3 eq) where dissolved in dimethylsulfoxide (3.80 mL.mmol$^{-1}$) and the reaction mixture placed in a ReactiVial™ and heated to 120° C. for 18 hours. The reaction mixture was diluted with water and the mixture extracted with ethyl acetate. The organic phase was dried over magnesium sulphate and concentrated in vacuo. The residue was taken up in dichloromethane (20-50 mL.mmol$^{-1}$), treated with trifluoroacetic acid (4-20 mL.mmol$^{-1}$) and the mixture stirred at room temperature for 5 hours. The mixture was then concentrated in vacuo and the residue taken up in ethyl acetate and washed with 10% sodium hydrogencarbonate solution. The organic phase was dried over magnesium sulphate and concentrated in vacuo. The residue was purified by column chromatography on silica gel eluting with dichloromethane:methanol 99:1 to 98:2 to yield the desired product.

| No. | R$^1$ | Data |
|---|---|---|
| 233 | pyridine with 2,3-diCH$_3$ | $^1$H NMR (CD$_3$OD, 400 MHz) δ: 1.11 (1, 3H), 1.86 (d, 1H), 2.03 (d, 1H), 2.35 (s, 3H), 2.41 (s, 3H), 2.47 (s, 3H), 3.14 (s, 2H), 3.60 (m, 3H), 3.70 (m, 1H), 3.89 (m, 2H), 3.97 (s, 1H), 4.66 (m, 2H), 4.88 (s, 1H), 7.99 (m, 1H), 8.73 (d, 1H). LRMS: m/z APCl+ 423 [MH]$^+$ |
| 234 | pyridine with 2,4-diCH$_3$ | $^1$H NMR (CD$_3$OD, 400 MHz) δ: 1.12 (1, 3H), 1.86 (m, 1H), 2.07 (m, 1H), 2.36 (s, 3H), 2.42 (s, 3H), 2.43.(s, 3H), 3.18 (q, 2H), 3.59 (q, 2H), 3.69 (m, 2H), 3.84 (m, 2H), 4.01 (s, 1H), 4.66 (m, 2H), 4.93 (s, 1H), 6.81 (s, 1H), 8.19 (br, s, 1H). LRMS: m/z APCl+ 423 [MH]$^+$ |
| 235 | pyridine with 2-CH$_3$ | $^1$H NMR (CD$_3$OD, 400 MHz) δ: 1.17 (t, 3H), 1.83 (m, 1H), 2.01 (m, 1H), 2.41 (s, 3H), 2.48 (s, 3H), 3.04 (m, 2H), 3.60 (m, 3H), 3.70 (m, 1H), 3.82 (s, 1H), 3.88 (t, 2H), 4.65 (m, 2H), 4.89 (s, 1H), 6.93 (d, 1H), 7.67 (dd, 1H), 8.23 (m, 1H). LRMS: m/z APCl+ 409 [MH]$^+$ |
| 236 | pyridine with 4-CH$_3$ | $^1$H NMR (CD$_3$OD, 400 MHz) δ: 1.10 (t, 3H), 1.92 (d, 2H), 2.41 (s, 3H), 2.43 (s, 3H), 3.18 (m, 2H), 3.59 (m, 3H), 3.70 (m, 1H), 3.83 (m, 3H), 4.63 (m, 2H), 4.86 (m, 1H), 6.92 (d, 1H), 8.13 (d, 1H), 8.38 (m, 1H). LRMS: m/z ES+ 409 [MH]$^+$ |

-continued

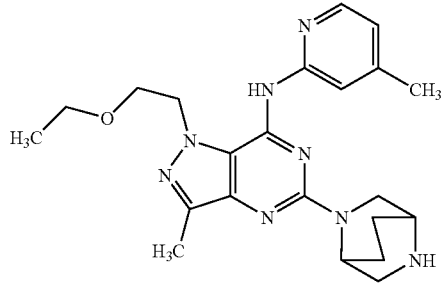

| 237 | ¹H NMR (CD₃OD, 400 MHz) δ: 1.11 (t, 3H), 1.92 (m, 2H), 2.12 (m, 2H), 2.39 (s, 3H), 2.41 (s, 3H), 3.23 (m, 1H), 3.38 (m, 2H), 3.58 (q, 2H), 3.81 (m, 1H), 3.85 (m, 2H), 4.00 (m, 1H), 4.64 (m, 2H), 4.81 (m, 1H), 6.91 (d, 1H), 8.15 (d, 1H), 8.29 (m, 1H). LRMS: m/z APCl+ 423 [MH]⁺ |

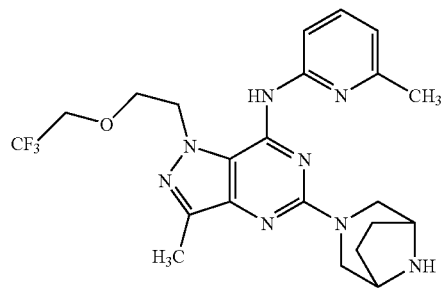

| 238 | ¹H NMR (CD₃OD, 400 MHz) δ: 1.92 (m, 4H), 2.42 (s, 3H), 2.48 (s, 3H), 3.22 (d, 2H), 3.83 (s, 2H), 4.06 (m, 4H), 4.40 (d, 2H), 4.75 (t, 2H), 6.95 (d, 1H), 7.70 (m, 1H), 8.08 (br s, 1H). LRMS: m/z APCl+ 477 [MH]⁺ |

EXAMPLE 239

N-[5-(3,8-Diazabicyclo[3.2.1]oct-3-yl)-3-methyl-1-(2-propoxyethyl)-1H-pyrazolo[4,3-d]pyrimidin-7-yl]-6-methylpyridin-2-ylamine

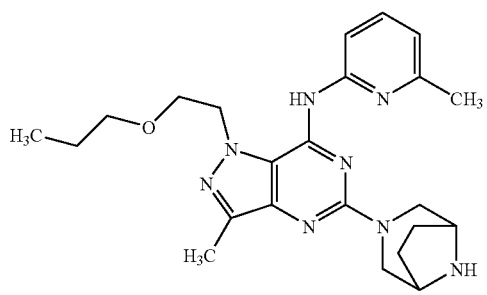

A mixture of the chloro compound from preparation 171 (150 mg, 0.42 mmol), tert-butyl 3,8-diazabicyclo[3.2.1]octane-8-carboxylate (Tet. Lett. 43 (2002), 899-902) (446 mg, 2.1 mmol), and caesium fluoride (63.8 mg, 0.42 mmol) in dimethylsulfoxide (3 mL) was heated at 110° C. for 18 hours in a sealed vessel. The reaction was poured into water, and the resulting precipitate filtered off. This solid was dissolved in dichloromethane, and the solution evaporated in vacuo. The solid was redissolved in dichloromethane (6 mL), trifluoroacetic acid (2 mL) added, and the solution stirred at room temperature for 3 hours. The mixture was concentrated in vacuo and the residue partitioned between dichloromethane and 2N hydrochloric acid and the layers separated. The aqueous solution was basified using solid sodium carbonate and then extracted with dichloromethane (3×). These organic extracts were dried over magnesium sulphate and evaporated in vacuo. The crude product was purified by column chromatography on silica gel using an elution gradient of dichloromethane:methanol:0.88 ammonia (100:0:0 to 98:2:0.25) to give the title compound as a yellow solid, 65 mg.

¹H NMR (CD₃OD, 400 MHz) δ: 0.73 (t, 3H), 1.57 (m, 2H), 1.75-1.86 (m, 4H), 2.40 (s, 3H), 2.44 (s, 3H), 3.11 (m, 2H), 3.48 (t, 2H), 3.60 (m, 2H), 3.84 (t, 2H), 4.27 (m, 2H), 4.65 (t, 2H), 6.90 (d, 1H), 7.66 (m, 1H), 8.10 (br d, 1H). LRMS:m/z APCl+437 [MH]⁺

EXAMPLES 240-243

The appropriate protected amine (1 eq) and trifluoroacetic acid (7.5-12.5 mL.mmol⁻¹) were added to dichloromethane (15-42 mL.mmol⁻¹) and the reaction mixture stirred at room temperature for 18 hours. The reaction mixture was concentrated in vacuo and the residue was partitioned between dichloromethane and sodium hydrogencarbonate solution, the phases were separated and the aqueous washed with dichloromethane. The organic layer was dried over magnesium sulphate and concentrated in vacuo. The residue was purified by column chromatography on silica gel eluting with dichloromethane:methanol:0.880 ammonia 100:0:0 to 90:10:1 to yield the desired product.

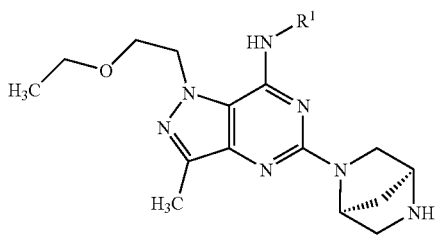

| No. | R¹ | Data |
|---|---|---|
| 240 | (pyridyl-CH₃) | ¹H NMR (CD₃OD, 400 MHz) δ: 1.12 (t, 3H), 1.82 (d, 1H), 1.98 (d, 1H), 2.32 (s, 3H), 2.42 (s, 3H), 3.07 (m, 2H), 3.56 (m, 3H), 3.68 (m, 1H), 3.86 (m, 3H), 4.63 (m, 3H), 7.62 (d, 1H), 8.11 (s, 1H), 8.32 (m, 1H). LRMS: m/z APCl+ 409 [MH]⁺ |
| 241 | (pyrimidinyl) | ¹H NMR (CD₃OD, 400 MHz) δ: 1.19 (t, 3H), 1.83 (m, 1H), 2.02 (m, 1H), 2.42 (s, 3H), 3.09 (m, 2H), 3.56–3.76 (m, 4H), 3.90 (m, 3H), 4.63 (m, 2H), 4.92 (s, 1H), 8.56 (m, 1H), 8.58 (d, 1H), 8.79 (s, 1H). LRMS: m/z ES+ 396 [MH]⁺ |

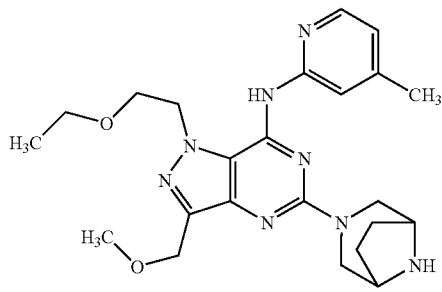

| 242 | ¹H NMR (CD₃OD, 400 MHz) δ: 1.11 (t, 3H), 1.82 (m, 4H), 2.38 (s, 3H), 3.16 (d, 2H), 3.43 (s, 3H), 3.58 (q, 2H), 3.64 (m, 2H), 3.87 (t, 2H), 4.33 (d, 2H), 4.67 (s, 2H), 4.70 (t, 2H), 6.91 (d, 1H), 8.13 (d, 1H), 8.20 (s, 1H). LRMS: m/z APCl+ 453 [MH]⁺ |
|---|---|

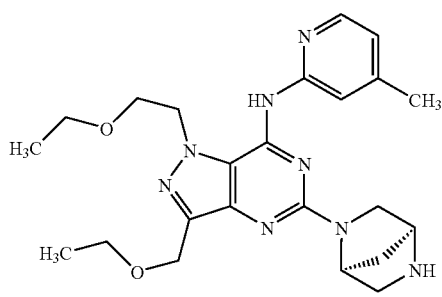

| 243 | ¹H NMR (CD₃OD, 400 MHz) δ: 1.10 (t, 3H), 1.21 (t, 3H), 1.85 (d, 1H), 2.02 (d, 1H), 2.41 (s, 3H), 3.12 (q, 2H), 3.56–3.70 (m, 5H), 3.73 (m, 1H), 3.89 (m, 3H), 4.73 (m, 4H), 4.91 (s, 1H), 6.93 (d, 1H), 8.15 (d, 1H), 8.39 (m, 1H). LRMS: m/z ES+ 453 [MH]⁺ |
|---|---|

EXAMPLE 244

N-[5-((1R,4R)-2,5-Diazabicyclo[2.2.1]hept-2-yl)-1-(2-ethoxyethyl)-3-methyl-1H-pyrazolo[4,3-d]pyrimidin-7-yl]-4-methylpyridin-2-ylamine

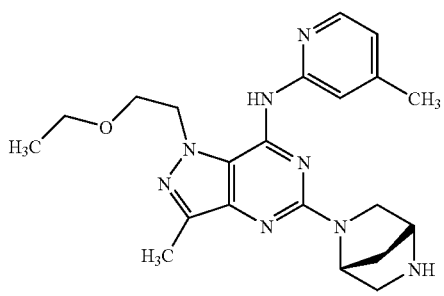

The protected product of preparation 168 (62 mg, 0.12 mmol) was dissolved in ethanol (5 mL) and the solution treated with palladium hydroxide (10 mg) and 2M hydrochloric acid (124 µL, 0.25 mmol). The reaction mixture was placed under 60 psi for 18 hours and was then treated with additional catalyst (20 mg) and placed under 60 psi for 18 hours. The reaction mixture was filtered through Arbocel® and the filtrate concentrated in vacuo. The residue was purified by column chromatography on silica gel eluting with dichloromethane:methanol:0.880 ammonia 95:5:0.5 to 90:10:1 to yield the title product, 16 mg.

¹H NMR (CD₃OD, 400 MHz) δ: 1.11 (t, 3H), 1.92 (m, 1H), 2.11 (m, 1H), 2.41 (2×s, 6H), 3.21 (m, 2H), 3.58 (m, 2H), 3.70 (q, 2H), 3.84 (m, 2H), 4.09 (s, 1H), 4.65 (m, 2H), 4.95 (s, 1H), 6.95 (m, 1H), 8.16 (d, 1H), 8.36 (m, 1H). LRMS:m/z APCI+409 [MH]⁺

EXAMPLES 245 to 257

The appropriate chloro compound (preparations 191 to 202) (1 eq), and the appropriate HNR³R⁴ amine (3-5 eq) were dissolved in dimethylsulfoxide (2.7-13.6 mL.mmol⁻¹) and the reaction mixture stirred at 120° C. for 18 hours in a sealed vessel. The reaction mixture was partitioned between water and ethyl acetate, and the layers separated. The organic layer was dried over magnesium sulphate and concentrated in vacuo. The residue was purified by column chromatography on silica gel eluting with dichloromethane:methanol:0.88 ammonia to yield the title product.

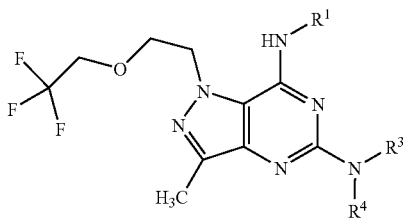

| No. | R¹ | —NR³R⁴ | Data |
|---|---|---|---|
| 245[A] | 4-methylpyridin-2-yl | (3R)-1-methyl-N-methylpyrrolidin-3-yl | ¹H NMR (CD₃OD, 400 MHz) δ: 2.14 (m, 1H), 2.41 (m, 7H), 2.71 (s, 3H), 2.91 (q, 1H), 3.11 (m, 1H), 3.23 (m, 4H), 3.35 (m, 1H), 3.98–4.09 (m, 4H), 4.73 (t, 2H), 5.24 (s, 1H), 6.96 (d, 1H), 8.15 (d, 1H), 8.22 (s, 1H). LRMS: m/z APCI+ 479 [MH]⁺ |
| 246[B] | 2-methylpyrimidin-4-yl | (3S)-3-methylpiperazin-1-yl | ¹H NMR (CD₃OD, 400 MHz) δ: 1.16 (d, 3H), 2.44 (s, 3H), 2.57 (s, 3H), 2.64 (m, 1H), 2.85 (m, 2H), 2.95–3.10 (m, 2H), 4.04–4.10 (m, 4H), 4.54 (m, 2H), 4.70 (t, 2H), 8.02 (m, 1H), 8.48 (d, 1H). LRMS: m/z APCI+ 466 [MH]⁺ |
| 247[B,C] | 4-methylpyrimidin-6-yl | 1-methyl-N-methylpiperidin-4-yl | ¹H NMR (CD₃OD, 400 MHz) δ: 2.00–2.45 (m, 4H), 2.42 (s, 3H), 2.50 (s, 3H), 2.88 (s, 3H), 3.15 (m, 5H), 3.60 (m, 2H), 4.06 (m, 4H), 4.72 (m, 2H), 5.00 (m, 1H), 8.22 (s, 1H), 8.68 (s, 1H). LRMS: m/z APCI+ 494 [MH]⁺ |

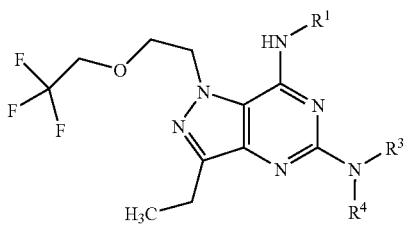

| No. | R¹ | —NR³R⁴ | Data |
|---|---|---|---|
| 248 | pyridazin-4-yl | (3S)-3-methylpiperazin-1-yl | ¹H NMR (CD₃OD, 400 MHz) δ: 1.18 (d, 3H), 1.36 (t, 3H), 2.68 (m, 1H), 2.88 (m, 4H), 3.02 (m, 1H), 3.09 (m, 1H), 3.96 (q, 2H), 4.03 (t, 2H), 4.55 (m, 2H), 4.78 (t, 2H), 8.02 (m, 1H), 8.97 (d, 1H), 9.45 (s, 1H). LRMS: m/z APCI+ 466 [MH]⁺ |
| 249[B,D] | pyrimidin-4-yl | (3S)-3-methylpiperazin-1-yl | ¹H NMR (CD₃OD, 400 MHz) δ: 1.20 (d, 3H), 1.35 (t, 3H), 2.60 (m, 1H), 2.80 (m, 4H), 3.05 (m, 2H), 4.05 (m, 4H), 4.50 (d, 2H), 4.70 (t, 2H), 8.20 (m, 1H), 8.60 (d, 1H), 8.80 (s, 1H). LRMS: m/z APCI– 464 [M – H]⁻ |
| 250 | 2-methylpyrimidin-4-yl | (3S)-3-methylpiperazin-1-yl | ¹H NMR (CD₃OD, 400 MHz) δ: 1.18 (d, 3H), 1.35 (t, 3H), 2.58 (s, 3H), 2.63 (m, 1H), 2.87 (m, 4H), 2.99–3.11 (m, 2H), 4.09 (m, 4H), 4.53 (m, 2H), 4.72 (m, 2H), 8.03 (s, 1H), 8.48 (d, 1H). LRMS: m/z APCI+ 480 [MH]⁺ |

-continued

| No. | R¹ | —NR³R⁴ | Data |
|---|---|---|---|
| 251 | 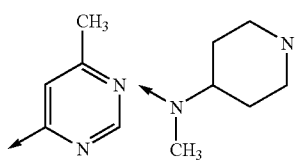 | | ¹H NMR (CD₃OD, 400 MHz) δ: 1.36 (t, 3H), 1.78 (m, 2H), 1.94 (m, 2H), 2.23 (m, 2H), 2.35 (s, 3H), 2.54 (s, 3H), 2.88 (q, 2H), 3.03 (m, 2H), 3.11 (s, 3H), 4.06 (m, 4H), 4.69 (m, 3H), 8.22 (m, 1H), 8.67 (s, 1H). LRMS: m/z APCl+ 508 [MH]⁺ |

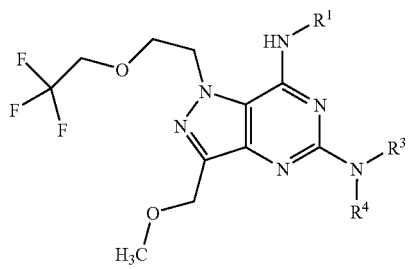

| No. | R¹ | —NR³R⁴ | Data |
|---|---|---|---|
| 252 | 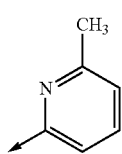 | 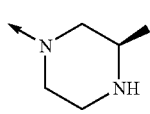 | ¹H NMR (CD₃OD, 400 MHz) δ: 1.20 (d, 3H), 2.50 (s, 3H), 2.62 (m, 1H), 2.85 (m, 2H), 3.00 (m, 2H), 3.42 (s, 3H), 4.05 (m, 2H), 4.15 (m, 2H), 4.54 (m, 2H), 4.70 (s, 2H), 4.82 (m, 2H), 6.99 (d, 1H), 7.70 (m, 1H), 8.10 (d, 1H). LRMS: m/z APCl+ 495 [MH]⁺ |
| 253 | 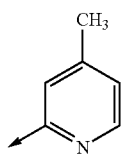 | 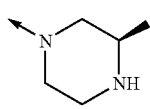 | ¹H NMR (CD₃OD, 400 MHz) δ: 1.18 (d, 3H), 2.39 (s, 3H), 2.60 (m, 1H), 2.80 (m, 2H), 2.90–3.05 (m, 2H), 3.42 (s, 3H), 4.00 (m, 2H), 4.10 (m, 2H), 4.50 (d, 2H), 4.65 (s, 2H), 4.75 (m, 2H), 6.90 (d, 1H), 8.10 (m, 2H). LRMS: m/z APCl+ 495 [MH]⁺ |
| 254[B,D] | 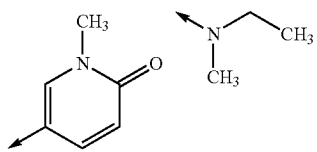 | | ¹H NMR (CD₃OD, 400 MHz) δ: 1.17 (t, 3H), 3.22 (s, 3H), 3.39 (s, 3H), 3.61–3.68 (m, 5H), 3.97 (q, 2H), 4.06 (t, 2H), 4.73 (s, 2H), 4.90 (t, 2H), 6.62 (d, 1H), 7.70 (m, 1H), 7.86 (d, 1H). LRMS: m/z APCl+ 470 [MH]⁺ |

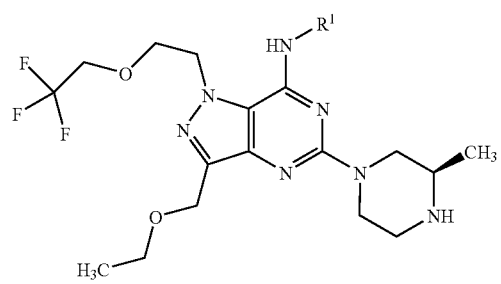

| No. | R¹ | Data |
|---|---|---|
| 255 | 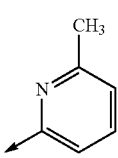 | ¹H NMR (CD₃OD, 400 MHz) δ: 1.20 (m, 6H), 2.42 (s, 3H), 2.62 (m, 1H), 2.85 (m, 2H), 3.00 (m, 2H), 3.65 (q, 2H), 4.10 (m, 2H), 4.15 (t, 2H), 4.60 (m, 2H), 4.75 (s, 2H), 4.85 (m, 2H), 6.95 (d, 1H), 7.70 (m, 1H), 8.10 (m, 1H). LRMS: m/z APCl+ 509 [MH]⁺ |

| | | |
|---|---|---|
| 256 | 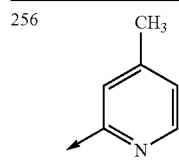 | ¹H NMR (CD₃OD, 400 MHz) δ: 1.20 (m, 6H), 2.40 (s, 3H), 2.60 (m, 1H), 2.85 (m, 2H), 3.00 (m, 2H), 3.65 (q, 2H), 4.05 (m, 2H), 4.10 (t, 2H), 4.59 (m, 2H), 4.70 (s, 2H), 4.80 (t, 2H), 6.95 (d, 1H), 8.20 (m, 2H). LRMS: m/z APCI+ 509 [MH]⁺ |
| 257ᴰ | 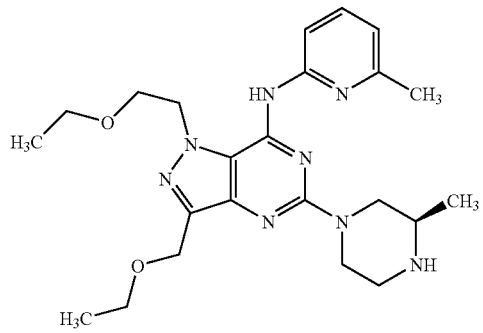 | ¹H NMR (CD₃OD, 400 MHz) δ: 1.21 (m, 9H), 2.42 (s, 3H), 2.62 (m, 1H), 2.81 (m, 2H), 3.00 (m, 2H), 3.30 (m, 2H), 3.63 (m, 4H), 3.92 (m, 2H), 4.59 (m, 2H), 4.80 (s, 2H), 6.98 (d, 1H), 7.65 (m, 1H), 8.05 (d, 1H). LRMS: m/z APCI+455 [MH]⁺ |

ᴬthe hydrochloride salt of the amine from preparation 115 was used, and an equimolar amount of N-ethyldiisoproplamine was added to the reaction.
ᴮthe reaction was not performed in a sealed vessel
ᶜproduct treated with ethereal HCl to provide the hydrochloride salt.
ᴰ1eq caesium fluoride was added to the reaction mixture

EXAMPLE 258

N-{3-Methyl-5-piperazin-1-yl-1-[2-(2,2,2-trifluoroethoxy)ethyl]-1H-pyrazolo[4,3-d]pyrimidin-7-yl}-6-methylpyridin-2-ylamine

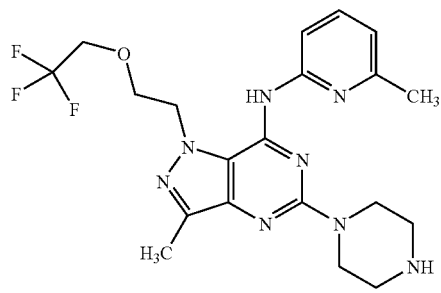

A mixture of the chloride from preparation 140 (200 mg, 0.5 mmol), tert-butyl 1-piperazinecarboxylate (165 mg, 0.89 mmol), caesium fluoride (76 mg, 0.5 mmol), and N-ethyldiisopropylamine (0.88 mL, 5.0 mmol) in dimethylsulfoxide (2 mL) was stirred at 110° C. for 18 hours. The cooled mixture was partitioned between ethyl acetate (25 mL) and water (25 mL), the layers separated, and the organic phase washed with brine, dried over magnesium sulphate and evaporated in vacuo. The product was dissolved in dichloromethane (9 mL), trifluoroacetic acid (3 mL) added and the reaction stirred for 1.5 hours. The reaction was evaporated in vacuo and the residue partitioned between ethyl acetate and aqueous sodium bicarbonate solution. The layers were separated, the organic phase dried over magnesium sulphate and evaporated in vacuo. The residue was triturated with ether/pentane to afford the title compound as an off-white solid, 117 mg.

¹H NMR (CD₃OD, 400 MHz) δ: 2.40 (s, 3H), 2.46 (s, 3H), 2.93 (m, 4H), 3.75 (m, 4H), 4.05 (m, 4H), 4.73 (t, 2H), 6.94 (d, 1H), 7.68 (dd, 1H), 8.05 (m, 1H). LRMS:m/z APCI+451 [MH]⁺

EXAMPLE 259

N-{5-(3,8-Diazabicyclo[3.2.1]oct-3-yl)-3-methoxymethyl-1-[2-(2,2,2-trifluoroethoxy)ethyl]-1H-pyrazolo[4,3-d]pyrimidin-7-yl}-4-methylpyridin-2-ylamine

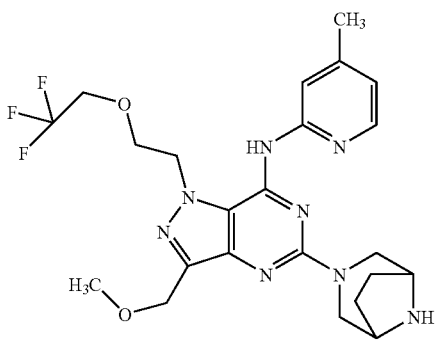

A mixture of the chloro compound from preparation 193 (150 mg, 0.35 mmol), tert-butyl 3,8-diazabicyclo[3.2.1]octane-8-carboxylate (J. Med. Chem. 1998, 41, 674) (160 mg, 0.72 mmol) and N-ethyldiisopropylamine (244 μL, 1.4 mmol) in dimethylsulfoxide (3 mL) were heated at 120° C.

for 18 hours in a Reactivial®. The mixture was poured into water, and extracted with dichloromethane (2×). The combined organic fractions were washed with water, dried over magnesium sulphate and evaporated in vacuo. The residual oil was dissolved in dichloromethane (6 mL), trifluoroacetic acid (2 mL) added, and the solution stirred at room temperature 3 hours. The reaction was concentrated in vacuo, the residue partitioned between dichloromethane and 2N hydrochloric acid and the layers separated. The aqueous phase was washed with dichloromethane, then basified using solid sodium bicarbonate. This solution was extracted with dichloromethane (3×), these combined organic extracts dried over magnesium sulphate and evaporated in vacuo. The crude product was purified by column chromatography on silica gel using an elution gradient of dichloromethane:methanol:0.88 ammonia (98:2:0.25 to 96:4:0.5) to afford the title compound as a yellow foam, 80 mg.

$^1$H NMR (CD$_3$OD, 400 MHz) δ: 1.76-1.84 (m, 4H), 2.39 (s, 3H), 3.15 (m, 2H), 3.42 (s, 3H), 3.59 (m, 2H), 4.02 (q, 2H), 4.10 (t, 2H), 4.28 (m, 2H), 4.68 (s, 2H), 4.77 (t, 2H), 6.92 (m, 1H), 8.13 (m, 2H). LRMS:m/z APCI+507 [MH]$^+$

EXAMPLE 260

N-{5-[(1S,4S)-2.5-Diazabicyclo[2.2.1]hept-2-yl]-1-(2-ethoxyethyl)-3-methoxymethyl-1H-pyrazolo[4,3-d]pyrimidin-7-yl}-4-methylpyridin-2-ylamine

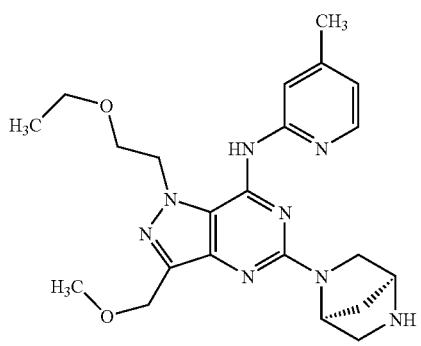

The title compound was obtained as a yellow solid from the chloride from preparation 159 and tert-butyl (1S,4S)-(−)-2,5-diazabicyclo[2.2.1]heptane-2-carboxylate, following a similar procedure to that described in example 259, except, the product was not purified by column chromatography.

$^1$H NMR (CD$_3$OD, 400 MHz) δ: 1.11 (t, 3H), 2.01 (m, 2H), 2.42 (s, 3H), 3.32 (m, 2H), 3.43 (s, 3H), 3.60 (q, 2H), 3.82 (m, 2H), 3.90 (t, 2H), 4.37 (m, 1H), 4.70 (s, 2H), 4.74 (m, 2H), 5.06 (m, 1H), 6.97 (d, 1H), 8.17 (d, 1H), 8.32 (s, 1H). LRMS:m/z APCI+439 [MH]$^+$

EXAMPLE 261

1-{3-Methyl-7-(4-methylpyridin-2-ylamino)-1-[2-(2,2,2-trifluoroethoxy)ethyl]-1H-pyrazolo[4,3-d]pyrimidin-5-yl}piperidine-4-carboxylic acid

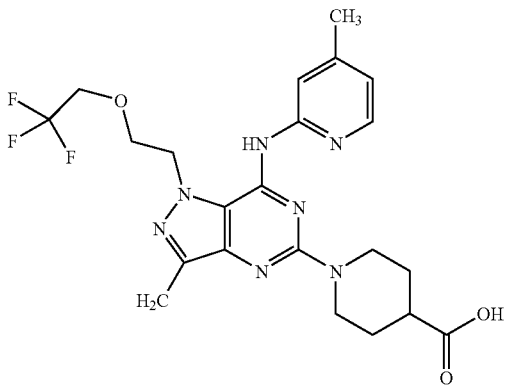

Sodium hydroxide solution (760 μL, 1M, 0.76 mmol) was added to a solution of the compound from preparation 203 (200 mg, 0.38 mmol) in dioxan (5 mL), and the reaction stirred at room temperature for 18 hours. The mixture was partitioned between ethyl acetate (20 mL) and water (20 mL) and the layers separated. The aqueous phase was acidified using 1M citric acid solution, then extracted with dichloromethane (2×50 mL). These combined organic extracts were dried over magnesium sulphate and evaporated in vacuo. The residue was purified by column chromatography on reverse phase silica gel using an elution gradient of water:methanol (100:0 to 20:80), and the appropriate fractions concentrated in vacuo. The residue was dissolved in dichloromethane (10 mL), the solution dried over magnesium sulphate and evaporated in vacuo to afford the title compound, 30 mg.

$^1$H NMR (DMSO-d$_6$, 400 MHz) δ: 1.52 (m, 2H), 1.84 (m, 2H), 2.30 (s, 3H), 2.50 (m, 4H), 3.00 (m, 2H), 3.95 (t, 2H), 4.06 (q, 2H), 4.47 (m, 2H), 4.64 (m, 2H), 6.78 (d, 1H), 7.94 (m, 1H), 8.14 (d, 1H). LRMS:m/z ES-492 [M−H]

EXAMPLE 262

1-{3-Methyl-7-(6-methylpyrimidin-4-ylamino)-1-[2-(2,2,2-trifluoroethoxy)ethyl]-1H-pyrazolo[4,3-d]pyrimidin-5-yl}piperidine-4-carboxylic acid

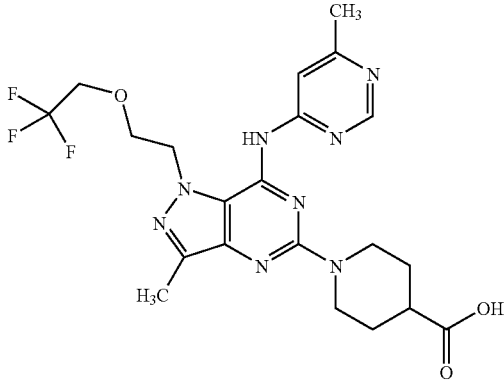

A mixture of the chloro compound from preparation 197 (150 mg, 0.37 mmol), and ethyl isonipecotate (188 μL, 1.22 mmol) in dimethylsulfoxide (2 mL) was heated at 120° C. for 3 hours. The cooled mixture was partitioned between dichloromethane (50 mL) and water (50 mL) and the phases separated. The organic layer was washed with water (2×25 mL), dried over magnesium sulphate and evaporated in vacuo. The residue was dissolved in dioxan (2 mL), sodium hydroxide (2.0 mL, 1M, 2.0 mmol) added, and the solution stirred at room temperature for 18 hours. The reaction was evaporated in vacuo, the residue partitioned between dichloromethane (20 mL) and water (20 mL), the layers separated, and the aqueous layer acidified with 1M citric acid. This solution was extracted into dichloromethane (2×50 mL) and the combined organic extracts dried over magnesium sulphate and evaporated in vacuo. The crude product was purified by column chromatography on silica gel using an elution gradient of dichloromethane:methanol:acetic acid (100:0:0 to 94:6:0.6) to give the title compound as a yellow solid, 87 mg.

$^1$H NMR (CD$_3$OD, 400 MHz) δ: 1.73 (m, 2H), 2.02 (m, 2H), 2.44 (s, 3H), 2.50 (s, 3H), 2.64 (m, 1H), 3.18 (m, 2H), 4.00-4.06 (m, 4H), 4.64 (m, 2H), 4.72 (t, 2H), 8.17 (m, 1H), 8.64 (s, 1H). LRMS:m/z APCI+495 [MH]$^+$

EXAMPLE 263

1-{3-Ethyl-7-(6-methylpyrimidin-4-ylamino)-1-[2-(2,2,2-trifluoroethoxy)ethyl]-1H-pyrazolo[4,3-d]pyrimidin-5-yl}piperidine-4-carboxylic acid

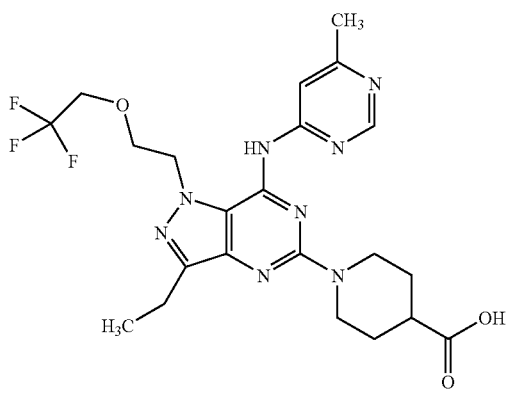

A mixture of the chloro compound from preparation 200 (150 mg, 0.36 mmol), and ethyl isonipecotate (277 μL, 1.80 mmol) in dimethylsulfoxide (1.5 mL) was heated in a Reactivial® at 120° C. for 18 hours. The cooled mixture was partitioned between ethyl acetate (50 mL) and water (50 mL) and the phases separated. The organic layer was washed with water (50 mL), dried over magnesium sulphate and evaporated in vacuo. The residue was dissolved in dioxan (3 mL), sodium hydroxide (2.5 mL, 1M, 2.5 mmol) added, and the solution stirred at room temperature for 72 hours. The reaction was evaporated in vacuo, the residue dissolved in water (2 mL) and the solution acidified using 10% citric acid solution. The resulting precipitate was filtered off, washed with water and dried in vacuo at 45° C. to afford the title compound as a yellow solid, 106 mg.

$^1$H NMR (CD$_3$OD, 400 MHz) δ: 1.35 (t, 3H), 1.73 (m, 2H), 1.99 (m, 2H), 2.50 (s, 3H), 2.62 (m, 1H), 2.89 (q, 2H), 3.15 (m, 2H), 3.96-4.09 (m, 4H), 4.60 (m, 2H), 4.70 (m, 2H), 8.17 (m, 1H), 8.66 (s, 1H). LRMS:m/z APCI+509 [MH]$^+$

The following preparations describe the preparation of certain intermediates used in the preceding examples.

Preparation 1

5-Isopropyl-4-nitro-2H-pyrazole-3-carboxamide

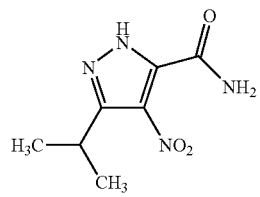

A solution of 5-isopropyl-4-nitro-2H-pyrazole-3-carboxylic acid (Farmaco, 46, 11, 1991, 1337-1350) (6 g, 0.03 mol) in N,N-dimethylformamide (69 μL) and dichloromethane (67 mL) was cooled to −5° C. in ice/acetone. Oxalyl chloride (11.48 g, 0.09 mol) was added over 30 minutes and the reaction mixture stirred for 1 hour, the reaction mixture was then allowed to return to room temperature for 2 hours. The reaction mixture was concentrated in vacuo and remaining solvent azeotroped with dichloromethane. The resulting solid was suspended in tetrahydrofuran (70 mL), cooled to 0° C. and 0.880 ammonia (25 mL) added. The reaction mixture was stirred for 30 minutes and then concentrated in vacuo. The resulting solid was suspended in water, filtered and dried at 70° C. under vacuum to yield the product.

$^1$H NMR (DMSO-d$_6$, 400 MHz) δ: 1.28 (d, 6H), 3.55 (m, 1H), 7.59 (s, 1H), 7.89 (s, 1H), 13.72 (br s, 1H). LRMS:m/z ES+199 [MH]$^+$

Preparation 2

4-Nitro-2H-pyrazole-3-carboxamide

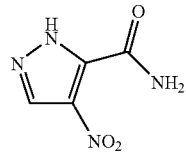

4-Nitro-2H-pyrazole-3-carboxylic acid (2.72 g, 17.4 mmol) was added to a solution of oxalyl chloride (2.42 mL, 27.7 mmol) and N,N-dimethylformamide (80 μL) in dichloromethane (45 mL) and the reaction mixture stirred at room temperature for 2 hours. The reaction mixture was concentrated in vacuo and azeotroped from dichloromethane (3×100 mL). The crude product was dissolved in tetrahydrofuran, cooled in an ice bath, and treated with 0.880 ammonia solution (20 mL). The reaction mixture was stirred at room temperature for 18 hours then concentrated in vacuo and the residue partitioned between dichloromethane (300 mL) and water (100 mL). The organic layer was separated, dried over magnesium sulphate and concentrated in vacuo to yield the title product. LRMS ES+m/z 157 [MH]$^+$

Preparation 3 tert-Butyl trans-2,5-dimethylpiperazine-1-carboxylate

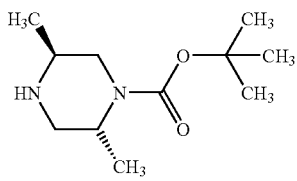

trans-2,5-Dimethylpiperazine (10 g, 0.087 mol) was dissolved in a mixture of dioxan (18 mL) and water (8 mL) and cooled in an ice bath. Di-tert-butyl dicarbonate (19.29 g, 0.089 mol) was added and the reaction mixture allowed to return to room temperature. Additional dioxan (9 mL) and water (4 mL) were added and the mixture stirred for 18 hours. The dioxan was removed in vacuo and the mixture basified to pH 9, extracted into ethyl acetate dried over magnesium sulphate and concentrated. The mixture was purified by column chromatography on silica gel using methanol:dichloromethane 20:80. The crude product was dissolved in ether and hydrochloric acid (0.5 eq) added to give the HCl salt of the title compound, (2.73 g).

$^1$H NMR (DMSO-d$_6$ 400 MHz) δ: 1.21 (2×d, 6H), 1.40 (s 9H), 2.90 (dd, 1H), 3.21 (dd 1H), 3.52 (m 2H), 3.62 (dd 1H), 4.25 (m 1H), 9.2 (br m 2H). LRMS: ES+m/z 215 [MH]$^+$

Preparation 4 tert-Butyl (3S)-3-methylpiperazine-1-carboxylate

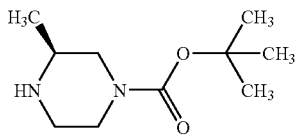

A solution of (2S)-2-methylpiperazine (3.8 g, 38 mmol) and N-(tert-butyloxycarbonyloxy)phthalimide (10 g, 38 mmol) in dichloromethane (100 mL) was stirred at room temperature for 3 hours. The mixture was washed with 2N sodium hydroxide solution, the organic solution dried over magnesium sulphate, and concentrated in vacuo to afford the title compound as a clear oil, 4.31 g.

$^1$H NMR (CDCl$_3$ 400 MHz) δ: 1.12 (m, 3H), 1.45 (s, 9H), 2.74-2.90 (br m, 3H), 3.00 (d, 2H), 3.78 (m, 1H), 3.88-3.98 (br m, 2H). LRMS ES+m/z 201 [MH]$^+$

Preparation 5

3-(Methylaminomethyl)-1-methylpiperidine

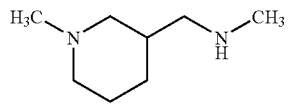

A solution of 3-(chloromethyl)-1-methylpiperidine (9.2 g, 50 mmol) (U.S. Pat. No. 6,184,338, example 5) and 33% methylamine in ethanol (60 mL) in ethanol (30 mL) was heated in a sealed vessel at 100° C. for 17 hours. The reaction mixture was concentrated in vacuo and diluted with water before being extracted into dichloromethane and dried over magnesium sulphate. The reaction mixture was filtered and concentrated in vacuo to yield the title product, 8.2 g.

Microanalysis: Observed C, 44.80%, H, 9.37, N, 13.21%. C$_8$H$_{18}$N$_2$ Calculated C, 44.65%, H, 9.37%, N, 13.02%.

Preparation 6 tert-Butyl 3-(methylamino)azetidine-1-carboxylate

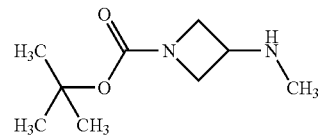

tert-Butyl 3-iodoazetidine-1-carboxylate (EP 1176142, pg. 23, ex. 2 (i)) (2.0 g, 7.07 mmol) was added to 33% methylamine in ethanol (45 mL) and the reaction mixture heated in a sealed vessel at 100° C. for 24 hours. The reaction mixture was concentrated in vacuo and the residue partitioned between ethyl acetate and 1M aqueous sodium hydroxide. The organic layer was separated and washed with brine, dried over magnesium sulphate and concentrated in vacuo. The crude product was purified by column chromatography on silica gel eluting with dichloromethane:methanol:0.880 ammonia 96:3.5:0.5 to yield the title product.

$^1$H NMR (CDCl$_3$, 400 MHz) δ: 1.43 (s, 9H), 1.94 (m, 1H), 2.41 (s, 3H), 3.49 (m, 1H), 3.67 (m, 2H), 4.06 (m, 2H). LRMS APCI+m/z 187 [MH]$^+$

Preparation 7

(3R)-3-Methoxypyrrolidine trifluoroacetate

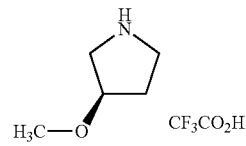

tert-Butyl (3R)-3-hydroxypyrrolidine-1-carboxylate (25 g, 133.4 mmol) was dissolved in tetrahydrofuran (668 mL) and the reaction mixture cooled to 0° C. on an ice bath. The reaction mixture was treated with sodium hydride (4.40 g, 80% dispersion in mineral oil, 146.6 mmol) and stirred until back at room temperature. The reaction mixture was then treated with methyl iodide (29.0 g, 200.0 mmol) and stirred at room temperature for 18 hours. The reaction mixture was diluted with water (200 mL) and concentrated in vacuo until just the aqueous remained. The reaction mixture was treated with ethyl acetate (1500 mL), the organic layer separated, dried over magnesium sulphate and concentrated in vacuo to yield the title product as a brown oil.

This oil (24.75 g, 123.0 mmol) was dissolved in diethyl ether (615 mL) and hydrogen chloride bubbled through the solution for 1 hour at room temperature. The reaction mixture was concentrated in vacuo and re-dissolved in ether and stirred for a further 2 hours. The ether was decanted off and the reaction mixture concentrated in vacuo. The crude product was dissolved in ethanol and treated with trifluoroacetic acid (200 mL) and stirred at room temperature for 2 hours. The reaction mixture was concentrated in vacuo to yield the title product.

1H NMR (CD$_3$OD, 400 MHz) δ: 1.96 (m, 1H), 2.09 (m, 1H), 3.08-3.37 (m, 4H), 4.06 (m, 1H), 4.80 (s, 3H).

Preparation 8

3-Amino-N-methylpropionamide hydrochloride

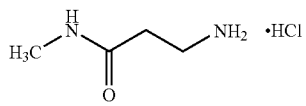

Benzyl (2-(methylcarbamoyl)ethyl)carbamate (7.92 g, 33.52 mmol) and 5% Pd/C (800 mg) were dissolved in ethanol (300 mL) and the reaction mixture stirred at room temperature under 50 psi of hydrogen for 4 hours. The reaction mixture was filtered through Arbocel®, washing through with ethanol, and 1M hydrochloric acid solution (37 mL) was added to the filtrate. The reaction mixture was concentrated in vacuo and the crude product was azeotroped with dichloromethane (×3) and dried in vacuo to yield the title product, 4.66 g.

$^1$H NMR (CDCl$_3$, 400 MHz) δ: 2.48 (m, 2H), 2.61 (s, 3H), 2.97 (m, 2H), 7.89-8.11 (br m, 3H)

Preparation 9

5-Vinylpyridin-2-amine

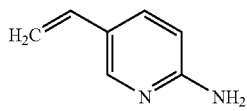

Vinyltributyltin (13 mL, 44.6 mmol), palladium(II) acetate (0.45 g, 2.1 mmol), triethylamine (12.4 mL, 89.1 mmol) and tri-(o-tolyl)phosphine (3.69 g, 12.15 mmol) were added to a solution of 5-bromopyridin-2-amine (7.0 g, 40.5 mmol) in acetonitrile (70 mL) and the reaction mixture refluxed for 18 hours. The reaction mixture was washed with 2M sodium carbonate solution (80 mL), the organics separated, dried over magnesium sulphate, filtered and concentrated in vacuo. The crude product was purified by column chromatography on silica gel using methanol:dichloromethane 3:97 to yield 3.6 g of product. This residue was dissolved in dichloromethane and washed with aqueous solutions of potassium fluoride and then sodium hydrogencarbonate. The organic solution was dried over magnesium sulphate, filtered and concentrated in vacuo to yield 1.9 g of final product.

$^1$H NMR (400 MHz, CDCl$_3$) δ: 4.52 (br s, 2H), 5.13 (d, 1H), 5.58 (d, 1H), 6.48 (d, 1H), 6.57 (m, 1H), 7.54 (d, 1H), 8.05 (s, 1H). LRMS APCI+m/z 121 [MH]$^+$

Preparation 10

5-Ethylpyridin-2-amine

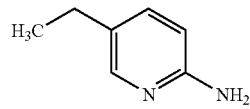

10% Palladium on carbon (300 mg) was added to a solution of the amine of preparation 9 (1.7 g, 14.1 mmol) in ethanol (80 mL) and the reaction mixture stirred under 15 psi of hydrogen for 18 hours. The reaction mixture was filtered through Arbocel® and the filtrate concentrated in vacuo. The resulting oil was dissolved in dichloromethane and washed with a solution of potassium fluoride (2×10 mL), the organic phase dried over magnesium sulphate, filtered and concentrated in vacuo to yield 650 mg product.

$^1$H NMR (400 MHz, CDCl$_3$) δ: 1.16 (t, 3H), 2.48 (q, 2H), 4.35 (br s, 2H), 6.46 (d, 1H), 7.26 (m, 1H), 7.89 (m, 1H)

Starting Materials

The following pyrazoles were used as starting materials:

5-Methyl-4-nitro-2H-pyrazole-3-carboxamide (U.S. Pat. No. 4,282,361, ex. 7)

5-Ethyl-4-nitro-2H-pyrazole-3-carboxamide (WO 02/10171, pg. 17, prep. 1, synthesis j.)

4-Nitro-5-propyl-2H-pyrazole-3-carboxamide (WO 02/10171, pg. 17, prep. 1, synthesis k.)

5-Isopropyl-4-nitro-2H-pyrazole-3-carboxamide—see Preparation 1

4-Nitro-2H-pyrazole-3-carboxamide—see Preparation 2

Preparations 11 to 23

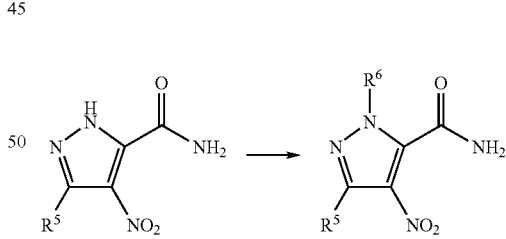

Potassium carbonate (1 eq) and the appropriate R$^6$Br (1 eq) were added to a solution of the appropriate pyrazole (see above starting materials) (1 eq) in N,N-dimethylformamide (2-3 mL.mmol$^{-1}$) and the reaction mixture stirred under nitrogen at room temperature for 18 hours. The reaction mixture was concentrated in vacuo and partitioned between ethyl acetate and water, the organic phase dried over magnesium sulphate and concentrated in vacuo. The crude product was purified using column chromatography on silica gel eluting with ethyl acetate:pentane 50:50 to 100:0 to yield the desired products.

Preparations 24 to 37

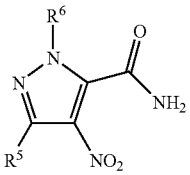

| Prep | | |
|---|---|---|
| 11 | $R^5$ = H; $R^6$ = —(CH$_2$)$_2$OCH$_2$CH$_3$ | |
| | $^1$H NMR (DMSO-d$_6$, 400 MHz) δ: 1.03 (t, 3H), 3.36 (q, 2H), 3.69 (t, 2H), 4.30 (t, 2H), 8.26 (br s, 1H), 8.29 (s, 1H), 8.42 (br s, 1H). LRMS: m/z APCl+ 229, [MH]$^+$ | |
| 12 | $R^5$ = —CH$_3$; $R^6$ = —(CH$_2$)$_3$OCH$_3$ | |
| | $^1$H NMR (CDCl$_3$, 400 MHz) δ: 2.13 (m, 2H), 2.52 (s, 3H), 3.27 (s, 3H), 3.42 (t, 2H), 4.42 (t, 2H), 5.97 (br s, 1H), 7.36 (br s, 1H). LRMS: m/z APCl+ 265, [MNa]$^+$ | |
| 13 | $R^5$ = —CH$_3$; $R^6$ = —(CH$_2$)$_2$OCH$_2$CH$_3$ | |
| | $^1$H NMR (CDCl$_3$, 400 MHz) δ: 1.12 (t, 3H), 2.51 (s, 3H), 3.46 (q, 2H), 3.78 (t, 2H), 4.44 (t, 2H), 6.07 (br s, 1H), 7.42 (br s, 1H). LRMS: m/z APCl+ 243, [MH]$^+$ | |
| 14 | $R^5$ = —CH$_3$; $R^6$ = —(CH$_2$)$_2$OCH$_3$ | |
| | $^1$H NMR (CDCl$_3$, 400 MHz) δ: 2.51 (s, 3H), 3.33 (s, 3H), 3.74 (t, 2H), 4.48 (t, 2H), 6.05 (br s, 1H), 7.36 (br s, 1H). LRMS: m/z APCl+ 251, [MNa]$^+$ | |
| 15 | $R^5$ = —CH$_2$CH$_3$; $R^6$ = —(CH$_2$)$_2$OCH$_3$ | |
| | LRMS: m/z APCl+ 243, [MH]$^+$ | |
| 16 | $R^5$ = —CH$_2$CH$_3$; $R^6$ = —(CH$_2$)$_2$OCH$_2$CH$_3$ | |
| | $^1$H NMR (DMSO-d$_6$, 400 MHz) δ: 1.03 (t, 3H), 1.18 (t, 3H), 2.84 (q, 2H), 3.37 (q, 2H), 3.69 (t, 2H), 4.22 (t, 2H), 8.18 (br s, 1H), 8.37 (br s, 1H). LRMS: m/z APCl+ 279, [MNa]$^+$ | |
| 17 | $R^5$ = —CH$_2$(CH$_3$)$_2$; $R^6$ = —(CH$_2$)$_2$OCH$_3$ | |
| | $^1$H NMR (DMSO-d$_6$, 400 MHz) δ: 1.26 (d, 6H), 3.18 (s, 3H), 3.42 (m, 1H), 3.65 (t, 2H), 4.25 (t, 2H), 8.17 (br s, 1H), 8.40 (br s, 1H). LRMS: m/z ES+ 279 [MNa]$^+$ | |
| 18 | $R^5$ = —CH$_3$; $R^6$ = —(CH$_2$)$_2$O(CH$_2$)$_2$CH$_3$ | |
| | $^1$H NMR (DMSO-d$_6$, 400 MHz) δ: 0.79 (t, 3H), 1.44 (m, 2H), 2.41 (s, 3H), 3.29 (t, 2H), 3.70 (t, 2H), 4.22 (t, 2H), 8.18 (s, 1H), 8.33 (s, 1H). LRMS m/z APCl+ 257 [MH]$^+$ | |
| 19 | $R^5$ = —CH$_3$; $R^6$ = —(CH$_2$)$_3$OCH$_2$CH$_3$ | |
| | $^1$H NMR (DMSO-d$_6$, 400 MHz) δ: 1.08 (t, 3H), 1.96 (m, 2H), 2.55 (s, 3H), 3.32 (m, 2H), 3.37 (m, 2H), 4.15 (t, 2H), 7.64 (br s, 1H), 7.89 (br s, 1H). | |
| 20 | $R^5$ = —CH$_3$; $R^6$ = —(CH$_2$)$_2$OCH(CH$_3$)$_2$ | |
| | $^1$H NMR (CDCl$_3$ 400 MHz) δ: 1.07 (d, 6H), 2.54 (s, 3H) 3.56 (m, 1H), 3.81 (t, 2H), 4.42 (t, 2H), 5.97 (br s, 1H), 7.54 (br s, 1H). LRMS APCl+ m/z 257 [MH]$^+$ | |
| 21 | $R^5$ = —(CH$_2$)$_2$CH$_3$; $R^6$ = —(CH$_2$)$_2$OCH$_3$ | |
| | $^1$H NMR (CDCl$_3$, 400 MHz) δ: 1.00 (t, 3H), 1.74 (m, 2H), 2.89 (t, 2H), 3.33 (s, 3H), 3.78 (t, 2H), 4.49 (t, 2H), 5.95 (br s, 1H), 7.25 (br s, 1H). MS ES+ m/z 257 [MH]$^+$ | |
| 22 | $R^5$ = —(CH$_2$)$_2$CH$_3$; $R^6$ = —CH$_3$ | |
| | $^1$H NMR (DMSO-d$_6$, 400 MHz) δ: 0.93 (t, 3H), 1.62 (m, 2H), 2.46 (m, 2H), 3.78 (s, 3H), 8.08 (m, 1H), 8.32 (m, 1H). LRMS APCl m/z 213 [MH]$^+$ | |
| 23 | $R^5$ = —CH$_3$; $R^6$ = —CH(CH$_3$)$_2$ | |
| | $^1$H NMR (DMSO-d$_6$, 400 MHz) δ: 1.38 (d, 6H), 2.42 (s, 3H), 4.45 (m, 1H), 8.21 (s, 1H), 8.43 (br s, 1H). LRMS: m/z APCl+ 213 [MH]$^+$ | |

Preparation 18—made using 1-(2-bromoethoxy)propane (EP 1072595)

Preparation 19—made using 1-ethoxy-3-iodopropane (EP 319479 pg21 ex. 23)

Preparation 20—made using 2-(2-bromoethoxy)propane (FR 2638745 pg7 ex. 4.1)

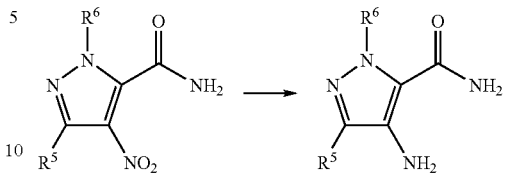

Ammonium formate (5 eq) was added portionwise to a suspension of 10% palladium(II) hydroxide on carbon (10% w/w) and the required 4-nitro pyrazole (1 eq) in ethanol (4-5 mL.mmol$^{-1}$) and the reaction mixture refluxed under nitrogen for 2 hours. The reaction mixture was filtered through Arbocel® and washed with ethanol and the filtrates concentrated in vacuo. If present, remaining ethanol was azeotroped with toluene, yielding the desired product.

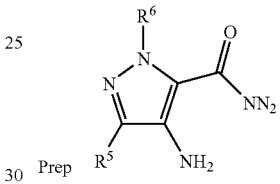

| Prep | | |
|---|---|---|
| 24 | $R^5$ = H; $R^6$ = —(CH$_2$)$_2$OCH$_2$CH$_3$ | |
| | $^1$H NMR (DMSO-d$_6$, 400 MHz) δ: 1.04 (t, 3H), 3.34 (q, 2H), 3.60 (t, 2H), 4.36 (s, 2H), 4.42 (t, 2H), 7.03 (s, 1H), 7.40 (br s, 2H). LRMS: m/z APCl+ 199, [MH]$^+$ | |
| 25 | $R^5$ = —CH$_3$; $R^6$ = H | |
| | $^1$H NMR (DMSO-d$_6$, 400 MHz) δ: 2.04 (s, 3H), 4.45 (br s, 2H), 7.13 (br s, 2H). LRMS: m/z APCl+ 399, [MH]$^+$ | |
| 26 | $R^5$ = —CH$_3$; $R^6$ = —(CH$_2$)$_3$OCH$_3$ | |
| | $^1$H NMR (DMSO-d$_6$, 400 MHz) δ: 1.82 (m, 2H), 2.04 (s, 3H), 3.17 (s, 3H), 3.22 (t, 2H), 4.01 (br s, 2H), 4.27 (t, 2H), 7.45 (br s, 2H). LRMS: m/z APCl+ 235, [MNa]$^+$ | |
| 27 | $R^5$ = —CH$_3$; $R^6$ = —(CH$_2$)$_2$OCH$_2$CH$_3$ | |
| | $^1$H NMR (DMSO-d$_6$, 400 MHz) δ: 1.03 (t, 3H), 2.02 (s, 3H), 3.35 (q, 2H), 3.56 (t, 2H), 4.12 (br s, 2H), 4.35 (t, 2H), 5.37 (br s, 1H), 7.50 (br s, 1H). LRMS: m/z APCl+ 213, [MH]$^+$ | |
| 28 | $R^5$ = —CH$_3$; $R^6$ = —(CH$_2$)$_2$OCH$_3$ | |
| | $^1$H NMR (DMSO-d$_6$, 400 MHz) δ: 2.04 (s, 3H), 3.16 (s, 3H), 3.53 (t, 2H), 4.07 (br s, 2H), 4.40 (t, 2H), 7.47 (br s, 2H). LRMS: m/z APCl+ 221, [MNa]$^+$ | |
| 29 | $R^5$ = —CH$_2$CH$_3$; $R^6$ = —(CH$_2$)$_2$OCH$_3$ | |
| | $^1$H NMR (CDCl$_3$, 400 MHz) δ: 1.20 (t, 3H), 2.53 (q, 2H), 3.32 (s, 3H), 3.80 (t, 2H), 4.46 (t, 2H). LRMS: m/z APCl+ 213, [MH]$^+$ | |
| 30 | $R^5$ = —CH$_2$CH$_3$; $R^6$ = —(CH$_2$)$_2$OCH$_2$CH$_3$ | |
| | $^1$H NMR (CDCl$_3$, 400 MHz) δ: 1.14 (t, 3H), 1.23 (t, 3H), 2.55 (q, 2H), 3.50 (q, 2H), 3.84 (t, 2H), 4.43 (t, 2H). LRMS: m/z APCl+ 227 [MH]$^+$ | |
| 31 | $R^5$ = —CH(CH$_3$)$_2$; $R^6$ = —(CH$_2$)$_2$OCH$_3$ | |
| | $^1$H NMR (DMSO-d$_6$, 400 MHz) δ: 1.15 (d, 6H), 2.95 (m, 1H), 3.17 (s, 3H), 3.55 (t, 2H), 4.07 (br s, 2H), 4.41 (t, 2H), 7.50 (br s, 2H). LRMS: m/z APCl+ 227, [MH]$^+$ | |
| 32 | $R^5$ = —CH$_3$; $R^6$ = —(CH$_2$)$_2$O(CH$_2$)$_2$CH$_3$ | |
| | $^1$H NMR (CDCl$_3$, 400 MHz) δ: 0.85 (t, 3H), 1.55 (m, 2H), 2.20 (s, 3H), 3.42 (t, 2H), 3.85 (t, 2H), 4.43 (t, 2H). LRMS: m/z APCl+ 227, [MH]$^+$ | |
| 33 | $R^5$ = —CH$_3$; $R^6$ = —(CH$_2$)$_2$OCH(CH$_3$)$_2$ | |
| | $^1$H NMR (CDCl$_3$, 400 MHz) δ: 1.08 (d, 6H), 2.23 (s, 3H), 3.58 (m, 1H), 3.83 (t, 2H), 4.39 (t, 2H). LRMS APCl+ m/z 227 [MH]$^+$ | |
| 34 | $R^5$ = —(CH$_2$)$_2$CH$_3$; $R^6$ = —(CH$_2$)$_2$OCH$_3$ | |
| | $^1$H NMR (CDCl$_3$, 400 MHz) δ: 0.83 (t, 3H), 1.62 (m, 2H), 2.43 (m, 2H), 3.36 (s, 3H), 3.78 (m, 2H), 4.46 (m, 2H). LRMS TSP+ m/z 227 [MH]$^+$ | |
| 35 | $R^5$ = —(CH$_2$)$_2$CH$_3$; $R^6$ = —CH$_3$ | |
| | $^1$H NMR (CDCl$_3$, 400 MHz) δ: 0.95 (t, 3H), 1.62 (m, 2H), 2.53 (t, 2H), 2.80 (br s, 2H), 4.10 (s, 3H). LRMS TSP+ m/z 205 [MNa]$^+$ | |

-continued

| Prep | | |
|---|---|---|

36  $R^5 = $ —$CH_3$; $R^6 = $ —$CH(CH_3)_2$
$^1$H NMR (CDCl$_3$, 400 MHz) δ: 1.42 (d, 6H), 2.23 (s, 3H), 5.55 (m, 1H). LRMS: m/z APCl+ 183, [MH]$^+$

37  $R^5 = $ —$CH_3$; $R^6 = $ —$(CH_2)_3OCH_2CH_3$
$^1$H NMR (CDCl$_3$, 400 MHz) δ: 1.03 (t, 3H), 1.82 (m, 2H), 2.02 (s, 3H), 3.24 (t, 2H), 3.48 (q, 2H), 4.05 (m, 2H), 4.28 (t, 2H), 7.48 (br m, 2H). LRMS APCl m/z 227 [MH]$^+$

Preparations 38 to 51

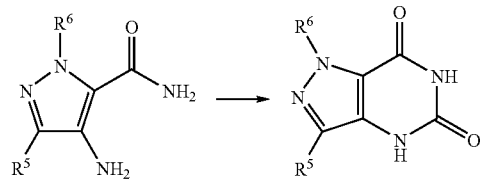

A mixture of the appropriate 4-aminopyrazole-5-carboxamide (see preparations 24-37) (1 eq) and carbonyl diimidazole (1 eq) in N,N-dimethylformamide (3.8 mL.mmol$^{-1}$) was stirred under nitrogen at room temperature for 1 hour. The reaction was then heated at 80° C. for 18 hours. The reaction mixture was concentrated in vacuo and the residue triturated with acetone. The resulting solid was filtered and dried to give the required product.

| Prep | | |
|---|---|---|

38  $R^5 = $ —$(CH_2)_2CH_3$; $R^6 = $ —$CH_3$
$^1$H NMR (DMSO-d$_6$, 400 MHz) δ: 0.9 (t, 3H), 1.55 (m, 2H), 2.55 (t, 2H), 3.95 (s, 3H), 11.0 (br m, 2H). LRMS: m/z 209 [MH]$^+$

39  $R^5 = $ —$CH_3$; $R^6 = $ —$CH(CH_3)_2$
$^1$H NMR (DMSO-d$_6$, 400 MHz) δ: 1.36 (d, 6H), 2.20 (s, 3H), 5.13 (m, 1H), 11.01 (s, 2H). LRMS: m/z APCl+ 209, [MH]$^+$

40  $R^5 = $ —$CH_2CH_3$; $R^6 = $ —$(CH_2)_2OCH_2CH_3$
$^1$H NMR (DMSO-d$_6$, 400 MHz) δ: 0.98 (t, 3H), 1.12 (t, 3H), 2.61 (q, 2H), 3.38 (q, 2H), 3.67 (t, 2H), 4.46 (t, 2H), 11.06 (s, 2H). LRMS: m/z APCl$^-$ 251, [M − H]$^-$

41  $R^5 = $ —$CH_3$; $R^6 = $ —$(CH_2)_2OCH_3$
$^1$H NMR (DMSO-d$_6$, 400 MHz) δ: 2.21 (s, 3H), 3.17 (s, 3H), 3.55 (t, 2H), 4.46 (t, 2H), 11.00 (br s, 2H). LRMS: m/z APCl$^-$ 223, [M − H]$^-$

42  $R^5 = $ —$CH_2CH_3$; $R^6 = $ —$(CH_2)_2OCH_3$
$^1$H NMR (DMSO-d$_6$, 400 MHz) δ: 1.12 (t, 3H), 2.63 (q, 2H), 3.26 (s, 3H), 3.67 (t, 2H), 4.46 (t, 2H), 11.00 (br s, 2H). LRMS: m/z APCl+ 239, [MH]$^+$

43  $R^5 = $ —$CH_3$; $R^6 = $ —$(CH_2)_2OCH_2CH_3$
$^1$H NMR (DMSO-d$_6$, 400 MHz) δ: 1.00 (t, 3H), 2.19 (s, 3H), 3.34 (q, 2H), 3.67 (t, 2H), 4.44 (t, 2H), 11.02 (br s, 2H). LRMS: m/z APCl$^-$ 237, [M − H]$^-$

44  $R^5 = $ H; $R^6 = $ —$(CH_2)_2OCH_2CH_3$
$^1$H NMR (DMSO-d$_6$, 400 MHz) δ: 0.97 (s, 3H), 3.36 (q, 2H), 3.70 (t, 2H), 4.51 (t, 2H), 7.34 (s, 1H), 10.93 (br s, 1H), 11.07 (br s, 1H)

45  $R^5 = $ —$CH_3$; $R^6 = $ —$(CH_2)_3OCH_3$
$^1$H NMR (DMSO-d$_6$, 400 MHz) δ: 1.82 (m, 2H), 2.18 (s, 3H), 3.17 (s, 3H), 3.26 (t, 2H), 4.32 (t, 2H), 11.00 (br s, 2H). LRMS: m/z (APCl−) 237, [M − H]$^-$

46  $R^5 = $ —$CH(CH_3)_2$; $R^6 = $ —$(CH_2)_2OCH_3$
$^1$H NMR (DMSO-d$_6$, 400 MHz) δ: 1.19 (d, 6H), 3.10 (m, 1H), 3.17 (s, 3H), 3.66 (t, 2H), 4.48 (t, 2H), 11.00 (s, 1H), 11.03 (s, 1H). LRMS: m/z APCl+ 253, [MH]$^+$

47  $R^5 = $ —$CH_3$; $R^6 = $ —$(CH_2)_2O(CH_2)_2CH_3$
$^1$H NMR (DMSO-d$_6$, 400 MHz) δ: 0.74 (t, 3H), 1.39 (m, 2H), 2.20 (s, 3H), 3.26 (t, 2H), 3.67 (t, 2H), 4.46 (t, 2H), 11.04 (s, 2H). LRMS: m/z APCl+ 253, [MH]$^+$

48  $R^5 = $ —$CH_3$; $R^6 = $ —$(CH_2)_2OCH(CH_3)_2$
$^1$H NMR (DMSO-d$_6$, 400 MHz) δ: 0.96 (d, 6H), 2.19 (s, 3H), 3.45 (m, 1H), 3.65 (t, 2H), 4.40 (t, 2H), 11.00 (br s, 2H). LRMS APCl− m/z 251 [M − H]$^-$

49  $R^5 = $ —$CH_3$; $R^6 = $ H
$^1$H NMR (DMSO-d$_6$, 400 MHz, tautomers) δ: 2.18 (s, 1.5H), 2.20 (s, 1.5H), 10.70 (br s, 1H), 10.90 (br s, 0.5H), 10.92 (br s, 0.5H), 13.45 (br s, 0.5H), 13.49 (br s, 0.5H). LRMS: m/z ES+ 189, [MNa]$^+$ 50  $R^5 = $ —$(CH_2)_2CH_3$; $R^6 = $ —$(CH_2)_2OCH_3$
$^1$H NMR (DMSO-d$_6$, 400 MHz) δ: 0.86 (t, 3H), 1.54 (m, 2H), 2.58 (t, 2H), 3.16 (s, 3H), 3.65 (t, 2H), 4.48 (t, 2H), 11.06 (s, 2H). LRMS APCl+ m/z 253 [MH]$^+$ 51  $R^5 = $ —$CH_3$; $R^6 = $ —$(CH_2)_3OCH_2CH_3$
$^1$H NMR (DMSO-d$_6$, 400 MHz) δ: 1.08 (t, 3H), 1.90 (m, 2H), 2.19 (s, 3H), 3.35 (m, 4H), 4.38 (t, 2H), 11.00 (br s, 2H). LRMS: m/z APCl$^-$ 237, [M − H]$^-$ Preparations 52 to 65

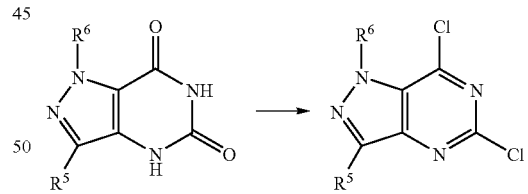

Method A (Preparations 52, 55, 56, 58 and 65): N-ethyldiisopropylamine (2-2.5 eq) was added to a solution of the appropriate dione (see preparations 38, 41, 42, 44 and 50) (1 eq) in phosphorous oxychloride (3 mL.mmol$^{-1}$) and the resulting solution heated under reflux for 18 hours. The cooled mixture was concentrated in vacuo, the residue dissolved in ethyl acetate (3.5 mL.mmol$^{-1}$) and carefully washed with water (3.5 mL.mmol$^{-1}$). The organic solution was evaporated in vacuo and the crude product purified by column chromatography on silica gel using ethyl acetate: pentane (20:80 to 60:40) to give the required compound.

Method B (Preparations 53, 54, 57, 59, 60, 61, 62 and 63): Tetraethylammonium chloride (3 eq) and phosphorous oxychloride (15 eq) were added to a solution of the appropriate dione (see preparations 39, 40, 43, 45-48 and 51) (1 eq) in acetonitrile (5-10 mL.mmol$^{-1}$) and the resulting solution heated under reflux for 18 hours. The cooled mixture was concentrated in vacuo, the residue dissolved in ethyl acetate (3.5 mL.mmol$^{-1}$) and carefully washed with water (3.5 mL.mmol$^{-1}$). The organic solution was evaporated in vacuo and the crude product purified by column chromatography on silica gel using ethyl acetate:pentane (20:80 to 60:40 to give the required compound.

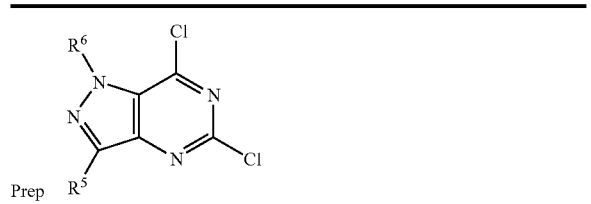

| Prep | |
|---|---|
| 52 | $R^5$ = —(CH$_2$)$_2$CH$_3$; $R^6$ = —CH$_3$<br>$^1$H NMR (CDCl$_3$ 400 MHz) δ: 1.00 (t, 3H), 1.80 (m, 2H), 2.95 (t, 2H), 4.30 (s, 3H). LRMS: m/z APCl+ 245 [MH]$^+$ |
| 53 | $R^5$ = —CH$_3$; $R^6$ = —CH(CH$_3$)$_2$<br>$^1$H NMR (CDCl$_3$, 400 MHz) δ: 1.60 (d, 6H), 2.62 (s, 3H), 5.43 (m, 1H). LRMS: m/z APCl+ 245, [MH]$^+$ |
| 54 | $R^5$ = —CH$_2$CH$_3$; $R^6$ = —(CH$_2$)$_2$OCH$_2$CH$_3$<br>$^1$H NMR (CDCl$_3$, 400 MHz) δ: 1.07 (t, 3H), 1.40 (t, 3H), 3.05 (q, 2H), 3.43 (q, 2H), 3.83 (t, 2H), 4.82 (t, 2H). LRMS: m/z APCl+ 289, [MH]$^+$ |
| 55 | $R^5$ = —CH$_3$; $R^6$ = —(CH$_2$)$_2$OCH$_3$<br>$^1$H NMR (CDCl$_3$, 400 MHz) δ: 2.60 (s, 3H), 3.28 (s, 3H), 3.79 (t, 2H), 4.82 (t, 2H). LRMS: m/z APCl+ 261, [MNa]$^+$ |
| 56 | $R^5$ = —CH$_2$CH$_3$; $R^6$ = —(CH$_2$)$_2$OCH$_3$<br>$^1$H NMR (CDCl$_3$, 400 MHz) δ: 1.30 (t, 3H), 2.94 (q, 2H), 3.16 (s, 3H), 3.73 (t, 2H), 4.77 (t, 2H). LRMS: m/z APCl+ 275, [MH]$^+$ |
| 57 | $R^5$ = —CH$_3$; $R^6$ = —(CH$_2$)$_2$OCH$_2$CH$_3$<br>$^1$H NMR (CDCl$_3$, 400 MHz) δ: 1.08 (t, 3H), 2.60 (s, 3H), 3.42 (q, 2H), 3.81 (t, 2H), 4.84 (t, 2H). LRMS APCl+ m/z 275 [MH]$^+$ |
| 58 | $R^5$ = H; $R^6$ = —(CH$_2$)$_2$OCH$_2$CH$_3$<br>$^1$H NMR (CDCl$_3$, 400 MHz) δ: 1.04 (t, 3H), 3.42 (q, 2H), 3.86 (t, 2H), 4.88 (t, 2H), 8.23 (s, 1H). LRMS: m/z APCl+ 261, [MH]$^+$ |
| 59 | $R^5$ = —CH$_3$; $R^6$ = —(CH$_2$)$_3$OCH$_3$<br>$^1$H NMR (DMSO-d$_6$, 400 MHz) δ: 2.05 (m, 2H), 2.49 (s, 3H), 3.16 (s, 3H), 3.32 (t, 2H), 4.65 (t, 2H). LRMS: m/z APCl+ 276, [MH]$^+$ |
| 60 | $R^5$ = —CH$_3$; $R^6$ = —(CH$_2$)$_2$OCH$_2$(CH$_3$)$_2$<br>$^1$H NMR (400 MHz, CDCl$_3$) δ: 0.91 (d, 6H), 2.50 (s, 3H), 3.40 (m, 1H), 3.70 (t, 2H), 4.70 (t, 2H). LRMS APCl+ m/z 289 [MH]$^+$ |
| 61 | $R^5$ = —CH(CH$_3$)$_2$; $R^6$ = —(CH$_2$)$_2$OCH$_3$<br>$^1$H NMR (DMSO-d$_6$, 400 MHz) δ: 1.38 (d, 6H), 3.18 (s, 3H), 3.39 (m, 1H), 3.74 (t, 2H), 4.77 (t, 2H). LRMS: m/z APCl+ 289, [MH]$^+$ |
| 62 | $R^5$ = —CH$_3$; $R^6$ = —(CH$_2$)$_2$O(CH$_2$)$_2$CH$_3$<br>$^1$H NMR (CDCl$_3$, 400 MHz) δ: 0.76 (t, 3H), 1.45 (m, 2H), 2.62 (s, 3H), 3.31 (t, 2H), 3.82 (t, 2H), 4.82 (t, 2H). LRMS: m/z APCl+ 289, [MH]$^+$ |
| 63 | $R^5$ = —CH$_3$; $R^6$ = —(CH$_2$)$_3$OCH$_2$CH$_3$<br>$^1$H NMR (CDCl$_3$, 400 MHz): δ: 0.97 (t, 3H), 2.06 (m, 2H), 2.51 (s, 3H), 3.36 (m, 4H), 4.66 (m, 2H) |
| 64 | $R^5$ = —CH$_3$; $R^6$ = H<br>$^1$H NMR (DMSO-d$_6$, 400 MHz) δ: 2.52 (m, 3H). LRMS ES- m/z 201 [M − H]$^-$ |
| 65 | $R^5$ = —(CH$_2$)$_2$CH$_3$; $R^6$ = —(CH$_2$)$_2$OCH$_3$<br>$^1$H NMR (CDCl$_3$, 400 MHz) δ: 0.99 (t, 3H), 1.83 (m, 2H), 2.99 (t, 2H), 3.28 (s, 3H), 3.80 (t, 2H), 4.83 (t, 2H). LRMS APCl+ m/z 289 [MH]$^+$ |

Preparation 66

N-(5-Chloro-1-methyl-3-propyl-1H-pyrazolo[4,3-d]pyrimidinyl-7-yl)-4-methylpyridin-2-ylamine

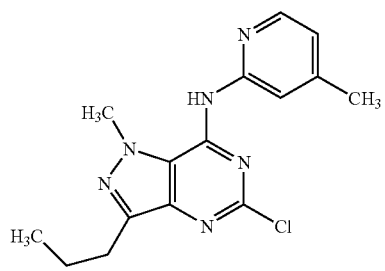

A solution of the dichloride of preparation 52 (8 g, 32.6 mmol) and 2-amino-4-methylpyridine (10.6 g, 97.9 mmol) in dimethylsulfoxide (60 mL) was stirred at 70° C. for 18 hours. The mixture was diluted with ethyl acetate (200 mL), and washed with water (3×100 mL) and brine (70 mL). The organic solution was dried over magnesium sulphate and concentrated in vacuo. The crude product was purified by column chromatography on silica gel using dichloromethane:acetonitrile 100:0 to 90:10, to give the title compound as a yellow solid, 5 g.

$^1$H-NMR (CDCl$_3$, 400 MHz) δ: 1.00 (t, 3H), 1.83 (m, 2H), 2.43 (s, 3H), 2.91 (t, 2H), 4.41 (s, 3H), 6.77 (br s, 1H), 7.89 (br m, 2H). LRMS:m/z ES+317 [MH]$^+$

Preparation 67

N-(5-Chloro-1-methyl-3-propyl-1H-pyrazolo[4,3-d]pyrimidin-7-yl)-5-methylpyridin-2-ylamine

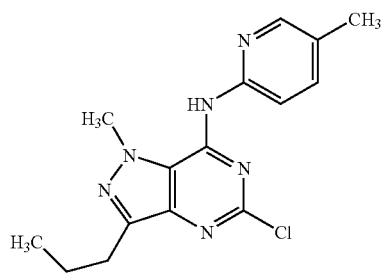

This compound was prepared by the method of preparation 66 using the dichloride of preparation 52 and 2-amino-5-methylpyridine as starting materials and a solvent of 50:50 1-methyl-2-pyrrolidinone:dimethylsulfoxide was used. The crude product was purified by column chromatography on silica gel using pentane:ethyl acetate 100:0 to 60:40.

$^1$H NMR (DMSO-d$_6$, 400 MHz) δ: 0.90 (t, 3H), 1.72 (m, 2H), 2.25 (s, 3H), 2.75 (t, 2H), 4.20 (s, 3H), 7.70 (d, 1H), 7.85 (d, 1H), 8.18 (s, 1H). LRMS: ES+m/z 339 [MNa]$^+$

Preparation 68

N-[5-Chloro-3-ethyl-1-(2-methoxyethyl)-1H-pyrazolo[4,3-d]pyrimidin-7-yl]-4-methylpyridin-2-ylamine

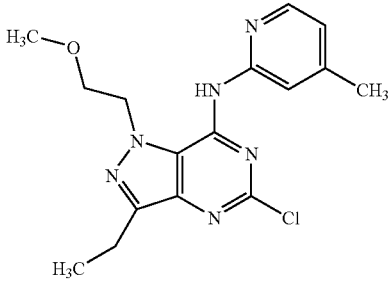

This compound was prepared following the method of preparation 66 using the dichloride of preparation 56 and 2-amino-4-methylpyridine as starting materials.

The crude product was purified by column chromatography on silica gel using dichloromethane:methanol 98:2.

$^1$H NMR (CDCl$_3$, 400 MHz) δ: 1.38 (t, 3H), 2.32 (s, 3H), 2.98 (q, 2H), 3.52 (s, 3H), 3.92 (t, 2H), 4.73 (t, 2H), 7.58 (d, 1H), 8.17 (s, 1H), 8.36 (d, 1H), 10.11 (br s, 1H). LRMS ES$^-$ m/z 345 [M−H]$^-$

Preparation 69

5-Chloro-1-methyl-3-propyl-N-(4-pyrimidinyl)-1H-pyrazolo[4,3-d]pyrimidin-7-amine

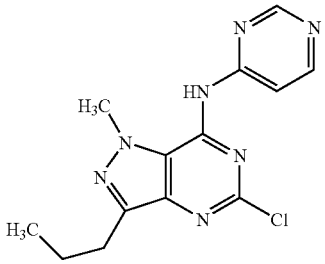

n-Butyllithium (6.53 mL, 2.5M in hexanes, 16.32 mmol) was added to a solution of 4-aminopyrimidine (1.55 g 16.32 mmol) in tetrahydrofuran (25 mL) and stirred for 10 minutes at room temperature. To this was added a solution of the dichloride from preparation 52 (1 g, 4.08 mmol) in tetrahydrofuran (25 mL). The reaction mixture was stirred for 2 hours. The mixture was then cooled in ice and an aqueous solution of ammonium choride was added and the mixture extracted with ethyl acetate. The combined organic solutions were dried over magnesium sulphate and purified by column chromatography on silica gel using dichloromethane:methanol 99:1 to give the title compound, 500 mg.

$^1$H NMR (DMSO-d$_6$, 400 MHz) δ: 0.93 (t, 3H), 1.74 (m, 2H), 2.81 (t, 2H), 4.19 (s, 3H), 7.99 (d, 1H), 8.63 (d, 1H), 8.86 (s, 1H). LRMS:m/z ESI$^-$:302, [M−H]$^-$

Preparations 70 to 77

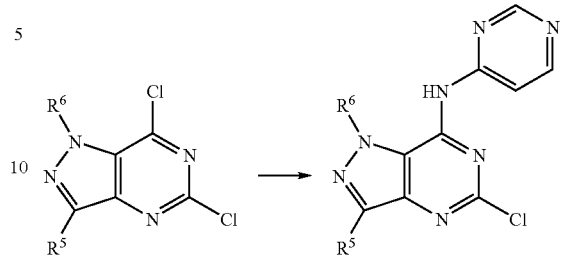

The following compounds, of the general structure below, were made in the way described in preparation 69 from the appropriate dichloride starting material (preparations 53, 54, 57-60, 62, and 64):

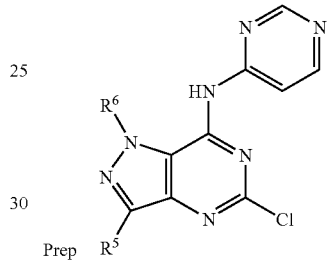

| Prep | R$^5$ | R$^6$ |
|---|---|---|
| 70 | R$^5$ = H; R$^6$ = —(CH$_2$)$_2$OCH$_2$CH$_3$ $^1$H NMR (DMSO-d$_6$, 400 MHz) δ: 1.05 (t, 3H), 3.52 (q, 2H), 3.83 (t, 2H), 4.80 (t, 2H), 8.16 (d, 1H), 8.26 (s, 1H), 8.72 (d, 1H), 8.88 (s, 1H), 10.6 (br s, 1H). LRMS: m/z APCl+ 320, [MH]$^+$ | |
| 71 | R$^5$ = —CH$_3$; R$^6$ = —(CH$_2$)$_2$OCH(CH$_3$)$_2$ $^1$H NMR (CDCl$_3$, 400 MHz) δ: 1.03 (d, 6H), 2.43 (s, 3H), 3.60 (m, 1H), 3.80 (t, 2H), 4.75 (t, 2H), 8.18 (d, 1H), 8.71 (s, 1H), 8.91 (s, 1H). LRMS APCl+ m/z 348 [MH]$^+$ | |
| 72 | R$^5$ = —CH$_3$; R$^6$ = —(CH$_2$)$_2$OCH$_2$CH$_3$ $^1$H NMR (CDCl$_3$, 400 MHz) δ: 1.23 (t, 3H), 2.57 (s, 3H), 3.69 (q, 2H), 3.95 (t, 2H), 4.73 (t, 2H), 8.44 (d, 1H), 8.67 (d, 1H), 8.91 (s, 1H), 10.41 (br s, 1H). LRMS: m/z ES+: 356, [MNa]$^+$ | |
| 73 | R$^5$ = —CH$_3$; R$^6$ = —(CH$_2$)$_2$O(CH$_2$)$_2$CH$_3$ $^1$H NMR (DMSO-d$_6$, 400 MHz) δ: 0.62 (t, 3H), 1.43 (m, 2H), 2.44 (s, 3H), 3.41 (t, 2H), 3.80 (t, 2H), 4.76 (t, 2H), 8.15 (d, 1H), 8.72 (d, 1H), 8.89 (s, 1H), 10.39 (br s, 1H). LRMS: m/z APCl+ 348, [MH]$^+$ | |
| 74 | R$^5$ = —CH$_2$CH$_3$; R$^6$ = —(CH$_2$)$_2$OCH$_2$CH$_3$ $^1$H NMR (CDCl$_3$, 400 MHz) δ: 1.25 (t, 3H), 1.41 (t, 3H), 3.02 (q, 2H), 3.71 (q, 2H), 3.97 (t, 2H), 4.75 (t, 2H), 8.49 (d, 1H), 8.67 (d, 1H), 8.93 (s, 1H). LRMS: m/z ES+ 348, [MH]$^+$ | |
| 75 | R$^5$ = —CH$_3$; R$^6$ = —(CH$_2$)$_3$OCH$_3$ $^1$H NMR (DMSO-d$_6$, 400 MHz) δ: 2.00 (m, 2H), 2.42 (s, 3H), 3.15 (s, 3H), 3.20 (m, 2H), 4.55 (t, 2H), 7.95 (d, 1H), 8.62 (d, 1H), 8.88 (s, 1H). LRMS: m/z (APCl$^+$) 320, [MH]$^+$ | |
| 76 | R$^5$ = —CH$_3$; R$^6$ = —(CH$_2$)$_3$OCH$_2$CH$_3$ $^1$H NMR (DMSO-d$_6$, 400 MHz) δ: 0.89 (t, 3H), 1.94 (m, 2H), 2.44 (s, 3H), 3.17 (t, 2H), 3.28 (q, 2H), 4.56 (t, 2H), 7.87 (d, 1H), 8.62 (d, 1H), 8.84 (s, 1H). LRMS APCl− m/z 346 [M − H]$^-$ | |
| 77 | R$^5$ = —CH$_3$; R$^6$ = —CH(CH$_3$)$_2$ $^1$H NMR (DMSO-d$_6$, 400 MHz) δ: 1.39 (d, 6H), 2.45 (s, 3H), 5.52 (br s, 1H), 7.78 (d, 1H), 8.58 (br s, 1H), 8.81 (s, 1H). LRMS: m/z APCl+ 304, [MH]$^+$ | |

Preparation 77: Sodium bis(trimethylsilyl)amide was used instead of butyl lithium

Preparation 78

N-[5-Chloro-3-isopropyl-1-(2-methoxyethyl)-1H-pyrazolo[4,3-d]pyrimidin-7-yl]-4-methylpyridin-2-ylamine

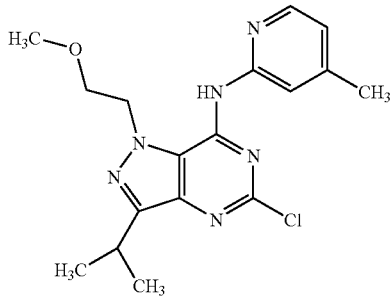

This compound was prepared by the method of preparation 69 using the dichloride of preparation 61 and 2-amino-4-methylpyridine as starting materials. The crude product was purified by column chromatography on silica gel eluting with methanol:dichloromethane 0:100 to 5:95.

$^1$H NMR (DMSO-$d_6$, 400 MHz) δ: 1.36 (d, 6H), 2.36 (s, 3H), 3.25 (s, 3H), 3.34 (m, 1H), 3.78 (t, 2H), 4.74, (m, 2H), 7.65 (m, 1H), 8.21 (m, 1H), 8.38 (m, 1H), LRMS:m/z APCI+361, [MH]$^+$

Preparation 79

N-[5-Chloro-3-methyl-1H-pyrazolo[4,3-d]pyrimidin-7-yl]-4-methylpyridin-2-ylamine

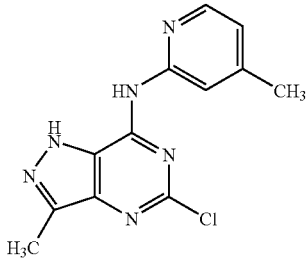

This compound was prepared by the method of preparation 69 using the dichloride of preparation 64 and 2-amino-4-methylpyridine as the starting materials. The crude product was triturated with ethyl acetate, filtered and concentrated in vacuo to yield the title product.

$^1$H NMR (DMSO-$d_6$, 400 MHz) δ: 2.35 (s, 3H), 2.43 (s, 3H), 7.00 (d, 1H), 7.84 (s, 1H), 8.30 (d, 1H). LRMS:m/z ES+273, [M−H]$^−$

Preparation 80

N-[5-Chloro-3-methyl-1-(2-propoxyethyl)-1H-pyrazolo[4,3-d]pyrimidin-7-yl]-4-methylpyridin-2-ylamine

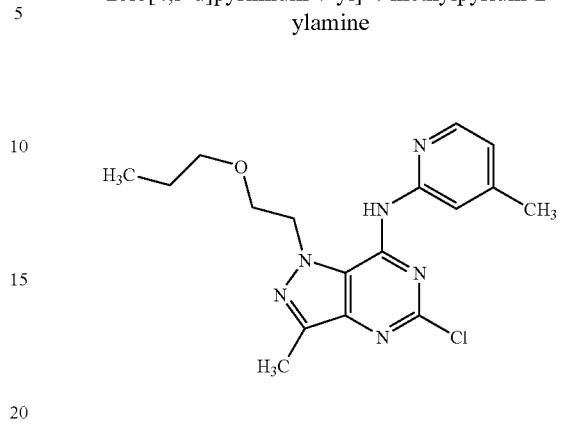

This compound was prepared by the method of preparation 69 using the dichloride of preparation 62 and 2-amino-4-methylpyridine as the starting materials. The crude product was purified by column chromatography on silica gel eluting with methanol:dichloromethane 0:100 to 5:95.

$^1$H NMR (CDCl$_3$, 400 MHz) δ: 0.71 (t, 3H), 1.56 (m, 2H), 2.47 (s, 3H), 2.56 (s, 3H), 3.51 (t, 2H), 3.91 (t, 2H), 4.79 (t, 2H), 6.91 (br s, 1H), 8.17 (br s, 1H), 8.42 (s, 1H). LRMS:m/z APCI+361, [MH]$^+$

Preparation 81

N-[5-Chloro-3-isopropyl-1-(2-methoxyethyl)-1H-pyrazolo[4,3-d]pyrimidin-7-yl]-5-methylpyridin-2-ylamine

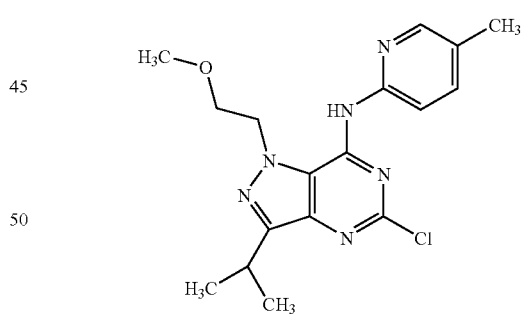

This compound was prepared by the method of preparation 69 using the dichloride of preparation 61 and 2-amino-5-methylpyridine as the starting materials. The crude product was purified by column chromatography on silica gel eluting with methanol:dichloromethane 0:100 to 5:95.

$^1$H NMR (DMSO-$d_6$, 400 MHz) δ: 1.36 (d, 6H), 2.27 (s, 3H), 3.25 (m, 1H), 3.35 (s, 3H), 3.77 (t, 2H), 4.72 (br s, 2H), 7.72 (br d, 1H), 8.05 (br d, 1H), 8.20 (s, 1H) LRMS:m/z APCI+361, [MH]$^+$

Preparation 82

N-[5-Chloro-3-methyl-1-(2-propoxyethyl)-1H-pyrazolo[4,3-d]pyrimidin-7-yl]-5-methylpyridin-2-ylamine

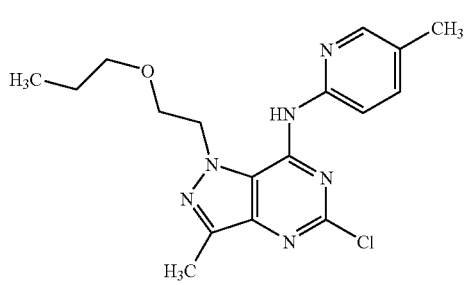

This compound was prepared by the method of preparation 69 using the dichloride of preparation 62 and 2-amino-5-methylpyridine as the starting materials. The crude product was purified by column chromatography on silica gel eluting with methanol:dichloromethane 0:100 to 5:95.

$^1$H NMR (CDCl$_3$, 400 MHz) δ: 0.74 (t, 3H), 1.60 (m, 2H), 2.32 (s, 3H), 2.55 (s, 3H), 3.53 (t, 2H), 3.92 (t, 2H), 4.72 (t, 2H), 7.58 (d, 1H), 8.15 (s, 1H), 8.38 (d, 1H) LRMS:m/z APCI+361, [MH]$^+$

Preparation 83

N-(5-Chloro-1-methyl-3-propyl-1H-pyrazolo[4,3-d]pyrimidin-7-yl)pyrazin-2-ylamine

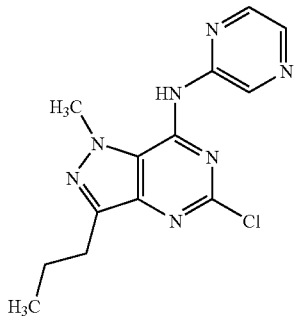

This compound was prepared by the method of preparation 69 using the dichloride of preparation 52 and 2-amino-1,4-pyrazine as the starting materials.

$^1$H NMR (CD$_3$OD, 400 MHz) δ: 0.99 (t, 3H), 1.80 (m, 2H), 2.89 (t, 2H), 4.23 (s, 3H), 8.33 (d, 1H), 8.42 (d, 1H), 9.48 (s, 1H). LRMS:m/z ES+326, [MNa]$^+$

Preparation 84

N-(5-Chloro-1-methyl-3-propyl-1H-pyrazolo[4,3-d]pyrimidin-7-yl)pyrimidin-2-ylamine

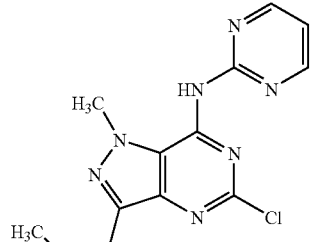

This compound was prepared by the method of preparation 69 using the dichloride of preparation 52 and 2-aminopyrimidine as the starting materials.

$^1$H NMR (400 MHz, CDCl$_3$) δ: 0.94 (t, 3H), 1.77 (m, 2H), 2.81 (m, 2H), 3.86 (s, 3H), 7.16 (m, 1H), 8.59 (m, 2H). LRMS APCI+m/z 304 [MH]$^+$

Preparation 85

N-[5-Chloro-1-(2-ethoxyethyl)-3-methyl-1H-pyrazolo[4,3-d]pyrimidin-7-yl]-6-methylpyrimidin-4-ylamine

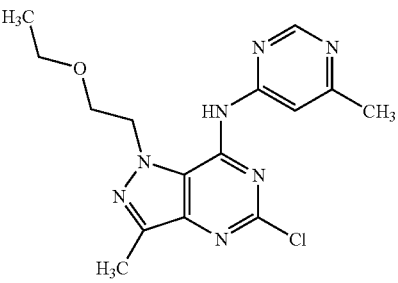

This compound was prepared by the method of preparation 69 using the dichloride of preparation 57 and 4-amino-6-methylpyrimidine as the starting materials. The crude product was purified by column chromatography on silica gel eluting with pentane:ethyl acetate 66:34.

$^1$H NMR (DMSO-d$_6$, 400 MHz) δ: 1.40 (t, 3H), 2.44 (s, 3H), 2.47 (s, 3H), 3.51 (q, 2H), 3.80 (t, 2H), 4.73 (t, 2H), 8.03 (s, 1H), 8.76 (s, 1H). LRMS:m/z APCI+348, [MH]$^+$

Preparation 86

N-(5-Chloro-1-methyl-3-propyl-1H-pyrazolo[4,3-d]pyrimidin-7-yl)pyridazin-3-ylamine

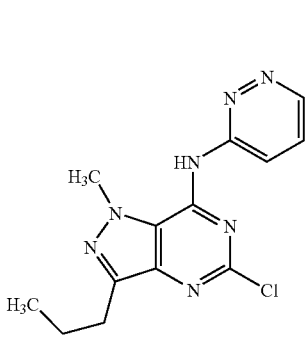

This compound was prepared by the method of preparation 69 using the dichloride of preparation 52 and 3-aminopyridiazine as the starting materials.

$^1$H NMR (DMSO-d$_6$, 400 MHz) δ: 0.90 (t, 3H), 1.72 (m, 2H), 2.79 (m, 2H), 4.27 (s, 3H), 7.77 (m, 2H), 8.22 (m, 1H). LRMS APCI+m/z 304 [MH]$^+$

Preparation 87

N-(5-Chloro-1-methyl-3-propyl-1H-pyrazolo[4,3-d]pyrimidin-7-yl)-5-methyl-[1,2,4]oxadiazol-3-ylamine

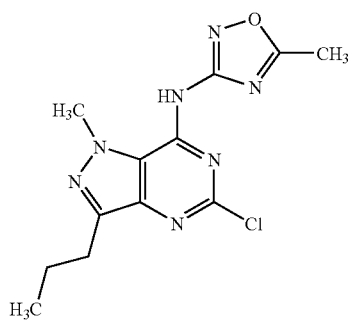

This compound was prepared by the method of preparation 69 using the dichloride of preparation 52 and 3-amino-5-methyl-[1,2,4]oxadiazole (Heterocycles, EN; 57; 5; 2002; 811) as the starting materials.

$^1$H NMR (DMSO-d$_6$, 400 MHz) δ: 0.94 (t, 3H), 1.77 (m, 2H), 2.14 (s, 3H), 2.83 (m, 2H), 4.24 (s, 3H), 11.20 (br s, 1H). LRMS ES+m/z 330 [MNa]$^+$

Preparation 88

N-(5-Chloro-1-methyl-3-propyl-1H-pyrazolo[4,3-d]pyrimidin-7-yl)-1H-imidazol-2-ylamine

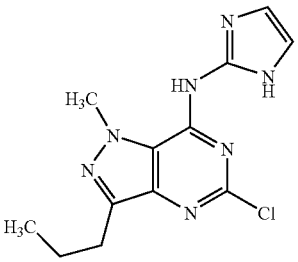

This compound was prepared by the method of preparation 69 using the dichloride of preparation 52 and 2-amino-1H-imidazole as the starting materials.

$^1$H NMR (CD$_3$OD, 400 MHz) δ: 1.01 (t, 3H), 1.72 (m, 2H), 2.81 (m, 2H), 4.33 (s, 3H), 6.95 (s, 2H). LRMS ES–m/z 290 [M–H]$^-$

Preparation 89

5-Chloro-N-(6-methoxy-4-pyrimidinyl)-1-methyl-3-propyl-1H-pyrazolo[4,3-d]pyrimidin-7-amine

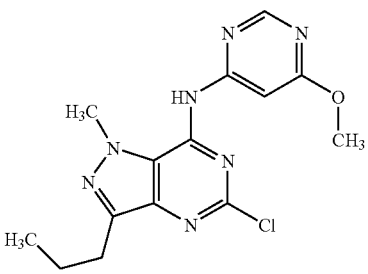

This compound was prepared by the method of preparation 69 using the dichloride of preparation 52 and 4-amino-6-methoxypyrimidine as staring materials. The crude product was purified by column chromatography on silica gel eluting with ethyl acetate:pentane 50:50 to 70:30.

$^1$H NMR (DMSO-d$_6$, 400 MHz) δ: 0.92 (t, 3H), 1.74 (m, 2H), 2.81 (t, 2H), 3.93 (s, 3H), 4.21 (s, 3H), 7.40 (s, 1H), 8.57 (s, 1H). LRMS:m/z ES+356, [MNa]$^+$

Preparation 90

N-(5-Chloro-1-isopropyl-3-methyl-1H-pyrazolo[4,3-d]pyrimidin-7-yl)-5-methylpyridin-2-ylamine

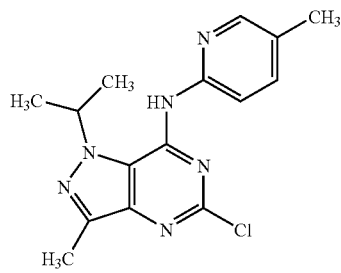

This compound was prepared by the method of preparation 69 using the dichloride of preparation 53 and 2-amino-5-methylpyridine as the starting materials.

$^1$H NMR (CDCl$_3$, 400 MHz) δ: 1.58 (d, 6H), 2.55 (s, 3H), 2.61 (s, 3H), 5.41 (m, 1H), 7.61 (m, 1H), 8.14 (m, 1H), 8.41 (m, 1H)

Preparation 91

N-[5-Chloro-1-(2-ethoxyethyl)-3-ethyl-1H-pyrazolo[4,3-d]pyrimidin-7-yl]-N-methylpyrimidin-4-ylamine

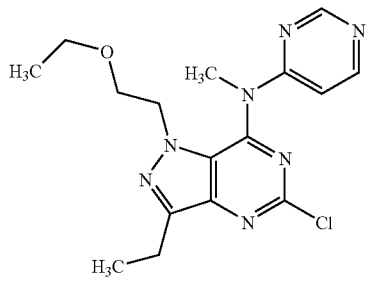

This compound was prepared by the method of preparation 69 using the dichloride of preparation 54 and N-methylpyrimidin-4-ylamine as the starting materials.

$^1$H NMR (CDCl$_3$, 400 MHz) δ: 1.25 (t, 3H), 1.41 (t, 3H), 3.02 (q, 2H), 3.71 (q, 2H), 3.97 (t, 2H), 4.05 (s, 3H), 4.75 (t, 2H), 8.49 (d, 1H), 8.67 (d, 1H), 8.93 (s, 1H)

Preparations 92 to 98

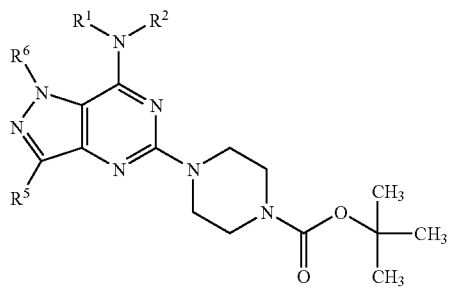

N-Ethyldiisopropylamine (3 eq) and the appropriate HNR$^1$R$^2$ amine (3 eq) were added to a solution of the appropriate dichloride (see preparations 56, 61 and 64) (1 eq) in dimethylsulfoxide (2-3 mL.mmol$^{-1}$) and stirred at 70° C. overnight. tert-Butyl piperazine-1-carboxylate (5 eq), and additional N-ethyldiisopropylamine (10 eq) were added to the cooled reaction mixture and the reaction stirred at 120° C. overnight. The cooled reaction mixture was partitioned between ether and water (3:1 by volume) and the organics were dried over magnesium sulphate and concentrated in vacuo to yield the product.

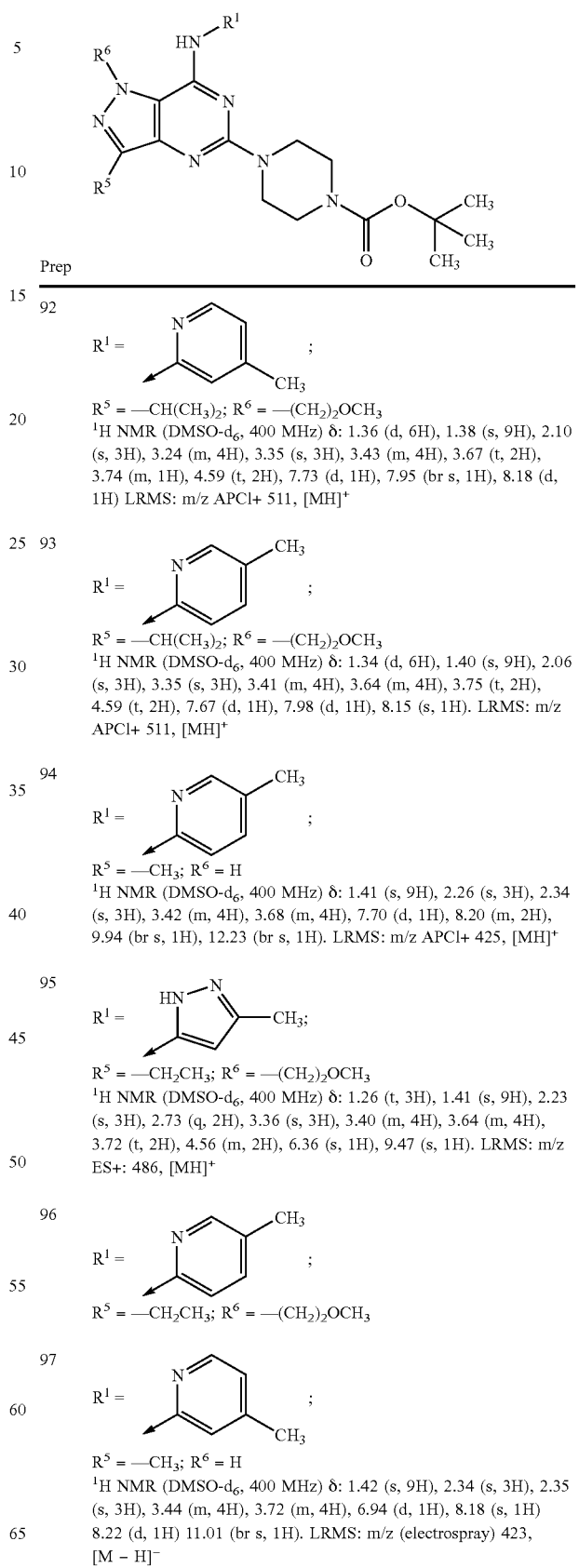

| Prep | | |
|---|---|---|
| 92 | R$^1$ = (4-methyl-pyridin-2-yl); R$^5$ = —CH(CH$_3$)$_2$; R$^6$ = —(CH$_2$)$_2$OCH$_3$ | $^1$H NMR (DMSO-d$_6$, 400 MHz) δ: 1.36 (d, 6H), 1.38 (s, 9H), 2.10 (s, 3H), 3.24 (m, 4H), 3.35 (s, 3H), 3.43 (m, 4H), 3.67 (t, 2H), 3.74 (m, 1H), 4.59 (t, 2H), 7.73 (d, 1H), 7.95 (br s, 1H), 8.18 (d, 1H) LRMS: m/z APCl+ 511, [MH]$^+$ |
| 93 | R$^1$ = (5-methyl-pyridin-2-yl); R$^5$ = —CH(CH$_3$)$_2$; R$^6$ = —(CH$_2$)$_2$OCH$_3$ | $^1$H NMR (DMSO-d$_6$, 400 MHz) δ: 1.34 (d, 6H), 1.40 (s, 9H), 2.06 (s, 3H), 3.35 (s, 3H), 3.41 (m, 4H), 3.64 (m, 4H), 3.75 (t, 2H), 4.59 (t, 2H), 7.67 (d, 1H), 7.98 (d, 1H), 8.15 (s, 1H). LRMS: m/z APCl+ 511, [MH]$^+$ |
| 94 | R$^1$ = (4-methyl-pyridin-2-yl); R$^5$ = —CH$_3$; R$^6$ = H | $^1$H NMR (DMSO-d$_6$, 400 MHz) δ: 1.41 (s, 9H), 2.26 (s, 3H), 2.34 (s, 3H), 3.42 (m, 4H), 3.68 (m, 4H), 7.70 (d, 1H), 8.20 (m, 2H), 9.94 (br s, 1H), 12.23 (br s, 1H). LRMS: m/z APCl+ 425, [MH]$^+$ |
| 95 | R$^1$ = (5-methyl-1H-pyrazol-3-yl); R$^5$ = —CH$_2$CH$_3$; R$^6$ = —(CH$_2$)$_2$OCH$_3$ | $^1$H NMR (DMSO-d$_6$, 400 MHz) δ: 1.26 (t, 3H), 1.41 (s, 9H), 2.23 (s, 3H), 2.73 (q, 2H), 3.36 (s, 3H), 3.40 (m, 4H), 3.64 (m, 4H), 3.72 (t, 2H), 4.56 (m, 2H), 6.36 (s, 1H), 9.47 (s, 1H). LRMS: m/z ES+: 486, [MH]$^+$ |
| 96 | R$^1$ = (4-methyl-pyridin-2-yl); R$^5$ = —CH$_2$CH$_3$; R$^6$ = —(CH$_2$)$_2$OCH$_3$ | |
| 97 | R$^1$ = (pyridin-2-yl, 4-methyl); R$^5$ = —CH$_3$; R$^6$ = H | $^1$H NMR (DMSO-d$_6$, 400 MHz) δ: 1.42 (s, 9H), 2.34 (s, 3H), 2.35 (s, 3H), 3.44 (m, 4H), 3.72 (m, 4H), 6.94 (d, 1H), 8.18 (s, 1H) 8.22 (d, 1H) 11.01 (br s, 1H). LRMS: m/z (electrospray) 423, [M − H]$^−$ |

-continued

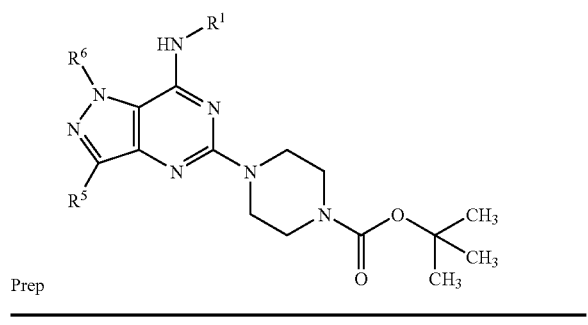

| Prep | | |
|---|---|---|
| 98 | $R^1 =$ 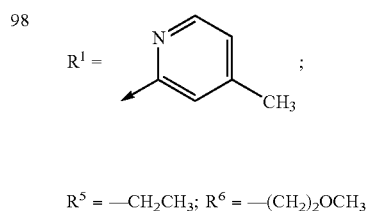 ; | |
| | $R^5 = —CH_2CH_3$; $R^6 = —(CH_2)_2OCH_3$ | |

Preparation 99

Dimethyl 1-(2-ethoxyethyl)-4-nitro-1H-pyrazole-3,5-dicarboxylate

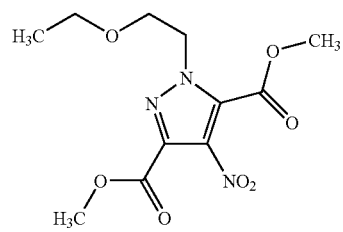

4-Nitro-1H-pyrazole-3,5-dicarboxylic acid dimethyl ester (2.0 g, 8.83 mmol) was added to a solution of 2-ethoxyethyl bromide (1.18 mL, 10.45 mmol) and potassium carbonate (1.32 g, 9.56 mmol) in N,N-dimethylformamide (35 mL) and the reaction mixture stirred for 48 hours at room temperature. The reaction mixture was concentrated in vacuo and partitioned between ethyl acetate (200 mL) and water (100 mL). The organic layer was separated, dried over magnesium sulphate and concentrated in vacuo. The crude product was purified by column chromatography on silica gel eluting with pentane:ethyl acetate 100:0 to 70:30 to yield the title product, 1.63 g.

$^1$H NMR (CDCl$_3$, 400 MHz) δ: 1.07 (t, 3H), 3.41 (q, 2H), 3.73 (t, 2H), 3.89 (s, 3H), 3.94 (s, 3H), 4.76 (t, 2H). LRMS:m/z APCI+302, [MH]$^+$

Preparation 100

1-(2-Ethoxyethyl)-4-nitro-1H-pyrazole-3,5-dicarboxylic acid 3-methyl ester

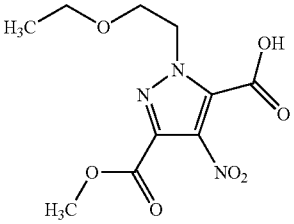

The di-ester of preparation 99 (1.63 g, 5.4 mmol) was added to a solution of potassium hydroxide (330 mg, 5.9 mmol) in methanol (20 mL) and the reaction mixture stirred at room temperature for 18 hours. The reaction mixture was concentrated in vacuo and the crude product dissolved in water and washed with ether. The aqueous phase was acidified with 2M hydrochloric acid and extracted into dichloromethane (3×100 mL). The organics were combined, dried over magnesium sulphate and concentrated in vacuo to yield the title product, 1.34 g.

$^1$H NMR (CD3OD, 400 MHz) δ: 1.07 (t, 3H), 3.47 (q, 2H), 3.80 (t, 2H), 3.88 (s, 3H), 4.77 (t, 2H). LRMS:m/z APCI+288, [MH]$^+$

Preparation 101

Methyl 5-carbamoyl-1-(2-ethoxyethyl)-4-nitro-1H-pyrazole-3-carboxylate

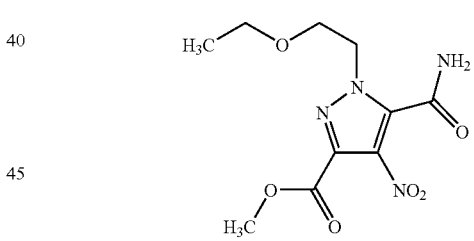

Oxalyl chloride (1.2 mL, 13.76 mmol) and N,N-dimethylformamide (39 μL) were added to a solution of the carboxylic acid of preparation 100 (1.33 g, 4.63 mmol) in dichloromethane (20 mL) and the reaction mixture stirred at room temperature for 2 hours. The reaction mixture was concentrated in vacuo and azeotroped from dichloromethane (3×50 mL). The reaction mixture was dissolved in tetrahydrofuran (50 mL), cooled in an ice bath and treated with 0.880 ammonia solution (10 mL). The reaction mixture was stirred for 18 hours at room temperature. The reaction mixture was concentrated in vacuo and the remaining solution partitioned between dichloromethane (200 mL) and water (50 mL). The organics were combined, dried over magnesium sulphate and concentrated in vacuo to yield the title product, 0.98 g.

$^1$H NMR (DMSO-d$_6$, 400 MHz) δ: 1.03 (t, 3H), 3.38 (q, 2H), 3.70 (t, 2H), 3.86 (s, 3H), 4.36 (t, 2H), 8.30 (br s, 1H), 8.46 (br s, 1H). LRMS APCI+m/z 287 [MH]$^+$

Preparation 102

Methyl 4-amino-5-carbamoyl-1-(2-ethoxyethyl)-1H-pyrazole-3-carboxylate

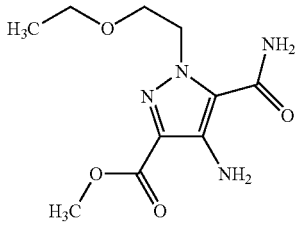

Pd(OH)$_2$ (100 mg) was added to a solution of the nitro compound of preparation 101 (970 mg, 3.39 mmol) in methanol (20 mL) and the reaction mixture warmed to reflux. Ammonium formate (1.07 g, 16.97 mmol) was added and the reaction mixture stirred at reflux for 2 hours. The catalyst was removed by filtration and the reaction mixture concentrated in vacuo to yield the title product, 870 mg.

$^1$H NMR (DMSO-d$_6$, 400 MHz) δ: 1.04 (t, 3H), 3.32 (q, 2H), 3.66 (t, 2H), 3.78 (s, 3H), 4.49 (t, 2H), 5.12 (br s, 2H), 7.50 (br s, 2H). LRMS APCI+m/z 257 [MH]$^+$

Preparation 103

Methyl 1-(2-ethoxyethyl)-5,7-dioxo-4,5,6,7-tetrahydro-1H-pyrazolo[4,3-d]pyrimidine-3-carboxylate

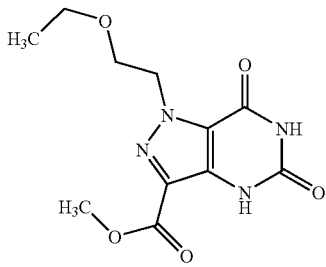

A solution of the amine of preparation 102 (570 mg, 3.38 mmol) in N,N-dimethylformamide (30 mL) was treated with carbonyl diimidazole (658 mg, 4.06 mmol) and the reaction mixture stirred at room temperature for 1 hour and then at 90° C. for 18 hours. The reaction mixture was concentrated in vacuo and the crude product suspended in acetone and sonicated for 30 minutes. The solid product was filtered off and dried in vacuo.

$^1$H NMR (DMSO-d$_6$, 400 MHz) δ: 1.03 (t, 3H), 3.40 (q, 2H), 3.87 (t, 2H), 4.06 (s, 3H), 4.98 (t, 2H). LRMS ES−m/z 281 [M−H]$^−$

Preparation 104

Methyl 5,7-dichloro-1-(2-ethoxyethyl)-1H-pyrazolo[4,3-d]pyrimidine-3-carboxylate

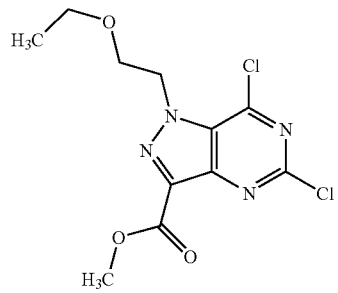

Phosphorous oxychloride (934 µL, 10.0 mmol) and tetraethylammonium chloride (195 mg, 1.50 mmol) were added to a solution of the dione of preparation 103 (140 mg, 0.50 mmol) in propionitrile (5 mL) and the reaction mixture refluxed for 18 hours. The reaction mixture was concentrated in vacuo and the crude product partitioned between ethyl acetate (50 mL) and water (50 mL). The organic layer was dried over magnesium sulphate and concentrated in vacuo. The crude product was purified by column chromatography on silica gel eluting with pentane:ethyl acetate 100:0 to 75:25 to yield the title product.

$^1$H NMR (CDCl$_3$, 400 MHz) δ: 1.03 (t, 3H), 3.40 (q, 2H), 3.87 (t, 2H), 4.06 (s, 3H), 4.98 (t, 2H). LRMS APCI+m/z 319 [MH]$^+$

Preparation 105

Methyl 5-chloro-1-(2-ethoxyethyl)-7-(4-methylpyridin-2-ylamino)-1H-pyrazolo[4,3-d]pyrimidine-3-carboxylate

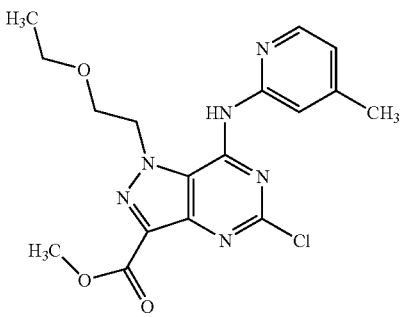

The dichloro compound of preparation 104 (1.98 g, 6.20 mmol) was dissolved in dimethylsulfoxide (10 mL) and the reaction mixture treated with 2-amino-4-methylpyridine (1.34 g, 12.4 mmol). The reaction mixture was stirred at 75° C. for 5 hours. The reaction mixture was partitioned between dichloromethane (300 mL) and water (500 mL) and the dichloromethane layer separated. The organics were washed with water (3×100 mL), dried over magnesium sulphate and concentrated in vacuo. The crude product was purified by column chromatography on silica gel eluting with dichloromethane:acetonitrile 100:0 to 98:2. The crude product was triturated with ether (50 mL), filtered and concentrated in vacuo to yield the title product, 1.2 g.

$^1$H NMR (CDCl3, 400 MHz) δ: 1.06 (t, 3H), 2.49 (s, 3H), 3.62 (q, 2H), 4.00 (t, 2H), 4.06 (s, 3H), 5.05 (br, 2H), 6.98 (br s, 1H), 8.16 (br s, 1H), 8.50 (br s, 1H) LRMS APCI+m/z 391 [MH]$^+$

Preparation 106

[5-Chloro-1-(2-ethoxyethyl)-7-(4-methylpyridin-2-ylamino)-1H-pyrazolo[4,3-d]pyrimidin-3-yl]methanol

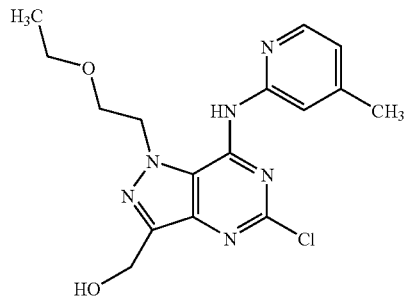

The chloro compound of preparation 105 (1.89 g, 4.84 mmol) was suspended in tetrahydrofuran (450 mL) and the reaction mixture cooled to −78° C. DIBAL (39 mL, 1M solution in toluene, 39 mmol) was added and the reaction mixture allowed to warm to −5° C. The reaction mixture was stirred at −5° C. for 15 minutes before being re-cooled to −78° C. and being quenched with aqueous ammonium chloride solution (10 mL). The reaction mixture was allowed to warm to room temperature and partitioned between dichloromethane (200 mL) and water (200 mL). The mixture was filtered through Arbocel® and the organic layer separated, dried over magnesium sulphate and concentrated in vacuo. The crude product was triturated with ethyl acetate and the solid filtered off to yield the title product.

$^1$H NMR (CDCl$_3$, 400 MHz) δ: 1.11 (t, 3H), 2.46 (s, 3H), 3.61 (m, 2H), 3.94 (m, 2H), 4.86 (m, 2H), 5.07 (m, 2H), 6.96 (m, 1H), 8.19 (m, 1H), 8.48 (m, 1H) LRMS APCI+m/z 363 [MH]$^+$

Preparation 107

[5,7-Dichloro-1-(2-ethoxyethyl)-1H-pyrazolo[4,3-d]pyrimidin-3-yl]methanol

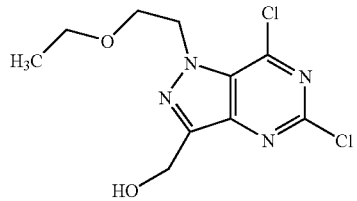

DIBAL (62.5 mL, 1M in tetrahydrofuran, 62.5 mmol) was added dropwise to a cooled (−78° C.) solution of the ester from preparation 104 (4 g, 12.5 mmol) in tetrahydrofuran (100 mL), and once addition was complete, the reaction was stirred for 10 minutes. The mixture was then allowed to warm to −10° C. over 1 hour, then re-cooled to −78° C. Saturated ammonium chloride solution (45 mL) was carefully added, the mixture warmed to room temperature and partitioned between water (175 mL) and dichloromethane (350 mL). The mixture was filtered through Arbocel®, washing through with dichloromethane (3×100 mL), the combined organic solutions dried over sodium sulphate and evaporated in vacuo. The crude product was purified by column chromatography on silica gel using methanol:dichloromethane (1:99) as eluant to afford the title compound, 2.56 g.

$^1$H NMR (CDCl$_3$, 400 MHz) δ: 1.07 (t, 3H), 3.44 (q, 2H), 3.84 (m, 2H), 4.86 (t, 2H), 5.09 (s, 2H).

Preparation 108

3-(tert-Butyldimethylsilanyloxymethyl)-5,7-dichloro-1-(2-ethoxyethyl)-1H-pyrazolo[4,3-d]pyrimidine

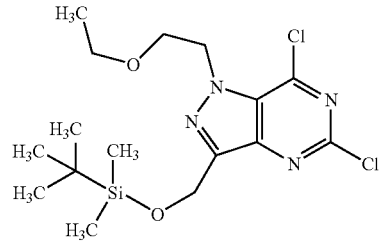

Imidazole (637 mg, 9.35 mmol) and tert-butyldimethylsilyl chloride (1.41 g, 9.35 mmol) were added to a solution of the alcohol from preparation 107 2.47 g, 8.5 mmol) in dichloromethane (50 mL), and the reaction stirred at room temperature for 18 hours. The mixture was diluted with dichloromethane (250 mL), and washed with 10% aqueous potassium carbonate solution (175 mL). The organic solution was dried over sodium sulphate and evaporated in vacuo. The residue was purified by column chromatography on silica gel using methanol:dichloromethane (1:99) as eluant to afford the title compound, 2.9 g.

$^1$H NMR (CDCl$_3$, 400 MHz) δ: 0.00 (s, 6H), 0.78 (s, 9H), 0.93 (t, 3H), 3.29 (q, 2H), 3.71 (m, 2H), 4.72 (m, 2H), 4.94 (s, 2H). LRMS: m/z APCI+405 [MH$^+$]

Preparation 109

N-[3-(tert-Butyldimethylsilanyloxymethyl)-5-chloro-1-(2-ethoxyethyl)-1H-pyrazolo[4,3-d]pyrimidin-7-yl]-pyrimidin-4-ylamine

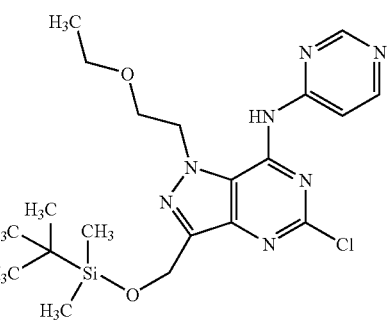

Sodium bis(trimethylsilyl)amide (1.12 g, 6.12 mmol) was added to a solution of 4-aminopyrimidine (580 mg, 6.12 mmol) in tetrahydrofuran (17 mL) and the solution stirred at room temperature for 20 minutes. The chloride from preparation 108 (825 mg, 2.04 mmol) in tetrahydrofuran (8 mL) was added and the reaction stirred at room temperature for 90 minutes. The reaction was diluted with saturated aqueous ammonium chloride solution (50 mL), and extracted with dichloromethane (100 mL). The organic extracts were dried over sodium sulphate and evaporated in vacuo. The crude product was purified by column chromatography on silica gel using methanol:dichloromethane (3:97) to afford the title compound 812 mg.

$^1$H NMR (CDCl$_3$, 400 MHz) δ: 0.00 (s, 6H), 0.78 (s, 9H), 1.08 (t, 3H), 3.54 (q, 2H), 3.82 (m, 2H), 4.63 (m, 2H), 4.91 (s, 2H), 8.29 (d, 1H), 8.53 (d, 1H), 8.76 (s, 1H).

Preparation 110

[5-Chloro-1-(2-ethoxyethyl)-7-(pyrimidin-4-ylamino)-1H-pyrazolo[4,3-d]pyrimidin-3-yl]methanol

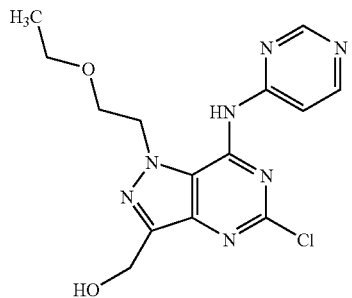

Tetrabutylammonium fluoride (3.1 mL, 1M in tetrahydrofuran, 3.1 mmol) was added to a solution of the compound from preparation 109 (715 mg, 1.54 mmol) in tetrahydrofuran (15 mL), and the reaction stirred at room temperature for 18 hours. The reaction was diluted with water (40 mL), and the mixture extracted with ethyl acetate (70 mL). The organic solution was dried over sodium sulphate and evaporated in vacuo. The residue was purified by column chromatography on silica gel using methanol:dichloromethane (5:95) as eluant to afford the title compound, 450 mg.

$^1$H NMR (CDCl$_3$, 400 MHz) δ: 1.22 (t, 3H), 3.69 (m, 2H), 3.98 (m, 2H) 4.77 (m, 2H), 5.08 (s, 2H), 8.58 (m, 1H), 8.64 (m, 1H), 8.97 (m, 1H). LRMS APCI+m/z 350 [MH]$^+$

Preparation 111

N-[3-Bromomethyl-5-chloro-1-(2-ethoxyethyl)-1H-pyrazolo[4,3-d]pyrimidin-7-yl]-4-methylpyridin-2-ylamine

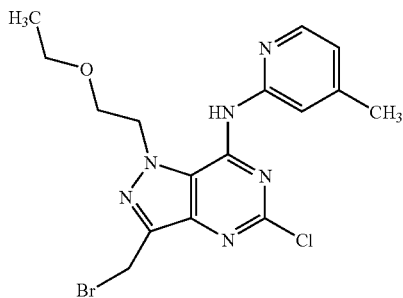

Tetrabromomethane (912 mg, 2.75 mmol) and triphenylphosphine (720 mg, 2.75 mmol) were added to a solution of the alcohol of preparation 106 (830 mg, 2.29 mmol) in dichloromethane (35 mL) and the reaction mixture stirred at room temperature for 1 hour. The reaction mixture was purified directly by column chromatography on silica gel eluting with dichloromethane:methanol 100:0 to 99:1 to yield the title product.

$^1$H NMR (CDCl$_3$, 400 MHz) δ: 0.92 (m, 3H), 2.63 (s, 3H), 3.58 (m, 2H), 3.91 (m, 2H), 4.81 (s, 2H), 5.20 (m, 2H), 7.14 (m, 1H), 8.16 (m, 1H), 8.97 (m, 1H) LRMS APCI+m/z 427 [MH]$^+$

Preparation 112

N-[3-Bromomethyl-5-chloro-1-(2-ethoxyethyl)-1H-pyrazolo[4,3-d]pyrimidin-7-yl]-pyrimidin-4-ylamine

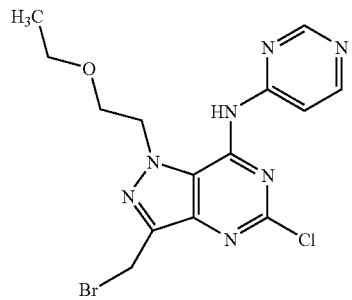

This compound was prepared by the method of preparation 111 using the alcohol of preparation 110 as a starting material.

$^1$H NMR (CDCl$_3$, 400 MHz) δ: 1.24 (t, 3H), 3.74 (m, 2H), 3.99 (m, 2H) 4.84 (m, 4H), 8.61 (m, 1H), 8.69 (m, 1H), 9.02 (m, 1H)

Preparation 113 tert-Butyl (3S)-3-(tert-butyloxycarbonylamino)pyrrolidine-1-carboxylate

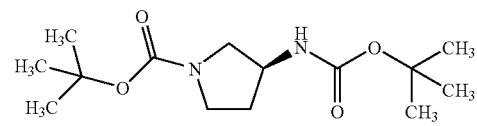

(3S)-3-(tert-Butyloxycarbonylamino)pyrrolidine (1 g, 5.37 mmol) and triethylamine (1.38 mL, 10.00 mmol) were dissolved in dichloromethane (15 mL) and the reaction mixture stirred for 10 minutes. The reaction mixture was then treated with di-tert-butyl dicarbonate (1.75 g, 8.00 mmol) and stirred at room temperature for 18 hours. The reaction mixture was concentrated in vacuo and the residue purified by column chromatography on silica gel eluting with pentane:ethyl acetate 80:20 to yield the title product as a white solid, 1.25 g.

$^1$H NMR (CDCl$_3$, 400 MHz) δ: 1.39 (s, 18H), 1.81 (m, 1H), 2.15 (m, 1H), 3.13 (m, 1H), 3.40 (m, 2H), 3.58 (m, 1H), 4.17 (m, 1H), 4.62 (m, 1H). LRMS ES+m/z 309 [MNa]$^+$

Preparation 114 tert-Butyl (3R)-3-(tert-butyloxycarbonylamino)pyrrolidine-1-carboxylate

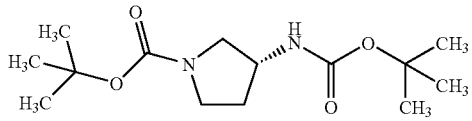

This compound was prepared by the method of preparation 113 using (3R)-3-(tert-butyloxycarbonylamino)pyrrolidine.

$^1$H NMR (CDCl$_3$, 400 MHz) δ: 1.37 (s, 18H), 1.79 (m, 1H), 2.15 (m, 1H), 3.13 (m, 1H), 3.40 (m, 2H), 3.58 (m, 1H), 4.16 (m, 1H), 4.62 (m, 1H). LRMS ES+m/z 309 [MNa]$^+$

Preparation 115

(3S)-1-Methyl-3-(methylamino)pyrrolidine

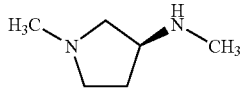

A solution of lithium aluminiumhydride (17 mL, 1M in tetrahydrofuran, 17 mmol) was added dropwise to a stirring solution of the pyrrolidine of preparation 113 (600 mg, 2.09 mmol) in tetrahydrofuran (10 mL) at 0° C. The reaction mixture was allowed to warm to room temperature and then heated to reflux for 5 hours. The reaction mixture was cooled to 0° C. with an ice bath and then quenched by addition of sodium sulphate solution. The reaction mixture was diluted with ethyl acetate (100 mL), the ethyl acetate decanted off and additional ethyl acetate used to wash the residues. The combined organics were dried over magnesium sulphate and concentrated in vacuo to yield the title product, 60 mg.

$^1$H NMR (CD$_3$OD, 400 MHz) δ: 2.25-2.46 (m, 4H), 2.75 (s, 3H), 3.02 (s, 3H), 3.73-4.08 (m, 3H), LRMS APCI+m/z 115 [MH]$^+$

Preparation 116

(3R)-1-Methyl-3-(methylamino)pyrrolidine

This compound was prepared by the method of preparation 115 using the pyrrolidine of preparation 114.

$^1$H NMR (CD$_3$OD, 400 MHz) δ: 2.23-2.47 (m, 4H), 2.75 (s, 3H), 2.99 (s, 3H), 3.74-4.06 (m, 3H). LRMS APCI+m/z 115 [MH]$^+$

Preparations 117-123

The appropriate HNR$^1$R$^2$ amine (6.20 mmol) was dissolved in tetrahydrofuran (30 mL) and the reaction mixture treated with sodium hexamethyldisilazide (1.36 g, 7.2 mmol) under nitrogen. The reaction mixture was stirred for 20 minutes at room temperature before being treated with the appropriate dichloro compound (3.1 mmol) from preparations 54, 55 or 57, and stirred for 3 hours. The reaction mixture was quenched by addition of methanol (10 mL) and concentrated in vacuo. The residue was purified by column chromatography on silica gel eluting with dichloromethane: methanol 100:0 to 95:5 to yield the desired product.

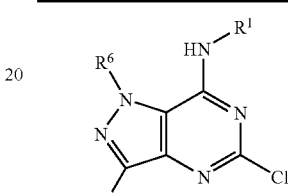

Prep

117

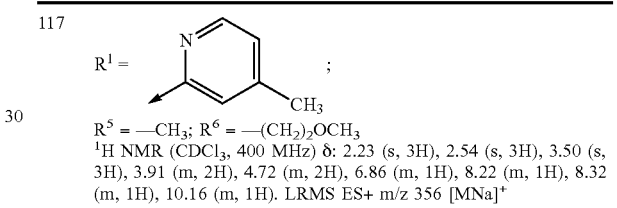

R$^5$ = —CH$_3$; R$^6$ = —(CH$_2$)$_2$OCH$_3$
$^1$H NMR (CDCl$_3$, 400 MHz) δ: 2.23 (s, 3H), 2.54 (s, 3H), 3.50 (s, 3H), 3.91 (m, 2H), 4.72 (m, 2H), 6.86 (m, 1H), 8.22 (m, 1H), 8.32 (m, 1H), 10.16 (m, 1H). LRMS ES+ m/z 356 [MNa]$^+$

118

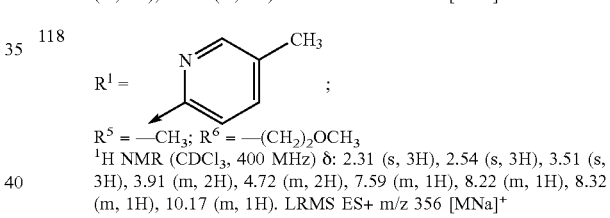

R$^5$ = —CH$_3$; R$^6$ = —(CH$_2$)$_2$OCH$_3$
$^1$H NMR (CDCl$_3$, 400 MHz) δ: 2.31 (s, 3H), 2.54 (s, 3H), 3.51 (s, 3H), 3.91 (m, 2H), 4.72 (m, 2H), 7.59 (m, 1H), 8.22 (m, 1H), 8.32 (m, 1H), 10.17 (m, 1H). LRMS ES+ m/z 356 [MNa]$^+$

119

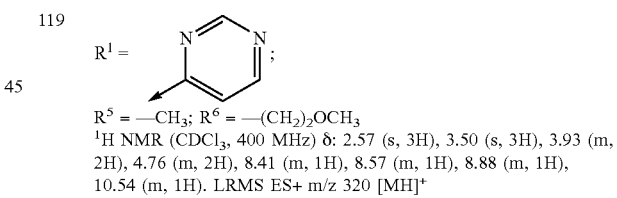

R$^5$ = —CH$_3$; R$^6$ = —(CH$_2$)$_2$OCH$_3$
$^1$H NMR (CDCl$_3$, 400 MHz) δ: 2.57 (s, 3H), 3.50 (s, 3H), 3.93 (m, 2H), 4.76 (m, 2H), 8.41 (m, 1H), 8.57 (m, 1H), 8.88 (m, 1H), 10.54 (m, 1H). LRMS ES+ m/z 320 [MH]$^+$

120

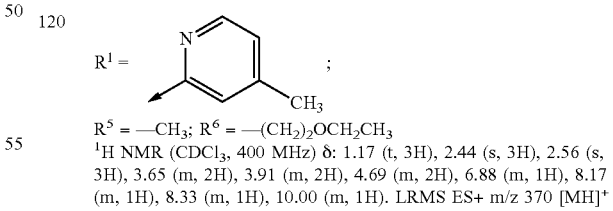

R$^5$ = —CH$_3$; R$^6$ = —(CH$_2$)$_2$OCH$_2$CH$_3$
$^1$H NMR (CDCl$_3$, 400 MHz) δ: 1.17 (t, 3H), 2.44 (s, 3H), 2.56 (s, 3H), 3.65 (m, 2H), 3.91 (m, 2H), 4.69 (m, 2H), 6.88 (m, 1H), 8.17 (m, 1H), 8.33 (m, 1H), 10.00 (m, 1H). LRMS ES+ m/z 370 [MH]$^+$

121

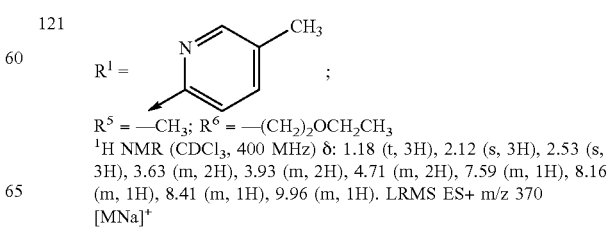

R$^5$ = —CH$_3$; R$^6$ = —(CH$_2$)$_2$OCH$_2$CH$_3$
$^1$H NMR (CDCl$_3$, 400 MHz) δ: 1.18 (t, 3H), 2.12 (s, 3H), 2.53 (s, 3H), 3.63 (m, 2H), 3.93 (m, 2H), 4.71 (m, 2H), 7.59 (m, 1H), 8.16 (m, 1H), 8.41 (m, 1H), 9.96 (m, 1H). LRMS ES+ m/z 370 [MNa]$^+$

-continued

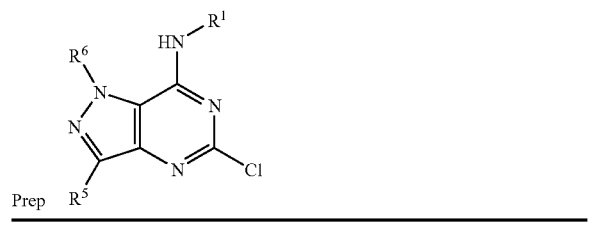

| Prep | R⁵ | |
|---|---|---|
| 122 | $R^1 = $ 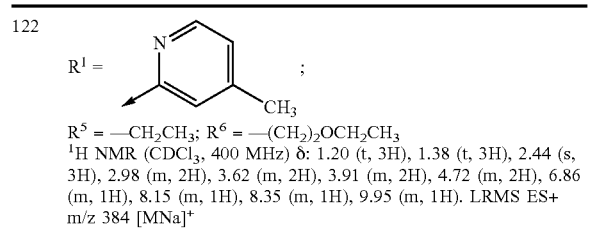 ; |
| | $R^5 = -CH_2CH_3$; $R^6 = -(CH_2)_2OCH_2CH_3$ |
| | $^1$H NMR (CDCl$_3$, 400 MHz) δ: 1.20 (t, 3H), 1.38 (t, 3H), 2.44 (s, 3H), 2.98 (m, 2H), 3.62 (m, 2H), 3.91 (m, 2H), 4.72 (m, 2H), 6.86 (m, 1H), 8.15 (m, 1H), 8.35 (m, 1H), 9.95 (m, 1H). LRMS ES+ m/z 384 [MNa]⁺ |
| 123 | $R^1 = $ 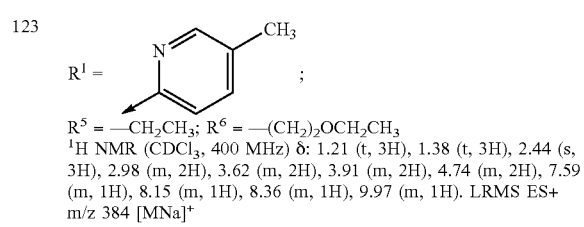 ; |
| | $R^5 = -CH_2CH_3$; $R^6 = -(CH_2)_2OCH_2CH_3$ |
| | $^1$H NMR (CDCl$_3$, 400 MHz) δ: 1.21 (t, 3H), 1.38 (t, 3H), 2.44 (s, 3H), 2.98 (m, 2H), 3.62 (m, 2H), 3.91 (m, 2H), 4.74 (m, 2H), 7.59 (m, 1H), 8.15 (m, 1H), 8.36 (m, 1H), 9.97 (m, 1H). LRMS ES+ m/z 384 [MNa]⁺ |

Preparation 124

(2R)-2-Ethylpiperazine dihydrochloride

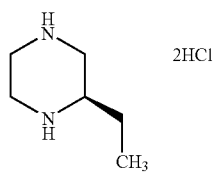

(2R)-2-Aminobutanoic acid (1.57 g, 15.22 mmol) was dissolved in ethanol (40 mL) and the solution treated with thionyl chloride (5 mL, 63.8 mmol). The reaction mixture was heated at reflux for 70 hours. The reaction mixture was cooled and concentrated in vacuo. The residue was azeotroped with toluene (50 mL) to give a clear oil. The oil (2.78 g, 16.58 mmol) was dissolved in dichloromethane (50 mL) and the solution treated with carbobenzyloxyglycine (3.47 g, 16.58 mmol), 1-hydroxybenzotriazole hydrate (2.55 g, 16.65 mmol), 1-(3-dimethylaminopropyl)-3-ethylcarbodiimide hydrochloride (3.18 g, 16.59 mmol) and triethylamine (6.9 mL, 49.5 mmol). The reaction mixture was stirred for 18 hours at room temperature. The reaction mixture was washed with water, citric acid, brine and sodium hydrogencarbonate solution and then dried over magnesium sulphate and concentrated in vacuo. The residue was purified by column chromatography on silica gel eluting with ethyl acetate:pentane 50:50. The crude product (4.22 g, 13.08 mmol) was dissolved in methanol (100 mL) and the solution treated with 10% Pd/C (450 mg) and stirred under 60 psi of hydrogen at room temperature for 18 hours. The reaction mixture was filtered through Arbocel® and the filtrate concentrated in vacuo. The residue (1.6 g, 11.25 mmol) was dissolved in 1,2-dimethoxyethane (25 mL) and the solution treated with a 1M solution of borane in tetrahydrofuran (45 mL, 45 mmol). The reaction mixture was heated to reflux for 18 hours, then quenched with methanol and stirred at room temperature for 30 minutes. The reaction mixture was concentrated in vacuo and the residue dissolved in methanol (50 mL) and treated with a saturated solution of hydrogen chloride in dioxane (15 mL). The solution was refluxed for 2 hours, then concentrated in vacuo and the residue dissolved in ether (50 mL). The solution was concentrated in vacuo to yield the title product as a yellow oil that solidifed on standing.

$^1$H NMR (DMSO-d$_6$, 400 MHz) δ: 0.84 (t, 3H), 1.30 (m, 1H), 1.70 (m, 1H), 3.00-4.10 (br m, 7H).

Preparation 125

3-Bromotetrahydropyran

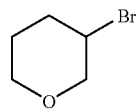

Tetrahydropyran-3-ol (J. Org. Chem., 1985, 50, 1582) (4.66 mL, 49 mmol) was dissolved in dichloromethane (137 mL) and the solution treated with tetrabromomethane (19.48 g, 58 mmol). The reaction mixture was cooled to 0° C. and treated dropwise with a solution of triphenylphosphine (17.98 g, 69 mmol) in dichloromethane. The reaction mixture was allowed to return to room temperature and stirred for 4 hours. The reaction mixture was concentrated in vacuo and the residue purified by column chromatography on silica gel eluting with dichloromethane:methanol 98:2 to yield the title product as a yellow oil, 6.3 g.

$^1$H NMR (CDCl$_3$, 400 MHz) δ: 2.02 (m, 2H), 2.18 (m, 2H), 3.54 (t, 2H), 3.96 (m, 2H), 4.31 (m, 1H).

Preparation 126

2-(2,2,2-Trifluoroethoxy)ethanol

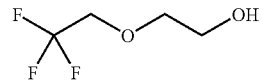

Trifluoroethanol (36 mL, 494 mmol), ethylene carbonate (66.0 g, 741 mmol), triethylamine (70 mL, 494 mmol) and tetrabutylammonium bromide (3.20 g, 9.90 mmol) were combined and the reaction mixture heated to reflux for 24 hours. The reaction mixture was distilled at atmospheric pressure, yielding the title product in the range 132° C. to 142° C.

$^1$H NMR (CDCl$_3$, 400 MHz) δ: 3.69-3.77 (m, 4H), 3.88 (m, 2H).

Preparation 127

5-Methyl-4-nitro-2-[2-(2,2,2-trifluoroethoxy)ethyl]-2H-pyrazole-3-carboxamide

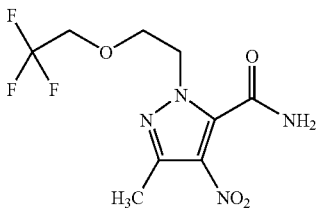

5-Methyl-4-nitro-2H-pyrazole-3-carboxamide (U.S. Pat. No. 4,282,361, ex 7) (2.0 g, 11.80 mmol), the alcohol of preparation 126 (2.03 g, 14.16 mmol) and triphenylphosphine (4.29 g, 16.52 mmol) were dissolved in tetrahydrofuran (30 mL) and the mixture cooled in an ice bath. A solution of diisopropyl azodicarboxylate (3.20 mL, 16.52 mmol) in tetrahydrofuran (5 mL) was added dropwise and the reaction mixture stirred for 2 hours at room temperature. The reaction mixture was concentrated in vacuo and the residue triturated with dichloromethane:ether 80:20 to yield a white solid, 884 mg. The mother liquors were concentrated in vacuo and the residue triturated again with dichloromethane and the solid filtered to yield another batch of white solid, 584 mg. The dichloromethane solution was then purified by column chromatography on silica gel eluting with dichloromethane:ether 70:30 to yield additional product, 1.49 g.

$^1$H NMR (CD$_3$OD, 400 MHz) δ: 2.46 (s, 3H), 3.91 (q, 2H), 4.02 (t, 2H), 4.35 (t, 2H)

Preparation 128

4-Amino-5-methyl-2-[2-(2,2,2-trifluoroethoxy)ethyl]-2H-pyrazole-3-carboxamide

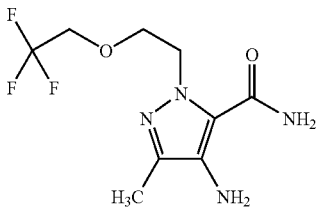

A mixture of the pyrazole from preparation 127 (1.46 g, 4.93 mmol), and palladium hydroxide (150 mg) in methanol (50 mL) was heated to reflux, and ammonium formate (1.55 g, 24.6 mmol) added portionwise. Once addition was complete, the reaction was stirred for a further hour under reflux. The cooled mixture was filtered through Arbocel®, and the filtrate evaporated in vacuo to give the title compound as an orange solid, 1.30 g.

$^1$H NMR (CD$_3$OD, 400 MHz) δ: 2.16 (s, 3H), 3.84 (q, 2H), 3.91 (t, 2H), 4.53 (t, 2H) LRMS:m/z ES+m/z 289 [MNa]$^+$

Preparation 129

3-Methyl-1-[2-(2,2,2-trifluoroethoxy)ethyl]-1,4-dihydropyrazolo[4,3-d]pyrimidine-5,7-dione

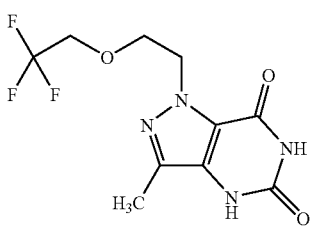

A solution of 1,1'-carbonyl diimidazole (1.2 g, 7.4 mmol) in acetonitrile (15 mL) was heated to reflux, and a solution of the pyrazole from preparation 128 (1.3 g, 4.93 mmol) in acetonitrile (15 mL) was added dropwise over 25 minutes. The reaction was heated under reflux for a further 1.5 hours, then additional 1,1'-carbonyl diimidazole (400 mg, 2.5 mmol) added, and the reaction heated under reflux for a further 18 hours. The cooled mixture was evaporated in vacuo and the residue triturated with ether, the resulting solid filtered off and dried to afford the title compound as a white solid, 864 mg.

$^1$H NMR (DMSO-d$_6$, 400 MHz) δ: 2.20 (s, 3H), 3.92 (t, 2H), 4.00 (q, 2H), 4.51 (t, 2H), 11.08 (s, 2H).

Preparation 130

5,7-Dichloro-3-methyl-1-[2-(2,2,2-trifluoroethoxy)ethyl]-1H-pyrazolo[4,3-d]pyrimidine

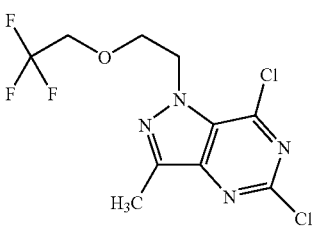

A mixture of the compound from preparation 129 (2.1 g, 7.18 mmol), phosphorous oxychloride (10.02 mL) and tetraethylammonium chloride (3.57 g, 21.6 mmol) in propionitrile (30 mL) was heated to 100° C. and stirred for 18 hours. The cooled mixture was evaporated in vacuo and the residue azeotroped with toluene. The residue was partitioned between ethyl acetate and water and the layers separated. The organic phase was dried over magnesium sulphate, concentrated in vacuo and the crude product purified by column chromatography on silica gel using dichloromethane:ethyl acetate (50:50) to give the title compound as a gum, 776 mg.

$^1$H NMR (CDCl$_3$, 400 MHz) δ: 2.62 (s, 3H), 3.72 (q, 2H), 4.03 (t, 2H), 4.89 (t, 2H)

Preparation 131

5-Amino-1-methyl-1H-pyridin-2-one

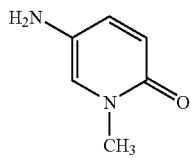

Trifluoroacetic acid (10 mL) was added dropwise to an ice-cooled solution of tert-butyl (1-methyl-6-oxo-1,6-dihydropyridin-3-yl)carbamate (Heterocycles 1995; 40; 2; 831-836) (2.87 g, 12.8 mmol) in dichloromethane (80 mL), and the reaction then stirred at room temperature for 18 hours. The mixture was concentrated in vacuo and the residue purified by column chromatography on silica gel using dichloromethane:methanol:0.88 ammonia (90:10:1) as eluant to afford the title compound as a red/brown solid, 1.90 g.

$^1$H NMR (CD$_3$OD, 400 MHz) δ: 3.50 (s, 3H), 6.47 (d, 1H), 7.04 (d, 1H), 7.26 (dd, 1H).

Preparation 132

5-Amino-2,3-dimethylpyridine hydrochloride

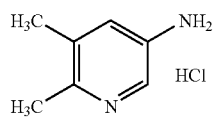

Cold 0.88 ammonia (344 mL, 6.2 mol) was added to 5-bromo-2,3-dimethylpyridine (Zeitschrift für Chemie 28; 2; 1988; 59-60) (35.1 g, 188.6 mmol) and copper oxide (330 mg, 2.3 mmol) and the mixture stirred vigorously then transferred to a sealed vessel and allowed to stand at 100° C. for 18 hours. The mixture was cooled to 10° C., the pH adjusted to 10, using 2M sulphuric acid, and the mixture extracted with ethyl acetate. The combined organic extracts were washed with brine, dried over sodium sulphate and concentrated in vacuo. The product was dissolved in ether, the solution cooled to 0° C., and 1M hydrochloric acid added dropwise. The resulting mixture was stirred for 30 minutes, the precipitate filtered off, washed with ether and dried in vacuo to afford the title compound, 32.9 g.

$^1$H NMR (DMSO-d$_6$, 400 MHz) δ: 2.23 (s, 3H), 2.50 (s, 3H), 7.10-7.80 (m, 5H). LRMS:m/z ES+123.6 [MH]$^+$

Preparation 133

4-Amino-6-methylpyrimidine

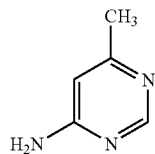

A mixture of 4-chloro-6-methylpyrimidine (Recl. Trav. Chim. Pays-Bas. 84; 1965, 1101-1106) (1 g, 7.81 mmol) and 0.88 ammonia (25 mL) were heated in a sealed vessel at 100° C. for 18 hours. The cooled mixture was concentrated in vacuo and the residue purified by column chromatography on silica gel using dichloromethane:methanol:0.88 ammonia (95:5:0.5) as eluant to give the title compound, 560 mg.

$^1$H NMR (CD$_3$OD, 400 MHz) δ: 2.30 (s, 3H), 6.40 (s, 1H), 8.23 (s, 1H).

Preparation 134

[5-Chloro-1-(2-ethoxyethyl)-3-methyl-1H-pyrazolo[4,3-d]pyrimidin-7-yl]-6-methylpyridin-2-ylamine

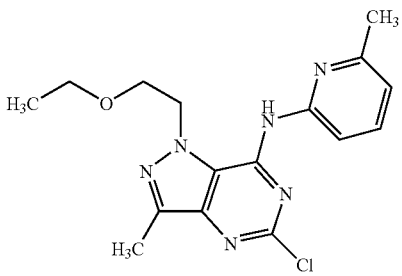

Sodium bis(trimethylsilyl)amide (1.99 g, 10.85 mmol) was added portionwise to a cooled solution of 2-amino-6-methylpyridine (1.17 g, 10.85 mmol) in tetrahydrofuran (10 mL), so as to maintain the temperature below 25° C. Once addition was complete, the solution was stirred for a further 20 minutes, and then a solution of the chloro compound from preparation 57 (1 g, 3.63 mmol) in tetrahydrofuran (15 mL) was added dropwise, so as to maintain the temperature below 25° C. The reaction was then stirred for a further 2 hours, and partitioned between ethyl acetate (100 mL) and 10% citric acid solution (100 mL). The organic layer was separated, dried over magnesium sulphate and evaporated in vacuo. The residue was triturated with ether, the solid filtered and dried to afford the title compound, 595 mg.

$^1$H NMR (CD$_3$OD, 400 MHz) δ: 0.93 (t, 3H), 2.45 (s, 3H), 2.49 (s, 3H), 3.61 (q, 2H), 3.92 (t, 2H), 4.88 (t, 2H), 6.98 (d, 1H), 7.71 (dd, 1H), 8.21 (br s, 1H). LRMS:m/z ES+m/z 369 [MNa]$^+$

Preparations 135 to 141

The following compounds were prepared following a similar procedure to that described in preparation 134.

| Prep. | —R¹ | Data |
|---|---|---|
| 135 | 4-CF₃-pyridin-2-yl | ¹H NMR (CD₃OD, 400 MHz) δ: 1.16 (t, 3H), 2.50 (s, 3H), 3.65 (q, 2H), 3.93 (m, 2H), 4.77 (m, 2H), 7.40 (d, 1H), 8.56 (d, 1H), 8.78 (m, 1H). LRMS: m/z ES+ 401 [MH]⁺ |
| 136ᴬ | 2-methylpyrimidin-4-yl | ¹H NMR (DMSO-d₆, 400 MHz) δ: 1.09 (t, 3H), 2.43 (s, 3H), 2.53 (s, 3H), 3.53 (q, 2H), 3.82 (m, 2H), 4.73 (m, 2H), 7.99 (m, 1H), 8.60 (m, 1H), 10.36 (m, 1H). LRMS: m/z ES+ 348 [MH]⁺ |
| 137ᴮ | 6-methylpyrimidin-4-yl | ¹H NMR (CD₃OD, 400 MHz) δ: 1.18 (t, 3H), 2.50 (s, 3H), 2.55 (s, 3H), 3.65 (q, 2H), 3.92 (t, 2H), 4.77 (t, 2H), 8.31 (s, 1H), 8.72 (s, 1H). LRMS: m/z APCl+ 348 [MH]⁺ |
| 138ᴮ | 4-methylpyrimidin-2-yl | ¹H NMR (CD₃OD, 400 MHz) δ: 1.23 (t, 3H), 2.50 (s, 3H), 2.51 (s, 3H), 3.62 (q, 2H), 3.81 (t, 2H), 4.75 (m, 2H), 7.05 (d, 1H), 8.49 (d, 1H). LRMS: m/z APCl+ 348 [MH]⁺ |
| 139ᶜ | 4,6-dimethylpyridin-2-yl | ¹H NMR (CD₃OD, 400 MHz) δ: 1.08 (t, 3H), 2.36 (s, 3H), 2.44 (m, 6H), 3.57 (m, 2H), 3.88 (m, 2H), 4.78 (m, 2H), 6.83 (m, 1H), 8.13 (m, 1H). LRMS: m/z APCl+ 361 [MH]⁺ |
| 140ᶜ | 6-methylpyridin-2-yl | ¹H NMR (CD₃OD, 400 MHz) δ: 2.36 (s, 3H), 2.43 (s, 3H), 3.94 (m, 4H), 4.81 (t, 2H), 7.16 (d, 1H), 7.83 (d, 1H), 8.00 (dd, 1H). LRMS: m/z APCl+ 423 [MNa]⁺ |
| 141 | 4-methylpyridin-2-yl | ¹H NMR (DMSO-d₆, 400 MHz) δ: 2.41 (s, 3H), 2.44 (s, 3H), 3.96 (t, 2H), 4.01 (q, 2H), 4.86 (t, 2H), 7.14 (d, 1H), 7.78 (s, 1H), 8.30 (d, 1H). LRMS: m/z ES+ 401 [MH]⁺ |

ᴬcompound purified by column chromatography on silica gel using methanol:dichloromethane as eluant, then recrystallised from ethyl acetate.
ᴮcompound purifed by column chromatography using ethyl acetate:pentane as eluant (50:50 to 100:0)
ᶜcompound purified by column chromatography using ethyl acetate:dichloromethane as eluant.

Prep 135: 2-amino-4-trifluoromethylpyridine prepared as in J. Med. Chem. 41 (1); 1998; 96-101

Prep 136: 4-amino-2-methylpyrimidine was prepared as described in J. Het. Chem. 14; 1413; 1977.

Prep 137: used amine from preparation 133

Preparation 142

5-[5-Chloro-1-(2-ethoxyethyl)-3-methyl-1H-pyrazolo[4,3-d]pyrimidin-7-ylamino]-1-methyl-1H-pyridin-2-one

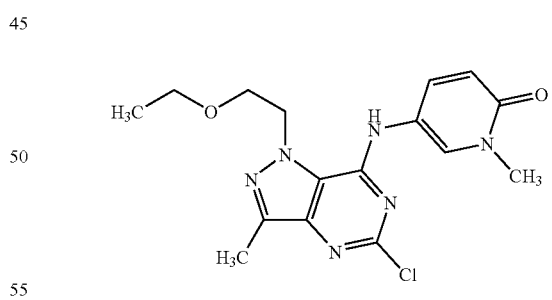

A mixture of the chloro compound from preparation 57 (100 mg, 0.36 mmol), and the amine from preparation 131 (230 mg, 1.85 mmol) in dimethylsulfoxide (3 mL) was stirred at room temperature for 4 hours. The mixture was partitioned between ethyl acetate (100 mL) and water (200 mL) and the phases separated. The aqueous layer was extracted with ethyl acetate (2×), and the combined organic solutions dried over magnesium sulphate and evaporated in vacuo. The residue was triturated with ether, the solid filtered off and dried to afford the title compound as a grey solid, 80 mg.

Preparation 143

[5-Chloro-1-(2-ethoxyethyl)-3-methyl-1H-pyrazolo[4,3-d]pyrimidin-7-yl]-5,6-dimethylpyridin-3-ylamine

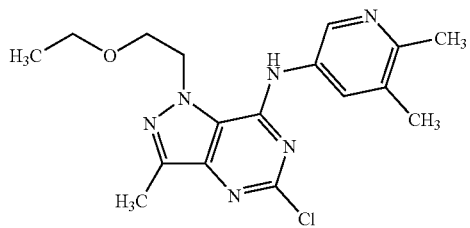

A mixture of the chloro compound from preparation 57 (230 mg, 0.84 mmol), N-ethyldiisopropylamine (437 μL, 2.52 mmol), and the amine from preparation 132 (398 mg, 2.52 mmol) in dimethylsulfoxide (3 mL) was stirred at room temperature for 2 hours. The mixture was diluted with water and extracted with ethyl acetate. The combined organic extracts were dried over magnesium sulphate, evaporated in vacuo and the residue purified by column chromatography on silica gel using dichloromethane:methanol (100:0 to 98:2) as eluant to afford the title compound, 160 mg.

$^1$H NMR (CD$_3$OD, 400 MHz) δ: 1.09 (t, 3H), 2.36 (s, 3H), 2.47 (s, 3H), 2.48 (s, 3H), 3.59 (q, 2H), 3.91 (t, 2H), 4.79 (t, 2H), 8.01 (d, 1H), 8.67 (d, 1H) LRMS:m/z APCI+361 [MH]$^+$

Preparation 144

[5-Chloro-1-(2-ethoxyethyl)-3-methyl-1H-pyrazolo[4,3-d]pyrimidin-7-yl]-6-methoxypyridin-3-ylamine

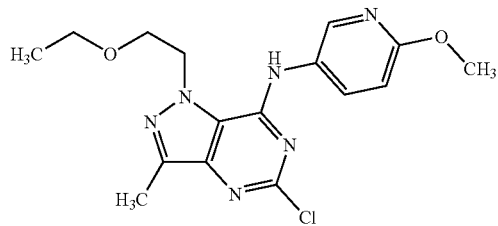

A solution of 5-amino-2-methoxypyridine (1.13 g, 9.1 mmol) in dichloromethane (2 mL) was added dropwise to a solution of the chloro compound from preparation 57 (500 mg, 1.82 mmol) in dichloromethane (8 mL) and the reaction then stirred at room temperature for 18 hours. The mixture was diluted with dichloromethane, washed with 10% citric acid solution (3×10 mL), dried over magnesium sulphate and evaporated under reduced pressure to give the title compound as a pale pink solid.

$^1$H NMR (DMSO-d$_6$, 400 MHz) δ: 0.95 (t, 3H), 2.38 (s, 3H), 3.40 (q, 2H), 3.72 (t, 2H), 3.86 (s, 3H), 4.80 (t, 2H), 6.91 (m, 1H), 7.92 (m, 1H), 8.38 (m, 1H), 9.13 (s, 1H). LRMS:m/z APCI+363 [MH]$^+$ $^1$H NMR (CD$_3$OD, 400 MHz) δ: 1.08 (t, 3H), 2.46 (s, 3H), 3.54 (q, 2H), 3.63 (s, 3H), 3.87 (t, 2H), 4.76 (t, 2H), 6.63 (d, 1H), 7.69 (dd, 1H), 8.24 (d, 1H) LRMS:m/z APCI+363 [MH]$^+$

Preparation 145

Dimethyl 4-nitro-1-(2-propoxyethyl)-1H-pyrazole-3,5-dicarboxylate

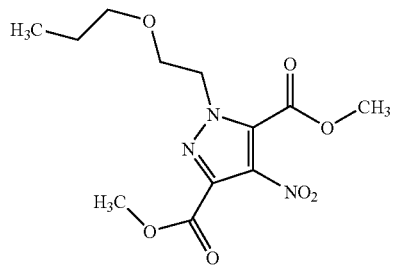

Diisopropyl azodicarboxylate (14.2 mL, 70 mmol) was added to an ice-cooled solution of 4-nitro-1H-pyrazole-3,5-dicarboxylic acid dimethyl ester (EP 1241170, prep 10) (15 g, 60 mmol), 2-propoxyethanol (8.2 mL, 70 mmol) and triphenylphosphine (18.9 g, 70 mmol) in tetrahydrofuran (150 mL), and the reaction stirred at 0° C. for 2.5 hours, then allowed to stir at room temperature for a further 18 hours. The reaction was concentrated in vacuo and the residue purified by column chromatography on silica gel using ethyl acetate:pentane as eluant, and then re-columned using dichloromethane as eluant to afford the title compound as a solid, 14 g.

$^1$H NMR (CD$_3$OD, 400 MHz) δ: 0.82 (t, 3H), 1.47 (m, 2H), 3.34 (t, 2H), 3.78 (t, 2H), 3.91 (s, 6H), 4.76 (t, 2H). LRMS:m/z APCI+316 [MH]$^+$

Preparation 146

3-(Methoxycarbonyl)-4-nitro-1-(2-propoxyethyl)-1H-pyrazole-5-carboxylic acid

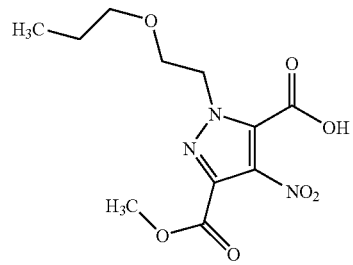

A mixture of the diester from preparation 145 (14 g, 44 mmol) and potassium hydroxide (2.74 g, 48 mmol) in methanol (200 mL) was stirred at room temperature for 18 hours. The reaction mixture was concentrated in vacuo and the residue suspended in water. The aqueous solution was washed with ether (3×), then acidified to pH 2-3 using hydrochloric acid, and the solution extracted with dichloromethane (9×). These combined organic extracts were dried over magnesium sulphate and evaporated in vacuo to afford the title compound as a white solid, 13.2 g.

$^1$H NMR (CD$_3$OD, 400 MHz) δ: 0.83 (t, 3H), 1.49 (m, 2H), 3.36 (t, 2H), 3.80 (t, 2H), 3.90 (s, 3H), 4.78 (t, 2H). LRMS:m/z APCI+302 [MH]$^+$

Preparation 147

Methyl 5-carbamoyl-4-nitro-1-(2-propoxyethyl)-1H-pyrazole-3-carboxylate

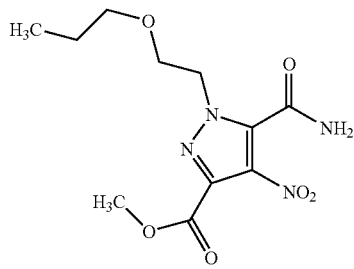

Oxalyl chloride (11.48 mL, 132 mmol) was added dropwise over 30 minutes to a cooled (−5° C.) solution of the acid from preparation 146 (13.2 g, 44 mmol) and N,N-dimethylformamide (150 μL) in dichloromethane (140 mL), and the solution stirred for an hour, then allowed to warm slowly to room temperature, and stirred for a further 1.5 hours. The solution was evaporated in vacuo and the residue azeotroped with dichloromethane. The product was dissolved in tetrahydrofuran (150 mL), the solution cooled in an ice-bath, and 0.88 ammonia (60 mL) added dropwise over 10 minutes. The reaction was allowed to warm to room temperature over an hour, then evaporated in vacuo. The residue was triturated with water, the resulting solid filtered off and dried at 70° C. to afford the title compound, 10.22 g.

$^1$H NMR (DMSO-$d_6$, 400 MHz) δ: 0.81 (t, 3H), 1.45 (m, 2H), 3.32 (t, 2H), 3.74 (t, 2H), 3.96 (s, 3H), 4.40 (t, 2H), 8.33 (br s, 1H), 8.48 (br s, 1H). LRMS:m/z APCI+301 [MH]$^+$

Preparation 148

Methyl 4-amino-5-carbamoyl-1-(2-propoxyethyl)-1H-pyrazole-3-carboxylate

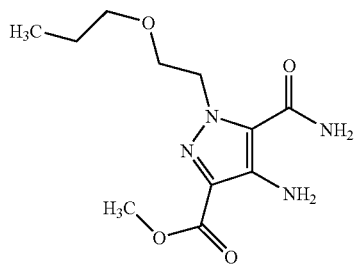

A solution of the nitro compound of preparation 147 (10 g, 33 mmol) and palladium hydroxide on carbon (933 mg) in ethanol (180 mL) was heated to 75° C., then ammonium formate (2.1 g, 33.3 mmol) added, and the reaction stirred for a further 3 hours. The mixture was filtered through Arbocel®, washing through with ethanol and the combined filtrate evaporated in vacuo to give the title compound as a pale pink solid, 9.1 g.

$^1$H NMR (CD$_3$OD, 400 MHz) δ: 0.84 (t, 3H), 1.51 (m, 2H), 3.40 (t, 2H), 3.83 (t, 2H), 3.89 (s, 3H), 4.56 (t, 2H). LRMS:m/z APCI+271 [MH]$^+$

Preparation 149

Methyl 5,7-dioxo-1-(2-propoxyethyl)-4,5,6,7-tetrahydro-1H-pyrazolo[4,3-d]pyrimidine-3-carboxylate

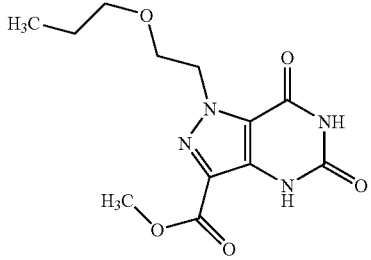

A mixture of the compound from preparation 148 (9 g, 33 mmol), 1,1'-carbonyl diimidazole (5.4 g, 33 mmol) and N,N-dimethylformamide (400 mL) was stirred for 30 minutes at room temperature then warmed to 75° C. for 18 hours. Tlc analysis showed starting material remaining, so additional 1,1'-carbonyl diimidazole (400 mg, 2.5 mmol) was added and the mixture stirred for a further 1.5 hours. The mixture was concentrated in vacuo, the residue suspended in water and stirred for 30 minutes. The resulting precipitate was filtered off and dried to afford the title compound as a pale pink solid, 6.05 g.

$^1$H NMR (DMSO-$d_6$, 400 MHz) δ: 0.72 (t, 3H), 1.37 (m, 2H), 3.28 (m, 2H), 3.76 (t, 2H), 3.82 (s, 3H), 4.64 (t, 2H), 10.77 (s, 1H), 11.37 (s, 1H).

Preparation 150

Methyl 5,7-dichloro-1-(2-propoxyethyl)-1H-pyrazolo[4,3-d]pyrimidine-3-carboxylate

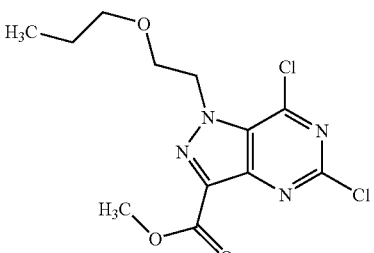

A mixture of the compound from preparation 149 (3 g, 10 mmol), phosphorous oxychloride (14.2 mL, 152 mmol) and tetraethylammonium chloride (3.95 g, 30 mmol) in propionitrile (80 mL) was heated at 115° C. for 18 hours. The mixture was evaporated in vacuo, and the residue re-suspended in phosphorous oxychloride (15 mL, 160 mmol) and propionitrile (80 mL), and the reaction stirred at 115° C. for a further 18 hours. The mixture wa concentrated in vacuo, and the residue azeotroped with toluene. The residue was partitioned carefully between water and ethyl acetate, the layers separated, and the aqueous phase extracted with further ethyl acetate. The combined organic solutions were washed with brine, dried over magneisum sulphate and evaporated in vacuo. The crude product was purified by column chromatography on silica gel using pentane:ethyl acetate (75:25) as eluant to afford the title compound, 3.1 g.
$^1$H NMR (DMSO-d$_6$, 400 MHz) δ: 0.65 (t, 3H), 1.33 (m, 2H), 3.26 (t, 2H), 3.82 (t, 2H), 3.93 (s, 3H), 4.94 (t, 2H).

Preparation 151

Methyl 5-chloro-7-(4-methylpyridin-2-ylamino)-1-(2-propoxyethyl)-1H-pyrazolo[4,3-d]pyrimidine-3-carboxylate

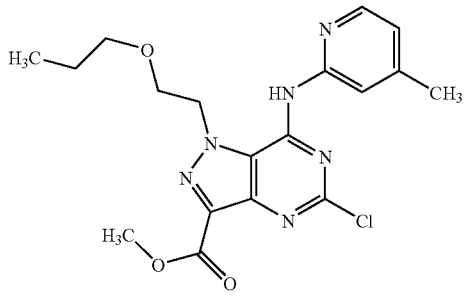

A mixture of the chloro compound from preparation 150 (1 g, 3 mmol), and 2-amino-4-methylpyridine (389 mg, 3.6 mmol) in dimethylsulfoxide (4.1 mL) was stirred at room temperature for 4 hours. The mixture was partitioned between ethyl acetate and water and the layers separated. The aqueous phase was extracted with ethyl acetate (3×), and the combined organic solutions were washed with water (3×) and brine, then dried over magnesium sulphate and evaporated in vacuo. The crude product was purified by column chromatography on silica gel using an elution gradient of ethyl acetate:pentane (20:80 to 50:50) to give the title compound, 452 mg.
$^1$H NMR (CDCl$_3$, 400 MHz) δ: 0.72 (m, 3H), 1.25 (m, 2H), 2.47 (s, 3H), 3.52 (t, 2H), 3.99 (m, 2H), 4.07 (s, 3H), 4.98 (m, 2H), 6.90 (s, 1H), 7.23 (s, 1H), 8.18 (s, 1H).

Preparation 152

N-[5-Chloro-3-hydroxymethyl-1-(2-propoxyethyl)-1H-pyrazolo[4,3-d]pyrimidin-7-yl]-4-methylpyridin-2-ylamine

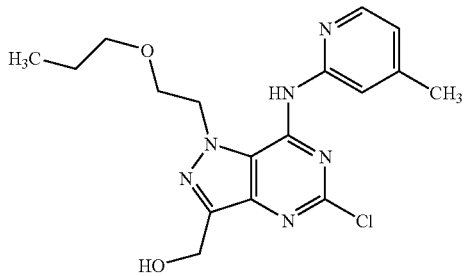

Diisobutylaluminium hydride (4.95 mL, 1M in tetrahydrofuran, 4.95 mmol) was added over 10 minutes to a cooled (−78° C.) solution of the compound from preparation 151 (250 mg, 0.62 mmol) in tetrahydrofuran (6.5 mL) and once addition was complete the reaction was allowed to warm to −10° C. and stirred for 10 minutes. The solution was re-cooled to −78° C., additional diisobutylaluminium hydride (2 mL, 1M in tetrahydrofuran, 2 mmol) was added and the mixture warmed to −5° C. and stirred for 30 minutes. The reaction was re-cooled to −78° C. and quenched with ammonium chloride solution (5 mL). The mixture was partitioned between water (50 mL) and dichloromethane (50 mL) and filtered through Arbocel®, washing through with dichloromethane. The filtrate was separated, the organic phase was dried over magnesium sulphate and evaporated in vacuo. The crude product was purified by column chromatography on silica gel using methanol:dichloromethane (1:99) to afford the title compound as a yellow solid, 112 mg.
$^1$H NMR (CD$_3$OD, 400 MHz) δ: 0.70 (t, 3H), 1.50 (m, 2H), 2.43 (s, 3H), 3.50 (m, 2H), 3.95 (t, 2H), 4.82 (m, 4H), 7.00 (s, 1H), 8.19 (s, 1H), 8.38 (s, 1H). LRMS:m/z APCI+ 377 [MH]$^+$ Preparation 153

N-[3-(tert-Butyldimethylsilanyloxymethyl)-5-chloro-1-(2-ethoxyethyl)-1H-pyrazolo[4,3-d]pyrimidin-7-yl]-6-methylpyridin-2-ylamine

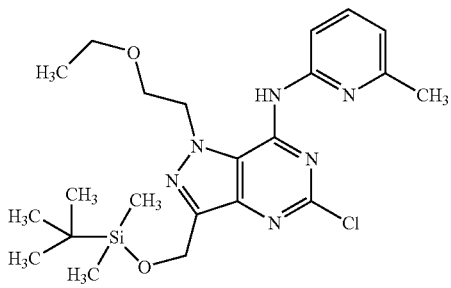

Sodium bis(trimethylsilyl)amide (677.1 mg, 3.7 mmol) was added portionwise to a cooled solution of 2-amino-6-methylpyridine (400 mg, 3.7 mmol) in tetrahydrofuran (5 mL) so as to maintain the temperature at 25° C., and once addition was complete the solution was stirred for 20 minutes. A solution of the chloro compound from preparation 108 (500 mg, 1.23 mmol) was added dropwise and the reaction then stirred for 1 hour at room temperature. The reaction was quenched by the addition of ammonium chloride solution, and the mixture partitioned between dichloromethane and water. The layers were separated and the organic phase washed with water and brine, then dried over magnesium sulphate and evaporated in vacuo. The crude product was purified by column chromatography on silica gel using dichloromethane:methanol (100:0 to 90:10) to afford the title compound as a yellow solid, 450 mg.
$^1$H NMR (CD$_3$OD, 400 MHz) δ: 0.12 (s, 6H), 0.90 (s, 9H), 1.13 (t, 3H), 2.49 (s, 3H), 3.61 (q, 2H), 3.93 (t, 2H), 4.84 (t, 2H), 4.98 (s, 2H), 6.98 (m, 1H), 7.73 (t, 1H), 8.25 (m, 1H). LRMS:m/z APCI+477 [MH]$^+$

Preparation 154

[5-Chloro-1-(2-ethoxyethyl)-7-(6-methylpyridin-2-ylamino)-1H-pyrazolo[4,3-d]pyrimidin-3-yl]methanol

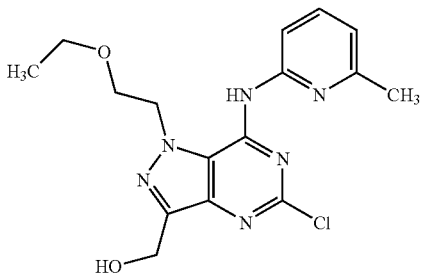

A mixture of the protected alcohol from preparation 153 (450 mg, 0.94 mmol) and tetrabutylammonium fluoride (1.89 mL, 1M in tetrahydrofuran, 1.89 mmol) in tetrahydrofuran (5 mL) was stirred at room temperature for 18 hours. The mixture was concentrated in vacuo and the residue partitioned between dichloromethane and water. The phases were separated, the organic layer washed with water and brine, then dried over magnesium sulphate and evaporated in vacuo. The product was triturated with ether to afford the title compound as a pale yellow solid, 260 mg.

$^1$H NMR (DMSO-$d_6$, 400 MHz) δ: 0.92 (t, 3H), 2.43 (s, 3H), 3.56 (q, 2H), 3.83 (t, 2H), 4.67 (d, 2H), 4.77 (t, 2H), 7.01 (d, 1H), 7.78 (m, 1H), 8.03 (d, 1H), 10.08 (s, 1H). LRMS:m/z APCI+363 [MH]$^+$

Preparation 155

N-[5-Chloro-3-chloromethyl-1-(2-ethoxyethyl)-1H-pyrazolo[4,3-d]pyrimidin-7-yl]-4-methylpyridin-2-ylamine

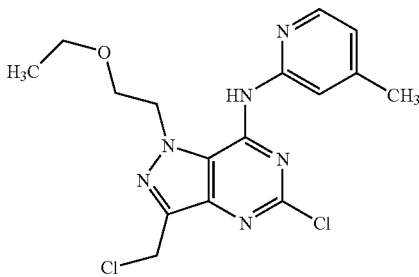

The alcohol of preparation 106 (1.80 g, 5.00 mmol) was dissolved in dichloromethane (15 mL) and the solution treated with thionyl chloride (1.50 mL, 17 mmol). The reaction mixture was stirred at room temperature for 18 hours and concentrated in vacuo. The residue was azeotroped with toluene and then dried in vacuo. The crude product was purified by column chromatography on silica gel eluting with dichloromethane:methanol (100:0 to 95:5) to yield the title product, 980 mg.

$^1$H NMR (CDCl$_3$, 400 MHz) δ: 0.92 (t, 3H), 2.63 (s, 3H), 3.58 (m, 2H), 3.91 (m, 2H), 4.81 (s, 2H), 5.20 (m, 2H), 7.14 (m, 1H), 8.16 (m, 1H), 8.97 (m, 1H) LRMS:m/z APCI+381 [MH]$^+$

Preparation 156

N-[5-Chloro-3-chloromethyl-1-(2-propoxyethyl)-1H-pyrazolo[4,3-d]pyrimidin-7-yl]-4-methylpyridin-2-ylamine

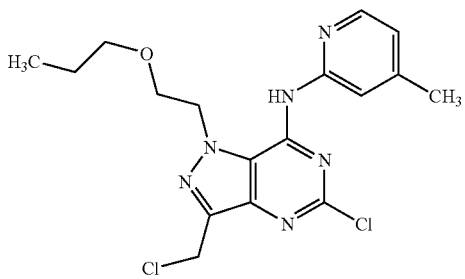

Thionyl chloride (170 μL, 23.4 mmol) was added to a solution of the hydroxy compound from preparation 152 (220 mg, 0.58 mmol) in dichloromethane (2 mL) and the solution stirred at room temperature for 2.5 hours. The reaction mixture was evaporated in vacuo to give the title compound as a pale yellow foam.

$^1$H NMR (CDCl$_3$, 400 MHz) δ: 0.60 (t, 3H), 1.30 (m, 2H), 2.69 (s, 3H), 3.41 (t, 2H), 3.91 (m, 2H), 4.96 (s, 2H), 5.24 (m, 2H), 7.23 (m, 1H), 8.16 (d, 1H), 9.06 (s, 1H). LRMS:m/z ES+395 [MH]$^+$

Preparation 157

N-[5-Chloro-3-chloromethyl-1-(2-ethoxyethyl)-1H-pyrazolo[4,3-d]pyrimidin-7-yl]-pyrimidin-4-ylamine

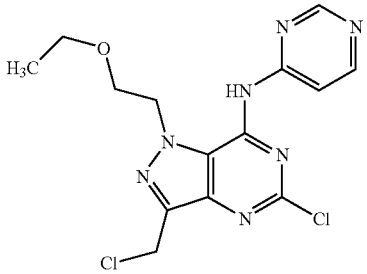

The title compound was obtained as a yellow solid from the alcohol from preparation 110, following a similar procedure to that described in preparation 156.

$^1$H NMR (CDCl$_3$, 400 MHz) δ: 1.20 (t, 3H), 3.68 (q, 2H), 3.96 (t, 2H), 4.75 (t, 2H), 4.88 (s, 2H), 8.62 (d, 1H), 8.69 (d, 1H), 9.00 (s, 1H). LRMS:m/z APCI+368 [MH]$^+$

Preparation 158

N-[5-Chloro-3-chloromethyl-1-(2-ethoxyethyl)-1H-pyrazolo[4,3-d]pyrimidin-7-yl]-6-methylpyridin-2-ylamine

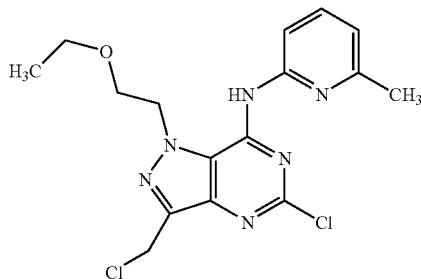

The title compound was obtained as a white foam from the alcohol from preparation 154, following a similar procedure to that described in preparation 156.

$^1$H NMR (CD$_3$OD, 400 MHz) δ: 0.87 (t, 3H), 2.90 (s, 3H), 3.47 (q, 2H), 3.89 (t, 2H), 4.96 (s, 2H), 5.30 (t, 2H), 7.19 (d, 1H), 8.19 (t, 1H), 9.04 (d, 1H). LRMS:m/z APCI+381 [MH]$^+$

Preparation 159

N-[5-Chloro-1-(2-ethoxyethyl)-3-methoxymethyl-1H-pyrazolo[4,3-d]pyrimidin-7-yl]-4-methylpyridin-2-ylamine

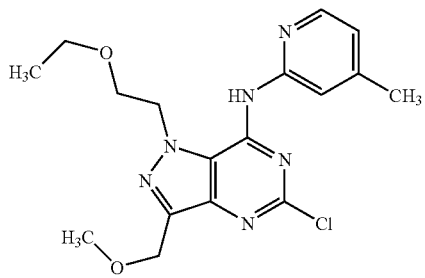

Sodium methoxide (25% in methanol, 8.4 mL, 39.5 mmol) was added to a solution of the chloro compound from preparation 155 (3 g, 7.9 mmol) in methanol (30 mL), and the reaction stirred at room temperature for 72 hours. The mixture was evaporated in vacuo, and the residue was partitioned between dichloromethane and water. The layers were separated, the organic phase washed with water, and evaporated in vacuo. The product was purified by column chromatography on silica gel using ethyl acetate as eluant to afford the title compound as a yellow solid.

$^1$H NMR (CD$_3$OD, 400 MHz) δ: 1.10 (t, 3H), 2.44 (s, 3H), 3.35 (m, 2H), 3.45 (s, 3H), 3.60 (q, 2H), 3.93 (t, 2H), 4.72 (s, 2H), 6.99 (s, 1H), 8.19 (s, 1H), 8.33 (s, 1H).

Preparation 160

N-[5-Chloro-3-methoxymethyl-1-(2-propoxyethyl)-1H-pyrazolo[4,3-d]pyrimidin-7-yl]-4-methylpyridin-2-ylamine

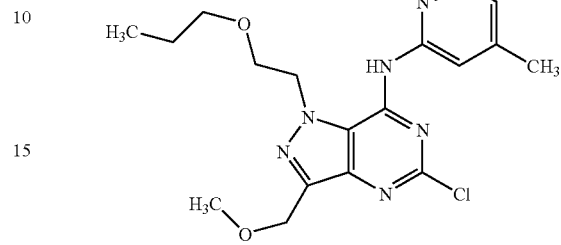

The title compound was obtained as a yellow solid in 80% yield from the chloro compound from preparation 156, following the procedure described in preparation 159.

$^1$H NMR (CD$_3$OD+TFA-d, 400 MHz) δ: 0.61 (t, 3H), 1.40 (m, 2H), 2.40 (s, 3H), 3.30 (s, 3H), 3.36 (t, 2H), 3.80 (t, 2H), 4.61 (s, 2H), 4.84 (t, 2H), 7.06 (d, 1H), 7.92 (s, 1H), 8.25 (d, 1H).

Preparation 161

N-[5-Chloro-1-(2-ethoxyethyl)-3-methoxymethyl-1H-pyrazolo[4,3-d]pyrimidin-7-yl]-6-methylpyridin-2-ylamine

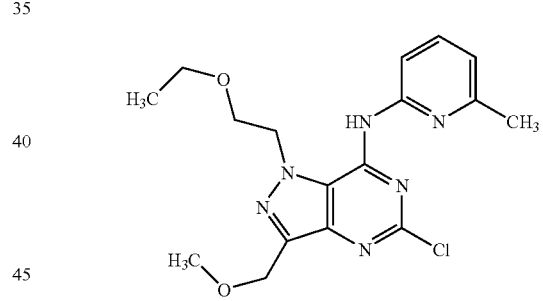

A mixture of the chloro compound from preparation 158 (280 mg, 0.73 mmol) and sodium methoxide (198 mg, 3.67 mmol) in methanol (4 mL) was stirred at room temperature for 18 hours. Tlc analysis showed starting material remaining, so additional sodium methoxide (79.2 mg, 1.46 mmol) was added and the reaction stirred for a further hour. The reaction was quenched by the addition of 10% aqueous citric acid solution, and the mixture evaporated in vacuo. The residue was partitioned between dichloromethane and water, and the layers separated. The organic phase was washed with 10% aqueous citric acid solution and water, then dried over magnesium sulphate and evaporated in vacuo. The crude product was purified by column chromatography on silica gel using an elution gradient of dichloromethane:methanol (100:0 to 98:2) to afford the title compound as a yellow solid, 190 mg.

$^1$H NMR (CDCl$_3$, 400 MHz) δ: 1.22 (t, 3H), 2.46 (s, 3H), 3.50 (s, 3H), 3.65 (q, 2H), 3.94 (t, 2H), 4.78 (m, 4H), 6.87 (d, 1H), 7.63 (t, 1H), 8.22 (d, 1H), 10.05 (br s, 1H). LRMS:m/z APCI+377 [MH]$^+$

Preparation 162

N-[5-Chloro-1-(2-ethoxyethyl)-3-methoxymethyl-1H-pyrazolo[4,3-d]pyrimidin-7-yl]-pyrimidin-4-yl-amine

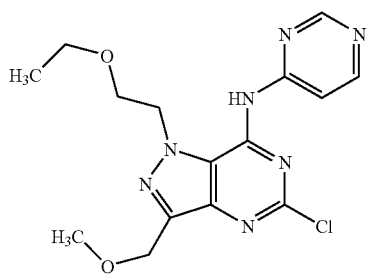

The title compound was obtained as a pale yellow solid from the chloro compound from preparation 157, following the procedure described in preparation 161.

$^1$H NMR (CD$_3$OD, 400 MHz) δ: 1.19 (t, 3H), 3.44 (s, 3H), 3.67 (q, 2H), 3.96 (t, 2H), 4.75 (s, 2H), 4.85 (t, 2H), 8.44 (d, 1H), 8.67 (d, 1H), 8.87 (s, 1H). LRMS:m/z APCI+364 [MH]$^+$

Preparation 163

N-[5-Chloro-1-(2-ethoxyethyl)-3-ethoxymethyl-1H-pyrazolo[4,3-d]pyrimidin-7-yl]-4-methylpyridin-2-ylamine

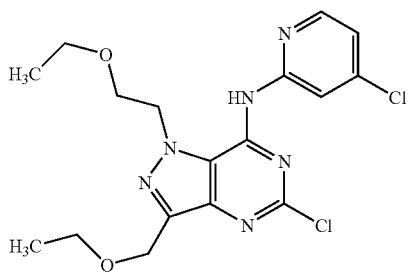

The title compound was obtained as an off-white solid in 70% yield, from the chloro compound from preparation 155 and sodium ethoxide in ethanol, following the procedure described in preparation 159, except ethyl acetate:pentane was the column eluant.

$^1$H NMR (CD$_3$OD, 400 MHz) δ: 1.10 (t, 3H), 1.21 (t, 3H), 2.43 (s, 3H), 3.55-3.68 (m, 4H), 3.92 (t, 2H), 4.76 (s, 2H), 4.84 (t, 2H), 6.99 (s, 1H), 8.19 (s, 1H), 8.34 (s, 1H). LRMS:m/z APCI+391 [MH]$^+$

Preparation 164 tert-Butyl 3-[1-(2-ethoxyethyl)-3-methoxymethyl-7-(4-methylpyridin-2-ylamino)-1H-pyrazolo[4,3-d]pyrimidin-5-yl]-3,8-diazabicyclo[3.2.1]octane-8-carboxylate

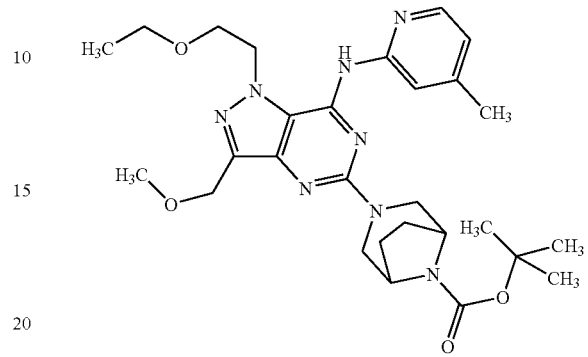

The monochloro compound of preparation 159 (100 mg, 0.27 mmol), tert-butyl 3,8-diazabicyclo[3.2.1]octane-8-carboxylate (Tet. Lett. 43 (2002), 899-902) (229 mg, 1.08 mmol) and N-ethyldiisoproylamine (232 μL, 1.33 mmol) were dissolved in dimethylsulfoxide (3 mL) and the reaction mixture heated to 120° C. for 18 hours in a sealed vessel. The reaction mixture was diluted with dichloromethane and washed with water (×2), 10% aqueous citric acid solution and brine. The organic phase was dried over magnesium sulphate and concentrated in vacuo. The residue was purified by column chromatography on silica gel eluting with dichloromethane:methanol (100:0 to 95:5) to yield the title product.

$^1$H NMR (CD$_3$OD, 400 MHz) δ: 1.11 (t, 3H), 1.50 (s, 9H), 1.79 (m, 2H), 1.92 (m, 2H), 2.39 (s, 3H), 3.14 (m, 2H), 3.43 (s, 3H), 3.58 (q, 2H), 3.87 (t, 2H), 4.33 (m, 2H), 4.39 (m, 2H), 4.67 (m, 4H), 6.91 (d, 1H), 8.13 (d, 1H), 8.18 (s, 1H). LRMS:m/z APCI+553 [MH]$^+$

Preparation 165 tert-Butyl (1S, 4S)-5-[1-(2-ethoxyethyl)-3-methyl-7-(5-methylpyridin-2-ylamino)-1H-pyrazolo[4,3-d]pyrimidin-5-yl]-2,5-diazabicyclo[2.2.1]heptane-2-carboxylate

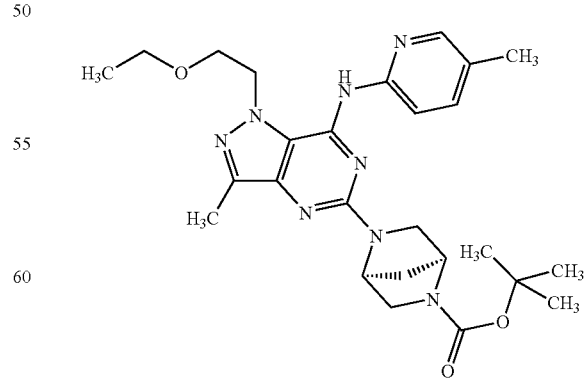

The title product was prepared by a method similar to that described for preparation 164 using the monochloro compound of preparation 121 and tert-butyl (1S, 4S)-2,5-diazabicyclo[2.2.1]heptane-2-carboxylate.

¹H NMR (CD₃OD, 400 MHz) δ: 1.11 (t, 3H), 1.39-1.46 (s, 9H), 2.00 (m, 2H), 2.28 (s, 3H), 2.40 (s, 3H), 3.43 (m, 2H), 3.54-3.67 (m, 4H), 3.85 (t, 2H), 4.55 (m, 1H), 4.62 (t, 2H), 4.92 (m, 1H), 7.60 (d, 1H), 8.08 (s, 1H), 8.26 (m, 1H). LRMS:m/z APCI+509 [MH]⁺

Preparation 166 tert-Butyl (1S, 4S)-5-[1-(2-ethoxyethyl)-3-methyl-7-(pyrimidin-4-ylamino)-1H-pyrazolo[4,3-d]pyrimidin-5-yl]-2,5-diazabicyclo[2.2.1]heptane-2-carboxylate

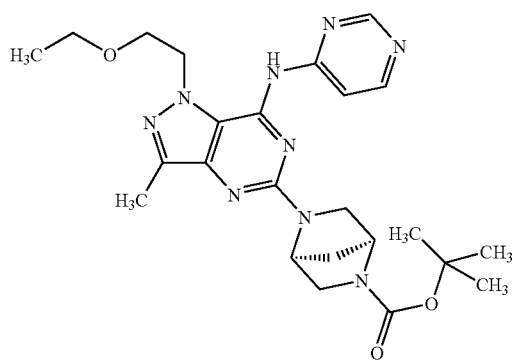

The title product was prepared by a method similar to that described for preparation 164 using the monochloro compound of preparation 72 and tert-butyl (1S, 4S)-2,5-diazabicyclo[2.2.1]heptane-2-carboxylate.

¹H NMR (CD₃OD, 400 MHz) δ: 1.22 (t, 3H), 1.33 (2×s, 9H), 2.01 (m, 2H), 2.43 (s, 3H), 3.47 (m, 3H), 3.65 (m, 4H), 3.91 (m, 2H), 4.63 (t, 2H), 5.01 (m, 1H), 8.35 (br s, 1H), 8.60 (d, 1H), 8.80 (s, 1H). LRMS:m/z APCI+496 [MH]⁺

Preparation 167 tert-Butyl (1S, 4S)-5-[1-(2-ethoxyethyl)-3-ethoxymethyl-7-(pyrimidin-4-ylamino)-1H-pyrazolo[4,3-d]pyrimidin-5-yl]-2,5-diazabicyclo[2.2.1]heptane-2-carboxylate

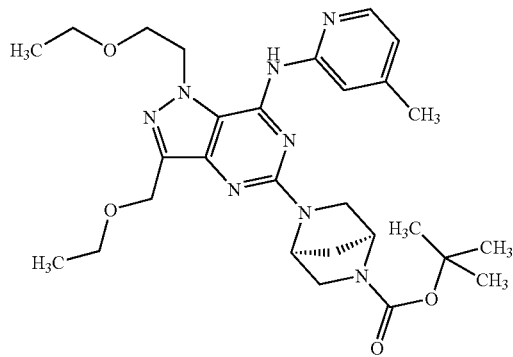

A mixture of the chloro compound from preparation 163 (100 mg, 0.26 mmol), tert-butyl (1S, 4S)-2,5-diazabicyclo[2.2.1]heptane-2-carboxylate (202.3 mg, 1.02 mmol) and N-ethyldiisoproylamine (226 μL, 1.3 mmol) in dimethylsulfoxide (3 mL) was heated at 120° C. for 18 hours in a sealed vessel. The cooled reaction was partitioned between dichloromethane and water, the layers separated, and the organic phase washed with water, then brine and dried over magnesium sulphate and evaporated in vacuo. The product was purified by column chromatography on silica gel using ethyl acetate as eluant to afford the title compound as an orange oil.

¹H NMR (CD₃OD, 400 MHz) δ: 1.10 (t, 3H), 1.19 (t, 3H), 1.40-1.48 (2×s, 9H), 2.00 (m, 2H), 2.40 (s, 3H), 3.49 (m, 2H), 3.56-3.71 (m, 6H), 3.89 (t, 2H), 4.57 (m, 1H), 4.69-4.75 (m, 4H), 4.95 (s, 1H), 6.92 (d, 1H), 8.14 (d, 1H), 8.34 (s, 1H). LRMS:m/z ES+553 [MH]⁺

Preparation 168

N-[5-((1R, 4R)-5-Benzyl-2,5-diazabicyclo[2.2.1]hept-2-yl)-1-(2-ethoxyethyl)-3-methyl-1H-pyrazolo[4,3-d]pyrimidin-7-yl]-4-methylpyridin-2-ylamine

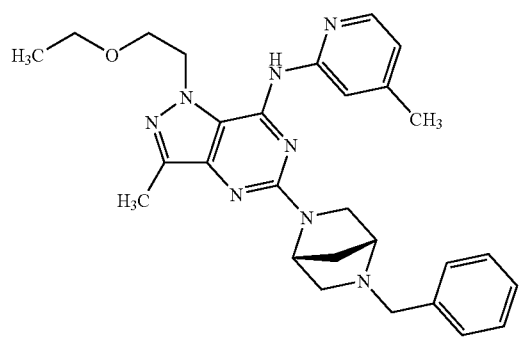

The monochloro compound of preparation 120 (180 mg, 0.52 mmol), (1R,4R)-2-benzyl-2,5-diazabicyclo[2.2.1]heptane dihydrobromide (EP 400661, ex 8) (545 mg, 2.90 mmol) and N-ethyldiisoproylamine (723 μL, 4.16 mmol) were dissolved in dimethylsulfoxide (3 mL) and the reaction mixture heated to 120° C. for 18 hours in a sealed vessel. The reaction mixture was partitioned between water (50 mL) and ethyl acetate (50 mL) and the aqueous separated and washed with ethyl acetate (50 mL). The organics were combined, dried over magnesium sulphate and concentrated in vacuo. The residue was purified by column chromatography on silica gel eluting with ethyl acetate:methanol (100:0 to 95:5) to yield the title product, 62 mg.

¹H NMR (CD₃OD, 400 MHz) δ: 0.12 (t, 3H), 1.96 (m, 1H), 2.09 (m, 1H), 2.38 (s, 3H), 2.42 (s, 3H), 2.88 (m, 1H), 3.08 (m, 1H), 3.59 (m, 3H), 3.80-3.95 (m, 7H), 4.62 (m, 2H), 6.92 (d, 1H), 7.35 (m, 5H), 8.12 (d, 1H), 8.35 (m, 1H). LRMS:m/z APCI+499 [MH]⁺

Preparation 169 tert-Butyl 3-dimethylaminoazetidine-1-carboxylate

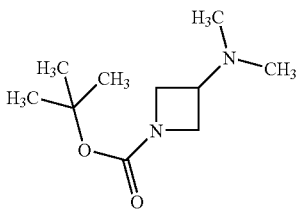

A mixture of tert-butyl 3-iodoazetidine-1-carboxylate (EP 1176147, prep 18) (5 g, 17.6 mmol) and dimethylamine (27 mL, 33% in ethanol, 176 mmol) was heated to 80° C. for 28 hours in a sealed vessel. The cooled mixture was evaporated in vacuo and the residue pre-adsorbed onto silica gel. This was then purified by column chromatography on silica gel using ethyl acetate:hexane (50:50) as eluant to afford the title compound as a yellow oil, 1.07 g.

$^1$H NMR (CDCl$_3$, 400 MHz) δ: 1.38 (s, 9H), 2.08 (s, 6H), 2.94 (m, 1H), 3.70 (m, 2H), 3.84 (m, 2H).

Preparation 170

3-Dimethylaminoazetidine bis(trifluoroacetate)

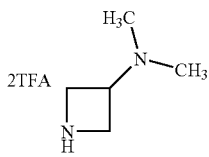

A mixture of the compound from preparation 169 (760 mg, 3.79 mmol) and trifluoroacetic acid (4 mL) in dichloromethane (12 mL) was stirred at room temperature for 1 hour. The solution was concentrated in vacuo and the residue azeotroped with toluene and dichloromethane. The product was triturated with ethyl acetate and the resulting solid filtered off and dried to afford the title compound, 600 mg.

$^1$H NMR (CD$_3$OD, 400 MHz) δ: 2.80 (s, 6H), 4.23 (m, 1H), 4.34 (m, 2H), 4.45 (m, 2H).

Preparation 171

N-[5-Chloro-3-methyl-1-(2-propoxyethyl)-1H-pyrazolo[4,3-d]pyrimidin-7-yl]-6-methylpyridin-2-ylamine

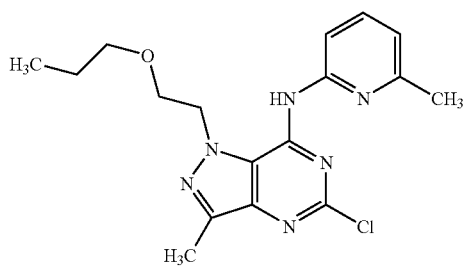

Sodium bis(trimethylsilyl)amide (1.43 g, 7.8 mmol) was added portionwise to a solution of 2-amino-6-methylpyridine (421.7 mg, 3.9 mmol) in tetrahydrofuran (7 mL), and the solution then stirred for 10 minutes. A solution of the chloro compound from preparation 62 (750 mg, 2.6 mmol) in tetrahydrofuran (7 mL) was added dropwise and the reaction stirred at room temperature for 2 hours. Aqueous saturated ammonium chloride solution was added dropwise and the mixture then extracted with dichloromethane. The organic solution was washed with water and brine, then dried over magnesium sulphate and evaporated in vacuo. The product was recrystallised from isopropyl acetate to afford the title compound as an off-white solid.

$^1$H NMR (CDCl$_3$, 400 MHz) δ: 0.79 (t, 3H), 1.69 (m, 2H), 2.46 (s, 3H), 2.55 (s, 3H), 3.56 (t, 2H), 3.93 (t, 2H), 4.72 (t, 2H), 6.88 (d, 1H), 7.64 (m, 1H), 8.23 (d, 1H), 9.94 (s, 1H). LRMS:m/z APCI+361 [MH]$^+$

Preparation 172

N-{5-Chloro-3-methyl-1-[2-(2,2,2-trifluoroethoxy)ethyl]-1H-pyrazolo[4,3-d]pyrimidin-7-yl}pyrimidin-4-ylamine

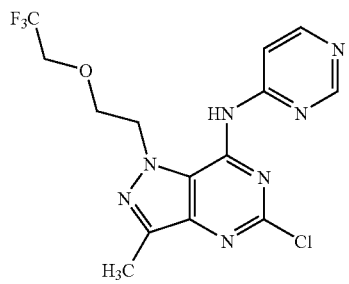

Sodium bis(trimethylsilyl)amide (1.46 g, 7.99 mmol) was added portionwise to a solution of 4-aminopyrimidine (864 mg, 8.0 mmol) in tetrahydrofuran (10 mL), and the solution then stirred for 15 minutes. A solution of the chloro compound from preparation 130 (1.17 g, 4.0 mmol) in tetrahydrofuran (10 mL) was added dropwise and the reaction stirred at room temperature for 2 hours. The mixture was partitioned between ethyl acetate (50 mL) and water (100 mL) and the layers separated. The aqueous phase was extracted with ethyl acetate (100 mL) and the combined organic solutions were dried over magnesium sulphate and evaporated in vacuo. The crude product was purified by column chromatography on silica gel using ethyl acetate as eluant, and the resulting solid triturated with ether to afford the title compound as a yellow solid, 1.02 g.

$^1$H NMR (CDCl$_3$, 400 MHz) δ: 2.50 (s, 3H), 4.00-4.10 (m, 2H), 4.12 (t, 2H), 4.85 (t, 2H), 8.40 (d, 1H), 8.60 (d, 1H), 8.85 (s, 1H). LRMS:m/z APCI+410 [MNa]$^+$

Preparation 173

3-(Methoxycarbonyl)-4-nitro-1-[2-(2,2,2,-trifluoroethoxy)ethyl]-1H-pyrazole-5-carboxylic acid

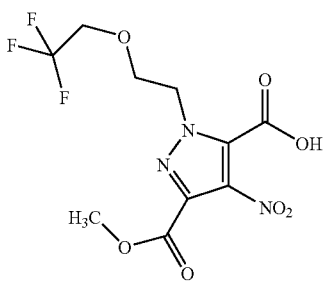

A solution of diisopropyl azodicarboxylate (71.9 mL, 366 mmol) in tetrahydrofuran (80 mL) was added dropwise to a solution of dimethyl 4-nitropyrazole-3,5-dicarboxylate (60 g, 260 mmol) and triphenylphosphine (96.15 g, 366 mmol) in tetrahydrofuran (650 mL) with stirring under nitrogen, keeping the reaction temperature between 0° C. and 10° C. by cooling in an ice bath. After the addition was complete, the mixture was allowed to warm to room temperature and stirred for 2 days. The solvent was removed under reduced pressure and the residue was dissolved in methanol (800 mL) and cooled to 0° C. A solution of potassium hydroxide (16.16 g, 288 mmol) in methanol (200 mL) was added at 0° C. and the reaction was allowed to warm to room temperature and stirred for 16 hours. The solvent was removed in vacuo and the residue was partitioned between water (600 mL) and ethyl acetate (600 mL). The aqueous layer was washed with ethyl acetate (2×200 mL) and the aqueous phase was acidified with hydrochloric acid to pH1. The aqueous solution was extracted with ethyl acetate (3×400 mL), and these combined extracts were dried over sodium sulphate and concentrated in vacuo to afford the title compound as a colourless solid, 52.86 g, 59%.

$^1$H NMR (CDCl$_3$, 400 MHz) δ: 3.77 (q, 2H), 3.93 (s, 3H), 4.00 (t, 2H), 4.84 (t, 2H).

Preparation 174

3-Ethyl-4-nitro-1-(2,2,2-trifluoroethoxy)ethylpyrazole-5-carboxamide

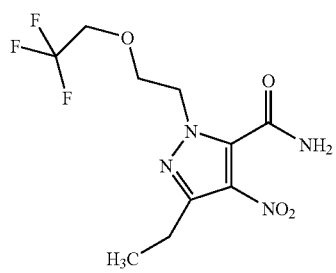

A solution of diisopropyl azodicarboxylate (53.74 g, 266 mmol) in tetrahydrofuran (50 mL) was added dropwise to a solution of 3-ethyl-4-nitropyrazole-5-carboxamide (EP 1176142, pg 18) (35.0 g, 190 mmol), and triphenylphosphine (69.79 g, 266 mmol) in tetrahydrofuran (450 mL) with stirring under nitrogen, keeping the reaction temperature between 0° C. and 10° C. by cooling in an ice bath. After the addition was complete, the mixture was allowed to stir for 2 hours, then warmed to room temperature. The solvent was removed in vacuo and the residue was recrystallised twice from hot isopropanol to afford the title compound as a colourless solid, 49.06 g.

$^1$H NMR (CDCl$_3$, 400 MHz) δ: 1.25 (t, 3H), 2.92 (q, 2H), 3.78 (q, 2H), 3.98 (t, 2H), 4.56 (t, 2H), 5.95 (br s, 1H), 7.11 (br s, 1H).

Preparation 175

Methyl 5-(carbamoyl)-4-nitro-1-[2-(2,2,2,-trifluoroethoxy)ethyl]-1H-pyrazole-3-carboxylate

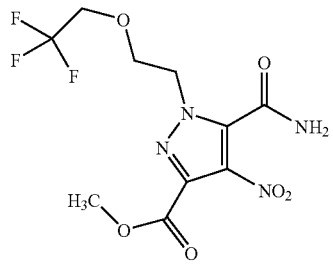

The acid from preparation 173 (70.0 g, 204 mmol) was dissolved in a mixture of dichloromethane (1000 mL) and N,N-dimethylformamide (1 mL) under nitrogen at 20° C. Oxalyl chloride (25 mL, 366 mmol) was added dropwise with stirring. The mixture was stirred for 16 hours then concentrated in vacuo, and the residue azeotroped with dichloromethane (3×200 mL). The residue was dissolved in tetrahydrofuran (1000 mL), cooled to −78° C. and 0.88 ammonia (70 mL) was added dropwise keeping the mixture at −78° C. After the addition was complete the mixture was stirred for 1 hour, and then an excess of hydrochloric acid was added at −78° C. (to give pH1). The mixture was allowed to warm to room temperature and the solvent was removed in vacuo. The resulting cream-coloured solid was collected by filtration and washed with water (3×100 mL). The solid was triturated with a mixture of diethyl ether and methanol (20:1, 20 mL/g) to give the title compound as a colourless solid, 40.0 g.

$^1$H NMR (CDCl$_3$, 400 MHz) δ: 3.78 (q, 2H), 3.95 (s, 3H), 3.98 (t, 2H), 4.76 (t, 2H), 5.91 (br s, 1H), 7.03 (br s, 1H).

Preparation 176

4-Amino-3-ethyl-1-(2,2,2-trifluoroethoxy)ethylpyrazole-5-carboxamide

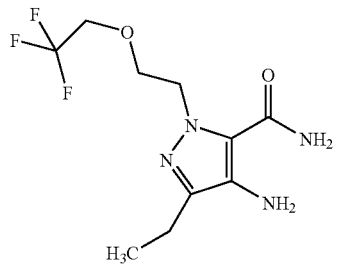

A solution of the compound from preparation 174 (23.34 g, 75 mmol) in methanol (400 mL) was hydrogenated over 10% palladium on charcoal (6.0 g) at 300 kPa and 50° C. for 2 hours. Another 2.0 g of catalyst was added and hydrogenation continued for another 14 hours. The hot solution was filtered through Arbocel® and the filter cake was washed with methanol (4×100 mL). The filtrate was concentrated in vacuo and the residue azeotroped with toluene (100 mL) to give the title compound as a red oil, 19.06 g.

$^1$H NMR (CDCl$_3$, 400 MHz) δ: 1.21 (t, 3H), 2.55 (q, 2H), 3.16 (br s, 2H), 3.79 (q, 2H), 3.99 (t, 2H), 4.61 (t, 2H),

Preparation 177

Methyl 4-amino-5-carbamoyl-1-[2-(2,2,2,-trifluoro-ethoxy)ethyl]-1H-pyrazole-3-carboxylate

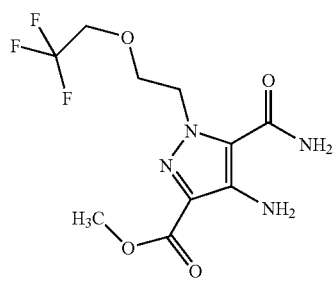

A solution of the compound from preparation 175 (40.0 g, 118 mmol) in methanol (640 mL) was hydrogenated over 10% palladium on charcoal (10 g) at 300 kPa and 50° C. for 3 hours. The hot solution was filtered through Arbocel® and the filter cake was washed with dichloromethane. The filtrate was concentrated in vacuo to give the title compound as an off-white solid, 34.2 g.

$^1$H NMR (CDCl$_3$, 400 MHz) δ: 3.80 (q, 2H), 3.91 (s, 3H), 4.07 (t, 2H), 4.63 (t, 2H), 6.29 (br s, 2H).

Preparation 178

3-Ethyl-1-[2-(2,2,2-trifluoroethoxy)ethyl]-1,4-dihydropyrazolo[4,3-d]pyrimidine-5,7-dione

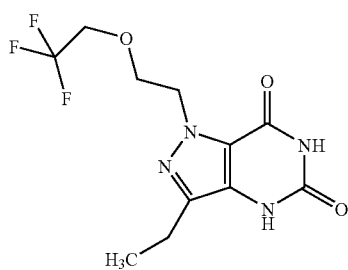

A solution of the compound from preparation 176 (19.06 g, 68.0 mmol) in acetonitrile (150 mL) was added dropwise over 2 hours to a stirred solution of N,N-carbonyl diimidazole (16.55 g, 100 mmol) in refluxing acetonitrile (850 mL) under nitrogen. The mixture was heated under reflux for 2 hours, cooled and the solvent was removed in vacuo. The residue was triturated with water (150 mL), the resulting colourless solid was filtered off and washed with water (100 mL), and dried in vacuo at 80° C., to afford the title compound, 17.53 g.

$^1$H NMR (CDCl$_3$, 400 MHz) δ: 1.26 (t, 3H), 2.67 (q, 2H), 3.78 (q, 2H), 4.00 (t, 2H), 4.63 (t, 2H), 7.94 (br s, 1H), 8.43 (br s, 1H). LRMS:m/z ES–305 [M–H]$^-$

Preparation 179

Methyl 5,7-dioxo-1-[2-(2,2,2-trifluoroethoxy)ethyl]-4,5,6,7-tetrahydro-1H-pyrazolo[4,3-d]pyrimidine-3-carboxylate

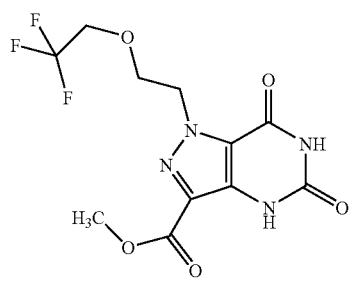

A solution of the compound from preparation 177 (21.7 g, 70.0 mmol) in acetonitrile (150 mL) was added dropwise over 2 hours to a stirred solution of N,N-carbonyl diimidazole (17.02 g, 105 mmol) in refluxing acetonitrile (850 mL) under nitrogen. The mixture was heated under reflux for 2 hours, cooled and the solvent was removed in vacuo. The residue was triturated with water (150 mL) and the resulting pale grey solid was filtered off, washed with water (3×100 mL), and dried in vacuo at 80° C., to afford the title compound, 21.26 g.

$^1$H NMR (CDCl$_3$, 400 MHz) δ: 3.79 (q, 2H), 3.98 (s, 3H), 4.07 (t, 2H), 4.77 (t, 2H), 7.87 (br s, 1H), 8.41 (br s, 1H). LRMS:m/z ES–335 [M–H]$^-$

Preparation 180

5,7-Dichloro-3-ethyl-1-[2-(2,2,2-trifluoroethoxy)ethyl]-1H-pyrazolo[4,3-d]pyrimidine

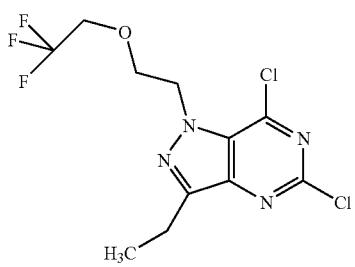

Phosphorous oxychloride (22.8 mL, 0.24 mol) was added to a suspension of the dione from preparation 178 (5 g, 16 mmol) and tetraethylammonium chloride (8.11 g, 48 mmol) in propionitrile (75 mL), and the mixture stirred at 106° C. for 18 hours. The cooled mixture was concentrated in vacuo and the residue azeotroped with toluene (2×50 mL). The residual oil was dissolved in ethyl acetate (50 mL), washed with water (200 mL), dried over magnesium sulphate and evaporated in vacuo, to afford the title compound, 4.98 g.

$^1$H NMR (CDCl$_3$, 400 MHz) δ: 1.40 (t, 3H), 3.05 (q, 2H), 3.70 (q, 2H), 4.05 (t, 2H), 4.90 (t, 2H).

Preparation 181

Methyl 5,7-dichloro-1-[2-(2,2,2,-trifluoroethoxy)ethyl]-1H-pyrazolo[4,3-d]pyrimidine-3-carboxylate

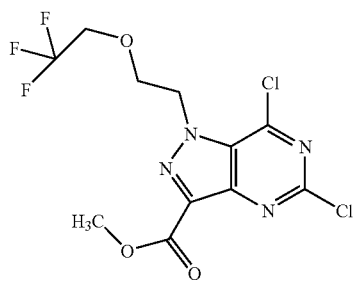

Phosphorous oxychloride (56 mL, 0.60 mol) was added to a suspension of the dione from preparation 179 (13.5 g, 40 mmol) and tetraethylammonium chloride (20.0 g, 120 mmol) in propionitrile (150 mL), and the mixture stirred under reflux for 18 hours. The cooled mixture was concentrated in vacuo and the residue azeotroped with toluene (2×50 mL). The residue was partitioned between dichloromethane (500 mL) and water (500 mL), the layers separated, and the aqueous extracted with further dichloromethane (500 mL). The combined organic solutions were washed with water (200 mL), brine (100 mL), dried over magnesium sulphate and evaporated in vacuo. The crude product was purified by column chromatography on silica gel using an elution gradient of ethyl acetate:pentane (34:66 to 50:50) to afford the title compound as a white solid, 9.4 g.

$^1$H NMR (CDCl$_3$, 400 MHz) δ: 3.75 (q, 2H), 4.10 (m, 5H), 5.05 (t, 2H).

Preparation 182

{5,7-Dichloro-1-[2-(2,2,2-trifluoroethoxy)ethyl]-1H-pyrazolo[4,3-d]pyrimidin-3-yl}methanol

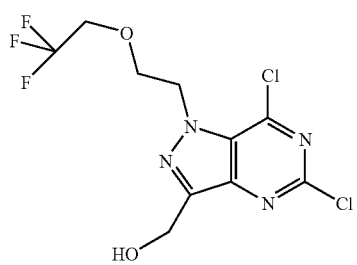

Diisobutylaluminium hydride (33.2 mL, 1M in tetrahydrofuran, 33.2 mmol) was added dropwise to a cooled (−78° C.) solution of the ester from preparation 181 (3.1 g, 8.31 mmol) in tetrahydrofuran (50 mL), so as to maintain the temperature below −70° C. Once addition was complete the reaction was allowed to warm to −10° C. and stirred for 1 hour. Tlc analysis showed starting material remaining, so the reaction was re-cooled to −78° C., additional diisobutylaluminium hydride (8.3 mL, 1M in tetrahydrofuran, 8.3 mmol) was added, the reaction warmed again to −10° C. and the reaction stirred for a further 20 minutes. The reaction was cooled again to −78° C., hydrochloric acid (2M, 30 mL) added and the mixture allowed to warm to room temperature and stirred for 18 hours. The mixture was diluted with water and extracted with dichloromethane (2×). The combined organic solutions were washed with water and brine, dried over magnesium sulphate and evaporated in vacuo. The crude product was purified by column chromatography on silica gel using an elution gradient of dichloromethane:methanol (100:0 to 97:3) to afford the title compound as an orange oil, 2.22 g.

$^1$H NMR (CDCl$_3$, 400 MHz) δ: 2.69 (s, 1H), 3.75 (q, 2H), 4.08 (t, 2H), 4.91 (t, 2H), 5.09 (s, 2H). LRMS:m/z APCI+ 345 [MH]$^+$

Preparation 183

5-{5-Chloro-3-hydroxymethyl-1-[2-(2,2,2-trifluoroethoxy)ethyl]-1H-pyrazolo[4,3-d]pyrimidin-7-ylamino}-1-methyl-1H-pyridin-2-one

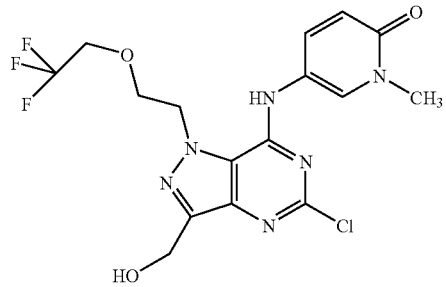

A mixture of the dichloro compound from preparation 182 (500 mg, 1.45 mmol), the amine from preparation 131 (198 mg, 1.6 mmol), and N-ethyldiisopropylamine (530 μL, 3.0 mmol) in dimethylsulfoxide (5 mL), was stirred at room temperature for 3 hours. The reaction was poured into water and the mixture acidified by the addition of hydrochloric acid. This mixture was extracted with dichloromethane (2×), the combined organic extracts washed with water (2×), dried over magnesium sulphate and evaporated in vacuo. The residual green solid was pre-adsorbed onto silica gel, and then purified by column chromatography on silica gel using an elution gradient of dichloromethane:methanol (98:2 to 90:10) to afford the title compound as a cream-white solid, 160 mg.

$^1$H NMR (DMSO-d$_6$, 400 MHz) δ: 3.45 (s, 3H), 3.92 (t, 2H), 4.01 (q, 2H), 4.13 (d, 2H), 4.87 (t, 2H), 5.24 (m, 1H), 6.46 (d, 1H), 7.51 (m, 1H), 7.81 (d, 1H), 8.81 (s, 1H). LRMS:m/z APCI+433 [MH]$^+$

Preparation 184

Methyl 5-chloro-7-(6-methylpyridin-2-ylamino)-1-[2-(2,2,2-trifluoroethoxy)ethyl]-1H-pyrazolo[4,3-d]pyrimidine-3-carboxylate

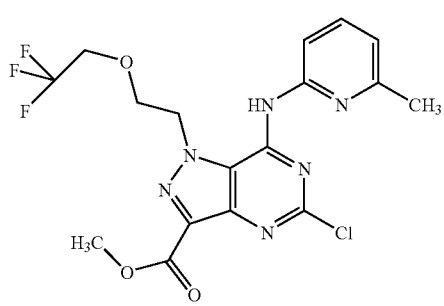

A mixture of the dichloro compound from preparation 181 (2 g, 5.36 mmol) and 2-amino-6-methylpyridine (1.74 g, 16.1 mmol) in acetonitrile (15 mL) were heated under reflux for 5 hours. The mixture was cooled in an ice-bath, and diluted with 10% citric acid solution (12 mL) and this mixture stirred for 15 minutes. The resulting precipitate was filtered off, washed with acetonitrile:water solution (50:50, 10 mL) and dried to afford the title compound as a pale pink solid, 1.8 g.

$^1$H NMR (DMSO-d$_6$+TFA-d, 400 MHz) δ: 2.59 (s, 3H), 3.90 (s, 3H), 4.10 (m, 4H), 5.15 (t, 2H), 7.05 (d, 1H), 7.90 (m, 1H), 8.02 (d, 1H).

Preparation 185

Methyl 5-chloro-7-(4-methylpyridin-2-ylamino)-1-[2-(2,2,2-trifluoroethoxy)ethyl]-1H-pyrazolo[4,3-d]pyrimidine-3-carboxylate

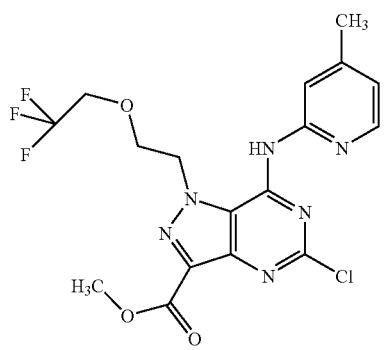

The title compound was obtained as a pale yellow solid from the dichloro compound from preparation 181, following the procedure described in preparation 184.

$^1$H NMR (DMSO-d$_6$+TFAd, 400 MHz) δ: 2.50 (s, 3H), 3.90 (s, 3H), 4.00-4.10 (m, 4H), 5.05 (t, 2H), 7.08 (d, 1H), 7.79 (s, 1H), 8.25 (d, 1H). LRMS:m/z APCI+445 [MH]$^+$

Preparation 186

{5-Chloro-7-(6-methylpyridin-2-ylamino)-1-[2-(2,2,2-trifluoroethoxy)ethyl]-1H-pyrazolo[4,3-d]pyrimidin-3-yl}methanol

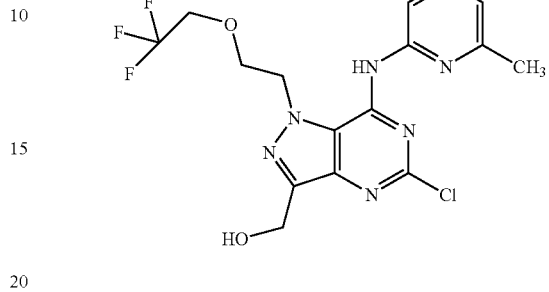

Diisobutylaluminium hydride (7 mL, 1M in tetrahydrofuran, 7 mmol) was added to a cooled (−10° C.) solution of the ester from preparation 184 (1.2 g, 2.7 mmol) in tetrahydrofuran (25 mL), and the reaction stirred for an hour at −10° C., followed by 1 hour at 0° C. Tlc analysis showed starting material remaining, so additional diisobutylaluminium hydride (5.4 mL, 1M in tetrahydrofuran, 5.4 mmol) was added and the reaction stirred at 10° C. for 10 minutes. The reaction was cooled to −5° C., hydrochloric acid (1N, 50 mL) added and the mixture poured into additional hydrochloric acid (2N, 50 mL). This mixture was stirred for 30 minutes, then extracted with dichloromethane (300 mL in total) and dichloromethane:methanol (95:5 by volume, 3×200 mL), and the combined organic extracts dried over magnesium sulphate and evaporated in vacuo. The product was triturated and sonicated with ether and the resulting solid dried in vacuo to afford the title compound as a yellow powder, 760 mg.

$^1$H NMR (CD$_3$OD, 400 MHz) δ: 2.70 (s, 3H), 3.95 (q, 2H), 4.10 (t, 2H), 4.85 (s, 2H), 5.05 (t, 2H), 7.40 (d, 1H), 7.98 (s, 1H), 8.30 (m, 1H).

Preparation 187

{5-Chloro-7-(4-methylpyridin-2-ylamino)-1-[2-(2,2,2-trifluoroethoxy)ethyl]-1H-pyrazolo[4,3-d]pyrimidin-3-yl}methanol

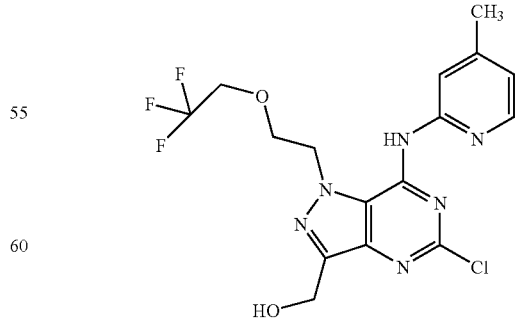

The title compound was prepared in 92% yield as a pink solid, from the compound from preparation 185, following a similar procedure to that described in preparation 186.

¹H NMR (CD₃OD, 400 MHz) δ: 2.52 (s, 3H), 3.98 (q, 2H), 4.10 (t, 2H), 4.85 (s, 2H), 5.00 (t, 2H), 7.19 (d, 1H), 7.82 (s, 1H), 8.21 (d, 1H).

Preparation 188

N-[5-Chloro-3-chloromethyl-1-[2-(2,2,2-trifluoroethoxy)ethyl]-1H-pyrazolo[4,3-d]pyrimidin-7-yl]-6-methylpyridin-2-ylamine

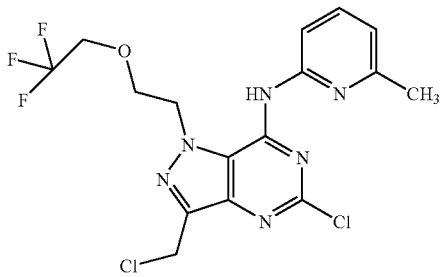

Thionyl chloride (0.3 mL, 3.84 mmol) was added to a suspension of the alcohol from preparation 186 (400 mg, 0.96 mmol) in dichloromethane (6 mL), and the reaction stirred for 10 minutes. The reaction mixture was concentrated in vacuo and the residue azeotroped with dichloromethane (3×10 mL) to afford the title compound.

LRMS:m/z APCI+435 [MH]⁺

Preparation 189

N-{5-Chloro-3-chloromethyl-1-[2-(2,2,2-trifluoroethoxy)ethyl]-1H-pyrazolo[4,3-d]pyrimidin-7-yl}-4-methylpyridin-2-ylamine

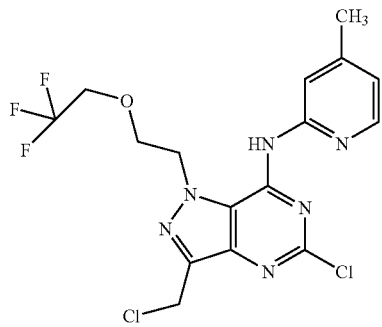

The title compound was obtained from the alcohol from preparation 187, following the procedure described in preparation 188.

LRMS:m/z APCI+435 [MH]⁺

Preparation 190

5-{5-Chloro-3-chloromethyl-1-[2-(2,2,2-trifluoroethoxy)ethyl]-1H-pyrazolo[4,3-d]pyrimidin-7-ylamino}-1-methyl-1H-pyridin-2-one

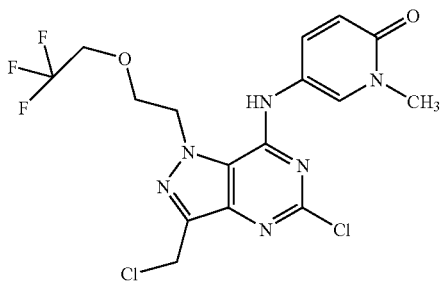

The title compound was obtained as an off-white solid, from the alcohol from preparation 183, following the procedure described in preparation 188.

LRMS:m/z APCI+451 [MH]⁺

Preparation 191

N-{5-Chloro-3-methoxymethyl-1-[2-(2,2,2-trifluoroethoxy)ethyl]-1H-pyrazolo[4,3-d]pyrimidin-7-yl}-6-methylpyridin-2-ylamine

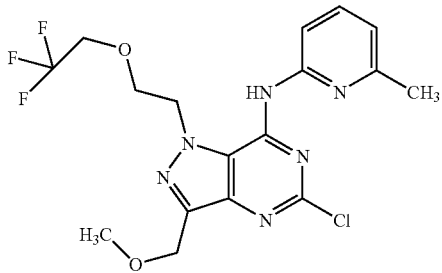

A mixture of the chloride from preparation 188 (100 mg, 0.23 mmol), sodium methoxide (25-30% solution in methanol, 0.2 mL, 0.91 mmol) and sodium iodide (10 mg) in tetrahydrofuran (1 mL) was stirred at room temperature for 30 minutes. The mixture was diluted with 10% citric acid solution, and extracted with dichloromethane (3×100 mL). The combined organic extracts were dried over magnesium sulphate, and evaporated in vacuo. The crude product was purified by column chromatography on silica gel using dichloromethane:methanol (99:1) as eluant to afford the title compound.

LRMS:m/z APCI+431 [MH]⁺

Preparations 192 to 195

The following compounds were prepared from the appropriate dichloro compounds of preparations 188-190, following the procedure described in preparation 191.

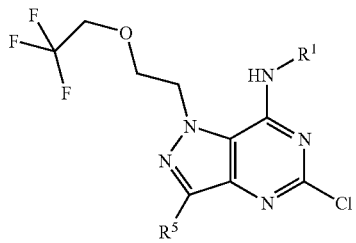

| Prep | R[1] | R[5] | Data |
|---|---|---|---|
| 192 | CH₃ pyridine (6-methyl-2-yl) | CH₃CH₂OCH₂— | ¹H NMR (CD₃OD, 400 MHz) δ: 1.20 (t, 3H), 2.40–2.60 (m, 3H), 3.65 (q, 2H), 3.90–4.18 (m, 4H), 4.80 (s, 2H), 4.90, 5.10 (mx2, 2H), 7.05 (m, 1H), 7.80 (m, 1H), 8.30 (m, 1H). LRMS: m/z APCl+ 445 [MH]⁺ |
| 193[a] | CH₃ pyridine (4-methyl-2-yl) | CH₃OCH₂— | LRMS: m/z ES+ 431.2 [MH]⁺ |
| 194 | CH₃ pyridine (4-methyl-2-yl) | CH₃CH₂OCH₂— | ¹H NMR (CD₃OD, 400 MHz) δ: 1.20 (t, 3H), 2.42 (s, 3H), 3.65 (q, 2H), 4.0 (m, 2H), 4.15 (t, 2H), 4.78 (m, 2H), 4.90, 5.10 (mx2, 2H), 6.90–8.30 (m, 3H). LRMS: m/z APCl+ 445 [MH]⁺ |
| 195[b] | CH₃ N-methyl-pyridin-2(1H)-one | CH₃OCH₂— | ¹H NMR (CDCl₃, 400 MHz) δ: 3.51 (s, 3H), 3.58 (s, 3H), 3.91 (q, 2H), 4.18 (t, 2H), 4.77–4.80 (m, 4H), 6.59 (d, 1H), 7.31 (m, 1H), 7.93 (s, 1H), 8.09 (d, 1H). LRMS: m/z APCl+ 447 [MH]⁺ |

[a]product was isolated by trituration/sonication with ether, and not purified by column chromatography.
[b]the reaction was performed with methanol as the solvent, for 18 hours in the absence of catalytic NaI.

Preparation 196

N-[5-Chloro-1-(2-ethoxyethyl)-3-ethoxymethyl-1H-pyrazolo[4,3-d]pyrimidin-7-yl]-6-methylpyridin-2-ylamine

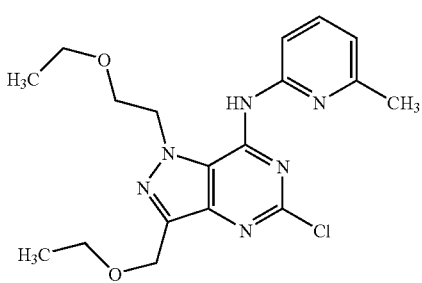

Sodium ethoxide (1.15 mL, 21% wt/vol in ethanol, 5.25 mmol) was added to a solution of the compound from preparation 158 (500 mg, 1.31 mmol) in ethanol (50 mL), and the reaction stirred at room temperature for 18 hours. Saturated ammonium chloride (50 mL) was added and the ethanol removed in vacuo. The aqueous residue was diluted with water (10 mL) and extracted with ethyl acetate (70 mL). The organic solution was dried over magnesium sulphate and concentrated in vacuo to afford the title compound, 420 mg.

¹H NMR (CDCl₃, 400 MHz) δ: 1.16 (t, 3H), 1.22 (t, 3H), 2.49 (s, 3H), 3.65 (q, 4H), 3.95 (t, 2H), 4.78 (s, 2H), 4.85 (m, 2H), 7.02 (d, 1H), 7.75 (m, 1H), 8.29 (d, 1H). LRMS:m/z APCl+391 [MH]⁺

Preparation 197

N-{5-Chloro-3-methyl-1-[2-(2,2,2-trifluoroethoxy)ethyl]-1H-pyrazolo[4,3-d]pyrimidin-7-yl}-6-methylpyrimidin-4-ylamine

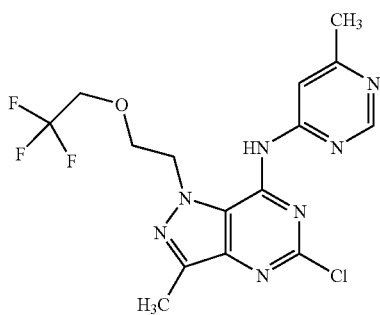

Sodium bis(trimethylsilyl)amide (917 mg, 15 mmol) was added to a suspension of the amine from preparation 133 (300 mg, 2.25 mmol) in tetrahydrofuran (30 mL), with ice cooling. The mixture was stirred for 10 minutes, then the compound from preparation 130 (822 mg, 2.5 mmol) was added and the reaction stirred for an hour at 0° C. 10% Citric acid solution (5 mL) was added and the mixture concentrated in vacuo. The residue was partitioned between ethyl acetate (150 mL) and water (100 mL), the layers separated, the organic phase dried over magnesium sulphate and evaporated in vacuo to give the title compound as a pale yellow solid, 968 mg.

$^1$H NMR (DMSO-d$_6$+TFA-d, 400 MHz) δ: 2.48 (s, 3H), 2.57 (s, 3H), 3.84-3.94 (m, 4H), 4.73 (t, 2H), 7.85 (s, 1H), 9.08 (s, 1H).
LRMS:m/z APCI+402 [MH]$^+$

Preparation 198

N-{5-Chloro-3-methyl-1-[2-(2,2,2-trifluoroethoxy)ethyl]-1H-pyrazolo[4,3-d]pyrimidin-7-yl}-2-methylpyrimidin-4-ylamine

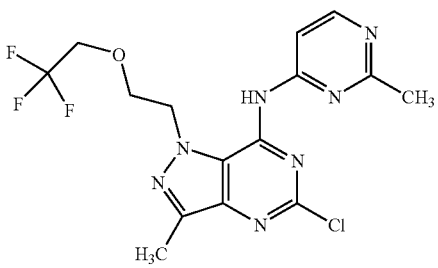

The title compound was obtained in 98% yield as an off-white solid from the compound from preparation 130 and 4-amino-2-methylpyrimidine (J. Het. Chem. 14; 1413; 197), following the procedure described in preparation 197.

$^1$H NMR (DMSO-d$_6$+TFA-d, 400 MHz) δ: 2.50 (s, 3H), 2.64 (s, 3H), 3.85-3.90 (m, 4H), 4.78 (t, 2H), 7.90 (d, 1H), 8.78 (d, 1H). LRMS:m/z APCI+402 [MH]$^+$

Preparation 199

N-{5-Chloro-3-ethyl-1-[2-(2,2,2-trifluoroethoxy)ethyl]-1H-pyrazolo[4,3-d]pyrimidin-7-yl}-2-methylpyrimidin-4-ylamine

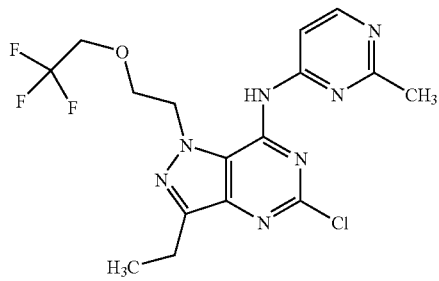

A solution of sodium bis(trimethylsilyl)amide (740 mg, 4.06 mmol) in tetrahydrofuran (10 mL) was added dropwise to a suspension of 4-amino-2-methylpyrimidine (J. Het. Chem. 14; 1413; 197), (445 mg, 4.06 mmol) in tetrahydrofuran (10 mL), with ice cooling. The mixture was stirred for 15 minutes, then a solution of the compound from preparation 180 (700 mg, 2.04 mmol) in tetrahydrofuran (10 mL) was added and the reaction stirred for an hour at room temperature. The mixture was partitioned between 10% citric acid solution (100 mL) and ethyl acetate (100 mL) and the layers separated. The organic phase was washed with water (100 mL) and brine (100 mL), then dried over magnesium sulphate and evaporated in vacuo to give the title compound as a yellow solid, 880 mg.

$^1$H NMR (CD$_3$OD, 400 MHz) δ: 1.37 (t, 3H), 2.60 (s, 3H), 2.96 (q, 2H), 4.06 (q, 2H), 4.13 (t, 2H), 4.86 (m, 2H), 8.20 (m, 1H), 8.55 (m, 1H). LRMS:m/z APCI−414 [M−H]$^-$

Preparation 200

N-{5-Chloro-3-ethyl-1-[2-(2,2,2-trifluoroethoxy)ethyl]-1H-pyrazolo[4,3-d]pyrimidin-7-yl}-6-methylpyrimidin-4-ylamine

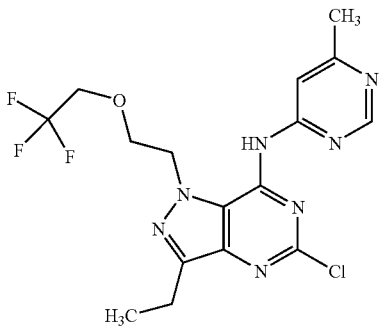

The title compound was obtained as a pale yellow solid from the compounds from preparation 133 and 180, following the procedure described in preparation 199.

$^1$H NMR (CD$_3$OD, 400 MHz) δ: 1.27 (t, 3H), 2.45 (s, 3H), 2.85 (q, 2H), 3.94 (q, 2H), 4.01 (t, 2H), 4.86 (m, 2H), 8.18 (m, 1H), 8.61 (m, 1H). LRMS:m/z APCI−414 [M−H]

Preparation 201

N-{5-Chloro-3-ethyl-1-[2-(2,2,2-trifluoroethoxy)ethyl]-1H-pyrazolo[4,3-d]pyrimidin-7-yl}pyridazin-4-ylamine

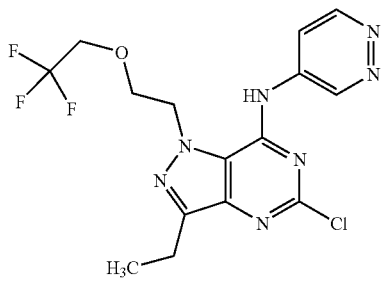

The title compound was obtained in 64% yield from the compound from preparation 180 and 4-aminopyridazine (J. Het. Chem. 19; 1285; 1982), following a similar procedure to that described in preparation 199, except, the compound was purified by column chromatography on silica gel using dichloromethane:methanol (90:10) as eluant.

$^1$H NMR (CD$_3$OD, 400 MHz) δ: 1.37 (t, 3H), 2.96 (q, 2H), 3.96 (q, 2H), 4.06 (t, 2H), 4.95 (t, 2H), 8.31 (m, 1H), 9.01 (m, 1H), 9.42 (m, 1H). LRMS:m/z APCI+403 [MH]$^+$

Preparation 202

N-{5-Chloro-3-ethyl-1-[2-(2,2,2-trifluoroethoxy)ethyl]-1H-pyrazolo[4,3-d]pyrimidin-7-yl}pyrimidin-4-ylamine

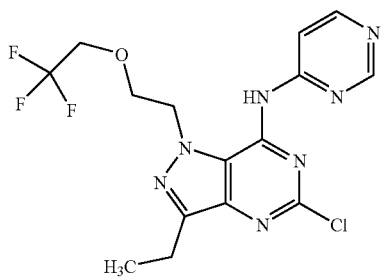

A solution of sodium bis(trimethylsilyl)amide (1.07 g, 5.82 mmol) in tetrahydrofuran (10 mL) was added to a solution of 4-aminopyrimidine (550 mg, 5.82 mmol) in tetrahydrofuran (10 mL) with ice cooling. The solution was stirred for 15 minutes, then a solution of the compound from preparation 180 (1 g, 2.91 mmol) in tetrahydrofuran (10 mL) was added and the reaction stirred at room temperature for 18 hours. The reaction was diluted with ethyl acetate (100 mL) and washed with water. The aqueous solution was extracted with ethyl acetate (100 mL) and the combined organic solutions dried over magnesium sulphate and evaporated in vacuo. The residue was purified by column chromatography on silica gel using ethyl acetate as eluant to afford the title compound as a yellow solid, 770 mg.

$^1$H NMR (CDCl$_3$, 400 MHz) δ: 1.40 (t, 3H), 3.00 (q, 2H), 4.05 (q, 2H), 4.20 (t, 2H), 4.80 (t, 2H), 8.40 (m, 1H), 8.70 (dd, 1H), 8.90 (s, 1H), 9.55 (br s, 1H). LRMS:m/z APCI+ 403 [MH]$^+$

Preparation 203

Ethyl 1-{3-methyl-7-(4-methylpyridin-2-ylamino)-1-[2-(2,2,2-trifluoroethoxy)ethyl]-1H-pyrazolo[4,3-d]pyrimidin-5-yl}piperidine-4-carboxylate

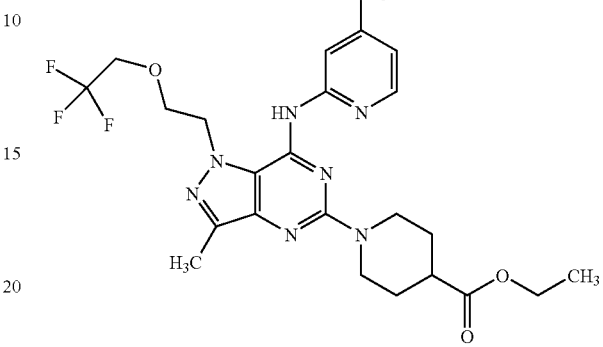

2-Amino-4-methylpyridine (162 mg, 1.5 mmol) was added to a solution of the dichloro compound from preparation 130 (165 mg, 0.5 mmol) in dimethylsulfoxide (2 mL) and the reaction stirred at 80° C. for 5 hours. Ethyl isonipecotate (308 μL, 2 mmol) was added, and the reaction stirred for a further 8 hours at 120° C. The cooled mixture was partitioned between dichloromethane (100 mL) and 0.5M citric acid solution (100 mL), and the layers separated. The organic layer was washed with water (100 mL), dried over magnesium sulphate and evaporated in vacuo. The crude product was purified by column chromatography on silica gel using an elution gradient of dichloromethane:methanol (100:0 to 98:2) to give the title compound as a yellow gum, 200 mg.

$^1$H NMR (CD$_3$OD, 400 MHz) δ: 1.25 (t, 3H), 1.70 (m, 2H), 1.95 (m, 2H), 2.38 (s, 3H), 2.40 (s, 3H), 2.62 (m, 1H), 3.10 (m, 2H), 4.00 (q, 2H), 4.06 (t, 2H), 4.12 (q, 2H), 4.60 (m, 2H), 4.71 (m, 2H), 6.93 (d, 1H), 8.14 (d, 1H), 8.20 (m, 1H). LRMS:m/z APCI+522 [MH]$^+$

Assay

The compounds of the invention are inhibitors of cyclic guanylate monophosphate (cGMP)-specific phosphodiesterase type 5 (PDE-5 inhibitors). Preferred compounds suitable for use in accordance with the present invention are potent and selective PDE-5 inhibitors. In vitro PDE inhibitory activities against cyclic guanosine 3',5'-monophosphate (cGMP) and cyclic adenosine 3',5'-monophosphate (cAMP) phosphodiesterases can be determined by measurement of their IC$_{50}$ values (the concentration of compound required for 50% inhibition of enzyme activity).

The required PDE enzymes can be isolated from a variety of sources, including human corpus cavernosum, human and rabbit platelets, human cardiac ventricle, human skeletal muscle and bovine retina, essentially by a modification of the method of Thompson, W J et al.; Biochemistry 18(23), 5228-5237, 1979, as described by Ballard S A et al.; J. Urology 159(6), 2164-2171, 1998. In particular, cGMP-specific PDE-5 and cGMP-inhibited cAMP PDE-3 can be obtained from human corpus cavernosum tissue, human platelets or rabbit platelets; cGMP-stimulated PDE-2 was obtained from human corpus cavernosum; calcium/calmodulin (Ca/CAM)-dependent PDE-1 from human cardiac ventricle; cAMP-specific PDE-4 from human skeletal muscle; and photoreceptor PDE-6 from bovine retina. Phosphodiesterases 7-11 can be generated from full length human recombinant clones transfected into SF9 cells.

Assays can be performed either using a modification of the "batch" method of Thompson W J and Appleman M M; Biochemistry 10(2),311-316, 1971, essentially as described by Ballard S A et al.; J. Urology 159(6), 2164-2171, 1998, or using a scintillation proximity assay for the direct detection of [$^3$H]-labelled AMP/GMP using a modification of the protocol described by Amersham plc under product code TRKQ7090/7100. In summary, for the scintillation proximity assay the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a concentration of ~⅓ Km or less) such that $IC_{50} \approx K_i$. The final assay volume was made up to 100 μL with assay buffer [20 mM Tris-HCl pH 7.4, 5 mM $MgCl_2$, 1 mg/mL bovine serum albumin]. Reactions were initiated with enzyme, incubated for 30-60 min at 30° C. to give <30% substrate turnover and terminated with 50 μL silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension.

All compounds of the invention have an activity against PDE-5 of less than 10,000 nm. $IC_{50}$ values for representative preferred compounds are listed in the table below.

| Example | $IC_{50}$ (nM) |
|---------|----------------|
| 2 | 0.50 |
| 11 | 0.31 |
| 15 | 0.11 |
| 20 | 0.64 |
| 23 | 0.47 |
| 91 | 22.6 |
| 138 | 0.33 |
| 141 | 0.15 |
| 161 | 0.5 |
| 162 | 0.24 |
| 181 | 0.41 |
| 184 | 2.94 |
| 185 | 1.32 |
| 191 | 2.4 |
| 193 | 1.01 |
| 211 | 2.7 |
| 224 | 0.2 |
| 247 | 0.47 |
| 248 | 0.30 |
| 249 | 0.16 |
| 250 | 2.37 |
| 251 | 0.25 |
| 252 | 2.81 |
| 253 | 1.20 |
| 255 | 1.43 |
| 256 | 3.89 |
| 258 | 1.99 |
| 261 | 0.57 |
| 262 | 0.93 |
| 263 | 0.27 |

What is claimed is:

1. A compound of formula (I)

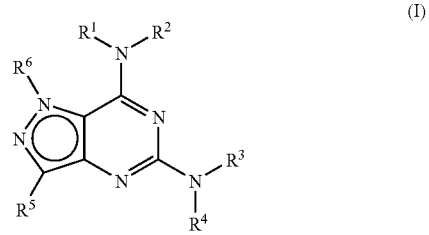

wherein $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ groups, or $R^E$, which is optionally substituted with one or more $R^9$ groups, or hydrogen;

or —$NR^3R^4$ forms $R^F$, which is optionally substituted with one or more $R^{10}$ groups;

$R^5$ is $C_1$-$C_6$ alkyl, $C_1$-$C_6$ haloalkyl, $C_2$-$C_6$ alkenyl, $C_2$-$C_6$ alkynyl or $C_3$-$C_7$ cycloalkyl, each of which is optionally substituted by one or more groups selected from hydroxy, $C_1$-$C_6$ alkoxy, $C_1$-$C_6$ haloalkoxy, $C_3$-$C_7$ cycloalkyl and $C_3$-$C_7$ cycloalkoxy, or hydrogen;

$R^6$ is $R^{6A}$;

$R^{6A}$ is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, $C_1$-$C_6$ haloalkoxy or a cyclic group selected from $R^J$, $R^K$, $R^L$ and $R^M$, or $R^{6A}$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ and $R^J$ are each independently a $C_3$-$C_{10}$ cycloalkyl or $C_3$-$C_{10}$ cycloalkenyl group, each of which may be either monocyclic or, when there are an appropriate number of ring atoms, polycyclic and which may be fused to either (a) a monocyclic aromatic ring selected from a benzene ring and a 5- or 6-membered heteroaromatic ring containing up to three heteroatoms selected from nitrogen, oxygen and sulphur, or (b) a 5-, 6- or 7-membered heteroalicyclic ring containing up to three heteroatoms selected from nitrogen, oxygen and sulphur;

$R^B$ and $R^K$ are each independently a phenyl or naphthyl group, each of which may be fused to (a) a $C_5$-$C_7$ cycloalkyl or $C_5$-$C_7$ cycloalkenyl ring, (b) a 5-, 6- or 7-membered heteroalicyclic ring containing up to three heteroatoms selected from nitrogen, oxygen and sulphur, or (c) a 5- or 6-membered heteroaromatic ring containing up to three heteroatoms selected from nitrogen, oxygen and sulphur;

$R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^D$ and $R^M$ are each independently a 5- or 6-membered heteroaromatic ring containing up to three heteroatoms independently selected from nitrogen, oxygen and sulphur, which ring may further be fused to (a) a second 5- or 6-membered heteroaromatic ring containing up to three heteroatoms selected from nitrogen, oxygen and sulphur;

(b) $C_5$-$C_7$ cycloalkyl or $C_5$-$C_7$ cycloalkenyl ring;

(c) a 5-, 6- or 7-membered heteroalicyclic ring containing up to three heteroatoms selected from nitrogen, oxygen and sulphur; or (d) a benzene ring;

$R^E$, $R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur; and $R^H$ is a 5- or 6-membered heteroaromatic ring containing up to three heteroatoms independently selected from nitrogen, oxygen and sulphur;

a tautomer thereof, or a pharmaceutically acceptable salt or polymorph of said compound or tautomer.

2. A compound according to claim 1 wherein $R^1$ is $R^D$, which is optionally substituted with one or more $R^7$ groups, or a tautomer thereof, or a pharmaceutically acceptable salt or polymorph of said compound or tautomer.

3. A compound according to claim 2 wherein $R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms, or a tautomer thereof, or a pharmaceutically acceptable salt or polymorph of said compound or tautomer.

4. A compound according to claim 3 wherein $R^D$ is pyrazolyl, imidazolyl, isoxazolyl, oxazolyl, oxadiazolyl, pyridyl, pyridazinyl, pyrimidyl or pyrazinyl, or a tautomer thereof, or a pharmaceutically acceptable salt or polymorph of said compound or tautomer.

5. A compound according to claim 4 wherein $R^7$ is fluoro, methyl, ethyl, hydroxy, methoxy, propoxy, trifluoromethyl, or $C(O)NHCH_3$, or a tautomer thereof, or a pharmaceutically acceptable salt or polymorph of said compound or tautomer.

6. A compound according to claim 5 wherein $R^2$ is hydrogen, or a tautomer thereof, or a pharmaceutically acceptable salt or polymorph of said compound or tautomer.

7. A compound according to claim 1 wherein $R^3$ is hydrogen, $C_1$-$C_6$ alkyl, which is optionally substituted with one or more $R^8$ groups, or $R^E$, which is optionally substituted with one or more $R^9$ groups; and wherein $R^E$ is a monocyclic or, when there are an appropriate number of ring atoms, polycyclic saturated ring system containing between 3 and 7 ring atoms, of which at least one is a heteroatom selected from nitrogen, oxygen and sulphur, or a tautomer thereof, or a pharmaceutically acceptable salt or polymorph of said compound or tautomer.

8. A compound according to claim 1 wherein $R^4$ is hydrogen, methyl or ethyl, or a tautomer thereof, or a pharmaceutically acceptable salt or polymorph of said compound or tautomer.

9. A compound according to claim 1 wherein —$NR^3R^4$ forms $R^F$, which is optionally substituted with one or more $R^{10}$ groups and $R^F$ is a monocyclic or, when there are an appropriate number of ring atoms, polycyclic saturated ring system containing between 3 and 10 ring atoms containing one or two nitrogen atoms and optionally one other atom selected from oxygen and sulphur, or a tautomer thereof, or a pharmaceutically acceptable salt or polymorph of said compound or tautomer.

10. A compound according to claim 1 wherein $R^5$ is methyl, ethyl or propyl, each of which is optionally substituted by hydroxy, methoxy or ethoxy, or a tautomer thereof, or a pharmaceutically acceptable salt or polymorph of said compound or tautomer.

11. A compound according to claim 1 wherein $R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy, cyclopropyl, cyclobutyl, tetrahydrofuranyl, tetrahydropyranyl or pyridinyl, or $R^{6A}$ is tetrahydropyranyl, or a tautomer thereof, or a pharmaceutically acceptable salt or polymorph of said compound or tautomer.

12. A compound according to claim 1 selected from:

1-(2-ethoxyethyl)-3-methyl-5-[(3R)-3-methylpiperazin-1-yl]-N-pyrimidin-4-yl-1H-pyrazolo[4,3-d]pyrimidin-7-amine, 1-(2-ethoxyethyl)-3-ethyl-5-[(3R)-3-methylpiperazin-1-yl]-N-pyrimidin-4-yl-1H-pyrazolo[4,3-d]pyrimidin-7-amine, 1-(2-ethoxyethyl)-3-ethyl-$N^5$-methyl-$N^5$-(1-methylpiperidin-4-yl)-$N^7$-pyrimidin-4-yl-1H-pyrazolo[4,3-d]pyrimidine-5,7-diamine, 3-methyl-5-[(3R)-3-methylpiperazin-1-yl]-1-(2-n-propoxyethyl)-N-pyrimidin-4-yl-1H-pyrazolo[4,3-d]pyrimidin-7-amine, 5-[(2R,5S)-2,5-dimethylpiperazin-1-yl]-1-(2-ethoxyethyl)-3-methyl-N-pyrimidin-4-yl-1H-pyrazolo[4,3-d]pyrimidin-7-amine, 5-[(2R,5S)-2,5-dimethylpiperazin-1-yl]-1-(2-ethoxyethyl)-3-ethyl-N-pyrimidin-4-yl-1H-pyrazolo[4,3-d]pyrimidin-7-amine, 1-(2-ethoxyethyl)-$N^5$,3-dimethyl-$N^7$-(4-methylpyridin-2-yl)-$N^5$-[(3S)-1-methylpyrrolidin-3-yl]-1H-pyrazolo[4,3-d]pyrimidine-5,7-diamine, 1-(2-ethoxyethyl)-3-ethyl-$N^5$-methyl-$N^7$-(4-methylpyridin-2-yl)-$N^5$-[(3S)-1-methylpyrrolidin-3-yl]-1H-pyrazolo[4,3-d]pyrimidine-5,7-diamine, 1-(2-ethoxyethyl)-3-(methoxymethyl)-5-[(3R)-3-methylpiperazin-1-yl]-N-(4-methylpyridin-2-yl)-1H-pyrazolo[4,3-d]pyrimidin-7-amine, 1-(2-ethoxyethyl)-3-(methoxymethyl)-$N^5,N^5$-dimethyl-$N^7$-(4-methylpyridin-2-yl)-1H-pyrazolo[4,3-d]pyrimidine-5,7-diamine, {1-(2-ethoxyethyl)-5-[N-ethyl-N-methylamino]-7-[(4-methylpyridin-2-yl)amino]-1H-pyrazolo[4,3-d]pyrimidin-3-yl}methanol, 1-(2-isopropoxyethyl)-3-methyl-5-[(3R)-3-methylpiperazin-1-yl]-N-pyrimidin-4-yl-1H-pyrazolo[4,3-d]pyrimidin-7-amine, 1-(2-ethoxyethyl)-$N^5$,3-dimethyl-$N^5$-[(3S)-1-methylpyrrolidin-3-yl]-$N^7$-pyrimidin-4-yl-1H-pyrazolo[4,3-d]pyrimidine-5,7-diamine, 1-(2-ethoxyethyl)-3-ethyl-$N^5$-methyl-$N^7$-(5-methylpyridin-2-yl)-$N^5$-[(3S)-1-methylpyrrolidin-3-yl]-1H-pyrazolo[4,3-d]pyrimidine-5,7-diamine, 1-methyl-5-[(3R)-3-methylpiperazin-1-yl]-3-propyl-N-pyrimidin-4-yl-1H-pyrazolo[4,3-d]pyrimidin-7-amine, and tautomers thereof, and pharmaceutically acceptable salts and polymorphs of said compounds and tautomers.

13. A pharmaceutical composition comprising a compound of formula (I) as claimed in claim 1 or 12, or a tautomer of said compound, or a pharmaceutically acceptable salt or polymorph of said compound or tautomer; and a pharmaceutically acceptable diluent or carrier.

14. A method of treating hypertension in a mammal, comprising administering to said mammal a therapeutically effective amount of a compound of formula (I) as claimed in claim 1 or 12, or a tautomer thereof, or a pharmaceutically acceptable salt or polymorph of said compound or tautomer.

15. A pharmaceutical composition comprising a compound of formula (I) as claimed in claim 1 or 12, or a tautomer thereof, or a pharmaceutically acceptable salt or polymorph of said compound or tautomer, and a second pharmaceutically active agent selected from aspirin, angiotensin II receptor antagonists, calcium channel blockers, beta-blockers CI1027, CCR5 receptor antagonists, imidazolines, soluble guanylate cyclase activators, diuretics, alpha adrenergic antagonists, ACE (angiotensin converting enzyme) inhibitors aldosterone receptor antagonists, neutral endopeptidase inhibitors, antidiabetic agents glitazones, cholesterol lowering agents, and alpha-2-delta ligands.

16. A compound of formula (VII)

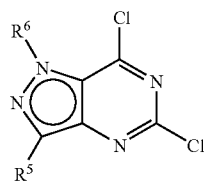

(VII)

wherein
$R^5$ is $C_1$-$C_6$ alkyl, $C_1$-$C_6$ haloalkyl, $C_2$-$C_6$ alkenyl, $C_2$-$C_6$ alkynyl or $C_3$-$C_7$ cycloalkyl, each of which is optionally substituted by one or more groups selected from hydroxy, $C_1$-$C_6$ alkoxy, $C_1$-$C_6$ haloalkoxy, $C_3$-$C_7$ cycloalkyl and $C_3$-$C_7$ cycloalkoxy, or hydrogen;
$R^6$ is $R^{6A}$;
$R^{6A}$ is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, $C_1$-$C_6$ haloalkoxy or a cyclic group selected from $R^J$, $R^K$, $R^L$ and $R^M$, or $R^{6A}$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy;

$R^J$ is a $C_3$-$C_{10}$ cycloalkyl or $C_3$-$C_{10}$ cycloalkenyl group, each of which may be either monocyclic or, when there are an appropriate number of ring atoms, polycyclic and which may be fused to either
(a) a monocyclic aromatic ring selected from a benzene ring and a 5- or 6-membered heteroaromatic ring containing up to three heteroatoms selected from nitrogen, oxygen and sulphur, or
(b) a 5-, 6- or 7-membered heteroalicyclic ring containing up to three heteroatoms selected from nitrogen, oxygen and sulphur;

$R^K$ is a phenyl or naphthyl group, each of which may be fused to
(a) a $C_5$-$C_7$ cycloalkyl or $C_5$-$C_7$ cycloalkenyl ring,
(b) a 5-, 6- or 7-membered heteroalicyclic ring containing up to three heteroatoms selected from nitrogen, oxygen and sulphur, or
(c) a 5- or 6-membered heteroaromatic ring containing up to three heteroatoms selected from nitrogen, oxygen and sulphur;

$R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^M$ is a 5- or 6-membered heteroaromatic ring containing up to three heteroatoms independently selected from nitrogen, oxygen and sulphur, which ring may further be fused to
(a) a second 5- or 6-membered heteroaromatic ring containing up to three heteroatoms selected from nitrogen, oxygen and sulphur;
(b) $C_5$-$C_7$ cycloalkyl or $C_5$-$C_7$ cycloalkenyl ring;
(c) a 5-, 6- or 7-membered heteroalicyclic ring containing up to three heteroatoms selected from nitrogen and sulphur; or
(d) a benzene ring.

17. A compound of formula (VIII)

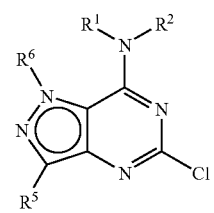

(VIII)

wherein
$R^1$ is a cyclic group selected from $R^A$, $R^B$, $R^C$ and $R^D$, each of which is optionally substituted with one or more $R^7$ groups;
$R^2$ is hydrogen or $C_1$-$C_2$ alkyl;
$R^6$ is $R^{6A}$;
$R^{6A}$ is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, $C_1$-$C_6$ haloalkoxy or a cyclic group selected from $R^J$, $R^K$, $R^L$ and $R^M$, or $R^{6A}$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_{12}R^{14}$, $C(O)R^{12}$, $CO_2R^{12}$, $CONR^{12}R^{13}$ or CN;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ and $R^J$ are each independently a $C_3$-$C_{10}$ cycloalkyl or $C_3$-$C_{10}$ cycloalkenyl group, each of which may be either monocyclic or, when there are an appropriate number of ring atoms, polycyclic and which may be fused to either (a) a monocyclic aromatic ring selected from a benzene ring and a 5- or 6-membered heteroaromatic ring containing up to three heteroatoms selected from nitrogen, oxygen and sulphur, or (b) a 5-, 6- or 7-membered heteroalicyclic ring containing up to three heteroatoms selected from nitrogen, oxygen and sulphur;

$R^B$ and $R^K$ are each independently a phenyl or naphthyl group, each of which may be fused to (a) a $C_5$-$C_7$ cycloalkyl or $C_5$-$C_7$ cycloalkenyl ring, (b) a 5-, 6- or 7-membered heteroalicyclic ring containing up to three heteroatoms selected from nitrogen, oxygen and sulphur, or (c) a 5- or 6-membered heteroaromatic ring containing up to three heteroatoms selected from nitrogen, oxygen and sulphur;

$R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^D$ and $R^M$ are each independently a 5- or 6-membered heteroaromatic ring containing up to three heteroatoms independently selected from nitrogen, oxygen and sulphur, which ring may further be fused to (a) a second 5- or 6-membered heteroaromatic ring containing up to three heteroatoms selected from nitrogen, oxygen and sulphur;

(b) $C_5$-$C_7$ cycloalkyl or $C_5$-$C_7$ cycloalkenyl ring;

(c) a 5-, 6- or 7-membered heteroalicyclic ring containing up to three heteroatoms selected from nitrogen, oxygen and sulphur; or (d) a benzene ring.

18. A process for the preparation of a compound of formula (I) as defined in claim 1 comprising the step of treating a compound of formula (VII) as defined in claim 16 with a compound $HNR^3R^4$, where $R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ groups, or $R^E$, which is optionally substituted with one or more $R^9$ groups, or hydrogen.

19. A compound of formula (I)

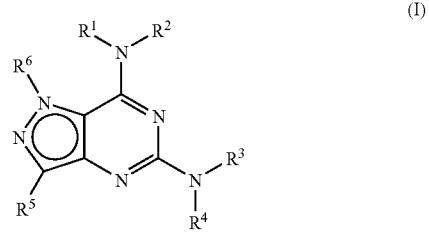

wherein:

$R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is $C_1$-$C_4$ alkyl or $C_1$-$C_4$ haloalkyl, each of which is optionally substituted by hydroxy, $C_1$-$C_4$ alkoxy or $C_1$-$C_4$ haloalkoxy;

$R^6$ is $R^{6A}$;

$R^{6A}$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^{6A}$ is $R^N$;

$R^7$ is halo, $C_1$-$C_6$ alkyl, $C_1$-$C_6$ haloalkyl, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^L$ and $R^N$ are each independently a monocyclic saturated ring system containing either 5 or 6 ring atoms, of which at least one is a heteroatom selected from nitrogen, oxygen and sulphur; and $R^M$ is a 5- or 6-membered heteroaromatic ring containing a heteroatom selected from nitrogen, oxygen and sulphur;

a tautomer thereof, or a pharmaceutically acceptable salt of said compound or tautomer.

20. A compound according to claim 19 wherein $R^2$ is hydrogen, or a tautomer thereof, or a pharmaceutically acceptable salt of said compound or tautomer.

21. A compound according to claim 20 wherein $R^5$ is methyl, ethyl or propyl, each of which is optionally substituted by hydroxy, methoxy or ethoxy, or a tautomer thereof, or a pharmaceutically acceptable salt of said compound or tautomer.

22. A compound according to claim 21 wherein $R^{6A}$ is $C_1$-$C_4$ alkyl or $C_1$-$C_4$ haloalkyl, each of which is optionally substituted by $C_1$-$C_4$ alkoxy, cyclopropyl, cyclobutyl, tetrahydrofuranyl, tetrahydropyranyl or pyridinyl, or $R^{6A}$ is tetrahydropyranyl, or a tautomer thereof, or a pharmaceutically acceptable salt of said compound or tautomer.

23. A compound according to claim 21 wherein $R^{6A}$ is methyl, ethyl, isopropyl, isobutyl, methoxyethyl, methoxypropyl, ethoxyethyl, ethoxypropyl, propoxyethyl, 2,2,2-trifluoroethyl, tetrahydrofuranylmethyl, tetrahydropyranylmethyl, tetrahydropyranyl or pyridinylmethyl, or a tautomer thereof, or a pharmaceutically acceptable salt of said compound or tautomer.

24. A compound according to claim 23 wherein:
—$NR^3R^4$ forms $R^F$, which is optionally substituted with one or more $R^{10}$ groups; and $R^F$ is azetidinyl, pyrrolidinyl, piperidinyl, piperazinyl, morpholinyl, 3-azabicyclo[3.1.0]hex-3-yl, homopiperazinyl, 2,5-diazabicyclo[2.2.1]hept-2-yl, 2,5-diazabicyclo[4.3.0]non-2-yl, 3,8-diazabicyclo[3.2.1]oct-3-yl, 3,8-diazabicyclo[3.2.1]oct-8-yl, 1,4-diazabicyclo[4.3.0]non-4-yl, or 1,4-diazabicyclo[3.2.2]non-4-yl, or a tautomer thereof, or a pharmaceutically acceptable salt of said compound or tautomer.

25. A compound according to claim 24 wherein $R^{10}$ is halo, methyl, ethyl, isopropyl, hydroxy, methoxy, $NH_2$, $NHCH_3$, $N(CH_3)_2$, $NHCO_2$(tert-butyl), $CO_2H$, $CO_2$(tert-butyl), oxo, benzyl, $CH_2NH_2$, $CH_2NHCH_3$, $CH_2N(CH_3)_2$, or $CH_2NCH_3CO_2$(tert-butyl), or a tautomer thereof, or a pharmaceutically acceptable salt of said compound or tautomer.

26. A compound according to claim 25 wherein $NR^3R^4$ forms a piperadine or piperazine ring each of which are optionally substituted by one or two $R^{10}$ groups, or a tautomer thereof, or a pharmaceutically acceptable salt of said compound or tautomer.

27. A compound according to claim 25 wherein $NR^3R^4$ forms a piperazine ring that is optionally substituted by one or two methyl groups, or a tautomer thereof, or a pharmaceutically acceptable salt of said compound or tautomer.

28. A compound according to claim 25 wherein $NR^3R^4$ is substituted with one $R^{10}$ group, and $R^{10}$ is $CO_2H$, or a tautomer thereof, or a pharmaceutically acceptable salt of said compound or tautomer.

29. A compound according to claim 26 wherein $R^1$ is $R^D$; $R^D$ is furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl or pyrazinyl, which is optionally substituted with one or more $R^7$ groups, or a tautomer thereof, or a pharmaceutically acceptable salt of said compound or tautomer.

30. A compound according to claim 26 wherein $R^1$ is $R^D$;

$R^D$ is pyrimidyl or pyridyl, each of which are optionally substituted with one or more $R^7$ groups, or a tautomer thereof, or a pharmaceutically acceptable salt of said compound or tautomer.

31. A compound according to claim 30 wherein $R^7$ is fluoro, methyl, ethyl, hydroxy, methoxy, propoxy, trifluoromethyl, or $CONHCH_3$, or a tautomer thereof, or a pharmaceutically acceptable salt of said compound or tautomer.

32. A compound according to claim 31 wherein $NR^3R^4$ is substituted with one $R^{10}$ group, and $R^{10}$ is $CO_2H$, or a tautomer thereof, or a pharmaceutically acceptable salt of said compound or tautomer.

33. A compound according to claim 27 wherein $R^D$ is pyrimidyl or pyridyl, each of which are optionally substituted with one or more $R^7$ groups, or a tautomer thereof, or a pharmaceutically acceptable salt of said compound or tautomer.

34. A compound according to claim 33 wherein $R^7$ is fluoro, methyl, ethyl, hydroxy, methoxy, propoxy, trifluoromethyl, or $CONHCH_3$, or a tautomer thereof, or a pharmaceutically acceptable salt of said compound or tautomer.

35. A pharmaceutical composition comprising a compound of formula (I) as claimed in claim 19, or a tautomer thereof, or a pharmaceutically acceptable salt of said compound or tautomer; and a pharmaceutically acceptable diluent or carrier.

36. A pharmaceutical composition comprising a compound of formula (I) as claimed in claim 30, or a tautomer thereof, or a pharmaceutically acceptable salt of said compound or tautomer; and a pharmaceutically acceptable diluent or carrier.

37. A pharmaceutical composition comprising a compound of formula (I) as claimed in claim 32, or a tautomer thereof, or a pharmaceutically acceptable salt of said compound or tautomer; and a pharmaceutically acceptable diluent or carrier.

38. A pharmaceutical composition comprising a compound of formula (I) as claimed in claim 34, or a tautomer thereof, or a pharmaceutically acceptable salt of said compound or tautomer; and a pharmaceutically acceptable diluent or carrier.

39. A method of treating hypertension in a mammal, comprising administering to said mammal a therapeutically effective amount of a compound of formula (I) as claimed in claim 19, or a tautomer thereof, or a pharmaceutically acceptable salt of said compound or tautomer.

40. A method of treating hypertension in a mammal, comprising administering to said mammal a therapeutically effective amount of a compound of formula (I) as claimed in claim 30, or a tautomer thereof, or a pharmaceutically acceptable salt of said compound or tautomer.

41. A method of treating hypertension in a mammal, comprising administering to said mammal a therapeutically effective amount of a compound of formula (I) as claimed in claim 32, or a tautomer thereof, or a pharmaceutically acceptable salt of said compound or tautomer.

42. A method of treating hypertension in a mammal, comprising administering to said mammal a therapeutically effective amount of a compound of formula (I) as claimed in claim 34, or a tautomer thereof, or a pharmaceutically acceptable salt of said compound or tautomer.

* * * * *